(12) United States Patent
Chang et al.

(10) Patent No.: US 9,062,351 B2
(45) Date of Patent: *Jun. 23, 2015

(54) DIAGNOSTIC, PROGNOSTIC AND THERAPEUTIC USES OF LONG NON-CODING RNAS FOR CANCER AND REGENERATIVE MEDICINE

(71) Applicant: The Board of Trustees of the Leland Stanford Junior University, Palo Alto, CA (US)

(72) Inventors: Howard Y. Chang, Stanford, CA (US); David J. Wong, Palo Alto, CA (US); Tiffany Hung, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/020,811

(22) Filed: Sep. 7, 2013

(65) Prior Publication Data
US 2014/0073525 A1   Mar. 13, 2014

Related U.S. Application Data

(62) Division of application No. 13/470,233, filed on May 11, 2012, now Pat. No. 8,557,787.

(60) Provisional application No. 61/486,025, filed on May 13, 2011.

(51) Int. Cl.
| | | |
|---|---|---|
| *C12N 15/11* | (2006.01) | |
| *A61K 38/00* | (2006.01) | |
| *C12Q 1/68* | (2006.01) | |
| *A61K 31/713* | (2006.01) | |

(52) U.S. Cl.
CPC ........ *C12Q 1/6886* (2013.01); *C12Q 2600/158* (2013.01); *C12Q 2600/178* (2013.01); *A61K 31/713* (2013.01)

(58) Field of Classification Search
None
See application file for complete search history.

(56) References Cited

U.S. PATENT DOCUMENTS

| 6,713,457 B2 | 3/2004 | Farrar et al. |
| 2008/0233101 A1 | 9/2008 | Sauer |
| 2012/0004278 A1 | 1/2012 | Chang et al. |
| 2012/0289581 A1 | 11/2012 | Chang et al. |

FOREIGN PATENT DOCUMENTS

WO    2011150453 A1    12/2011

OTHER PUBLICATIONS

Huarte et al. (2010) A large intergenic noncoding RNA induced by p53 mediates global gene repression in the p53 response. Cell 142(3):409-419.
Loewer et al. (2010) Large intergenic non-coding RNA-RoR modulates reprogramming of human induced pluripotent stem cells. Nat. Genet. 42(12):1113-1117. Epub Nov. 7, 2010.
Guttman et al. (2009) Chromatin signature reveals over a thousand highly conserved large non-coding RNAs in mammals. Nature 458(7235):223-7. Epub Feb. 1, 2009.
Guttman et al. (2010) Ab initio reconstruction of cell type-specific transcriptomes in mouse reveals the conserved multi-exonic structure of lincRNAs. Nat. Biotechnol. 28(5):503-510. Epub May 2, 2010.
Ponjavic et al. (2009) Genomic and transcriptional co-localization of protein-coding and long non-coding RNA pairs in the developing brain. PLoS Genet. 5(8):e1000617. Epub Aug. 21, 2009.
Gupta et al. (2010) Long non-coding RNA HOTAIR reprograms chromatin state to promote cancer metastasis. Nature 464(7291):1071-1076.
Mazar et al. (2010) Protein-coding and non-coding gene expression analysis in differentiating human keratinocytes using a three-dimensional epidermal equivalent. Mol. Genet. Genomics 284(1):1-9. Epub May 25, 2010.

*Primary Examiner* — Tracy Vivlemore
*Assistant Examiner* — Kate Poliakova
(74) *Attorney, Agent, or Firm* — Jenny Buchbinder

(57) ABSTRACT

Long non-coding RNAs (lncRNAs) and methods of using them diagnostically and therapeutically for treatment of cancer, stem cell therapy, or regenerative medicine are disclosed. In particular, the invention relates to lncRNAs that that play roles in regulation of genes involved in cell proliferation, differentiation, and apoptosis. Such lncRNAs can be used as biomarkers to monitor cell proliferation and differentiation during cancer progression or tissue regeneration. One of the identified lncRNAs, referred to as PANDA (a P21-Associated NcRNA, DNA damage Activated), inhibits the expression of apoptotic genes normally activated by the transcription factor NF-YA. Inhibitors of PANDA sensitize cancerous cells to chemotherapy and can be used in combination with chemotherapeutic agents for treatment of cancer.

5 Claims, 31 Drawing Sheets

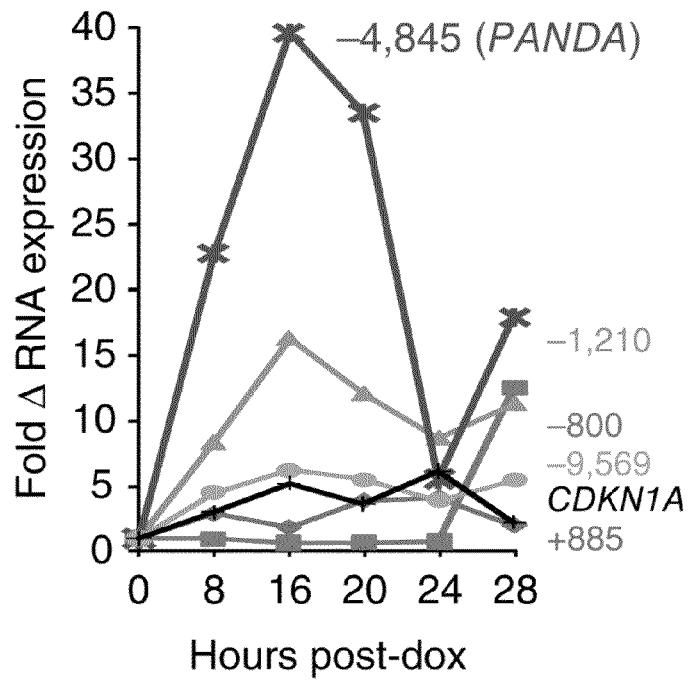
FIG. 5C
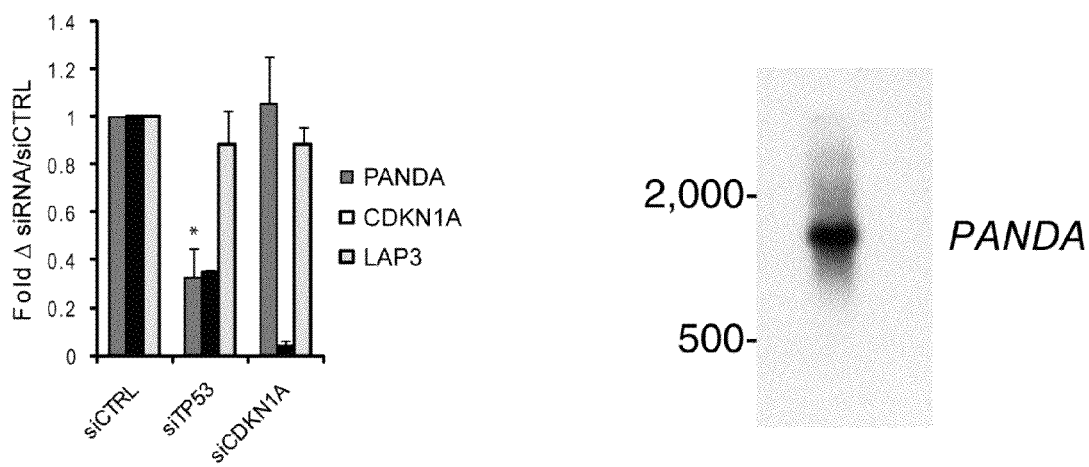
FIG. 5D
FIG. 5E

DIAGNOSTIC, PROGNOSTIC AND THERAPEUTIC USES OF LONG NON-CODING RNAS FOR CANCER AND REGENERATIVE MEDICINE

CROSS-REFERENCE TO RELATED APPLICATION

This application is a divisional application of U.S. application Ser. No. 13/470,233, filed May 11, 2012, which claims benefit under 35 U.S.C. §119(e) of provisional application 61/486,025, filed May 13, 2011, all of which applications are hereby incorporated herein by reference in their entireties.

STATEMENT REGARDING FEDERALLY SPONSORED RESEARCH OR DEVELOPMENT

This invention was made with Government support under contracts CA118750 and AR054615 awarded by the National Institutes of Health. The Government has certain rights in this invention.

TECHNICAL FIELD

The present invention pertains generally to long non-coding RNAs (lncRNAs) and methods of using them diagnostically and therapeutically. In particular, the invention relates to lncRNAs that that play roles in regulation of genes involved in cell proliferation, differentiation, and apoptosis, and their uses in treatment of cancer, stem cell therapy, or regenerative medicine.

BACKGROUND

Mammalian genomes are more pervasively transcribed than previously expected (Bertone et al. (2004) Science 306: 2242-2246; Carninci et al. (2005) Science 309:1559-1563; Calin et al. (2007) Cancer Cell 12: 215-229; and Carninci (2008) Nat. Cell Biol. 10:1023-1024). In addition to the protein-coding regions of genes, much of the genome is transcribed as non-coding RNAs (ncRNAs). These non-coding genomic transcripts include many different types of small regulatory ncRNAs and long ncRNAs (lncRNAs).

Included among the small non-coding RNAs are small interfering RNAs (siRNAs), microRNAs (miRNAs) and Piwi-associated RNAs (piRNAs), which function in genome defense and post-transcriptional regulation (Mattick et al. (2005) Hum. Mol. Genet. 14 Spec No 1, R121-R132; He et al. (2004) Nat. Rev. Genet. 5:522-531; and Hutvagner et al. (2008) Nat. Rev. Mol. Cell. Biol. 9:22-32). In addition, divergent transcription by RNA polymerase near transcriptional start sites (TSS) can result in generation of small ncRNAs, ranging from 20 to 200 nucleotides. These ncRNAs have been variously named promoter-associated small RNAs (PASRs), transcription-initiation RNAs (tiRNAs) and TSS-associated RNAs (TSSa-RNAs) (Kapranov et al. (2007) Science 316: 1484-1488; Seila et al. (2008) Science 322:1849-1851; Taft et al. (2009) Nat. Genet. 41:572-578; and Core (2008) Science 322:1845-1848). It remains uncertain, however, if these ncRNAs are functional or just represent byproducts of RNA polymerase infidelity (Ponjavic et al. (2007) Genome Res. 17:556-565; Struhl (2007) Nat. Struct. Mol. Biol. 14:103-105).

Long ncRNAs vary in length from several hundred bases to tens of kilobases and may be located separate from protein coding genes (long intergenic ncRNAs or lincRNAs), or reside near or within protein coding genes (Guttman et al. (2009) Nature 458:223-227; Katayama et al. (2005) Science 309:1564-1566). Recent evidence indicates that active enhancer elements may also be transcribed as lncRNAs (Kim et al. (2010) Nature 465:182-187; De Santa et al. (2010) PLoS Biol. 8:e1000384).

Several lncRNAs have been implicated in transcriptional regulation. For example, in the CCND1 (encoding cyclin D1) promoter, an ncRNA transcribed 2 kb upstream of CCND1 is induced by ionizing radiation and regulates transcription of CCND1 in cis by forming a ribonucleoprotein repressor complex (Wang et al. (2008) Nature 454:126-130). This ncRNA binds to and allosterically activates the RNA-binding protein TLS (translated in liposarcoma), which inhibits histone acetyltransferases, resulting in repression of CCND1 transcription. Another example is the antisense ncRNA CDKN2B-AS1 (also known as p15AS or ANRIL), which overlaps the p15 coding sequence. Expression of CDKN2B-AS is increased in human leukemias and inversely correlated with p15 expression (Pasmant et al. (2007) Cancer Res. 67:3963-3969; Yu et al. (2008) Nature 451:202-206). CDKN2B-AS1 can transcriptionally silence p15 directly as well as through induction of heterochromatin formation. Many well-studied lncRNAs, such as those involved in dosage compensation and imprinting, regulate gene expression in cis (Lee (2009) Genes Dev. 23:1831-1842). Other lincRNAs, such as HOTAIR and linc-p21 regulate the activity of distantly located genes in trans (Rinn et al. (2007) Cell 129: 1311-1323; Gupta et al. (2010) Nature 464:1071-1076; and Huarte et al. (2010) Cell 142:409-419).

A number of the identified lncRNAs are differentially expressed in association with cell proliferation, differentiation, or apoptosis and could have important roles in regulating cell function (Huarte et al. (2010) Cell 142(3):409-419; Loewer et al. (2010) Nat. Genet. 42(12):1113-1117; Ponjavic et al. (2009) PLoS Genet. 5(8):e1000617; Gupta et al. (2010) Nature 464(7291):1071-1076; and Mazar et al. (2010) Mol. Genet. Genomics 284:1-9). Such lncRNAs may potentially be useful diagnostically or therapeutically; however, the functions of only a few of these lncRNAs have been studied in detail, and many more functional lncRNAs have yet to be discovered. Thus, there remains a need in the art for identifying and characterizing lncRNAs that can be used in developing diagnostics and therapeutics.

SUMMARY

The invention relates to long non-coding RNAs (lncRNAs) and their diagnostic, prognostic, and therapeutic uses for cancer, stem cell therapy, and regenerative medicine. In particular, the invention relates to lncRNAs that that play roles in regulation of genes involved in cell proliferation, differentiation, and apoptosis. Such lncRNAs can be used as biomarkers to monitor cell proliferation and differentiation during cancer progression, stem cell therapy, or tissue regeneration. One of the identified lncRNAs, referred to as PANDA (a P21-Associated NcRNA, DNA damage Activated), inhibits the expression of apoptotic genes normally activated by the transcription factor NF-YA Inhibitors of PANDA sensitize cancerous cells to chemotherapy and can be used in combination with chemotherapeutic agents for treating cancer.

Biomarkers that can be used in the practice of the invention include lncRNAs, such as, but not limited to int:CDK6:143, dst:CDKN2A:43877, upst:CCNF:−1721, upst:CCNI:−6398, upst:CCNI:−6621, upst:CCNI:−6883, upst:CDKN1A:−4845, upst:CDK5R1:−4044, upst:CDK5R1:−4410, upst:CCNL2:−1391, upst:CCNL2:−2253, upst:CCNL2:−767, int: CDKN2D:1417, upst:CCNL2:−5540, int:CDKN1A:1420, int:CCNT1:602, upst:CCNL2:−3110, upst:CDK5R1:−5717, upst:CCNL2:−982, upst:CCNE2:−682, int:CDK5R1:183, upst:CDK5R1:−482, upst:CDK8:−798, upst:CDK9:−646, upst:CDK6:−1860, int:CDK6:1276, upst:CDK6:−533, upst:CDKN2C:−8037, upst:CCNK:−899, upst:CNNM3:−248, upst:CDKN1C:−4619, int:CDKN2A:6667, int:ARF:4530, upst:CDKN2B:−15913, upst:CDK6:−1679, upst:CDKN1A:−1210, int:CDKN2B:1926, dst:CDKN2A:39498, upst:CCNL1:−1968, upst:CCNL1:−2234, upst:CCNL1:−2383, upst:CCNL1:−2767, upst:CDK5R2:−6418, upst:CDK4:−7794, upst:CDKN1A:−5830, int:CDKN2C:159, upst:CCNYL2:−36, upst:CCNC:−6760, upst:CDKN2B:−2817, upst:CNNM3:−970, upst:CDK5R2:−6045, upst:CDKN1C:−2196, int:CCND1:874, int:CCND2:1205, upst:CDKN1C:−446, int:CCNG2:390, upst:CDK3:−4148, upst:CCNA2:−250, int:CDKL5:64, upst:CCND2: 3165, int:CCNK:210, int:CDKN1A:885, upst:CDK5R2:−9197, int:CNNM3:1459, upst:CCND1:−1659, int:CCNL2:463, upst:CCNE1:−1190, upst:CDK5R2:−8037, upst:CDKL3:−867, int:CCNG1:381, upst:CCND2:−2874, upst:CDKN2B:−130736, int:CCNI:1042, upst:CCND2:−4757, int:CDK9:352, int:CCND2:1689, int:CDKL5:1682, upst:CDK5R2:−4541, upst:CDK5:−7855, upst:CDK9:−1536, upst:CCND2:−1291, upst:CCND1:−377, int:CCNL1:1097, upst:CDK5R2:−648, upst:CCNL2:−7336, upst:CCND1:−2768, upst:CDK2:−1390, upst:CCNYL3:−8181, dst:CDKN2A:8650, upst:CDK8:−265, upst:CDK4:−4462, upst:CDKN2A:−44, int:CDKN2A:5270, upst:CCNJL:−2749, upst:CNNM4:−1843, upst:CDK5R2:−7376, int:CCNO:1417, upst:CDKN1C:−5, upst:CDKN1C:−6280, upst:ARF:−840, upst:CCND2:−1830, upst:CDK5R1:−206, upst:CCNA1:−1163, int:CCNE2:647, upst:CDK9:−909, upst:CCNYL3:−293, upst:CDKN3:−271, int:CCNT2:640, upst:CCND1:−2574, upst:CCNT2:−319, upst:CDK5R1:−3023, upst:CDK9:−3159, upst:CDK9:−8667, upst:CCNE2:−4956, int:CCND3:2384, upst:CDKN1B:−1362, upst:CCNI:−7899, upst:CCNT2:−6751, int:CDK5:1993, upst:CDK9:−8509, upst:CCND1:−7190, upst:CDKN1C:−7144, upst:CDKN3:−4479, upst:CCNB3:−3258, upst:CCND3:−9303, upst:CDK8:−8337, int:CDKN2C:643, upst:CCNYL3:−1019, upst:CDK5:−2373, int:CNNM4:1658, upst:CCNE2:−8552, upst:CCNG1:−9141, upst:CCND2:−4886, upst:CCNK:−8357, upst:CDK5:−9105, upst:CDKN2B:−108997, int:CCNB2:547, upst:CDKN3:−2291, dst:CDKN2A:30203, upst:CDK2:−5210, upst:CCNL1:−3430, upst:CCNF:−3964, upst:CCNK:−4426, upst:CCNF:−3743, upst:CDK5:−3754, upst:CDKN2B:−35359, upst:CDKN2B:−87467, upst:CDK5R2:−4915, upst:CCNF:−2075, upst:CDK6:−8726, upst:CDKN2B:−90566, int:CDKN2A:4904, int:CDKN2A:4432, upst:ARF:−2148, upst:CDKN2B:−130339, upst:CNNM3:−9238, upst:CCNG1:−4532, int:ARF:15754, upst:CCNF:−1085, upst:CDKN2B:−23831, upst:CDKN1A:−9569, int:CCNI:1874, dst:CDKN2A:45866, int:CCNC:816, upst:CCNC:−5405, upst:CDK4:−1632, upst:CCNK:−3241, upst:CDK10:−1805, upst:CCNJL:−671, upst:CDKN3:−5723, upst:CDKN2B:−15114, upst:CCNE2:−5939, upst:CCNJL:−7299, upst:CCND3:−4248, int:CDK9:1811, upst:CDKN2C:−8538, upst:ARF:−1395, upst:CCND2:−6904, upst:CDK4:−977, upst:CCNE1:−5422, upst:CCNE2:−2828, upst:CDK4:−2133, upst:CDK8:−9630, upst:CDK3:−4497, upst:CCND3:−6423, upst:CCND1:−8918, upst:CDKN2B:−119804, upst:CDKN3:−5438, upst:CDKN2C:−7397, upst:CCNYL1:−3709, upst:CDKL4:−6205, upst:CDKN1A:−2237, upst:CDKN1C:−4093, upst:CCND2:−9042, int:CDK8:566, upst:CDKN2B:−804, upst:CCNE1:−4445, upst:CDKN2B:−74328, upst:CDKN2B:−53107, upst:CCNE1:−9426, upst:CDKN2C:−3161, upst:CCNG2:−2953, upst:CNNM1:−2645, upst:CDKN1A:−1902, upst:CDKN3:−1974, upst:CDK10:−4173, upst:CDK9:−9782, upst:CDKN1C:−5693, upst:CDK5:−9871, upst:CNNM4:−4755, upst:CDKN2B:−31120, upst:CDK2:−8040, upst:CDKN2B:−75214, upst:CDKN2C:−127, upst:CDKN1C:−1017, and upst:CNNM4:−3840; polynucleotide fragments thereof, and variants comprising nucleotide sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto. Biomarkers can be used alone or in combination with additional biomarkers or relevant clinical parameters in prognosis, diagnosis, or monitoring treatment of cancer, stem cell therapy, or regenerative medicine.

Biomarker polynucleotides (e.g., lncRNAs) can be detected, for example, by microarray analysis, polymerase chain reaction (PCR), reverse transcriptase polymerase chain reaction (RT-PCR), Northern blot, serial analysis of gene expression (SAGE), immunoassay, or mass spectrometry.

In one aspect, the invention provides a method for diagnosing cancer in a subject, comprising measuring the level of a plurality of biomarkers in a biological sample derived from a subject suspected of having cancer, and analyzing the levels of the biomarkers and comparing with respective reference value ranges for the biomarkers, wherein differential expression of one or more biomarkers in the biological sample compared to one or more biomarkers in a control sample indicates that the subject has cancer. In one embodiment, the plurality of biomarkers comprises one or more lncRNAs selected from the group consisting of upst:CCNL1:−2767, int:CDKN1A:+885, upst: CDKN1A: −4845, upst:CDKN2B:−2,817, upst:CDK9:−9782, int:ARF:+4,517, int:ARF:+4530, upst:CDKN1C:−1017, int:CCNG1:+381, and upst:CCNG2:−2953. In certain embodiments, PANDA (upst:CDKN1A:−4845) is used alone or in combination with one or more additional biomarkers or relevant clinical parameters in prognosis, diagnosis, or monitoring treatment of cancer. In certain embodiments, the cancer comprises a mutation in the TP53 gene.

In certain embodiments, the level of one or more biomarkers is compared with reference value ranges for the biomarkers. The reference value ranges can represent the level of one or more biomarkers found in one or more samples of one or more subjects without cancer (i.e., normal or control samples). Alternatively, the reference values can represent the level of one or more biomarkers found in one or more samples of one or more subjects with cancer. More specifically, the reference value ranges can represent the level of one or more biomarkers at particular stages of disease (e.g., mild, moderate, or severe dysplasia, cancer in situ, or invasive cancer) to facilitate a determination of the stage of disease progression in an individual and an appropriate treatment regimen.

In another embodiment, the invention includes a method for monitoring the efficacy of a therapy for treating cancer in a subject, the method comprising: analyzing the level of each of one or more biomarkers in samples derived from the subject before and after the subject undergoes said therapy, in conjunction with respective reference value ranges for said one or more biomarkers, wherein the one or more biomarkers comprises one or more lncRNAs selected from the group consisting of upst:CCNL1:−2767, int:CDKN1A:+885, upst: CDKN1A: −4845, upst:CDKN2B:−2,817, upst:CDK9:−9782, int:ARF:+4,517, int:ARF:+4530, upst:CDKN1C:−1017, int:CCNG1:+381, and upst:CCNG2:−2953.

In another embodiment, the invention includes a method for evaluating the effect of an agent for treating cancer in a subject, the method comprising: analyzing the level of each of one or more biomarkers in samples derived from the subject before and after the subject is treated with said agent, in conjunction with respective reference value ranges for said one or more biomarkers, wherein one or more biomarkers comprises one or more lncRNAs selected from the group consisting of upst:CCNL1:−2767, int:CDKN1A:+885, upst:CDKN1A: −4845, upst:CDKN2B:−2,817, upst:CDK9:−9782, int:ARF:+4,517, int:ARF:+4530, upst:CDKN1C:−1017, int:CCNG1:+381, and upst:CCNG2:−2953.

In another aspect, the invention includes a method for monitoring tissue regeneration in a subject, the method comprising measuring the level of a plurality of biomarkers in a biological sample derived from the subject, wherein the plurality of biomarkers comprises one or more lncRNAs selected from the group consisting of upst:CCNG2:−2953, upst:CDKN1A: −4845, upst: CDKN1A: −9569, upst:CCNL1:−2767, int:CCNG1:+381, upst:CDK9:−9782, int:ARF:+4530, upst:CDKN1C:−1017; and analyzing the levels of the biomarkers in conjunction with respective reference value ranges for said plurality of biomarkers, wherein differential expression of one or more biomarkers in the biological sample compared to one or more biomarkers in a control sample indicates whether the tissue is regenerating.

In another embodiment, the invention includes a method for monitoring cell differentiation in a tissue grown in culture, the method comprising measuring the level of a plurality of biomarkers in a cell derived from the tissue, wherein the plurality of biomarkers comprises one or more lncRNAs selected from the group consisting of upst:CCNG2:−2953, upst: CDKN1A: −4845, upst: CDKN1A: −9569, upst: CCNL1:−2767, int:CCNG1:+381, upst:CDK9:−9782, int:ARF:+4530, upst:CDKN1C:−1017; and analyzing the levels of the biomarkers in conjunction with respective reference value ranges for said plurality of biomarkers, wherein differential expression of one or more biomarkers in the biological sample compared to one or more biomarkers in a control sample indicates the state of differentiation of the tissue. In certain embodiments, the tissue is derived from a stem cell. The stem cell can be an embryonic stem cell, an adult stem cell, or a cord blood stem cell, and can be totipotent, pluripotent, multipotent, or unipotent.

In another embodiment, the invention includes a method for evaluating the effect of an agent for regenerating tissue in a subject, the method comprising: analyzing the level of each of one or more biomarkers in samples derived from the subject before and after the subject is treated with said agent, in conjunction with respective reference value ranges for said one or more biomarkers, wherein one or more biomarkers comprises one or more lncRNAs selected from the group consisting of upst:CCNG2:−2953, upst: CDKN1A: −4845, upst: CDKN1A: −9569, upst:CCNL1:−2767, int:CCNG1:+381, upst:CDK9:−9782, int:ARF:+4530, upst:CDKN1C:−1017.

In another embodiment, the invention includes a method for monitoring the efficacy of a therapy for regenerating tissue in a subject, the method comprising: analyzing the level of each of one or more biomarkers in samples derived from the subject before and after the subject undergoes said therapy, in conjunction with respective reference value ranges for said one or more biomarkers, wherein the one or more biomarkers comprises one or more lncRNAs selected from the group consisting of upst:CCNG2:−2953, upst: CDKN1A: −4845, upst: CDKN1A: −9569, upst:CCNL1:−2767, int:CCNG1:+381, upst:CDK9:−9782, int:ARF:+4530, upst:CDKN1C:−1017.

In another embodiment, the invention includes a method for evaluating the effect of an agent for inducing differentiation of a stem cell in a subject, the method comprising: analyzing the level of each of one or more biomarkers in samples derived from the subject before and after the subject is treated with said agent, in conjunction with respective reference value ranges for said one or more biomarkers, wherein one or more biomarkers comprises one or more lncRNAs selected from the group consisting of upst:CCNG2:−2953, upst: CDKN1A: −4845, upst: CDKN1A: −9569, upst:CCNL1:−2767, int:CCNG1:+381, upst:CDK9:−9782, int:ARF:+4530, upst:CDKN1C:−1017.

In another embodiment, the invention includes a method for monitoring the efficacy of stem cell therapy in a subject, the method comprising: analyzing the level of each of one or more biomarkers in samples derived from the subject before and after the subject undergoes said stem cell therapy, in conjunction with respective reference value ranges for said one or more biomarkers, wherein the one or more biomarkers comprises one or more lncRNAs selected from the group consisting of upst:CCNG2:−2953, upst: CDKN1A: −4845, upst: CDKN1A: −9569, upst:CCNL1:−2767, int:CCNG1:+381, upst:CDK9:−9782, int:ARF:+4530, upst:CDKN1C:−1017.

In another embodiment, the invention includes a method for evaluating the effect of an agent for inducing differentiation of a stem cell, the method comprising growing the stem cell in culture; treating the culture with the agent; measuring the level of a plurality of biomarkers in a cultured cell derived from the stem cell after treating the culture with the agent, wherein the plurality of biomarkers comprises one or more lncRNAs selected from the group consisting of upst: CCNG2:−2953, upst: CDKN1A: −4845, upst: CDKN1A: −9569, upst:CCNL1:−2767, int:CCNG1:+381, upst:CDK9:−9782, int:ARF:+4530, upst:CDKN1C:−1017; and analyzing the levels of the biomarkers in conjunction with respective reference value ranges for said plurality of biomarkers.

In certain embodiments, a panel of biomarkers is used for diagnosing cancer or monitoring cancer progression, stem cell therapy, or regenerative medical treatments. Biomarker panels of any size can be used in the practice of the invention. Biomarker panels typically comprise at least 4 biomarkers and up to 30 biomarkers, including any number of biomarkers in between, such as 4, 5, 6, 7, 8, 9, 10, 11, 12, 13, 14, 15, 16, 17, 18, 19, 20, 21, 22, 23, 24, 25, 26, 27, 28, 29, or 30 biomarkers. In certain embodiments, the invention includes a biomarker panel comprising at least 4, or at least 5, or at least 6, or at least 7, or at least 8, or at least 9, or at least 10 or more biomarkers. Although smaller biomarker panels are usually more economical, larger biomarker panels (i.e., greater than 30 biomarkers) have the advantage of providing more detailed information and can also be used in the practice of the invention.

In certain embodiments, the invention includes a biomarker panel comprising a plurality of lncRNAs selected from the group consisting of int:CDK6:143, dst:CDKN2A:43877, upst:CCNF:−1721, upst:CCNI:−6398, upst:CCNI:−6621, upst:CCNI:−6883, upst:CDKN1A:−4845, upst:CDK5R1:−4044, upst:CDK5R1:−4410, upst:CCNL2:−1391, upst: CCNL2:−2253, upst:CCNL2:−767, int:CDKN2D:1417, upst:CCNL2:−5540, int:CDKN1A:1420, int:CCNT1:602, upst:CCNL2:−3110, upst:CDK5R1:−5717, upst:CCNL2:−982, upst:CCNE2:−682, int:CDK5R1:183, upst:CDK5R1:−482, upst:CDK8:−798, upst:CDK9:−646, upst:CDK6:−1860, int:CDK6:1276, upst:CDK6:−533, upst:CDKN2C:−8037, upst:CCNK:−899, upst:CNNM3:−248, upst:

CDKN1C:−4619, int:CDKN2A:6667, int:ARF:4530, upst: CDKN2B:−15913, upst:CDK6:−1679, upst:CDKN1A:− 1210, int:CDKN2B:1926, dst:CDKN2A:39498, upst: CCNL1:−1968, upst:CCNL1:−2234, upst:CCNL1:−2383, upst:CCNL1:−2767, upst:CDK5R2:−6418, upst:CDK4:− 7794, upst:CDKN1A:−5830, int:CDKN2C:159, upst: CCNYL2:−36, upst:CCNC:−6760, upst:CDKN2B:−2817, upst:CNNM3:−970, upst:CDK5R2:−6045, upst:CDKN1C:− 2196, int:CCND1:874, int:CCND2:1205, upst:CDKN1C:− 446, int:CCNG2:390, upst:CDK3:−4148, upst:CCNA2:− 250, int:CDKL5:64, upst:CCND2: 3165, upst:CCNK:210, int: CDKN1A:885, upst:CDK5R2:−9197, int:CNNM3:1459, upst:CCND1:−1659, int:CCNL2:463, upst:CCNE1:−1190, upst:CDK5R2:−8037, upst:CDKL3:−867, int:CCNG1:381, upst:CCND2:−2874, upst:CDKN2B:−130736, int:CCNI: 1042, upst:CCND2:−4757, int:CDK9:352, int:CCND2: 1689, int:CDKL5:1682, upst:CDK5R2:−4541, upst:CDK5:− 7855, upst:CDK9:−1536, upst:CCND2:−1291, upst: CCND1:−377, int:CCNL1:1097, upst:CDK5R2:−648, upst: CCNL2:−7336, upst:CCND1:−2768, upst:CDK2:−1390, upst:CCNYL3:−8181, dst:CDKN2A:8650, upst:CDK8:− 265, upst:CDK4:−4462, upst:CDKN2A:−44, int:CDKN2A: 5270, upst:CCNJL:−2749, upst:CNNM4:−1843, upst: CDK5R2:−7376, int:CCNO:1417, upst:CDKN1C:−5, upst: CDKN1C:−6280, upst:ARF:−840, upst:CCND2:−1830, upst:CDK5R1:−206, upst:CCNA1:−1163, int:CCNE2:647, upst:CDK9:−909, upst:CCNYL3:−293, upst:CDKN3:−271, int:CCNT2:640, upst:CCND1:−2574, upst:CCNT2:−319, upst:CDK5R1:−3023, upst:CDK9:−3159, upst:CDK9:− 8667, upst:CCNE2:−4956, int:CCND3:2384, upst: CDKN1B:−1362, upst:CCNI:−7899, upst:CCNT2:−6751, int:CDK5:1993, upst:CDK9:−8509, upst:CCND1:−7190, upst:CDKN1C:−7144, upst:CDKN3:−4479, upst:CCNB3:− 3258, upst:CCND3:−9303, upst:CDK8:−8337, int: CDKN2C:643, upst:CCNYL3:−1019, upst:CDK5:−2373, int:CNNM4:1658, upst:CCNE2:−8552, upst:CCNG1:− 9141, upst:CCND2:−4886, upst:CCNK:−8357, upst: CDK5:−9105, upst:CDKN2B:−108997, int:CCNB2:547, upst:CDKN3:−2291, dst:CDKN2A:30203, upst:CDK2:− 5210, upst:CCNL1:−3430, upst:CCNF:−3964, upst: CCNK:−4426, upst:CCNF:−3743, upst:CDK5:−3754, upst: CDKN2B:−35359, upst:CDKN2B:−87467, upst:CDK5R2:− 4915, upst:CCNF:−2075, upst:CDK6:−8726, upst: CDKN2B:−90566, int:CDKN2A:4904, int:CDKN2A:4432, upst:ARF:−2148, upst:CDKN2B:−130339, upst:CNNM3:− 9238, upst:CCNG1:−4532, int:ARF:15754, upst:CCNF:− 1085, upst:CDKN2B:−23831, upst:CDKN1A:−9569, int:C-CNI:1874, dst:CDKN2A:45866, int:CCNC:816, upst: CCNC:−5405, upst:CDK4:−1632, upst:CCNK:−3241, upst: CDK10:−1805, upst:CCNJL:−671, upst:CDKN3:−5723, upst:CDKN2B:−15114, upst:CCNE2:−5939, upst:CCNJL:− 7299, upst:CCND3:−4248, int:CDK9:1811, upst: CDKN2C:−8538, upst:ARF:−1395, upst:CCND2:−6904, upst:CDK4:−977, upst:CCNE1:−5422, upst:CCNE2:−2828, upst:CDK4:−2133, upst:CDK8:−9630, upst:CDK3:−4497, upst:CCND3:−6423, upst:CCND1:−8918, upst:CDKN2B:− 119804, upst:CDKN3:−5438, upst:CDKN2C:−7397, upst: CCNYL1:−3709, upst:CDKL4:−6205, upst:CDKN1A:− 2237, upst:CDKN1C:−4093, upst:CCND2:−9042, int: CDK8:566, upst:CDKN2B:−804, upst:CCNE1:−4445, upst: CDKN2B:−74328, upst:CDKN2B:−53107, upst:CCNE1:− 9426, upst:CDKN2C:−3161, upst:CCNG2:−2953, upst: CNNM1:−2645, upst:CDKN1A:−1902, upst:CDKN3:− 1974, upst:CDK10:−4173, upst:CDK9:−9782, upst: CDKN1C:−5693, upst:CDK5:−9871, upst:CNNM4:−4755, upst:CDKN2B:−31120, upst:CDK2:−8040, upst: CDKN2B:−75214, upst:CDKN2C:−127, upst:CDKN1C:− 1017, and upst:CNNM4:−3840.

In one embodiment, the invention includes a biomarker panel comprising a plurality of lncRNAs selected from the group consisting of int:CDK6:1276, upst:CDK6:−533, upst: CDKN2C:−8037, int:CDKN2D:1417, upst:CCNL2:−5540, int:CDKN1A:1420, int:CCNT1:602, upst:CCNL2:−3110, upst:CDK5R1:−5717, upst:CCNL2:−982, upst:CCNE2:− 682, int:CDK5R1:183, upst:CDK5R1:−482, upst:CDK8:− 798, upst:CDK9:−646, upst:CDK6:−1860, int:CDKN2B: 1926, int:CDK6:143, dst:CDKN2A:43877, upst:CCNF:− 1721, upst:CCNI:−6398, upst:CCNI:−6621, upst:CCNI:− 6883, upst:CDKN1A:−4845, upst:CDK5R1:−4044, upst: CDK5R1:−4410, upst:CCNL2:−1391, upst:CCNL2:−2253, upst:CCNL2:−767, dst:CDKN2A:39498, upst:CCNL1:− 1968, upst:CCNL1:−2234, upst:CCNL1:−2383, upst: CCNL1:−2767, upst:CDK5R2:−6418, upst:CDK4:−7794, upst:CDKN1A:−5830, int:CDKN2C:159, upst:CCNYL2:− 36, upst:CCNC:−6760, upst:CDKN2B:−2817, upst: CNNM3:−970, upst:CDK5R2:−6045, and upst:CDKN1C:− 2196.

In another embodiment, the biomarker panel comprises upst:CCNG2:−2953, upst: CDKN1A: −4845, upst: CDKN1A: −9569, upst:CCNL1:−2767, int:CCNG1:+381, upst:CDK9:−9782, int:ARF:+4530, and upst:CDKN1C:− 1017.

In a further embodiment, the biomarker panel comprises upst:CCNL1:−2767, upst: CDKN1A: −4845, upst:CDK9:− 9782, int:ARF:+4530, upst:CDKN1C:−1017, upst: CCNG2:−2953, int:CCNG1:+381.

In another aspect, the invention includes a method for treating cancer comprising administering to a subject in need thereof a therapeutically effective amount of at least one chemotherapeutic agent in combination with a therapeutically effective amount of at least one PANDA inhibitor. Exemplary PANDA inhibitors include antisense oligonucleotides, inhibitory RNA molecules, such as miRNAs, siRNAs, piRNAs, and snRNAs, and ribozymes. In one embodiment, the inhibitory RNA molecule is an siRNA comprising a nucleotide sequence selected from the group consisting of SEQ ID NOS:12-14.

In another embodiment, the invention includes a method for inhibiting PANDA in a subject comprising administering an effective amount of a PANDA inhibitor to the subject.

In another embodiment, the invention includes a method of increasing the activity of the transcription factor NF-YA in a cell, the method comprising introducing an effective amount of a PANDA inhibitor into the cell.

In yet another aspect, the invention provides kits for use in diagnosing cancer or monitoring cancer progression, stem cell therapy or regenerative medical treatments in a subject. The kit may include at least one agent that specifically detects an lncRNA biomarker, a container for holding a biological sample isolated from the subject, and printed instructions for reacting the agent with the biological sample or a portion of the biological sample to detect the presence or amount of at least one lncRNA biomarker in the biological sample. The agents may be packaged in separate containers. The kit may further comprise one or more control reference samples and reagents for performing an immunoassay, microarray analysis, a Northern, PCR, or SAGE for detection of biomarkers as described herein.

In yet another aspect, the invention provides kits comprising compositions containing PANDA, or at least one PANDA inhibitor, and/or at least one chemotherapeutic agent, or any combination thereof. The kit may also include one or more transfection reagents to facilitate delivery of oligonucleotides or polynucleotides to cells. The kit may further contain means for administering a PANDA inhibitor to a subject.

These and other embodiments of the subject invention will readily occur to those of skill in the art in view of the disclosure herein.

BRIEF DESCRIPTION OF THE FIGURES

FIG. 1A shows a flow chart of the strategy for systematic discovery of cell-cycle ncRNAs. FIG. 1B shows a representative tiling array data. The RNA hybridization intensity and H3K36me3 and H3K4me3 ChIP-chip signals are shown relative to the input at the CCNE1 locus in human fetal lung fibroblasts. The predicted transcripts are shown in gray boxes. Known mRNA exons are shown in black boxes. Each bar represents a significant peak from one of the 108 array channels. FIG. 1C shows the chromatin state at the transcribed regions. The average ChIP-chip signal is shown relative to the input calculated across transcriptional peaks expressed in human fetal lung fibroblasts with or without doxorubicin treatment. FIG. 1D shows a codon substitution frequency (CSF) analysis with a graph of the average evolutionary CSF of the exons of coding genes and their predicted transcripts. A CSF <10 indicates no protein coding potential. FIG. 1E shows the transcriptional landscape of cell-cycle promoters. We aligned all of the cell-cycle promoters at the TSS and calculated the average RNA hybridization signal across a 12 kb window. The output represents a 150 bp running window of the average transcription signals across all 54 arrays.

FIG. 2A shows a hierarchical clustering of 216 predicted ncRNAs across 54 arrays, representing 108 conditions. Light gray indicates that the cell cycle perturbation induced transcription of the ncRNA. Dark gray indicates that the cell cycle perturbation repressed transcription of the ncRNA. Black indicates no significant expression change. FIG. 2B shows a close up view of the ncRNAs in cluster 1.

FIG. 3A shows lncRNA expression patterns do not correlate with those of the mRNAs in cis. Histogram of Pearson correlations between each of the 216 ncRNAs and the cis mRNA across 108 samples are shown. FIG. 3B shows that lncRNA expression patterns have a positive correlation with neighboring lncRNA transcripts. Histogram of Pearson correlations between each of the 216 ncRNAs and nearby transcripts on the same locus across 108 samples are shown. FIG. 3C shows that the genes co-expressed with lncRNAs are enriched for functional groups in the cell cycle and in the DNA damage response. A module map of lncRNA gene sets (columns) versus Gene Ontology Biological Processes gene sets (rows) across 17 samples (P<0.05, false discovery rate <0.05) is shown. A light gray entry indicates that the Gene Ontology gene set is positively associated with the lncRNA gene set. A dark gray entry indicates that the Gene Ontology gene set is negatively associated with the lncRNA gene set. A black entry indicates no significant association. Representative enriched Gene Ontology gene sets are listed.

FIGS. 4A and 4B show periodic expression of lncRNAs (dark gray) during synchronized cell cycle progression in HeLa cells (FIG. 4A) and foreskin fibroblasts (FIG. 4B). Cell cycle phases were confirmed by fluorescence-activated cell sorting and expression of genes with known periodic expression in the cell cycle (light gray). FIG. 4C shows a comparison of regulated expression of lncRNAs in human ESCs and fetal pancreas (d, day). FIG. 4D shows a comparison of differential expression of lncRNAs in normal breast epithelium and breast cancer samples.

FIGS. 5A-5E show that ncRNAs at the CDKN1A locus are induced by DNA damage. FIG. 5A shows: at the top, a map of all detected transcripts at the CDKN1A promoter; in the middle, two tracks are examples of RNA hybridization intensity in the control or in human fetal lung fibroblasts treated with doxorubicin (dox) (200 ng/ml) for 24 hours. Note that we did not observe all DNA-damage-inducible transcripts in one single time point. At the bottom, the p53 ChIP-chip signal relative to input confirmed the p53 binding site immediately upstream of the CDKN1A TSS after DNA damage. The RACE clone of upst:CDKN1A:−4,845 closely matches the predicted transcript on the tiling array. FIG. 5B shows quantitative RT-PCR of lncRNAs with coordinate induction or repression across a 24 hour time course of doxorubicin treatment. A cluster of lncRNAs transcribed from the CDKN1A locus are induced. FIG. 5C shows the expression of transcripts from the CDKN1A locus over a 24 hour time course after doxorubicin treatment of normal human fibroblasts (FL3). FIG. 5D shows an RNA blot of PANDA confirming that the transcript size of 1.5 kb. FIG. 5E shows that doxorubicin induction of PANDA requires p53 but not CDKN1A. The mean±s.d. are shown (*P<0.05 relative to siCTRL (control siRNA) determined by student's t-test). FIG. 5F shows that expression of wild-type p53 in p53-null H1299 cells restores DNA damage induction of CDKN1A and PANDA. The p53 (p.Val272Cys) loss-of-function mutant fails to restore induction, whereas a gain-of-function Li-Fraumeni allele, p53 (p.Arg273His), selectively retains the ability to induce PANDA.

FIG. 6A shows the results of siRNA knockdown of PANDA in the presence of DNA damage with doxorubicin in human fibroblasts (FL3). Custom siRNAs specifically target PANDA with no discernable effect on the LAP3 mRNA. The mean±s.d. is shown in all bar graphs (*P<0.05 compared to siCTRL for all panels determined by Student's t-test). FIG. 6B shows a heat map of gene expression changes with siPANDA relative to control siRNA after 24 hours of doxorubicin treatment in FL3 cells. FIG. 6C shows that quantitative RT-PCR of canonical apoptosis pathway genes revealed induction with siPANDA relative to control siRNA after 28 hours of doxorubicin treatment (in FL3 cells). FIG. 6D shows that quantitative RT-PCR of CDKN1A and TP53 in FL3 cells revealed no reduction in expression with siPANDA relative to control siRNA. FIG. 6E shows TUNEL immunofluorescence of control and siPANDA FL3 fibroblasts after 28 hours of doxorubicin treatment (scale bar, 20 µm). FIG. 6F shows quantification of three independent TUNEL assays (P<0.05 for each siPANDA sample compared to siCTRL determined by student's t-test). FIG. 6G shows a protein blot of PARP cleavage in control and PANDA siRNA FL3 fibroblasts after 24 hours of doxorubicin treatment.

FIG. 7A shows RNA chromatography of PANDA from doxorubicin-treated FL3 cell lysates. We visualized the retrieved proteins by immunoblot analysis. FIG. 7B shows that immunoprecipitation of NF-YA from doxorubicin-treated FL3 lysates specifically retrieves PANDA, as measured by qRT-PCR. The immunoblot confirms immunoprecipitation of NF-YA, as shown at the bottom. FIG. 7C shows ChIP of NF-YA in FL3 fibroblasts nucleofected with siCTRL or siPANDA. ChIP-qPCR is shown for known NF-YA target sites on promoters of CCNB1, FAS, NOXA, BBC3 (PUMA) or a control downstream region in the FAS promoter lacking the NF-YA motif. Mean+s.d. is shown in all bar graphs (*P<0.05 determined by Student's t-test). FIG. 7D shows that concomitant knockdown of NF-YA attenuates induction of apoptotic genes by PANDA depletion, as measured by qRT-PCR. FIG. 7E shows that concomitant knockdown of NF-YA rescues apoptosis induced by PANDA depletion. Quantification of TUNEL staining is shown. The legend for this panel is as in FIG. 7D.

FIG. 16A shows a comparison of the expression in p53 mutant and p53 wild-type tumors. Human primary breast tumors were derived from the fresh-frozen tissue bank of the Netherlands Cancer Institute/Antoni van Leeuwenhoek Hospital. TP53 mutations were identified by DNA sequencing of exons 2-11. FIG. 16B shows a comparison of the expression of PANDA in 5 normal breast tissues and 5 metastatic ductal carcinomas, also obtained from the same tissue depository as FIG. 16A.

DETAILED DESCRIPTION

Figure 1A:
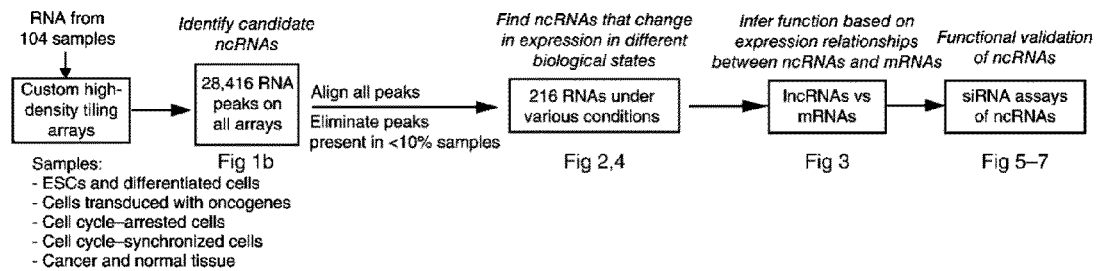
FIGS. 1A-1E show the identification of ncRNAs near and within cell-cycle genes.

The practice of the present invention will employ, unless otherwise indicated, conventional methods of pharmacology, chemistry, biochemistry, recombinant DNA techniques and immunology, within the skill of the art. Such techniques are explained fully in the literature. See, e.g., *Handbook of Experimental Immunology*, Vols. I-IV (D. M. Weir and C.C. Blackwell eds., Blackwell Scientific Publications); A. L. Lehninger, *Biochemistry* (Worth Publishers, Inc., current addition); Sambrook, et al., *Molecular Cloning: A Laboratory Manual* (3$^{rd}$ Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

I. Definitions

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "an lncRNA" includes a mixture of two or more lncRNAs, and the like.

The term "about," particularly in reference to a given quantity, is meant to encompass deviations of plus or minus five percent.

"PANDA" refers to upst:CDKN1A:−4845, also known as P21-Associated, Non-coding RNA, DNA damage Activated, a long non-coding RNA transcript produced from chromosome 6 at nucleotide positions 36749619-36750963. A representative human sequence of PANDA is shown in SEQ ID NO:1.

The terms "microRNA," "miRNA," and MiR" are interchangeable and refer to endogenous or artificial non-coding RNAs that are capable of regulating gene expression. It is believed that miRNAs function via RNA interference. When used herein in the context of inactivation, the use of the term microRNAs is intended to include also long non-coding RNAs, piRNAs, siRNAs, and the like. Endogenous (e.g., naturally occurring) miRNAs are typically expressed from RNA polymerase II promoters and are generated from a larger transcript.

The terms "siRNA" and "short interfering RNA" are interchangeable and refer to single-stranded or double-stranded RNA molecules that are capable of inducing RNA interference. SiRNA molecules typically have a duplex region that is between 18 and 30 base pairs in length.

The terms "piRNA" and "Piwi-interacting RNA" are interchangeable and refer to a class of small RNAs involved in gene silencing. PiRNA molecules typically are between 26 and 31 nucleotides in length.

The terms "snRNA" and "small nuclear RNA" are interchangeable and refer to a class of small RNAs involved in a variety of processes including RNA splicing and regulation of transcription factors. The subclass of small nucleolar RNAs (snoRNAs) is also included. The term is also intended to include artificial snRNAs, such as antisense derivatives of snRNAs comprising antisense sequences directed against the lncRNA, PANDA.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing normucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, microRNA, DNA:RNA hybrids, and hybrids between PNAs and DNA or RNA, and also include known types of modifications, for example, labels which are known in the art, methylation, "caps," substitution of one or more of the naturally occurring nucleotides with an analog (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, 0(6)-methylguanine, and 2-thiocytidine), internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. The term also includes locked nucleic acids (e.g., comprising a ribonucleotide that has a methylene bridge between the 2'-oxygen atom and the 4'-carbon atom). See, for example, Kurreck et al. (2002) Nucleic Acids Res. 30: 1911-1918; Elayadi et al. (2001) Curr. Opinion Invest. Drugs 2: 558-561; Orum et al. (2001) Curr. Opinion Mol. Ther. 3: 239-243; Koshkin et al. (1998) Tetrahedron 54: 3607-3630; Obika et al. (1998) Tetrahedron Lett. 39: 5401-5404.

The term "homologous region" refers to a region of a nucleic acid with homology to another nucleic acid region. Thus, whether a "homologous region" is present in a nucleic acid molecule is determined with reference to another nucleic acid region in the same or a different molecule. Further, since a nucleic acid is often double-stranded, the term "homologous, region," as used herein, refers to the ability of nucleic acid molecules to hybridize to each other. For example, a single-stranded nucleic acid molecule can have two homologous regions which are capable of hybridizing to each other. Thus, the term "homologous region" includes nucleic acid segments with complementary sequence. Homologous regions may vary in length, but will typically be between 4 and 40 nucleotides (e.g., from about 4 to about 40, from about 5 to about 40, from about 5 to about 35, from about 5 to about 30, from about 5 to about 20, from about 6 to about 30, from about 6 to about 25, from about 6 to about 15, from about 7 to about 18, from about 8 to about 20, from about 8 to about 15, etc.).

The term "complementary" and "complementarity" are interchangeable and refer to the ability of polynucleotides to form base pairs with one another. Base pairs are typically formed by hydrogen bonds between nucleotide units in anti-parallel polynucleotide strands or regions. Complementary polynucleotide strands or regions can base pair in the Watson-Crick manner (e.g., A to T, A to U, C to G). 100% complementary refers to the situation in which each nucleotide unit of one polynucleotide strand or region can hydrogen bond with each nucleotide unit of a second polynucleotide strand or region. Less than perfect complementarity refers to the situation in which some, but not all, nucleotide units of two strands or two regions can hydrogen bond with each other and can be expressed as a percentage.

A "target site" or "target sequence" is the nucleic acid sequence recognized (i.e., sufficiently complementary for hybridization) by an antisense oligonucleotide or inhibitory RNA molecule.

The term "hairpin" and "stem-loop" can be used interchangeably and refer to stem-loop structures. The stem results from two sequences of nucleic acid or modified nucleic acid annealing together to generate a duplex. The loop lies between the two strands comprising the stem.

The term "loop" refers to the part of the stem-loop between the two homologous regions (the stem) that can loop around to allow base-pairing of the two homologous regions. The loop can be composed of nucleic acid (e.g., DNA or RNA) or non-nucleic acid material(s), referred to herein as nucleotide or non-nucleotide loops. A non-nucleotide loop can also be situated at the end of a nucleotide molecule with or without a stem structure.

"Administering" a nucleic acid, such as a microRNA, siRNA, piRNA, snRNA, antisense nucleic acid, or lncRNA to a cell comprises transducing, transfecting, electroporating, translocating, fusing, phagocytosing, shooting or ballistic methods, etc., i.e., any means by which a nucleic acid can be transported across a cell membrane.

The term "transfection" is used to refer to the uptake of foreign DNA or RNA by a cell. A cell has been "transfected" when exogenous DNA or RNA has been introduced inside the cell membrane. A number of transfection techniques are generally known in the art. See, e.g., Graham et al. (1973) Virology, 52:456, Sambrook et al. (2001) Molecular Cloning, a laboratory manual, 3rd edition, Cold Spring Harbor Laboratories, New York, Davis et al. (1995) Basic Methods in Molecular Biology, 2nd edition, McGraw-Hill, and Chu et al. (1981) Gene 13:197. Such techniques can be used to introduce one or more exogenous DNA or RNA moieties into suitable host cells. The term refers to both stable and transient uptake of the genetic material, and includes uptake, for example, of microRNA, siRNA, piRNA, lncRNA, or antisense nucleic acids.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

The terms "tumor," "cancer" and "neoplasia" are used interchangeably and refer to a cell or population of cells whose growth, proliferation or survival is greater than growth, proliferation or survival of a normal counterpart cell, e.g. a cell proliferative, hyperproliferative or differentiative disorder. Typically, the growth is uncontrolled. The term "malignancy" refers to invasion of nearby tissue. The term "metastasis" or a secondary, recurring or recurrent tumor, cancer or neoplasia refers to spread or dissemination of a tumor, cancer or neoplasia to other sites, locations or regions within the subject, in which the sites, locations or regions are distinct from the primary tumor or cancer. Neoplasia, tumors and cancers include benign, malignant, metastatic and non-metastatic types, and include any stage (I, II, III, IV or V) or grade (G1, G2, G3, etc.) of neoplasia, tumor, or cancer, or a neoplasia, tumor, cancer or metastasis that is progressing, worsening, stabilized or in remission. In particular, the terms "tumor," "cancer" and "neoplasia" include carcinomas, such as squamous cell carcinoma, adenocarcinoma, adenosquamous carcinoma, anaplastic carcinoma, large cell carcinoma, and small cell carcinoma. These terms include, but are not limited to, breast cancer, prostate cancer, lung cancer, ovarian cancer, testicular cancer, colon cancer, pancreatic cancer, gastric cancer, hepatic cancer, leukemia, lymphoma, adrenal cancer, thyroid cancer, pituitary cancer, renal cancer, brain cancer, skin cancer, head cancer, neck cancer, oral cavity cancer, tongue cancer, and throat cancer.

An "effective amount" of a PANDA inhibitor (e.g., microRNA, siRNA, piRNA, snRNA, antisense nucleic acid, ribozyme, or small molecule inhibitor) is an amount sufficient to effect beneficial or desired results, such as an amount that inhibits the activity of the lncRNA, PANDA, for example by interfering with transcription of PANDA or interfering with binding of PANDA to the transcription factor NF-YA. An effective amount can be administered in one or more administrations, applications, or dosages.

By "anti-tumor activity" is intended a reduction in the rate of cell proliferation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Such activity can be assessed using animal models.

By "therapeutically effective dose or amount" of a PANDA inhibitor is intended an amount that, when administered as described herein, brings about a positive therapeutic response, such as anti-tumor activity. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

The term "tumor response" as used herein means a reduction or elimination of all measurable lesions. The criteria for tumor response are based on the WHO Reporting Criteria [WHO Offset Publication, 48-World Health Organization, Geneva, Switzerland, (1979)]. Ideally, all uni- or bidimensionally measurable lesions should be measured at each assessment. When multiple lesions are present in any organ, such measurements may not be possible and, under such circumstances, up to 6 representative lesions should be selected, if available.

The term "complete response" (CR) as used herein means a complete disappearance of all clinically detectable malignant disease, determined by 2 assessments at least 4 weeks apart.

The term "partial response" (PR) as used herein means a 50% or greater reduction from baseline in the sum of the products of the longest perpendicular diameters of all measurable disease without progression of evaluable disease and without evidence of any new lesions as determined by at least two consecutive assessments at least four weeks apart. Assessments should show a partial decrease in the size of lytic lesions, recalcifications of lytic lesions, or decreased density of blastic lesions.

"Substantially purified" generally refers to isolation of a substance (compound, polynucleotide, protein, polypeptide, polypeptide composition) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macromolecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

"Homology" refers to the percent identity between two polynucleotide or two polypeptide moieties. Two nucleic acid, or two polypeptide sequences are "substantially homologous" to each other when the sequences exhibit at least about 50% sequence identity, preferably at least about 75% sequence identity, more preferably at least about 80%-85% sequence identity, more preferably at least about 90% sequence identity, and most preferably at least about 95%-98% sequence identity over a defined length of the molecules. As used herein, substantially homologous also refers to sequences showing complete identity to the specified sequence.

In general, "identity" refers to an exact nucleotide to nucleotide or amino acid to amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in Atlas of Protein Sequence and Structure M. O. Dayhoff ed., 5 Suppl. 3:353 358, National biomedical Research Foundation, Washington, D.C., which adapts the local homology algorithm of Smith and Waterman Advances in Appl. Math. 2:482 489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single stranded specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Recombinant host cells", "host cells," "cells", "cell lines," "cell cultures", and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

"Operably linked" refers to an arrangement of elements wherein the components so described are configured so as to perform their usual function. Thus, a given promoter operably linked to a coding sequence is capable of effecting the expression of the coding sequence when the proper enzymes are present. Expression is meant to include the transcription of any one or more of transcription of a microRNA, siRNA, piRNA, snRNA, lncRNA, antisense nucleic acid, or mRNA from a DNA or RNA template and can further include translation of a protein from an mRNA template. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Purified polynucleotide" refers to a polynucleotide of interest or fragment thereof which is essentially free, e.g., contains less than about 50%, preferably less than about 70%, and more preferably less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

The terms "variant" refers to biologically active derivatives of the reference molecule that retain desired activity, such as RNA interference (RNAi), lncRNA inhibition, or transcription factor inhibition. In general, the term "variant" refers to molecules (e.g., lncRNAs, miRNAs, siRNAs, piRNAs, snRNAs, antisense nucleic acids, or other inhibitors of lncRNAs) having a native sequence and structure with one or more additions, substitutions (generally conservative in nature) and/or deletions, relative to the native molecule, so long as the modifications do not destroy biological activity and which are "substantially homologous" to the reference molecule. In general, the sequences of such variants will have a high degree of sequence homology to the reference sequence, e.g., sequence homology of more than 50%, generally more than 60%-70%, even more particularly 80%-85% or more, such as at least 90%-95% or more, when the two sequences are aligned.

"Gene transfer" or "gene delivery" refers to methods or systems for reliably inserting DNA or RNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, alphaviruses, pox viruses and vaccinia viruses.

The term "derived from" is used herein to identify the original source of a molecule but is not meant to limit the method by which the molecule is made which can be, for example, by chemical synthesis or recombinant means.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

A "biomarker" in the context of the present invention refers to an lncRNA which is differentially expressed in a biological sample (e.g., a biopsy taken from a subject having cancer or a tissue undergoing regeneration or a stem cell undergoing differentiation) as compared to a control sample (e.g., a comparable sample taken from a person with a negative diagnosis, a normal or healthy subject, or normal, untreated tissue or cells). The biomarker can be an lncRNA that can be detected and/or quantified. Biomarkers include, but are not limited to int:CDK6:143, dst:CDKN2A:43877, upst:CCNF:−1721, upst:CCNI:−6398, upst:CCNI:−6621, upst:CCNI:−6883, upst:CDKN1A:−4845, upst:CDK5R1:−4044, upst:CDK5R1:−4410, upst:CCNL2:−1391, upst:CCNL2:−2253, upst:CCNL2:−767, int:CDKN2D:1417, upst:CCNL2:−5540, int:CDKN1A:1420, int:CCNT1:602, upst:CCNL2:−3110, upst:CDK5R1:−5717, upst:CCNL2:−982, upst:CCNE2:−682, int:CDK5R1:183, upst:CDK5R1:−482, upst:CDK8:−798, upst:CDK9:−646, upst:CDK6:−1860, int:CDK6:1276, upst:CDK6:−533, upst:CDKN2C:−8037, upst:CCNK:−899, upst:CNNM3:−248, upst:CDKN1C:−4619, int:CDKN2A:6667, int:ARF:4530, upst:CDKN2B:−15913, upst:CDK6:−1679, upst:CDKN1A:−1210, int:CDKN2B:1926, dst:CDKN2A:39498, upst:CCNL1:−1968, upst:CCNL1:−2234, upst:CCNL1:−2383, upst:CCNL1:−2767, upst:CDK5R2:−6418, upst:CDK4:−7794, upst:CDKN1A:−5830, int:CDKN2C:159, upst:CCNYL2:−36, upst:CCNC:−6760, upst:CDKN2B:−2817, upst:CNNM3:−970, upst:CDK5R2:−6045, upst:CDKN1C:−2196, int:CCND1:874, int:CCND2:1205, upst:CDKN1C:−446, int:CCNG2:390, upst:CDK3:−4148, upst:CCNA2:−250, int:CDKL5:64, upst:CCND2: 3165, int:CCNK:210, int:CDKN1A:885, upst:CDK5R2:−9197, int:CNNM3:1459, upst:CCND1:−1659, int:CCNL2:463, upst:CCNE1:−1190, upst:CDK5R2:−8037, upst:CDKL3:−867, int:CCNG1:381, upst:CCND2:−2874, upst:CDKN2B:−130736, int:CCNI:1042, upst:CCND2:−4757, int:CDK9:352, int:CCND2:1689, int:CDKL5:1682, upst:CDK5R2:−4541, upst:CDK5:−7855, upst:CDK9:−1536, upst:CCND2:−1291, upst:CCND1:−377, int:CCNL1:1097, upst:CDK5R2:−648, upst:CCNL2:−7336, upst:CCND1:−2768, upst:CDK2:−1390, upst:CCNYL3:−8181, dst:CDKN2A:8650, upst:CDK8:−265, upst:CDK4:−4462, upst:CDKN2A:−44, int:CDKN2A:5270, upst:CCNJL:−2749, upst:CNNM4:−1843, upst:CDK5R2:−7376, int:CCNO:1417, upst:CDKN1C:−5, upst:CDKN1C:−6280, upst:ARF:−840, upst:CCND2:−1830, upst:CDK5R1:−206, upst:CCNA1:−1163, int:CCNE2:647, upst:CDK9:−909, upst:CCNYL3:−293, upst:CDKN3:−271, int:CCNT2:640, upst:CCND1:−2574, upst:CCNT2:−319, upst:CDK5R1:−3023, upst:CDK9:−3159, upst:CDK9:−8667, upst:CCNE2:−4956, int:CCND3:2384, upst:CDKN1B:−1362, upst:CCNI:−7899, upst:CCNT2:−6751, int:CDK5:1993, upst:CDK9:−8509, upst:CCND1:−7190, upst:CDKN1C:−7144, upst:CDKN3:−4479, upst:CCNB3:−3258, upst:CCND3:−9303, upst:CDK8:−8337, int:CDKN2C:643, upst:CCNYL3:−1019, upst:CDK5:−2373, int:CNNM4:1658, upst:CCNE2:−8552, upst:CCNG1:−9141, upst:CCND2:−4886, upst:CCNK:−8357, upst:CDK5:−9105, upst:CDKN2B:−108997, int:CCNB2:547, upst:CDKN3:−2291, dst:CDKN2A:30203, upst:CDK2:−5210, upst:CCNL1:−3430, upst:CCNF:−3964, upst:CCNK:−4426, upst:CCNF:−3743, upst:CDK5:−3754, upst:CDKN2B:−35359, upst:CDKN2B:−87467, upst:CDK5R2:−4915, upst:CCNF:−2075, upst:CDK6:−8726, upst:CDKN2B:−90566, int:CDKN2A:4904, int:CDKN2A:4432, upst:ARF:−2148, upst:CDKN2B:−130339, upst:CNNM3:−9238, upst:CCNG1:−4532, int:ARF:15754, upst:CCNF:−1085, upst:CDKN2B:−23831, upst:CDKN1A:−9569, int:CCNI:1874, dst:CDKN2A:45866, int:CCNC:816, upst:CCNC:−5405, upst:CDK4:−1632, upst:CCNK:−3241, upst:CDK10:−1805, upst:CCNJL:−671, upst:CDKN3:−5723, upst:CDKN2B:−15114, upst:CCNE2:−5939, upst:CCNJL:−7299, upst:CCND3:−4248, int:CDK9:1811, upst:CDKN2C:−8538, upst:ARF:−1395, upst:CCND2:−6904, upst:CDK4:−977, upst:CCNE1:−5422, upst:CCNE2:−2828, upst:CDK4:−2133, upst:CDK8:−9630, upst:CDK3:−4497, upst:CCND3:−6423, upst:CCND1:−8918, upst:CDKN2B:−119804, upst:CDKN3:−5438, upst:CDKN2C:−7397, upst:CCNYL1:−3709, upst:CDKL4:−6205, upst:CDKN1A:−2237, upst:CDKN1C:−4093, upst:CCND2:−9042, int:CDK8:566, upst:CDKN2B:−804, upst:CCNE1:−4445, upst:CDKN2B:−74328, upst:CDKN2B:−53107, upst:CCNE1:−9426, upst:CDKN2C:−3161, upst:CCNG2:−2953, upst:CNNM1:−2645, upst:CDKN1A:−1902, upst:CDKN3:−1974, upst:CDK10:−4173, upst:CDK9:−9782, upst:CDKN1C:−5693, upst:CDK5:−9871, upst:CNNM4:−4755, upst:CDKN2B:−31120, upst:CDK2:−8040, upst:CDKN2B:−75214, upst:CDKN2C:−127, upst:CDKN1C:−1017, and upst:CNNM4:−3840.

The phrase "differentially expressed" refers to differences in the quantity and/or the frequency of a biomarker present in a sample taken from patients having, for example, cancer or undergoing tissue regeneration or stem cell therapy as compared to a control subject. For example, a biomarker can be an lncRNA which is present at an elevated level or at a decreased level in samples of patients with cancer or undergoing tissue regeneration or stem cell therapy compared to samples of control subjects. Alternatively, a biomarker can be an lncRNA which is detected at a higher frequency or at a lower frequency in samples of patients with cancer or undergoing tissue regeneration or stem cell therapy compared to samples of control subjects or control tissues. A biomarker can be differentially present in terms of quantity, frequency or both.

An lncRNA is differentially expressed between two samples if the amount of the lncRNA in one sample is statistically significantly different from the amount of the lncRNA in the other sample. For example, an lncRNA is differentially expressed in two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively or additionally, an lncRNA is differentially expressed in two sets of samples if the frequency of detecting the lncRNA in samples (e.g., tissue or cells from patient suffering from cancer, undergoing stem cell therapy, or regenerative medical treatment) is statistically significantly higher or lower than in the control samples. For example, an lncRNA is differentially expressed in two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

The terms "subject," "individual," and "patient," are used interchangeably herein and refer to any mammalian subject for whom diagnosis, prognosis, treatment, or therapy is desired, particularly humans. Other subjects may include cattle, dogs, cats, guinea pigs, rabbits, rats, mice, horses, and so on. In some cases, the methods of the invention find use in experimental animals, in veterinary application, and in the development of animal models for disease, including, but not limited to, rodents including mice, rats, and hamsters; primates, and transgenic animals.

As used herein, a "biological sample" refers to a sample of tissue or fluid isolated from a subject, including but not limited to, for example, urine, blood, plasma, serum, fecal matter, bone marrow, bile, spinal fluid, lymph fluid, samples of the skin, external secretions of the skin, respiratory, intestinal, and genitourinary tracts, tears, saliva, milk, blood cells, organs, biopsies, and also samples containing cells or tissues derived from the subject and grown in culture, and in vitro cell culture constituents, including but not limited to, conditioned media resulting from the growth of cells and tissues in culture, recombinant cells, stem cells, and cell components.

The term "stem cell" refers to a cell that retains the ability to renew itself through mitotic cell division and that can differentiate into a diverse range of specialized cell types. Mammalian stem cells can be divided into three broad categories: embryonic stem cells, which are derived from blastocysts, adult stem cells, which are found in adult tissues, and cord blood stem cells, which are found in the umbilical cord. In a developing embryo, stem cells can differentiate into all of the specialized embryonic tissues. In adult organisms, stem cells and progenitor cells act as a repair system for the body by replenishing specialized cells. Totipotent stem cells are produced from the fusion of an egg and sperm cell. Cells produced by the first few divisions of the fertilized egg are also totipotent. These cells can differentiate into embryonic and extraembryonic cell types. Pluripotent stem cells are the descendants of totipotent cells and can differentiate into cells derived from any of the three germ layers. Multipotent stem cells can produce only cells of a closely related family of cells (e.g., hematopoietic stem cells differentiate into red blood cells, white blood cells, platelets, etc.). Unipotent cells can produce only one cell type, but have the property of self-renewal, which distinguishes them from non-stem cells.

The terms "quantity," "amount," and "level" are used interchangeably herein and may refer to an absolute quantification of a molecule or an analyte in a sample, or to a relative quantification of a molecule or analyte in a sample, i.e., relative to another value such as relative to a reference value as taught herein, or to a range of values for the biomarker. These values or ranges can be obtained from a single patient or from a group of patients.

A "test amount" of a biomarker refers to an amount of a biomarker present in a sample being tested. A test amount can be either an absolute amount (e.g., µg/ml) or a relative amount (e.g., relative intensity of signals).

A "diagnostic amount" of a biomarker refers to an amount of a biomarker in a subject's sample that is consistent with a diagnosis of cancer. A diagnostic amount can be either an absolute amount (e.g., µg/ml) or a relative amount (e.g., relative intensity of signals).

A "control amount" of a marker can be any amount or a range of amount which is to be compared against a test amount of a biomarker. For example, a control amount of a biomarker can be the amount of a biomarker in a person without cancer, or normal tissue or cells, or untreated tissue or cells. A control amount can be either in absolute amount (e.g., µg/ml) or a relative amount (e.g., relative intensity of signals).

The term "antibody" encompasses polyclonal and monoclonal antibody preparations, as well as preparations including hybrid antibodies, altered antibodies, chimeric antibodies and, humanized antibodies, as well as: hybrid (chimeric) antibody molecules (see, for example, Winter et al. (1991) Nature 349:293-299; and U.S. Pat. No. 4,816,567); F(ab')2 and F(ab) fragments; Fv molecules (noncovalent heterodimers, see, for example, Inbar et al. (1972) Proc Natl Acad Sci USA 69:2659-2662; and Ehrlich et al. (1980) Biochem 19:4091-4096); single-chain Fv molecules (sFv) (see, e.g., Huston et al. (1988) Proc Natl Acad Sci USA 85:5879-5883); dimeric and trimeric antibody fragment constructs; minibodies (see, e.g., Pack et al. (1992) Biochem 31:1579-1584; Cumber et al. (1992) J Immunology 149B:120-126); humanized antibody molecules (see, e.g., Riechmann et al. (1988) Nature 332:323-327; Verhoeyan et al. (1988) Science 239:1534-1536; and U.K. Patent Publication No. GB 2,276, 169, published 21 Sep. 1994); and, any functional fragments obtained from such molecules, wherein such fragments retain specific-binding properties of the parent antibody molecule.

"Immunoassay" is an assay that uses an antibody to specifically bind an antigen (e.g., a biomarker). The immunoassay is characterized by the use of specific binding properties of a particular antibody to isolate, target, and/or quantify the antigen. An immunoassay for a biomarker may utilize one antibody or several antibodies. Immunoassay protocols may be based, for example, upon competition, direct reaction, or sandwich type assays using, for example, labeled antibody. The labels may be, for example, fluorescent, chemiluminescent, or radioactive.

The phrase "specifically (or selectively) binds" to an antibody or "specifically (or selectively) immunoreactive with," when referring to a biomarker, refers to a binding reaction that is determinative of the presence of the biomarker in a heterogeneous population of proteins, nucleic acids, and other biologics. Thus, under designated immunoassay conditions, the specified antibodies bind to a particular biomarker at least two times the background and do not substantially bind in a significant amount to other nucleic acids present in the sample. Specific binding to an antibody under such conditions may require an antibody that is selected for its specificity for a particular lncRNA. For example, polyclonal antibodies raised to a biomarker from specific species such as rat, mouse, or human can be selected to obtain only those polyclonal antibodies that are specifically immunoreactive with the biomarker and not with other nucleic acids, except for polymorphic variants and alleles of the biomarker. This selection may be achieved by subtracting out antibodies that cross-react with biomarker molecules from other species. A variety of immunoassay formats may be used to select antibodies specifically immunoreactive with a particular biomarker. For example, solid-phase ELISA immunoassays are routinely used to select antibodies specifically immunoreactive with an antigen (see, e.g., Harlow & Lane. Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

"Capture reagent" refers to a molecule or group of molecules that specifically bind to a specific target molecule or group of target molecules. For example, a capture reagent can comprise two or more antibodies each antibody having specificity for a separate target molecule. Capture reagents can be any combination of organic or inorganic chemicals, or biomolecules, and all fragments, analogs, homologs, conjugates, and derivatives thereof that can specifically bind a target molecule.

The capture reagent can comprise a single molecule that can form a complex with multiple targets, for example, a multimeric fusion protein with multiple binding sites for different targets. The capture reagent can comprise multiple molecules each having specificity for a different target, thereby resulting in multiple capture reagent-target complexes. In certain embodiments, the capture reagent is comprised of proteins, such as antibodies.

The capture reagent can be directly labeled with a detectable moiety. For example, an anti-biomarker antibody can be directly conjugated to a detectable moiety and used in the inventive methods, devices, and kits. In the alternative, detection of the capture reagent-biomarker complex can be by a secondary reagent that specifically binds to the biomarker or the capture reagent-biomarker complex. The secondary reagent can be any biomolecule, and is preferably an antibody. The secondary reagent is labeled with a detectable moiety. In some embodiments, the capture reagent or secondary reagent is coupled to biotin, and contacted with avidin or streptavidin having a detectable moiety tag.

"Detectable moieties" or "detectable labels" contemplated for use in the invention include, but are not limited to, radioisotopes, fluorescent dyes such as fluorescein, phycoerythrin, Cy-3, Cy-5, allophycoyanin, DAPI, Texas Red, rhodamine, Oregon green, Lucifer yellow, and the like, green fluorescent protein (GFP), red fluorescent protein (DsRed), Cyan Fluorescent Protein (CFP), Yellow Fluorescent Protein (YFP), Cerianthus Orange Fluorescent Protein (cOFP), alkaline phosphatase (AP), beta-lactamase, chloramphenicol acetyltransferase (CAT), adenosine deaminase (ADA), aminoglycoside phosphotransferase (neor, G418r) dihydrofolate reductase (DHFR), hygromycin-B-phosphotransferase (HPH), thymidine kinase (TK), lacZ (encoding alpha-galactosidase), and xanthine guanine phosphoribosyltransferase (XGPRT), Beta-Glucuronidase (gus), Placental Alkaline Phosphatase (PLAP), Secreted Embryonic Alkaline Phosphatase (SEAP), or Firefly or Bacterial Luciferase (LUC). Enzyme tags are used with their cognate substrate. The terms also include color-coded microspheres of known fluorescent light intensities (see e.g., microspheres with xMAP technology produced by Luminex (Austin, Tex.); microspheres containing quantum dot nanocrystals, for example, containing different ratios and combinations of quantum dot colors (e.g., Qdot nanocrystals produced by Life Technologies (Carlsbad, Calif.); glass coated metal nanoparticles (see e.g., SERS nanotags produced by Nanoplex Technologies, Inc. (Mountain View, Calif.); barcode materials (see e.g., sub-micron sized striped metallic rods such as Nanobarcodes produced by Nanoplex Technologies, Inc.), encoded microparticles with colored bar codes (see e.g., CellCard produced by Vitra Bioscience, vitrabio.com), and glass microparticles with digital holographic code images (see e.g., CyVera microbeads produced by Illumina (San Diego, Calif.). As with many of the standard procedures associated with the practice of the invention, skilled artisans will be aware of additional labels that can be used.

"Diagnosis" as used herein generally includes determination as to whether a subject is likely affected by a given disease, disorder or dysfunction. The skilled artisan often makes a diagnosis on the basis of one or more diagnostic indicators, i.e., a biomarker, the presence, absence, or amount of which is indicative of the presence or absence of the disease, disorder or dysfunction.

"Prognosis" as used herein generally refers to a prediction of the probable course and outcome of a clinical condition or disease. A prognosis of a patient is usually made by evaluating factors or symptoms of a disease that are indicative of a favorable or unfavorable course or outcome of the disease. It is understood that the term "prognosis" does not necessarily refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition.

MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery of lncRNAs that play roles in regulation of genes involved in cell proliferation, differentiation, and apoptosis. Such lncRNAs can be used as biomarkers to monitor cell proliferation and differentiation during cancer progression or tissue regeneration. In particular, the inentors have shown that an lncRNA, referred to as PANDA (a P21-Associated NcRNA, DNA damage Activated), inhibits the expression of apoptotic genes normally activated by the transcription factor NF-YA. The inventors have further shown that inhibitors of PANDA sensitize cancerous cells to chemotherapy and can be used in combination with chemotherapeutic agents for treating cancer (see Example 1). In order to further an understanding of the invention, a more detailed discussion is provided below regarding the identified lncRNAs and their diagnostic and therapeutic uses for cancer, stem cell therapy, and regenerative medicine.

A. Biomarkers

Biomarkers that can be used in the practice of the invention include lncRNAs such as, but not limited to int:CDK6:143, dst:CDKN2A:43877, upst:CCNF:−1721, upst:CCNI:−6398, upst:CCNI:−6621, upst:CCNI:−6883, upst:CDKN1A:−4845, upst:CDK5R1:−4044, upst:CDK5R1:−4410, upst:CCNL2:−1391, upst:CCNL2:−2253, upst:CCNL2:−767, int:CDKN2D:1417, upst:CCNL2:−5540, int:CDKN1A:1420, int:CCNT1:602, upst:CCNL2:−3110, upst:CDK5R1:−5717, upst:CCNL2:−982, upst:CCNE2:−682, int:CDK5R1:183, upst:CDK5R1:−482, upst:CDK8:−798, upst:CDK9:−646, upst:CDK6:−1860, int:CDK6:1276, upst:CDK6:−533, upst:CDKN2C:−8037, upst:CCNK:−899, upst:CNNM3:−248, upst:CDKN1C:−4619, int:CDKN2A:6667, int:ARF:4530, upst:CDKN2B:−15913, upst:CDK6:−1679, upst:CDKN1A:−1210, int:CDKN2B:1926, dst:CDKN2A:39498, upst:CCNL1:−1968, upst:CCNL1:−2234, upst:CCNL1:−2383, upst:CCNL1:−2767, upst:CDK5R2:−6418, upst:CDK4:−7794, upst:CDKN1A:−5830, int:CDKN2C:159, upst:CCNYL2:−36, upst:CCNC:−6760, upst:CDKN2B:−2817, upst:CNNM3:−970, upst:CDK5R2:−6045, upst:CDKN1C:−2196, int:CCND1:874, int:CCND2:1205, upst:CDKN1C:−446, int:CCNG2:390, upst:CDK3:−4148, upst:CCNA2:−250, int:CDKL5:64, upst:CCND2: 3165, int:

CCNK:210, int:CDKN1A:885, upst:CDK5R2:−9197, int: CNNM3:1459, upst:CCND1:−1659, int:CCNL2:463, upst: CCNE1:−1190, upst:CDK5R2:−8037, upst:CDKL3:−867, int:CCNG1:381, upst:CCND2:−2874, upst:CDKN2B:− 130736, int:CCNI:1042, upst:CCND2:−4757, int:CDK9: 352, int:CCND2:1689, int:CDKL5:1682, upst:CDK5R2:− 4541, upst:CDK5:−7855, upst:CDK9:−1536, upst: CCND2:−1291, upst:CCND1:−377, int:CCNL1:1097, upst: CDK5R2:−648, upst:CCNL2:−7336, upst:CCND1:−2768, upst:CDK2:−1390, upst:CCNYL3:−8181, dst:CDKN2A: 8650, upst:CDK8:−265, upst:CDK4:−4462, upst: CDKN2A:−44, int:CDKN2A:5270, upst:CCNJL:−2749, upst:CNNM4:−1843, upst:CDK5R2:−7376, int:CCNO: 1417, upst:CDKN1C:−5, upst:CDKN1C:−6280, upst:ARF:− 840, upst:CCND2:−1830, upst:CDK5R1:−206, upst: CCNA1:−1163, int:CCNE2:647, upst:CDK9:−909, upst: CCNYL3:−293, upst:CDKN3:−271, int:CCNT2:640, upst: CCND1:−2574, upst:CCNT2:−319, upst:CDK5R1:−3023, upst:CDK9:−3159, upst:CDK9:−8667, upst:CCNE2:−4956, int:CCND3:2384, upst:CDKN1B:−1362, upst:CCNI:−7899, upst:CCNT2:−6751, int:CDK5:1993, upst:CDK9:−8509, upst:CCND1:−7190, upst:CDKN1C:−7144, upst:CDKN3:− 4479, upst:CCNB3:−3258, upst:CCND3:−9303, upst: CDK8:−8337, int:CDKN2C:643, upst:CCNYL3:−1019, upst:CDK5:−2373, int:CNNM4:1658, upst:CCNE2:−8552, upst:CCNG1:−9141, upst:CCND2:−4886, upst:CCNK:− 8357, upst:CDK5:−9105, upst:CDKN2B:−108997, int: CCNB2:547, upst:CDKN3:−2291, dst:CDKN2A:30203, upst:CDK2:−5210, upst:CCNL1:−3430, upst:CCNF:−3964, upst:CCNK:−4426, upst:CCNF:−3743, upst:CDK5:−3754, upst:CDKN2B:−35359, upst:CDKN2B:−87467, upst: CDK5R2:−4915, upst:CCNF:−2075, upst:CDK6:−8726, upst:CDKN2B:−90566, int:CDKN2A:4904, int:CDKN2A: 4432, upst:ARF:−2148, upst:CDKN2B:−130339, upst: CNNM3:−9238, upst:CCNG1:−4532, int:ARF:15754, upst: CCNF:−1085, upst:CDKN2B:−23831, upst:CDKN1A:− 9569, int:CCNI:1874, dst:CDKN2A:45866, int:CCNC:816, upst:CCNC:−5405, upst:CDK4:−1632, upst:CCNK:−3241, upst:CDK10:−1805, upst:CCNJL:−671, upst:CDKN3:− 5723, upst:CDKN2B:−15114, upst:CCNE2:−5939, upst:C-CNJL:−7299, upst:CCND3:−4248, int:CDK9:1811, upst: CDKN2C:−8538, upst:ARF:−1395, upst:CCND2:−6904, upst:CDK4:−977, upst:CCNE1:−5422, upst:CCNE2:−2828, upst:CDK4:−2133, upst:CDK8:−9630, upst:CDK3:−4497, upst:CCND3:−6423, upst:CCND1:−8918, upst:CDKN2B:− 119804, upst:CDKN3:−5438, upst:CDKN2C:−7397, upst: CCNYL1:−3709, upst:CDKL4:−6205, upst:CDKN1A:− 2237, upst:CDKN1C:−4093, upst:CCND2:−9042, int: CDK8:566, upst:CDKN2B:−804, upst:CCNE1:−4445, upst: CDKN2B:−74328, upst:CDKN2B:−53107, upst:CCNE1:− 9426, upst:CDKN2C:−3161, upst:CCNG2:−2953, upst: CNNM1:−2645, upst:CDKN1A:−1902, upst:CDKN3:− 1974, upst:CDK10:−4173, upst:CDK9:−9782, upst: CDKN1C:−5693, upst:CDK5:−9871, upst:CNNM4:−4755, upst:CDKN2B:−31120, upst:CDK2:−8040, upst: CDKN2B:−75214, upst:CDKN2C:−127, upst:CDKN1C:− 1017, and upst:CNNM4:−3840; polynucleotide fragments thereof, and variants comprising nucleotide sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto. Differential expression of these biomarkers is associated with cell proliferation, differentiation, or apoptosis, and therefore expression profiles of these biomarkers are useful for diagnosing cancer and monitoring differentiation and regeneration of tissues and cells.

Accordingly, in one aspect, the invention provides a method for diagnosing cancer in a subject, comprising measuring the level of a plurality of biomarkers in a biological sample derived from a subject suspected of having cancer, and analyzing the levels of the biomarkers and comparing with respective reference value ranges for the biomarkers, wherein differential expression of one or more biomarkers in the biological sample compared to one or more biomarkers in a control sample indicates that the subject has cancer. The biomarkers can be used alone or in combination with relevant clinical parameters in prognosis, diagnosis, or monitoring treatment of cancer. In one embodiment, the plurality of biomarkers comprises one or more lncRNAs selected from the group consisting of upst:CCNL1:−2767, int:CDKN1A:+ 885, upst: CDKN1A: −4845, upst:CDKN2B:−2,817, upst: CDK9:−9782, int:ARF:+4,517, int:ARF:+4530, upst: CDKN1C:−1017, int:CCNG1:+381, and upst:CCNG2:− 2953. In another embodiment, PANDA is used alone or in combination with one or more additional biomarkers or clinical parameters in diagnosing cancer. In certain embodiments, the cancer comprises a mutation in the TP53 gene.

When analyzing the levels of biomarkers in a biological sample, the reference value ranges used for comparison can represent the level of one or more biomarkers found in one or more samples of one or more subjects without cancer (i.e., normal or control samples). Alternatively, the reference values can represent the level of one or more biomarkers found in one or more samples of one or more subjects with cancer. More specifically, the reference value ranges can represent the level of one or more biomarkers at particular stages of disease (e.g., mild, moderate, or severe dysplasia, cancer in situ, or invasive cancer) to facilitate a determination of the stage of disease progression in an individual.

In another embodiment, the invention includes a method for monitoring the efficacy of a therapy for treating cancer in a subject, the method comprising: analyzing the level of each of one or more biomarkers in samples derived from the subject before and after the subject undergoes said therapy, in conjunction with respective reference value ranges for said one or more biomarkers, wherein the one or more biomarkers comprises one or more lncRNAs selected from the group consisting of upst:CCNL1:−2767, int:CDKN1A:+885, upst: CDKN1A: −4845, upst:CDKN2B:−2,817, upst:CDK9:− 9782, int:ARF:+4,517, int:ARF:+4530, upst:CDKN1C:− 1017, int:CCNG1:+381, and upst:CCNG2:−2953.

In another embodiment, the invention includes a method for evaluating the effect of an agent for treating cancer in a subject, the method comprising: analyzing the level of each of one or more biomarkers in samples derived from the subject before and after the subject is treated with said agent, in conjunction with respective reference value ranges for said one or more biomarkers, wherein one or more biomarkers comprises one or more lncRNAs selected from the group consisting of upst:CCNL1:−2767, int:CDKN1A:+885, upst: CDKN1A: −4845, upst:CDKN2B:−2,817, upst:CDK9:− 9782, int:ARF:+4,517, int:ARF:+4530, upst:CDKN1C:− 1017, int:CCNG1:+381, and upst:CCNG2:−2953.

In another aspect, the invention includes a method for monitoring tissue regeneration in a subject, the method comprising measuring the level of a plurality of biomarkers in a biological sample derived from the subject, wherein the plurality of biomarkers comprises one or more lncRNAs selected from the group consisting of upst:CCNG2:−2953, upst: CDKN1A: −4845, upst: CDKN1A: −9569, upst:CCNL1:− 2767, int:CCNG1:+381, upst:CDK9:−9782, int:ARF:+4530, upst:CDKN1C:−1017; and analyzing the levels of the biomarkers in conjunction with respective reference value ranges for said plurality of biomarkers.

In another embodiment, the invention includes a method for monitoring cell differentiation in a tissue grown in culture, the method comprising measuring the level of a plurality of biomarkers in a cell derived from the tissue, wherein the plurality of biomarkers comprises one or more lncRNAs selected from the group consisting of upst:CCNG2:−2953, upst: CDKN1A: −4845, upst: CDKN1A: −9569, upst: CCNL1:−2767, int:CCNG1:+381, upst:CDK9:−9782, int: ARF:+4530, upst:CDKN1C:−1017; and analyzing the levels of the biomarkers in conjunction with respective reference value ranges for said plurality of biomarkers. In certain embodiments, the tissue is derived from a stem cell. The stem cell can be an embryonic stem cell, an adult stem cell, or a cord blood stem cell, and can be totipotent, pluripotent, multipotent, or unipotent.

In another embodiment, the invention includes a method for evaluating the effect of an agent for regenerating tissue in a subject, the method comprising: analyzing the level of each of one or more biomarkers in samples derived from the subject before and after the subject is treated with said agent, in conjunction with respective reference value ranges for said one or more biomarkers, wherein one or more biomarkers comprises one or more lncRNAs selected from the group consisting of upst:CCNG2:−2953, upst: CDKN1A: −4845, upst: CDKN1A: −9569, upst:CCNL1:−2767, int:CCNG1:+381, upst:CDK9:−9782, int:ARF:+4530, upst:CDKN1C:−1017.

In another embodiment, the invention includes a method for monitoring the efficacy of a therapy for regenerating tissue in a subject, the method comprising: analyzing the level of each of one or more biomarkers in samples derived from the subject before and after the subject undergoes said therapy, in conjunction with respective reference value ranges for said one or more biomarkers, wherein the one or more biomarkers comprises one or more lncRNAs selected from the group consisting of upst:CCNG2:−2953, upst: CDKN1A: −4845, upst: CDKN1A: −9569, upst:CCNL1:−2767, int:CCNG1:+381, upst:CDK9:−9782, int:ARF:+4530, upst:CDKN1C:−1017.

In another embodiment, the invention includes a method for evaluating the effect of an agent for inducing differentiation of a stem cell in a subject, the method comprising: analyzing the level of each of one or more biomarkers in samples derived from the subject before and after the subject is treated with said agent, in conjunction with respective reference value ranges for said one or more biomarkers, wherein one or more biomarkers comprises one or more lncRNAs selected from the group consisting of upst:CCNG2:−2953, upst: CDKN1A: −4845, upst: CDKN1A: −9569, upst:CCNL1:−2767, int:CCNG1:+381, upst:CDK9:−9782, int:ARF:+4530, upst:CDKN1C:−1017.

In another embodiment, the invention includes a method for monitoring the efficacy of stem cell therapy in a subject, the method comprising: analyzing the level of each of one or more biomarkers in samples derived from the subject before and after the subject undergoes said stem cell therapy, in conjunction with respective reference value ranges for said one or more biomarkers, wherein the one or more biomarkers comprises one or more lncRNAs selected from the group consisting of upst:CCNG2:−2953, upst: CDKN1A: −4845, upst: CDKN1A: −9569, upst:CCNL1:−2767, int:CCNG1:+381, upst:CDK9:−9782, int:ARF:+4530, upst:CDKN1C:−1017.

In another embodiment, the invention includes a method for evaluating the effect of an agent for inducing differentiation of a stem cell, the method comprising growing the stem cell in culture; treating the culture with the agent; measuring the level of a plurality of biomarkers in a cultured cell derived from the stem cell after treating the culture with the agent, wherein the plurality of biomarkers comprises one or more lncRNAs selected from the group consisting of upst: CCNG2:−2953, upst: CDKN1A: −4845, upst: CDKN1A: −9569, upst:CCNL1:−2767, int:CCNG1:+381, upst: CDK9:−9782, int:ARF:+4530, upst:CDKN1C:−1017; and analyzing the levels of the biomarkers in conjunction with respective reference value ranges for said plurality of biomarkers.

In cases in which biomarkers are used to monitor stem therapy or cell or tissue differentiation, the reference value ranges used for comparison can represent the level of one or more biomarkers found in one or more samples of one or more healthy or untreated subjects or normal or untreated tissues or cells (i.e., normal or control samples). Alternatively, the reference values can represent the level of one or more biomarkers found in one or more samples of one or more subjects in need of stem cell therapy or regenerative medical treatment. More specifically, the reference value ranges can represent the level of one or more biomarkers in tissues or cells at particular stages of differentiation or treatment to aid in determining an appropriate treatment regimen.

In cases in which the subject is being diagnosed for cancer, the biological sample obtained from the subject to be diagnosed is typically a biopsy of abnormal tissue suspected of containing cancerous or dysplastic cells, but can be any sample of tissue or cells that contains the expressed biomarkers. In cases in which the subject is undergoing stem cell therapy or regenerative medical treatment, the biological sample may include samples from in vitro cell culture resulting from the growth of cells, tissues, or organs, which are to be transferred to the subject, in culture, or a biopsy of tissue from the subject. The biological sample can be obtained from the subject by conventional techniques. For example, samples of tissue or cells can be obtained by surgical techniques well known in the art.

In certain embodiments, the biological sample may comprise a tissue sample including a portion, piece, part, segment, or fraction of a tissue which is obtained or removed from an intact tissue of a subject. Tissue samples can be obtained, for example, from the breast, pancreas, stomach, liver, secretory gland, bladder, lung, prostate gland, ovary, cervix, uterus, brain, eye, connective tissue, bone, muscles, vasculature, skin, oral cavity, tongue, head, neck, or throat. A tissue biopsy may be obtained by methods including, but not limited to, an aspiration biopsy, a brush biopsy, a surface biopsy, a needle biopsy, a punch biopsy, an excision biopsy, an open biopsy, an incision biopsy or an endoscopic biopsy.

In certain embodiments, the biological sample is a tumor sample, including the entire tumor or a portion, piece, part, segment, or fraction of a tumor. A tumor sample can be obtained from a solid tumor or from a non-solid tumor, for example, from a squamous cell carcinoma, skin carcinoma, oral cavity carcinoma, head carcinoma, throat carcinoma, neck carcinoma, breast carcinoma, lung carcinoma, basal cell carcinoma, a colon carcinoma, a cervical carcinoma, Kaposi sarcoma, prostate carcinoma, an adenocarcinoma, a melanoma, hemangioma, meningioma, astrocytoma, neuroblastoma, carcinoma of the pancreas, gastric carcinoma, colorectal carcinoma, colon carcinoma, transitional cell carcinoma of the bladder, carcinoma of the larynx, chronic myeloid leukemia, acute lymphocytic leukemia, acute promyelocytic leukemia, multiple myeloma, T-cell lymphoma, B-cell lymphomas, retinoblastoma, sarcoma gallbladder, or bronchial cancer. The tumor sample may be obtained from a primary tumor or from a metastatic lesion.

In other embodiments, the biological sample is a stem cell, a population of stem cells, or a differentiated cell, tissue or organ derived from stem cells. Stem cells may be embryonic stem cells, adult stem cells, or cord blood stem cells, and may be totipotent, pluripotent, multipotent, or unipotent.

A "control" sample as used herein refers to a biological sample, such as tissue or cells that are not diseased. That is, a control sample is obtained from a normal subject (e.g. an individual known to not have cancer or dysplasia or any condition or symptom associated with abnormal cell maturation or proliferation).

In certain embodiments, a panel of biomarkers is used for diagnosing cancer or monitoring cancer progression, stem cell therapy or regenerative medical treatments. Biomarker panels of any size can be used in the practice of the invention. Biomarker panels typically comprise at least 4 biomarkers and up to 30 biomarkers, including any number of biomarkers in between, such as 4, 5, 6, 7, 8, 9, 10, 11, 12, 13, 14, 15, 16, 17, 18, 19, 20, 21, 22, 23, 24, 25, 26, 27, 28, 29, or 30 biomarkers. In certain embodiments, the invention includes a biomarker panel comprising at least 4, or at least 5, or at least 6, or at least 7, or at least 8, or at least 9, or at least 10 or more biomarkers. Although smaller biomarker panels are usually more economical, larger biomarker panels (i.e., greater than 30 biomarkers) have the advantage of providing more detailed information and can also be used in the practice of the invention.

In certain embodiments, the invention includes a biomarker panel comprising a plurality of lncRNAs selected from the group consisting of int:CDK6:143, dst:CDKN2A:43877, upst:CCNF:−1721, upst:CCNI:−6398, upst:CCNI:−6621, upst:CCNI:−6883, upst:CDKN1A:−4845, upst:CDK5R1:−4044, upst:CDK5R1:−4410, upst:CCNL2:−1391, upst:CCNL2:−2253, upst:CCNL2:−767, int:CDKN2D:1417, upst:CCNL2:−5540, int:CDKN1A:1420, int:CCNT1:602, upst:CCNL2:−3110, upst:CDK5R1:−5717, upst:CCNL2:−982, upst:CCNE2:−682, int:CDK5R1:183, upst:CDK5R1:−482, upst:CDK8:−798, upst:CDK9:−646, upst:CDK6:−1860, int:CDK6:1276, upst:CDK6:−533, upst:CDKN2C:−8037, upst:CCNK:−899, upst:CNNM3:−248, upst:CDKN1C:−4619, int:CDKN2A:6667, int:ARF:4530, upst:CDKN2B:−15913, upst:CDK6:−1679, upst:CDKN1A:−1210, int:CDKN2B:1926, dst:CDKN2A:39498, upst:CCNL1:−1968, upst:CCNL1:−2234, upst:CCNL1:−2383, upst:CCNL1:−2767, upst:CDK5R2:−6418, upst:CDK4:−7794, upst:CDKN1A:−5830, int:CDKN2C:159, upst:CCNYL2:−36, upst:CCNC:−6760, upst:CDKN2B:−2817, upst:CNNM3:−970, upst:CDK5R2:−6045, upst:CDKN1C:−2196, int:CCND1:874, int:CCND2:1205, upst:CDKN1C:−446, int:CCNG2:390, upst:CDK3:−4148, upst:CCNA2:−250, int:CDKL5:64, upst:CCND2: 3165, int:CCNK:210, int:CDKN1A:885, upst:CDK5R2:−9197, int:CNNM3:1459, upst:CCND1:−1659, int:CCNL2:463, upst:CCNE1:−1190, upst:CDK5R2:−8037, upst:CDKL3:−867, int:CCNG1:381, upst:CCND2:−2874, upst:CDKN2B:−130736, int:CCNI:1042, upst:CCND2:−4757, int:CDK9:352, int:CCND2:1689, int:CDKL5:1682, upst:CDK5R2:−4541, upst:CDK5:−7855, upst:CDK9:−1536, upst:CCND2:−1291, upst:CCND1:−377, int:CCNL1:1097, upst:CDK5R2:−648, upst:CCNL2:−7336, upst:CCND1:−2768, upst:CDK2:−1390, upst:CCNYL3:−8181, dst:CDKN2A:8650, upst:CDK8:−265, upst:CDK4:−4462, upst:CDKN2A:−44, int:CDKN2A:5270, upst:CCNJL:−2749, upst:CNNM4:−1843, upst:CDK5R2:−7376, int:CCNO:1417, upst:CDKN1C:−5, upst:CDKN1C:−6280, upst:ARF:−840, upst:CCND2:−1830, upst:CDK5R1:−206, upst:CCNA1:−1163, int:CCNE2:647, upst:CDK9:−909, upst:CCNYL3:−293, upst:CDKN3:−271, int:CCNT2:640, upst:CCND1:−2574, upst:CCNT2:−319, upst:CDK5R1:−3023, upst:CDK9:−3159, upst:CDK9:−8667, upst:CCNE2:−4956, int:CCND3:2384, upst:CDKN1B:−1362, upst:CCNI:−7899, upst:CCNT2:−6751, int:CDK5:1993, upst:CDK9:−8509, upst:CCND1:−7190, upst:CDKN1C:−7144, upst:CDKN3:−4479, upst:CCNB3:−3258, upst:CCND3:−9303, upst:CDK8:−8337, int:CDKN2C:643, upst:CCNYL3:−1019, upst:CDK5:−2373, int:CNNM4:1658, upst:CCNE2:−8552, upst:CCNG1:−9141, upst:CCND2:−4886, upst:CCNK:−8357, upst:CDK5:−9105, upst:CDKN2B:−108997, int:CCNB2:547, upst:CDKN3:−2291, dst:CDKN2A:30203, upst:CDK2:−5210, upst:CCNL1:−3430, upst:CCNF:−3964, upst:CCNK:−4426, upst:CCNF:−3743, upst:CDK5:−3754, upst:CDKN2B:−35359, upst:CDKN2B:−87467, upst:CDK5R2:−4915, upst:CCNF:−2075, upst:CDK6:−8726, upst:CDKN2B:−90566, int:CDKN2A:4904, int:CDKN2A:4432, upst:ARF:−2148, upst:CDKN2B:−130339, upst:CNNM3:−9238, upst:CCNG1:−4532, int:ARF:15754, upst:CCNF:−1085, upst:CDKN2B:−23831, upst:CDKN1A:−9569, int:CCNI:1874, dst:CDKN2A:45866, int:CCNC:816, upst:CCNC:−5405, upst:CDK4:−1632, upst:CCNK:−3241, upst:CDK10:−1805, upst:CCNJL:−671, upst:CDKN3:−5723, upst:CDKN2B:−15114, upst:CCNE2:−5939, upst:CCNJL:−7299, upst:CCND3:−4248, int:CDK9:1811, upst:CDKN2C:−8538, upst:ARF:−1395, upst:CCND2:−6904, upst:CDK4:−977, upst:CCNE1:−5422, upst:CCNE2:−2828, upst:CDK4:−2133, upst:CDK8:−9630, upst:CDK3:−4497, upst:CCND3:−6423, upst:CCND1:−8918, upst:CDKN2B:−119804, upst:CDKN3:−5438, upst:CDKN2C:−7397, upst:CCNYL1:−3709, upst:CDKL4:−6205, upst:CDKN1A:−2237, upst:CDKN1C:−4093, upst:CCND2:−9042, int:CDK8:566, upst:CDKN2B:−804, upst:CCNE1:−4445, upst:CDKN2B:−74328, upst:CDKN2B:−53107, upst:CCNE1:−9426, upst:CDKN2C:−3161, upst:CCNG2:−2953, upst:CNNM1:−2645, upst:CDKN1A:−1902, upst:CDKN3:−1974, upst:CDK10:−4173, upst:CDK9:−9782, upst:CDKN1C:−5693, upst:CDK5:−9871, upst:CNNM4:−4755, upst:CDKN2B:−31120, upst:CDK2:−8040, upst:CDKN2B:−75214, upst:CDKN2C:−127, upst:CDKN1C:−1017, and upst:CNNM4:−3840.

In one embodiment, the invention includes a biomarker panel comprising a plurality of lncRNAs selected from the group consisting of int:CDK6:1276, upst:CDK6:−533, upst:CDKN2C:−8037, int:CDKN2D:1417, upst:CCNL2:−5540, int:CDKN1A:1420, int:CCNT1:602, upst:CCNL2:−3110, upst:CDK5R1:−5717, upst:CCNL2:−982, upst:CCNE2:−682, int:CDK5R1:183, upst:CDK5R1:−482, upst:CDK8:−798, upst:CDK9:−646, upst:CDK6:−1860, int:CDKN2B:1926, int:CDK6:143, dst:CDKN2A:43877, upst:CCNF:−1721, upst:CCNI:−6398, upst:CCNI:−6621, upst:CCNI:−6883, upst:CDKN1A:−4845, upst:CDK5R1:−4044, upst:CDK5R1:−4410, upst:CCNL2:−1391, upst:CCNL2:−2253, upst:CCNL2:−767, dst:CDKN2A:39498, upst:CCNL1:−1968, upst:CCNL1:−2234, upst:CCNL1:−2383, upst:CCNL1:−2767, upst:CDK5R2:−6418, upst:CDK4:−7794, upst:CDKN1A:−5830, int:CDKN2C:159, upst:CCNYL2:−36, upst:CCNC:−6760, upst:CDKN2B:−2817, upst:CNNM3:−970, upst:CDK5R2:−6045, and upst:CDKN1C:−2196.

In another embodiment, the biomarker panel comprises upst:CCNG2:−2953, upst: CDKN1A: −4845, upst:CDKN1A: −9569, upst:CCNL1:−2767, int:CCNG1:+381, upst:CDK9:−9782, int:ARF:+4530, and upst:CDKN1C:−1017. In a further embodiment, the biomarker panel comprises upst:CCNL1:−2767, upst: CDKN1A: −4845, upst: CDK9:−9782, int:ARF:+4530, upst:CDKN1C:−1017, upst: CCNG2:−2953, int:CCNG1:+381.

The methods of the invention, as described herein, can also be used for determining the prognosis of a subject and for monitoring treatment of a subject having cancer. The inventors have shown that some lncRNAs, including upst: CCNL1:−2,767 and int:CDKN1A:+885 are repressed in metastatic breast cancers relative to normal mammary tissues, whereas others, including upst:CDKN1A:−4,845, upst: CDKN2B:−2,817 and int:ARF:+4,517, are induced (See Example 1). Thus, a medical practitioner can monitor the progress of disease by measuring the levels of these lncRNAs in a biological sample from the patient. For example, an increase in a CCNL1:−2,767 or int:CDKN1A:+885 level as compared to a prior level (e.g., in a prior biological sample from the same area of lesion) indicates the disease or condition in the subject is improving or has improved, while a decrease of the CCNL1:−2,767 or int:CDKN1A:+885 level as compared to a prior level (e.g., in a prior biological sample from the same area of lesion) indicates the disease or condition in the subject has worsened or is worsening. In another example, a decrease in a CDKN1A:−4,845, upst:CDKN2B:− 2,817 or int:ARF:+4,517 level as compared to a prior level (e.g., in a prior biological sample from the same area of lesion) indicates the disease or condition in the subject is improving or has improved, while an increase of the CDKN1A:−4,845, upst:CDKN2B:−2,817 and int:ARF:+4, 517 level as compared to a prior level (e.g., in a prior biological sample from the same area of lesion) indicates the disease or condition in the subject has worsened or is worsening.

The methods described herein for prognosis or diagnosis of cancer may be used in individuals who have not yet been diagnosed (for example, preventative screening), or who have been diagnosed, or who are suspected of having cancer (e.g., display one or more characteristic symptoms), or who are at risk of developing cancer (e.g., have a genetic predisposition or presence of one or more developmental, environmental, or behavioral risk factors). The methods may also be used to detect various stages of progression or severity of disease. The methods may also be used to detect the response of disease to prophylactic or therapeutic treatments or other interventions. The methods can furthermore be used to help the medical practitioner in determining prognosis (e.g., worsening, status-quo, partial recovery, or complete recovery) of the patient, and the appropriate course of action, resulting in either further treatment or observation, or in discharge of the patient from the medical care center.

B. Detecting and Measuring Levels of Biomarkers

It is understood that the expression level of the biomarkers in a sample can be determined by any suitable method known in the art. Measurement of the level of a biomarker can be direct or indirect. For example, the abundance levels of lncRNAs can be directly quantitated. Alternatively, the amount of a biomarker can be determined indirectly by measuring abundance levels of cDNAs, amplified RNAs or DNAs, or by measuring quantities or activities of RNAs, or other molecules that are indicative of the expression level of the biomarker.

LncRNAs can be detected and quantitated by a variety of methods including, but not limited to, microarray analysis, polymerase chain reaction (PCR), reverse transcriptase polymerase chain reaction (RT-PCR), Northern blot, serial analysis of gene expression (SAGE), immunoassay, and mass spectrometry. See, e.g., Draghici *Data Analysis Tools for DNA Microarrays*, Chapman and Hall/CRC, 2003; Simon et al. *Design and Analysis of DNA Microarray Investigations*, Springer, 2004; *Real-Time PCR: Current Technology and Applications*, Logan, Edwards, and Saunders eds., Caister Academic Press, 2009; Bustin *A-Z of Quantitative PCR* (IUL Biotechnology, No. 5), International University Line, 2004; Velculescu et al. (1995) Science 270: 484-487; Matsumura et al. (2005) Cell. Microbiol. 7: 11-18; *Serial Analysis of Gene Expression (SAGE): Methods and Protocols (Methods in Molecular Biology)*, Humana Press, 2008, Hoffmann and Stroobant *Mass Spectrometry: Principles and Applications*, Third Edition, Wiley, 2007; herein incorporated by reference in their entireties.

In one embodiment, microarrays are used to measure the levels of biomarkers. An advantage of microarray analysis is that the expression of each of the biomarkers can be measured simultaneously, and microarrays can be specifically designed to provide a diagnostic expression profile for a particular disease or condition (e.g., cancer, regenerative medicine).

Microarrays are prepared by selecting probes which comprise a polynucleotide sequence, and then immobilizing such probes to a solid support or surface. For example, the probes may comprise DNA sequences, RNA sequences, or copolymer sequences of DNA and RNA. The polynucleotide sequences of the probes may also comprise DNA and/or RNA analogues, or combinations thereof. For example, the polynucleotide sequences of the probes may be full or partial fragments of genomic DNA. The polynucleotide sequences of the probes may also be synthesized nucleotide sequences, such as synthetic oligonucleotide sequences. The probe sequences can be synthesized either enzymatically in vivo, enzymatically in vitro (e.g., by PCR), or non-enzymatically in vitro.

Probes used in the methods of the invention are preferably immobilized to a solid support which may be either porous or non-porous. For example, the probes may be polynucleotide sequences which are attached to a nitrocellulose or nylon membrane or filter covalently at either the 3' or the 5' end of the polynucleotide. Such hybridization probes are well known in the art (see, e.g., Sambrook, et al., *Molecular Cloning: A Laboratory Manual* (3rd Edition, 2001). Alternatively, the solid support or surface may be a glass or plastic surface. In one embodiment, hybridization levels are measured to microarrays of probes consisting of a solid phase on the surface of which are immobilized a population of polynucleotides, such as a population of DNA or DNA mimics, or, alternatively, a population of RNA or RNA mimics. The solid phase may be a nonporous or, optionally, a porous material such as a gel.

In one embodiment, the microarray comprises a support or surface with an ordered array of binding (e.g., hybridization) sites or "probes" each representing one of the biomarkers described herein. Preferably the microarrays are addressable arrays, and more preferably positionally addressable arrays. More specifically, each probe of the array is preferably located at a known, predetermined position on the solid support such that the identity (i.e., the sequence) of each probe can be determined from its position in the array (i.e., on the support or surface). Each probe is preferably covalently attached to the solid support at a single site.

Microarrays can be made in a number of ways, of which several are described below. However they are produced, microarrays share certain characteristics. The arrays are reproducible, allowing multiple copies of a given array to be produced and easily compared with each other. Preferably, microarrays are made from materials that are stable under binding (e.g., nucleic acid hybridization) conditions. Microarrays are generally small, e.g., between 1 cm$^2$ and 25 cm$^2$; however, larger arrays may also be used, e.g., in screening arrays. Preferably, a given binding site or unique set of binding sites in the microarray will specifically bind (e.g., hybridize) to the product of a single gene in a cell (e.g., to a specific mRNA, lncRNA, or to a specific cDNA derived therefrom). However, in general, other related or similar sequences will cross hybridize to a given binding site.

As noted above, the "probe" to which a particular polynucleotide molecule specifically hybridizes contains a complementary polynucleotide sequence. The probes of the microarray typically consist of nucleotide sequences of no more than 1,000 nucleotides. In some embodiments, the probes of the array consist of nucleotide sequences of 10 to 1,000 nucleotides. In one embodiment, the nucleotide sequences of the probes are in the range of 10-200 nucleotides in length and are genomic sequences of one species of organism, such that a plurality of different probes is present, with sequences complementary and thus capable of hybridizing to the genome of such a species of organism, sequentially tiled across all or a portion of the genome. In other embodiments, the probes are in the range of 10-30 nucleotides in length, in the range of 10-40 nucleotides in length, in the range of 20-50 nucleotides in length, in the range of 40-80 nucleotides in length, in the range of 50-150 nucleotides in length, in the range of 80-120 nucleotides in length, or are 60 nucleotides in length.

The probes may comprise DNA or DNA "mimics" (e.g., derivatives and analogues) corresponding to a portion of an organism's genome. In another embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone (e.g., phosphorothioates).

DNA can be obtained, e.g., by polymerase chain reaction (PCR) amplification of genomic DNA or cloned sequences. PCR primers are preferably chosen based on a known sequence of the genome that will result in amplification of specific fragments of genomic DNA. Computer programs that are well known in the art are useful in the design of primers with the required specificity and optimal amplification properties, such as Oligo version 5.0 (National Biosciences). Typically each probe on the microarray will be between 10 bases and 50,000 bases, usually between 300 bases and 1,000 bases in length. PCR methods are well known in the art, and are described, for example, in Innis et al., eds., *PCR Protocols: A Guide To Methods And Applications*, Academic Press Inc., San Diego, Calif. (1990); herein incorporated by reference in its entirety. It will be apparent to one skilled in the art that controlled robotic systems are useful for isolating and amplifying nucleic acids.

An alternative, preferred means for generating polynucleotide probes is by synthesis of synthetic polynucleotides or oligonucleotides, e.g., using N-phosphonate or phosphoramidite chemistries (Froehler et al., Nucleic Acid Res. 14:5399-5407 (1986); McBride et al., Tetrahedron Lett. 24:246-248 (1983)). Synthetic sequences are typically between about 10 and about 500 bases in length, more typically between about 20 and about 100 bases, and most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., Nature 363:566-568 (1993); U.S. Pat. No. 5,539,083).

Probes are preferably selected using an algorithm that takes into account binding energies, base composition, sequence complexity, cross-hybridization binding energies, and secondary structure. See Friend et al., International Patent Publication WO 01/05935, published Jan. 25, 2001; Hughes et al., Nat. Biotech. 19:342-7 (2001).

A skilled artisan will also appreciate that positive control probes, e.g., probes known to be complementary and hybridizable to sequences in the target polynucleotide molecules, and negative control probes, e.g., probes known to not be complementary and hybridizable to sequences in the target polynucleotide molecules, should be included on the array. In one embodiment, positive controls are synthesized along the perimeter of the array. In another embodiment, positive controls are synthesized in diagonal stripes across the array. In still another embodiment, the reverse complement for each probe is synthesized next to the position of the probe to serve as a negative control. In yet another embodiment, sequences from other species of organism are used as negative controls or as "spike-in" controls.

The probes are attached to a solid support or surface, which may be made, e.g., from glass, plastic (e.g., polypropylene, nylon), polyacrylamide, nitrocellulose, gel, or other porous or nonporous material. One method for attaching nucleic acids to a surface is by printing on glass plates, as is described generally by Schena et al, Science 270:467-470 (1995). This method is especially useful for preparing microarrays of cDNA (See also, DeRisi et al, Nature Genetics 14:457-460 (1996); Shalon et al., Genome Res. 6:639-645 (1996); and Schena et al., Proc. Natl. Acad. Sci. U.S.A. 93:10539-11286 (1995); herein incorporated by reference in their entireties).

A second method for making microarrays produces high-density oligonucleotide arrays. Techniques are known for producing arrays containing thousands of oligonucleotides complementary to defined sequences, at defined locations on a surface using photolithographic techniques for synthesis in situ (see, Fodor et al., 1991, Science 251:767-773; Pease et al., 1994, Proc. Natl. Acad. Sci. U.S.A. 91:5022-5026; Lockhart et al., 1996, Nature Biotechnology 14:1675; U.S. Pat. Nos. 5,578,832; 5,556,752; and 5,510,270; herein incorporated by reference in their entireties) or other methods for rapid synthesis and deposition of defined oligonucleotides (Blanchard et al., Biosensors & Bioelectronics 11:687-690; herein incorporated by reference in its entirety). When these methods are used, oligonucleotides (e.g., 60-mers) of known sequence are synthesized directly on a surface such as a derivatized glass slide. Usually, the array produced is redundant, with several oligonucleotide molecules per RNA.

Other methods for making microarrays, e.g., by masking (Maskos and Southern, 1992, Nuc. Acids. Res. 20:1679-1684; herein incorporated by reference in its entirety), may also be used. In principle, any type of array, for example, dot blots on a nylon hybridization membrane (see Sambrook, et al., *Molecular Cloning: A Laboratory Manual*, 3rd Edition, 2001) could be used. However, as will be recognized by those skilled in the art, very small arrays will frequently be preferred because hybridization volumes will be smaller.

Microarrays can also be manufactured by means of an ink jet printing device for oligonucleotide synthesis, e.g., using the methods and systems described by Blanchard in U.S. Pat. No. 6,028,189; Blanchard et al., 1996, Biosensors and Bioelectronics 11:687-690; Blanchard, 1998, in Synthetic DNA Arrays in Genetic Engineering, Vol. 20, J. K. Setlow, Ed., Plenum Press, New York at pages 111-123; herein incorporated by reference in their entireties. Specifically, the oligonucleotide probes in such microarrays are synthesized in arrays, e.g., on a glass slide, by serially depositing individual nucleotide bases in "microdroplets" of a high surface tension solvent such as propylene carbonate. The microdroplets have small volumes (e.g., 100 µL or less, more preferably 50 µL or less) and are separated from each other on the microarray (e.g., by hydrophobic domains) to form circular surface tension wells which define the locations of the array elements (i.e., the different probes). Microarrays manufactured by this ink jet method are typically of high density, preferably having a density of at least about 2,500 different probes per 1 cm$^2$. The polynucleotide probes are attached to the support covalently at either the 3' or the 5' end of the polynucleotide.

Biomarker polynucleotides which may be measured by microarray analysis can be expressed lncRNAs or a nucleic acid derived therefrom (e.g., cDNA or amplified RNA derived from cDNA that incorporates an RNA polymerase promoter), including naturally occurring nucleic acid molecules, as well as synthetic nucleic acid molecules. In one embodiment, the target polynucleotide molecules comprise RNA, including, but by no means limited to, total cellular RNA, lncRNA, poly(A)$^+$ messenger RNA (mRNA) or a fraction thereof, cytoplasmic mRNA, or RNA transcribed from cDNA (i.e., cRNA; see, e.g., Linsley & Schelter, U.S. patent application Ser. No. 09/411,074, filed Oct. 4, 1999, or U.S. Pat. Nos. 5,545,522, 5,891,636, or 5,716,785). Methods for preparing total and poly(A)$^+$ RNA are well known in the art, and are described generally, e.g., in Sambrook, et al., *Molecular Cloning: A Laboratory Manual* (3rd Edition, 2001). RNA can be extracted from a cell of interest using guanidinium thiocyanate lysis followed by CsCl centrifugation (Chirgwin et al., 1979, Biochemistry 18:5294-5299), a silica gel-based column (e.g., RNeasy (Qiagen, Valencia, Calif.) or StrataPrep (Stratagene, La Jolla, Calif.)), or using phenol and chloroform, as described in Ausubel et al., eds., 1989, *Current Protocols In Molecular Biology*, Vol. III, Green Publishing Associates, Inc., John Wiley & Sons, Inc., New York, at pp. 13.12.1-13.12.5). Poly(A)$^+$ RNA can be selected, e.g., by selection with oligo-dT cellulose or, alternatively, by oligo-dT primed reverse transcription of total cellular RNA. RNA can be fragmented by methods known in the art, e.g., by incubation with $ZnCl_2$, to generate fragments of RNA.

In one embodiment, total RNA, lncRNAs, or nucleic acids derived therefrom, are isolated from a sample taken from a patient undergoing cancer treatment, stem cell therapy, or regenerative medical treatment. Biomarker lncRNAs that are poorly expressed in particular cells may be enriched using normalization techniques (Bonaldo et al., 1996, Genome Res. 6:791-806).

As described above, the biomarker polynucleotides can be detectably labeled at one or more nucleotides. Any method known in the art may be used to label the target polynucleotides. Preferably, this labeling incorporates the label uniformly along the length of the RNA, and more preferably, the labeling is carried out at a high degree of efficiency. For example, polynucleotides can be labeled by oligo-dT primed reverse transcription. Random primers (e.g., 9-mers) can be used in reverse transcription to uniformly incorporate labeled nucleotides over the full length of the polynucleotides. Alternatively, random primers may be used in conjunction with PCR methods or T7 promoter-based in vitro transcription methods in order to amplify polynucleotides.

The detectable label may be a luminescent label. For example, fluorescent labels, bioluminescent labels, chemiluminescent labels, and colorimetric labels may be used in the practice of the invention. Fluorescent labels that can be used include, but are not limited to, fluorescein, a phosphor, a rhodamine, or a polymethine dye derivative. Additionally, commercially available fluorescent labels including, but not limited to, fluorescent phosphoramidites such as FluorePrime (Amersham Pharmacia, Piscataway, N.J.), Fluoredite (Miilipore, Bedford, Mass.), FAM (ABI, Foster City, Calif.), and Cy3 or Cy5 (Amersham Pharmacia, Piscataway, N.J.) can be used. Alternatively, the detectable label can be a radiolabeled nucleotide.

In one embodiment, biomarker polynucleotide molecules from a patient sample are labeled differentially from the corresponding polynucleotide molecules of a reference sample. The reference can comprise lncRNAs from a normal biological sample (i.e., control sample, e.g., biopsy from a subject not having cancer, or untreated cells or tissue) or from a reference biological sample, (e.g., sample from a subject having cancer, sample of cells or tissue at different stages of differentiation or treatment).

Nucleic acid hybridization and wash conditions are chosen so that the target polynucleotide molecules specifically bind or specifically hybridize to the complementary polynucleotide sequences of the array, preferably to a specific array site, wherein its complementary DNA is located. Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self-complementary sequences.

Optimal hybridization conditions will depend on the length (e.g., oligomer versus polynucleotide greater than 200 bases) and type (e.g., RNA, or DNA) of probe and target nucleic acids. One of skill in the art will appreciate that as the oligonucleotides become shorter, it may become necessary to adjust their length to achieve a relatively uniform melting temperature for satisfactory hybridization results. General parameters for specific (i.e., stringent) hybridization conditions for nucleic acids are described in Sambrook, et al., *Molecular Cloning: A Laboratory Manual* (3rd Edition, 2001), and in Ausubel et al., *Current Protocols In Molecular Biology*, vol. 2, Current Protocols Publishing, New York (1994). Typical hybridization conditions for the cDNA microarrays of Schena et al. are hybridization in 5.times.SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Schena et al., Proc. Natl. Acad. Sci. U.S.A. 93:10614 (1993)). Useful hybridization conditions are also provided in, e.g., Tijessen, 1993, *Hybridization with Nucleic Acid Probes*, Elsevier Science Publishers B. V.; and Kricka, 1992, *Nonisotopic Dna Probe Techniques*, Academic Press, San Diego, Calif. Particularly preferred hybridization conditions include hybridization at a temperature at or near the mean melting temperature of the probes (e.g., within 51° C., more preferably within 21° C.) in 1 M NaCl, 50 mM MES buffer (pH 6.5), 0.5% sodium sarcosine and 30% formamide.

When fluorescently labeled gene products are used, the fluorescence emissions at each site of a microarray may be, preferably, detected by scanning confocal laser microscopy. In one embodiment, a separate scan, using the appropriate excitation line, is carried out for each of the two fluorophores used. Alternatively, a laser may be used that allows simultaneous specimen illumination at wavelengths specific to the two fluorophores and emissions from the two fluorophores can be analyzed simultaneously (see Shalon et al., 1996, "A DNA microarray system for analyzing complex DNA samples using two-color fluorescent probe hybridization,"

Genome Research 6:639-645, which is incorporated by reference in its entirety for all purposes). Arrays can be scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Schena et al., Genome Res. 6:639-645 (1996), and in other references cited herein. Alternatively, the fiber-optic bundle described by Ferguson et al., Nature Biotech. 14:1681-1684 (1996), may be used to monitor mRNA abundance levels at a large number of sites simultaneously.

In one embodiment, the invention includes a microarray comprising a plurality of probes that hybridize to one or more lncRNAs selected from the group consisting of int:CDK6: 143, dst:CDKN2A:43877, upst:CCNF:−1721, upst:CCNI:− 6398, upst:CCNI:−6621, upst:CCNI:−6883, upst: CDKN1A:−4845, upst:CDK5R1:−4044, upst:CDK5R1:− 4410, upst:CCNL2:−1391, upst:CCNL2:−2253, upst: CCNL2:−767, int:CDKN2D:1417, upst:CCNL2:−5540, int: CDKN1A:1420, int:CCNT1:602, upst:CCNL2:−3110, upst: CDK5R1:−5717, upst:CCNL2:−982, upst:CCNE2:−682, int:CDK5R1:183, upst:CDK5R1:−482, upst:CDK8:−798, upst:CDK9:−646, upst:CDK6:−1860, int:CDK6:1276, upst: CDK6:−533, upst:CDKN2C:−8037, upst:CCNK:−899, upst: CNNM3:−248, upst:CDKN1C:−4619, int:CDKN2A:6667, int:ARF:4530, upst:CDKN2B:−15913, upst:CDK6:−1679, upst:CDKN1A:−1210, int:CDKN2B:1926, dst:CDKN2A: 39498, upst:CCNL1:−1968, upst:CCNL1:−2234, upst: CCNL1:−2383, upst:CCNL1:−2767, upst:CDK5R2:−6418, upst:CDK4:−7794, upst:CDKN1A:−5830, int:CDKN2C: 159, upst:CCNYL2:−36, upst:CCNC:−6760, upst: CDKN2B:−2817, upst:CNNM3:−970, upst:CDK5R2:− 6045, upst:CDKN1C:−2196, int:CCND1:874, int:CCND2: 1205, upst:CDKN1C:−446, int:CCNG2:390, upst:CDK3:− 4148, upst:CCNA2:−250, int:CDKL5:64, upst:CCND2: 3165, int:CCNK:210, int:CDKN1A:885, upst:CDK5R2:− 9197, int:CNNM3:1459, upst:CCND1:−1659, int:CCNL2: 463, upst:CCNE1:−1190, upst:CDK5R2:−8037, upst: CDKL3:−867, int:CCNG1:381, upst:CCND2:−2874, upst: CDKN2B:−130736, int:CCNI:1042, upst:CCND2:−4757, int:CDK9:352, int:CCND2:1689, int:CDKL5:1682, upst: CDK5R2:−4541, upst:CDK5:−7855, upst:CDK9:−1536, upst:CCND2:−1291, upst:CCND1:−377, int:CCNL1:1097, upst:CDK5R2:−648, upst:CCNL2:−7336, upst:CCND1:− 2768, upst:CDK2:−1390, upst:CCNYL3:−8181, dst: CDKN2A:8650, upst:CDK8:−265, upst:CDK4:−4462, upst: CDKN2A:−44, int:CDKN2A:5270, upst:CCNJL:−2749, upst:CNNM4:−1843, upst:CDK5R2:−7376, int:CCNO: 1417, upst:CDKN1C:−5, upst:CDKN1C:−6280, upst:ARF:− 840, upst:CCND2:−1830, upst:CDK5R1:−206, upst: CCNA1:−1163, int:CCNE2:647, upst:CDK9:−909, upst: CCNYL3:−293, upst:CDKN3:−271, int:CCNT2:640, upst: CCND1:−2574, upst:CCNT2:−319, upst:CDK5R1:−3023, upst:CDK9:−3159, upst:CDK9:−8667, upst:CCNE2:−4956, int:CCND3:2384, upst:CDKN1B:−1362, upst:CCNI:−7899, upst:CCNT2:−6751, int:CDK5:1993, upst:CDK9:−8509, upst:CCND1:−7190, upst:CDKN1C:−7144, upst:CDKN3:− 4479, upst:CCNB3:−3258, upst:CCND3:−9303, upst: CDK8:−8337, int:CDKN2C:643, upst:CCNYL3:−1019, upst:CDK5:−2373, int:CNNM4:1658, upst:CCNE2:−8552, upst:CCNG1:−9141, upst:CCND2:−4886, upst:CCNK:− 8357, upst:CDK5:−9105, upst:CDKN2B:−108997, upst: CCNB2:547, upst:CDKN3:−2291, dst:CDKN2A:30203, upst:CDK2:−5210, upst:CCNL1:−3430, upst:CCNF:−3964, upst:CCNK:−4426, upst:CCNF:−3743, upst:CDK5:−3754, upst:CDKN2B:−35359, upst:CDKN2B:−87467, upst: CDK5R2:−4915, upst:CCNF:−2075, upst:CDK6:−8726, upst:CDKN2B:−90566, int:CDKN2A:4904, int:CDKN2A: 4432, upst:ARF:−2148, upst:CDKN2B:−130339, upst: CNNM3:−9238, upst:CCNG1:−4532, int:ARF:15754, upst: CCNF:−1085, upst:CDKN2B:−23831, upst:CDKN1A:− 9569, int:CCNI:1874, dst:CDKN2A:45866, int:CCNC:816, upst:CCNC:−5405, upst:CDK4:−1632, upst:CCNK:−3241, upst:CDK10:−1805, upst:CCNJL:−671, upst:CDKN3:− 5723, upst:CDKN2B:−15114, upst:CCNE2:−5939, upst:C- CNJL:−7299, upst:CCND3:−4248, int:CDK9:1811, upst: CDKN2C:−8538, upst:ARF:−1395, upst:CCND2:−6904, upst:CDK4:−977, upst:CCNE1:−5422, upst:CCNE2:−2828, upst:CDK4:−2133, upst:CDK8:−9630, upst:CDK3:−4497, upst:CCND3:−6423, upst:CCND1:−8918, upst:CDKN2B:− 119804, upst:CDKN3:−5438, upst:CDKN2C:−7397, upst: CCNYL1:−3709, upst:CDKL4:−6205, upst:CDKN1A:− 2237, upst:CDKN1C:−4093, upst:CCND2:−9042, int: CDK8:566, upst:CDKN2B:−804, upst:CCNE1:−4445, upst: CDKN2B:−74328, upst:CDKN2B:−53107, upst:CCNE1:− 9426, upst:CDKN2C:−3161, upst:CCNG2:−2953, upst: CNNM1:−2645, upst:CDKN1A:−1902, upst:CDKN3:− 1974, upst:CDK10:−4173, upst:CDK9:−9782, upst: CDKN1C:−5693, upst:CDK5:−9871, upst:CNNM4:−4755, upst:CDKN2B:−31120, upst:CDK2:−8040, upst: CDKN2B:−75214, upst:CDKN2C:−127, upst:CDKN1C:− 1017, and upst:CNNM4:−3840.

In another embodiment, the invention includes a microarray comprising a plurality of probes that hybridize to int: CDK6:1276, upst:CDK6:−533, upst:CDKN2C:−8037, int: CDKN2D:1417, upst:CCNL2:−5540, int:CDKN1A:1420, int:CCNT1:602, upst:CCNL2:−3110, upst:CDK5R1:−5717, upst:CCNL2:−982, upst:CCNE2:−682, int:CDK5R1:183, upst:CDK5R1:−482, upst:CDK8:−798, upst:CDK9:−646, upst:CDK6:−1860, int:CDKN2B:1926, int:CDK6:143, dst: CDKN2A:43877, upst:CCNF:−1721, upst:CCNI:−6398, upst:CCNI:−6621, upst:CCNI:−6883, upst:CDKN1A:− 4845, upst:CDK5R1:−4044, upst:CDK5R1:−4410, upst:C- NL2:−1391, upst:CCNL2:−2253, upst:CCNL2:−767, dst: CDKN2A:39498, upst:CCNL1:−1968, upst:CCNL1:−2234, upst:CCNL1:−2383, upst:CCNL1:−2767, upst:CDK5R2:− 6418, upst:CDK4:−7794, upst:CDKN1A:−5830, int: CDKN2C:159, upst:CCNYL2:−36, upst:CCNC:−6760, upst:CDKN2B:−2817, upst:CNNM3:−970, upst:CDK5R2:− 6045, and upst:CDKN1C:−2196.

In another embodiment, the invention includes a microarray comprising a plurality of probes that hybridize to upst: CCNG2:−2953, upst: CDKN1A: −4845, upst: CDKN1A: −9569, upst:CCNL1:−2767, int:CCNG1:+381, upst: CDK9:−9782, int:ARF:+4530, and upst:CDKN1C:−1017.

In another embodiment, the invention includes a microarray comprising a plurality of probes that hybridize to upst: CCNL1:−2767, int:CDKN1A:+885, upst: CDKN1A: −4845, upst:CDKN2B:−2,817, upst:CDK9:−9782, int:ARF:+4,517, int:ARF:+4530, upst:CDKN1C:−1017, int:CCNG1:+381, and upst:CCNG2:−2953.

Polynucleotides can also be analyzed by other methods including, but not limited to, northern blotting, nuclease protection assays, RNA fingerprinting, polymerase chain reaction, ligase chain reaction, Qbeta replicase, isothermal amplification method, strand displacement amplification, transcription based amplification systems, nuclease protection (S1 nuclease or RNAse protection assays), SAGE as well as methods disclosed in International Publication Nos. WO 88/10315 and WO 89/06700, and International Applications Nos. PCT/US87/00880 and PCT/US89/01025; herein incorporated by reference in their entireties.

A standard Northern blot assay can be used to ascertain an RNA transcript size, identify alternatively spliced RNA transcripts, and the relative amounts of mRNA or lncRNA in a sample, in accordance with conventional Northern hybridization techniques known to those persons of ordinary skill in the art. In Northern blots, RNA samples are first separated by size by electrophoresis in an agarose gel under denaturing conditions. The RNA is then transferred to a membrane, cross-linked, and hybridized with a labeled probe. Nonisotopic or high specific activity radiolabeled probes can be used, including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes. The labeled probe, e.g., a radiolabelled cDNA, either containing the full-length, single stranded DNA or a fragment of that DNA sequence may be at least 20, at least 30, at least 50, or at least 100 consecutive nucleotides in length. The probe can be labeled by any of the many different methods known to those skilled in this art. The labels most commonly employed for these studies are radioactive elements, enzymes, chemicals that fluoresce when exposed to ultraviolet light, and others. A number of fluorescent materials are known and can be utilized as labels. These include, but are not limited to, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. Isotopes that can be used include, but are not limited to, $^3$H, $^{14}$C, $^{32}$P, $^{35}$S, $^{36}$Cl, $^{35}$Cr, $^{57}$Co, $^{58}$Co, $^{59}$Fe, $^{90}$Y, $^{125}$I, $^{131}$I, and $^{186}$Re. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Any enzymes known to one of skill in the art can be utilized. Examples of such enzymes include, but are not limited to, peroxidase, beta-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

Nuclease protection assays (including both ribonuclease protection assays and S1 nuclease assays) can be used to detect and quantitate specific mRNAs and lncRNAs. In nuclease protection assays, an antisense probe (labeled with, e.g., radiolabeled or nonisotopic) hybridizes in solution to an RNA sample. Following hybridization, single-stranded, unhybridized probe and RNA are degraded by nucleases. An acrylamide gel is used to separate the remaining protected fragments. Typically, solution hybridization is more efficient than membrane-based hybridization, and it can accommodate up to 100 µg of sample RNA, compared with the 20-30 µg maximum of blot hybridizations.

The ribonuclease protection assay, which is the most common type of nuclease protection assay, requires the use of RNA probes. Oligonucleotides and other single-stranded DNA probes can only be used in assays containing S1 nuclease. The single-stranded, antisense probe must typically be completely homologous to target RNA to prevent cleavage of the probe:target hybrid by nuclease.

Serial Analysis Gene Expression (SAGE), can also be used to determine RNA (e.g., lncRNA) abundances in a cell sample. See, e.g., Velculescu et al., 1995, Science 270:484-7; Carulli, et al., 1998, Journal of Cellular Biochemistry Supplements 30/31:286-96; herein incorporated by reference in their entireties. SAGE analysis does not require a special device for detection, and is one of the preferable analytical methods for simultaneously detecting the expression of a large number of transcription products. First, RNA is extracted from cells. Next, the RNA is converted into cDNA using a biotinylated oligo (dT) primer, and treated with a four-base recognizing restriction enzyme (Anchoring Enzyme: AE) resulting in AE-treated fragments containing a biotin group at their 3' terminus. Next, the AE-treated fragments are incubated with streptoavidin for binding. The bound cDNA is divided into two fractions, and each fraction is then linked to a different double-stranded oligonucleotide adapter (linker) A or B. These linkers are composed of: (1) a protruding single strand portion having a sequence complementary to the sequence of the protruding portion formed by the action of the anchoring enzyme, (2) a 5' nucleotide recognizing sequence of the IIS-type restriction enzyme (cleaves at a predetermined location no more than 20 bp away from the recognition site) serving as a tagging enzyme (TE), and (3) an additional sequence of sufficient length for constructing a PCR-specific primer. The linker-linked cDNA is cleaved using the tagging enzyme, and only the linker-linked cDNA sequence portion remains, which is present in the form of a short-strand sequence tag. Next, pools of short-strand sequence tags from the two different types of linkers are linked to each other, followed by PCR amplification using primers specific to linkers A and B. As a result, the amplification product is obtained as a mixture comprising myriad sequences of two adjacent sequence tags (ditags) bound to linkers A and B. The amplification product is treated with the anchoring enzyme, and the free ditag portions are linked into strands in a standard linkage reaction. The amplification product is then cloned. Determination of the clone's nucleotide sequence can be used to obtain a readout of consecutive ditags of constant length. The presence of mRNA corresponding to each tag can then be identified from the nucleotide sequence of the clone and information on the sequence tags.

Quantitative reverse transcriptase PCR (qRT-PCR) can also be used to determine the expression profiles of biomarkers (see, e.g., U.S. Patent Application Publication No. 2005/0048542A1; herein incorporated by reference in its entirety). The first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TAQ-MAN PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TAQMAN RT-PCR can be performed using commercially available equipment, such as, for example, ABI PRISM 7700 sequence detection system. (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700 sequence detection system. The system consists of a thermocycler, laser, charge-coupled device (CCD), camera and computer. The system includes software for running the instrument and for analyzing the data. 5'-Nuclease assay data are initially expressed as Ct, or the threshold cycle. Fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and beta-actin.

A more recent variation of the RT-PCR technique is the real time quantitative PCR, which measures PCR product accumulation through a dual-labeled fluorigenic probe (i.e., TAQMAN probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., Genome Research 6:986-994 (1996).

Mass spectrometry, and particularly SELDI mass spectrometry, is a particularly useful method for detection of the biomarkers of this invention. Laser desorption time-of-flight mass spectrometer can be used in embodiments of the invention. In laser desorption mass spectrometry, a substrate or a probe comprising biomarkers is introduced into an inlet system. The biomarkers are desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of markers of specific mass to charge ratio.

Matrix-assisted laser desorption/ionization mass spectrometry (MALDI-MS) can also be used for detecting the biomarkers of this invention. MALDI-MS is a method of mass spectrometry that involves the use of an energy absorbing molecule, frequently called a matrix, for desorbing proteins intact from a probe surface. MALDI is described, for example, in U.S. Pat. No. 5,118,937 (Hillenkamp et al.) and U.S. Pat. No. 5,045,694 (Beavis and Chait). In MALDI-MS, the sample is typically mixed with a matrix material and placed on the surface of an inert probe. Exemplary energy absorbing molecules include cinnamic acid derivatives, sinapinic acid ("SPA"), cyano hydroxy cinnamic acid ("CHCA") and dihydroxybenzoic acid. Other suitable energy absorbing molecules are known to those skilled in this art. The matrix dries, forming crystals that encapsulate the analyte molecules. Then the analyte molecules are detected by laser desorption/ionization mass spectrometry.

Surface-enhanced laser desorption/ionization mass spectrometry, or SELDI-MS represents an improvement over MALDI for the fractionation and detection of biomolecules, such as lncRNAs, in complex mixtures. SELDI is a method of mass spectrometry in which biomolecules, such as lncRNAs, are captured on the surface of a biochip using capture reagents that are bound there. Typically, non-bound molecules are washed from the probe surface before interrogation. SELDI is described, for example, in: U.S. Pat. No. 5,719,060 ("Method and Apparatus for Desorption and Ionization of Analytes," Hutchens and Yip, Feb. 17, 1998,) U.S. Pat. No. 6,225,047 ("Use of Retentate Chromatography to Generate Difference Maps," Hutchens and Yip, May 1, 2001) and Weinberger et al., "Time-of-flight mass spectrometry," in Encyclopedia of Analytical Chemistry, R. A. Meyers, ed., pp 11915-11918 John Wiley & Sons Chichesher, 2000.

Biomarkers on the substrate surface can be desorbed and ionized using gas phase ion spectrometry. Any suitable gas phase ion spectrometer can be used as long as it allows biomarkers on the substrate to be resolved. Preferably, gas phase ion spectrometers allow quantitation of biomarkers. In one embodiment, a gas phase ion spectrometer is a mass spectrometer. In a typical mass spectrometer, a substrate or a probe comprising biomarkers on its surface is introduced into an inlet system of the mass spectrometer. The biomarkers are then desorbed by a desorption source such as a laser, fast atom bombardment, high energy plasma, electrospray ionization, thermospray ionization, liquid secondary ion MS, field desorption, etc. The generated desorbed, volatilized species consist of preformed ions or neutrals which are ionized as a direct consequence of the desorption event. Generated ions are collected by an ion optic assembly, and then a mass analyzer disperses and analyzes the passing ions. The ions exiting the mass analyzer are detected by a detector. The detector then translates information of the detected ions into mass-to-charge ratios. Detection of the presence of biomarkers or other substances will typically involve detection of signal intensity. This, in turn, can reflect the quantity and character of biomarkers bound to the substrate. Any of the components of a mass spectrometer (e.g., a desorption source, a mass analyzer, a detector, etc.) can be combined with other suitable components described herein or others known in the art in embodiments of the invention.

Biomarkers can also be detected with assays based on the use of antibodies that specifically recognize the lncRNA biomarkers or polynucleotide or oligonucleotide fragments of the biomarkers. Such assays include, but are not limited to, immunohistochemistry (IHC), enzyme-linked immunosorbent assay (ELISA), radioimmunoassays (RIA), "sandwich" immunoassays, fluorescent immunoassays, immunoprecipitation assays, the procedures of which are well known in the art (see, e.g., Ausubel et al, eds, 1994, Current Protocols in Molecular Biology, Vol. 1, John Wiley & Sons, Inc., New York, which is incorporated by reference herein in its entirety).

Antibodies that specifically bind to a biomarker can be prepared using any suitable methods known in the art. See, e.g., Coligan, Current Protocols in Immunology (1991); Harlow & Lane, Antibodies: A Laboratory Manual (1988); Goding, Monoclonal Antibodies: Principles and Practice (2d ed. 1986); and Kohler & Milstein, Nature 256:495-497 (1975). A biomarker antigen can be used to immunize a mammal, such as a mouse, rat, rabbit, guinea pig, monkey, or human, to produce polyclonal antibodies. If desired, a biomarker antigen can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (bacilli Calmette-Guerin) and *Corynebacterium parvum* are especially useful.

Monoclonal antibodies which specifically bind to a biomarker antigen can be prepared using any technique which provides for the production of antibody molecules by continuous cell lines in culture. These techniques include, but are not limited to, the hybridoma technique, the human B cell hybridoma technique, and the EBV hybridoma technique (Kohler et al., Nature 256, 495-97, 1985; Kozbor et al., J. Immunol. Methods 81, 3142, 1985; Cote et al., Proc. Natl. Acad. Sci. 80, 2026-30, 1983; Cole et al., Mol. Cell. Biol. 62, 109-20, 1984).

In addition, techniques developed for the production of "chimeric antibodies," the splicing of mouse antibody genes to human antibody genes to obtain a molecule with appropriate antigen specificity and biological activity, can be used (Morrison et al., Proc. Natl. Acad. Sci. 81, 6851-55, 1984; Neuberger et al., Nature 312, 604-08, 1984; Takeda et al., Nature 314, 452-54, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions.

Alternatively, humanized antibodies can be produced using recombinant methods, as described below. Antibodies which specifically bind to a particular antigen can contain antigen binding sites which are either partially or fully humanized, as disclosed in U.S. Pat. No. 5,565,332. Human monoclonal antibodies can be prepared in vitro as described in Simmons et al., PLoS Medicine 4(5), 928-36, 2007.

Alternatively, techniques described for the production of single chain antibodies can be adapted using methods known in the art to produce single chain antibodies which specifically bind to a particular antigen. Antibodies with related specificity, but of distinct idiotypic composition, can be generated by chain shuffling from random combinatorial immunoglobulin libraries (Burton, Proc. Natl. Acad. Sci. 88, 11120-23, 1991).

Single-chain antibodies also can be constructed using a DNA amplification method, such as PCR, using hybridoma cDNA as a template (Thirion et al., Eur. J. Cancer Prev. 5, 507-11, 1996). Single-chain antibodies can be mono- or bispecific, and can be bivalent or tetravalent. Construction of tetravalent, bispecific single-chain antibodies is taught, for example, in Coloma & Morrison, Nat. Biotechnol. 15, 159-63, 1997. Construction of bivalent, bispecific single-chain antibodies is taught in Mallender & Voss, J. Biol. Chem. 269, 199-206, 1994.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar et al., Int. J. Cancer 61, 497-501, 1995; Nicholls et al., J. Immunol. Meth. 165, 81-91, 1993).

Antibodies which specifically bind to a biomarker antigen also can be produced by inducing in vivo production in the lymphocyte population or by screening immunoglobulin libraries or panels of highly specific binding reagents as disclosed in the literature (Orlandi et al., Proc. Natl. Acad. Sci. 86, 3833 3837, 1989; Winter et al., Nature 349, 293 299, 1991).

Chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies can be purified by methods well known in the art. For example, antibodies can be affinity purified by passage over a column to which the relevant antigen is bound. The bound antibodies can then be eluted from the column using a buffer with a high salt concentration.

Antibodies may be used in diagnostic assays to detect the presence or for quantification of the biomarkers in a biological sample. Such a diagnostic assay may comprise at least two steps; (i) contacting a biological sample with the antibody, wherein the sample is a tissue (e.g., human, animal, etc.), cell (e.g., stem cell), biological fluid (e.g., blood, urine, sputum, semen, amniotic fluid, saliva, etc.), biological extract (e.g., tissue or cellular homogenate, etc.), or a chromatography column, etc; and (ii) quantifying the antibody bound to the substrate. The method may additionally involve a preliminary step of attaching the antibody, either covalently, electrostatically, or reversibly, to a solid support, before subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogenous phases (Zola, Monoclonal Antibodies: A Manual of Techniques, CRC Press, Inc., (1987), pp 147-158). The antibodies used in the diagnostic assays can be labeled with a detectable moiety. The detectable moiety should be capable of producing, either directly or indirectly, a detectable signal. For example, the detectable moiety may be a radioisotope, such as $^2H$, $^{14}C$, $^{32}P$, or $^{125}I$, a fluorescent or chemiluminescent compound, such as fluorescein isothiocyanate, rhodamine, or luciferin, or an enzyme, such as alkaline phosphatase, beta-galactosidase, green fluorescent protein, or horseradish peroxidase. Any method known in the art for conjugating the antibody to the detectable moiety may be employed, including those methods described by Hunter et al., Nature, 144:945 (1962); David et al., Biochem., 13:1014 (1974); Pain et al., J. Immunol. Methods, 40:219 (1981); and Nygren, J. Histochem. and Cytochem., 30:407 (1982).

Immunoassays can be used to determine the presence or absence of a biomarker in a sample as well as the quantity of a biomarker in a sample. First, a test amount of a biomarker in a sample can be detected using the immunoassay methods described above. If a biomarker is present in the sample, it will form an antibody-biomarker complex with an antibody that specifically binds the biomarker under suitable incubation conditions, as described above. The amount of an antibody-biomarker complex can be determined by comparing to a standard. A standard can be, e.g., a known compound or another lncRNA known to be present in a sample. As noted above, the test amount of a biomarker need not be measured in absolute units, as long as the unit of measurement can be compared to a control.

Kits

In yet another aspect, the invention provides kits for use in diagnosing cancer or monitoring stem cell therapy or regenerative medical treatments, wherein the kits can be used to detect the lncRNA biomarkers of the present invention. For example, the kits can be used to detect any one or more of the biomarkers described herein, which are differentially expressed in samples of a patient with cancer, or undergoing stem cell therapy, or regenerative medical treatment and normal subjects. The kit may include one or more agents for detection of lncRNA biomarkers, a container for holding a biological sample isolated from a human subject; and printed instructions for reacting agents with the biological sample or a portion of the biological sample to detect the presence or amount of at least one lncRNA biomarker in the biological sample. The agents may be packaged in separate containers. The kit may further comprise one or more control reference samples and reagents for performing an immunoassay, a Northern blot, PCR, microarray analysis, or SAGE.

In certain embodiments, the kit contains at least one probe that selectively hybridizes to a biomarker, or at least one antibody that selectively binds to a biomarker, or at least one set of PCR primers for amplifying a biomarker. In one embodiment, the kit comprises at least one agent for measuring the level of PANDA.

The kit can comprise one or more containers for compositions contained in the kit. Compositions can be in liquid form or can be lyophilized. Suitable containers for the compositions include, for example, bottles, vials, syringes, and test tubes. Containers can be formed from a variety of materials, including glass or plastic. The kit can also comprise a package insert containing written instructions for methods of diagnosing cancer or monitoring stem cell therapy or regenerative medical treatments.

The kits of the invention have a number of applications. For example, the kits can be used for monitoring cell proliferation and differentiation during cancer progression, tissue regeneration, or growth of human cells, tissues, or organs in culture for tissue or organ replacement. In another example, the kits can be used for evaluating the efficacy of a treatment for cancer, stem cell therapy, or regenerative medicine. In a further example, the kits can be used to identify compounds that modulate expression of one or more of the biomarkers in in vitro or in vivo animal models to determine the effects of treatment.

C. PANDA and Inhibitors

In another aspect, an inhibitor of PANDA is used in the practice of the invention. Inhibitors of PANDA can include, but are not limited to, antisense oligonucleotides, inhibitory RNA molecules, such as miRNAs, siRNAs, piRNAs, and snRNAs, ribozymes, and small molecule inhibitors. Various types of inhibitors for inhibiting nucleic acid function are well known in the art. See e.g., International patent application WO/2012/018881; U.S. patent application 2011/0251261; U.S. Pat. No. 6,713,457; Kole et al. (2012) Nat. Rev. Drug Discov. 11(2):125-40; Sanghvi (2011) Curr. Protoc. Nucleic Acid Chem. Chapter 4:Unit 4.1.1-22; herein incorporated by reference in their entireties.

Inhibitors can be single stranded or double stranded polynucleotides and may contain one or more chemical modifications, such as, but not limited to, locked nucleic acids, peptide nucleic acids, sugar modifications, such as 2'-O-alkyl (e.g., 2'-O-methyl, 2'-O-methoxyethyl), 2'-fluoro, and 4'-thio modifications, and backbone modifications, such as one or more phosphorothioate, morpholino, or phosphonocarboxylate linkages. In addition, inhibitory RNA molecules may have a "tail" covalently attached to their 3'- and/or 5'-end, which may be used to stabilize the RNA inhibitory molecule or enhance cellular uptake. Such tails include, but are not limited to, intercalating groups, various kinds of reporter groups, and lipophilic groups attached to the 3' or 5' ends of the RNA molecules. In certain embodiments, the RNA inhibitory molecule is conjugated to cholesterol or acridine. See, for example, the following for descriptions of syntheses of 3'-cholesterol or 3'-acridine modified oligonucleotides: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993); herein incorporated by reference in their entireties. Additional lipophilic moieties that can be used, include, but are not limited to, oleyl, retinyl, and cholesteryl residues, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, $O_3$-(oleoyl)lithocholic acid, $O_3$-(oleoyl)cholenic acid, dimethoxytrityl, or phenoxazine. Additional compounds, and methods of use, are set out in US Patent Publication Nos. 2010/0076056, 2009/0247608 and 2009/0131360; herein incorporated by reference in their entireties.

In one embodiment, inhibition of PANDA function may be achieved by administering antisense oligonucleotides targeting PANDA. The antisense oligonucleotides may be ribonucleotides or deoxyribonucleotides. Preferably, the antisense oligonucleotides have at least one chemical modification. Antisense oligonucleotides may be comprised of one or more "locked nucleic acids". "Locked nucleic acids" (LNAs) are modified ribonucleotides that contain an extra bridge between the 2' and 4' carbons of the ribose sugar moiety resulting in a "locked" conformation that confers enhanced thermal stability to oligonucleotides containing the LNAs. Alternatively, the antisense oligonucleotides may comprise peptide nucleic acids (PNAs), which contain a peptide-based backbone rather than a sugar-phosphate backbone. The antisense oligonucleotides may contain one or more chemical modifications, including, but are not limited to, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages (see, for example, U.S. Pat. Nos. 6,693,187 and 7,067,641, which are herein incorporated by reference in their entireties). In some embodiments, suitable antisense oligonucleotides are 2'-O-methoxyethyl "gapmers" which contain 2'-O-methoxyethyl-modified ribonucleotides on both 5' and 3' ends with at least ten deoxyribonucleotides in the center. These "gapmers" are capable of triggering RNase H-dependent degradation mechanisms of RNA targets. Other modifications of antisense oligonucleotides to enhance stability and improve efficacy, such as those described in U.S. Pat. No. 6,838,283, which is herein incorporated by reference in its entirety, are known in the art and are suitable for use in the methods of the invention. Antisense oligonucleotides may comprise a sequence that is at least partially complementary to a PANDA target sequence, e.g., at least about 75%, 80%, 85%, 90%, 91%, 92%, 93%, 94%, 95%, 96%, 97%, 98%, or 99% complementary to the PANDA target sequence. In some embodiments, the antisense oligonucleotide may be substantially complementary to the PANDA target sequence, that is at least about 95%, 96%, 97%, 98%, or 99% complementary to a target polynucleotide sequence. In one embodiment, the antisense oligonucleotide comprises a sequence that is 100% complementary to the PANDA target sequence.

In another embodiment, the inhibitor of PANDA is an inhibitory RNA molecule (e.g., a miRNA, a siRNA, a piRNA, or a snRNA) having a single-stranded or double-stranded region that is at least partially complementary to the target sequence of PANDA, e.g., about 75%, 80%, 85%, 90%, 91%, 92%, 93%, 94%, 95%, 96%, 97%, 98%, or 99% complementary to the target sequence of PANDA. In some embodiments, the inhibitory RNA comprises a sequence that is substantially complementary to the target sequence of PANDA, e.g., about 95%, 96%, 97%, 98%, or 99% complementary to a target polynucleotide sequence. In other embodiments, the inhibitory RNA molecule may contain a region that has 100% complementarity to the target sequence. The inhibitory molecules may target the PANDA sequence of SEQ ID NO:1. In certain embodiments, the inhibitory RNA molecule may be a double-stranded, small interfering RNA or a short hairpin RNA molecule (shRNA) comprising a stem-loop structure. In one embodiment, the PANDA inhibitor is an siRNA comprising a nucleotide sequence selected from the group consisting of SEQ ID NOS:12-14.

An "effective amount" of a PANDA inhibitor (e.g., microRNA, siRNA, piRNA, snRNA, antisense oligonucleotide, ribozyme, or small molecule inhibitor) is an amount sufficient to effect beneficial or desired results, such as an amount that reduces PANDA activity, for example, by interfering with transcription of PANDA or interfering with binding of PANDA to the transcription factor NF-YA. In some embodiments, a PANDA inhibitor reduces the amount and/or activity of PANDA by at least about 10% to about 100%, 20% to about 100%, 30% to about 100%, 40% to about 100%, 50% to about 100%, 60% to about 100%, 70% to about 100%, 10% to about 90%, 20% to about 85%, 40% to about 84%, 60% to about 90%, including any percent within these ranges, such as but not limited to 15%, 20%, 25%, 30%, 35%, 40%, 45%, 50%, 55%, 60%, 65%, 70%, 75%, 80%, 85%, 90%, 95%, 96%, 97%, 98%, and 99%.

In certain embodiments, the invention includes a method of modulating the activity of the transcription factor NF-YA in a cell, the method comprising introducing into the cell PANDA or an inhibitor of PANDA. In one embodiment, the activity of NF-YA is increased in the cell following administration of an inhibitor of PANDA. In another embodiment, the activity of NF-YA is decreased in the cell following administration of PANDA.

In certain embodiments, the invention includes a method of modulating the expression of one or more apoptotic genes in a cell, the method comprising introducing into the cell PANDA or an inhibitor of PANDA. In one embodiment, the expression of one or more apoptotic genes is increased in the cell following administration of an inhibitor of PANDA. In another embodiment, the expression of one or more apoptotic genes is decreased in the cell following administration of PANDA.

Inhibitors can be detectably labeled by well-known techniques. Detectable labels include, for example, radioactive isotopes, fluorescent labels, chemiluminescent labels, bioluminescent labels and enzyme labels. Such labeled inhibitors can be used to determine cellular uptake efficiency, quantitate binding of inhibitors at target sites, or visualize inhibitor localization.

In certain embodiments, PANDA or a PANDA inhibitor is expressed in vivo from a vector. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, lentiviral vectors, and the like. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention.

In one embodiment, an expression vector for expressing PANDA or a PANDA inhibitor comprises a promoter "operably linked" to a polynucleotide encoding PANDA or a PANDA inhibitor. The phrase "operably linked" or "under transcriptional control" as used herein means that the promoter is in the correct location and orientation in relation to a polynucleotide to control the initiation of transcription by RNA polymerase and expression of the polynucleotide.

In certain embodiments, the nucleic acid encoding a polynucleotide of interest is under transcriptional control of a promoter. A "promoter" refers to a DNA sequence recognized by the synthetic machinery of the cell, or introduced synthetic machinery, required to initiate the specific transcription of a gene. The term promoter will be used here to refer to a group of transcriptional control modules that are clustered around the initiation site for RNA polymerase I, II, or III. Typical promoters for mammalian cell expression include the SV40 early promoter, a CMV promoter such as the CMV immediate early promoter (see, U.S. Pat. Nos. 5,168,062 and 5,385,839, incorporated herein by reference in their entireties), the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. These and other promoters can be obtained from commercially available plasmids, using techniques well known in the art. See, e.g., Sambrook et al., supra. Enhancer elements may be used in association with the promoter to increase expression levels of the constructs. Examples include the SV40 early gene enhancer, as described in Dijkema et al., EMBO J. (1985) 4:761, the enhancer/promoter derived from the long terminal repeat (LTR) of the Rous Sarcoma Virus, as described in Gorman et al., Proc. Natl. Acad. Sci. USA (1982b) 79:6777 and elements derived from human CMV, as described in Boshart et al., Cell (1985) 41:521, such as elements included in the CMV intron A sequence.

Typically, transcription terminator/polyadenylation signals will also be present in the expression construct. Examples of such sequences include, but are not limited to, those derived from SV40, as described in Sambrook et al., supra, as well as a bovine growth hormone terminator sequence (see, e.g., U.S. Pat. No. 5,122,458). Additionally, 5'-UTR sequences can be placed adjacent to the coding sequence in order to enhance expression of the same. Such sequences include UTRs which include an Internal Ribosome Entry Site (IRES) present in the leader sequences of picornaviruses such as the encephalomyocarditis virus (EMCV) UTR (Jang et al. J. Virol. (1989) 63:1651-1660. Other picornavirus UTR sequences that will also find use in the present invention include the polio leader sequence and hepatitis A virus leader and the hepatitis C IRES.

In certain embodiments of the invention, the cells containing nucleic acid constructs of the present invention may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Fluorescent markers (e.g., green fluorescent protein (GFP), EGFP, or Dronpa), or immunologic markers can also be employed. The selectable marker employed is not believed to be important, so long as it is capable of being expressed simultaneously with the nucleic acid encoding a gene product. Further examples of selectable markers are well known to one of skill in the art.

There are a number of ways in which expression vectors may be introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express a polynucleotide that has been cloned therein. The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

The typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

Retroviral vectors are also suitable for expressing PANDA or PANDA inhibitors in cells. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Porter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding PANDA or the PANDA inhibitor of interest may be positioned and expressed at different sites. In certain embodiments, the nucleic acid encoding PANDA or a PANDA inhibitor may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ohosh and Bachhawat, 1991). Also contemplated are lipofectamine-DNA complexes.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-I) (Kato et al., 1991). In yet further embodiments, the liposome may be complexed or employed in conjunction with both HVJ and HMG-I. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular lncRNA or inhibitor into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes. For example, epidermal growth factor (EGF) may be used as the receptor for mediated delivery of a nucleic acid into cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In a particular example, the oligonucleotide may be administered in combination with a cationic lipid. Examples of cationic lipids include, but are not limited to, lipofectin, DOTMA, DOPE, and DOTAP. The publication of WO/0071096, which is specifically incorporated by reference, describes different formulations, such as a DOTAP: cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008,336, 6,077,835, 5,972,901, 6,200,801, and 5,972,900, which are incorporated by reference for those aspects.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

The present invention also encompasses pharmaceutical compositions comprising PANDA or one or more PANDA inhibitors and a pharmaceutically acceptable carrier. Where clinical applications are contemplated, pharmaceutical compositions will be prepared in a form appropriate for the intended application. Generally, this will entail preparing compositions that are essentially free of pyrogens, as well as other impurities that could be harmful to humans or animals.

Colloidal dispersion systems, such as macromolecule complexes, nanocapsules, microspheres, beads, and lipid-based systems including oil-in-water emulsions, micelles, mixed micelles, and liposomes, may be used as delivery vehicles for PANDA or PANDA inhibitors described herein. Commercially available fat emulsions that are suitable for delivering the nucleic acids of the invention to tissues, such as cardiac muscle tissue and smooth muscle tissue, include Intralipid, Liposyn, Liposyn II, Liposyn III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. Nos. 5,981,505; 6,217,900; 6,383,512; 5,783,565; 7,202,227; 6,379,965; 6,127,170; 5,837,533; 6,747,014; and WO 03/093449, which are herein incorporated by reference in their entireties.

One will generally desire to employ appropriate salts and buffers to render delivery vehicles stable and allow for uptake by target cells. Buffers also will be employed when recombinant cells are introduced into a patient. Aqueous compositions of the present invention comprise an effective amount of the delivery vehicle, dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the nucleic acids of the compositions.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like).

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

D. Administration

At least one therapeutically effective dose of a PANDA inhibitor and at least one chemotherapeutic agent will be administered. The PANDA inhibitor may be an antisense oligonucleotide or inhibitory RNA molecule such as, a miRNA, siRNA, piRNA, or snRNA, as described herein. Chemotherapeutic agents that can be used include, but are not limited to, abitrexate, adriamycin, adrucil, amsacrine, asparaginase, anthracyclines, azacitidine, azathioprine, bicnu, blenoxane, busulfan, bleomycin, camptosar, camptothecins, carboplatin, carmustine, cerubidine, chlorambucil, cisplatin, cladribine, cosmegen, cytarabine, cytosar, cyclophosphamide, cytoxan, dactinomycin, docetaxel, doxorubicin, daunorubicin, ellence, elspar, epirubicin, etoposide, fludarabine, fluorouracil, fludara, gemcitabine, gemzar, hycamtin, hydroxyurea, hydrea, idamycin, idarubicin, ifosfamide, ifex, irinotecan, lanvis, leukeran, leustatin, matulane, mechlorethamine, mercaptopurine, methotrexate, mitomycin, mitoxantrone, mithramycin, mutamycin, myleran, mylosar, navelbine, nipent, novantrone, oncovin, oxaliplatin, paclitaxel, paraplatin, pentostatin, platinol, plicamycin, procarbazine, purinethol, ralitrexed, taxotere, taxol, teniposide, thioguanine, tomudex, topotecan, valrubicin, velban, vepesid, vinblastine, vindesine, vincristine, vinorelbine, VP-16, and vumon.

By "therapeutically effective dose or amount" of each of these agents is intended an amount that when administered in combination brings about a positive therapeutic response with respect to treatment of an individual for cancer. Of particular interest is an amount of these agents that provides an anti-tumor effect, as defined herein. By "positive therapeutic response" is intended the individual undergoing the combination treatment according to the invention exhibits an improvement in one or more symptoms of the cancer for which the individual is undergoing therapy.

Thus, for example, a "positive therapeutic response" would be an improvement in the disease in association with the combination therapy, and/or an improvement in one or more symptoms of the disease in association with the combination therapy. Therefore, for example, a positive therapeutic response would refer to one or more of the following improvements in the disease: (1) reduction in tumor size; (2) reduction in the number of cancer cells; (3) inhibition (i.e., slowing to some extent, preferably halting) of tumor growth; (4) inhibition (i.e., slowing to some extent, preferably halting) of cancer cell infiltration into peripheral organs; (5) inhibition (i.e., slowing to some extent, preferably halting) of tumor metastasis; and (6) some extent of relief from one or more symptoms associated with the cancer. Such therapeutic responses may be further characterized as to degree of improvement. Thus, for example, an improvement may be characterized as a complete response. By "complete response" is documentation of the disappearance of all symptoms and signs of all measurable or evaluable disease confirmed by physical examination, laboratory, nuclear and radiographic studies (i.e., CT (computer tomography) and/or MRI (magnetic resonance imaging)), and other non-invasive procedures repeated for all initial abnormalities or sites positive at the time of entry into the study. Alternatively, an improvement in the disease may be categorized as being a partial response. By "partial response" is intended a reduction of greater than 50% in the sum of the products of the perpendicular diameters of all measurable lesions when compared with pretreatment measurements.

The actual dose to be administered will vary depending upon the age, weight, and general condition of the subject as well as the severity of the condition being treated, the judgment of the health care professional, and conjugate being administered. Therapeutically effective amounts can be determined by those skilled in the art, and will be adjusted to the particular requirements of each particular case. Generally, a therapeutically effective amount will range from about 0.50 mg to 5 grams NSAID daily, more preferably from about 5 mg to 2 grams daily, even more preferably from about 7 mg to 1.5 grams daily. Preferably, such doses are in the range of 10-600 mg four times a day (QID), 200-500 mg QID, 25-600 mg three times a day (TID), 25-50 mg TID, 50-100 mg TID, 50-200 mg TID, 300-600 mg TID, 200-400 mg TID, 200-600 mg TID, 100 to 700 mg twice daily (BID), 100-600 mg BID, 200-500 mg BID, or 200-300 mg BID.

In certain embodiments, multiple therapeutically effective doses of each of at least one PANDA inhibitor and at least one chemotherapeutic agent will be administered according to a daily dosing regimen, or intermittently. For example, a therapeutically effective dose can be administered, one day a week, two days a week, three days a week, four days a week, or five days a week, and so forth. By "intermittent" administration is intended the therapeutically effective dose can be administered, for example, every other day, every two days, every three days, and so forth. For example, in some embodiments, at least one PANDA inhibitor and at least one chemotherapeutic agent, will be administered twice-weekly or thrice-weekly for an extended period of time, such as for 1, 2, 3, 4, 5, 6, 7, 8 . . . 10 . . . 15 . . . 24 weeks, and so forth. By "twice-weekly" or "two times per week" is intended that two therapeutically effective doses of the agent in question is administered to the subject within a 7 day period, beginning on day 1 of the first week of administration, with a minimum of 72 hours, between doses and a maximum of 96 hours between doses. By "thrice weekly" or "three times per week" is intended that three therapeutically effective doses are administered to the subject within a 7 day period, allowing for a minimum of 48 hours between doses and a maximum of 72 hours between doses. For purposes of the present invention, this type of dosing is referred to as "intermittent" therapy. In accordance with the methods of the present invention, a subject can receive intermittent therapy (i.e., twice-weekly or thrice-weekly administration of a therapeutically effective dose) for one or more weekly cycles until the desired therapeutic response is achieved. The agents can be administered by any acceptable route of administration as noted herein below.

A PANDA inhibitor can be administered prior to, concurrent with, or subsequent to at least one chemotherapeutic agent. If provided at the same time as the chemotherapeutic agent, the PANDA inhibitor can be provided in the same or in a different composition. Thus, the agents can be presented to the individual by way of concurrent therapy. By "concurrent therapy" is intended administration to a human subject such that the therapeutic effect of the combination of the substances is caused in the subject undergoing therapy. For example, concurrent therapy may be achieved by administering at least one therapeutically effective dose of a pharmaceutical composition comprising a PANDA inhibitor and at least one therapeutically effective dose of a pharmaceutical composition comprising at least one chemotherapeutic agent according to a particular dosing regimen. Administration of the separate pharmaceutical compositions can be at the same time (i.e., simultaneously) or at different times (i.e., sequentially, in either order, on the same day, or on different days), so long as the therapeutic effect of the combination of these substances is caused in the subject undergoing therapy.

In certain embodiments, the PANDA inhibitor is administered for a brief period prior to administration of the chemotherapeutic agent and continued for a brief period after treatment with the chemotherapeutic agent is discontinued in order to ensure that the PANDA inhibitor levels are adequate in the subject during chemotherapy. For example, the PANDA inhibitor can be administered starting one week before administration of the first dose of the chemotherapeutic agent and continued for one week after administration of the last dose of the chemotherapeutic agent to the subject.

In other embodiments of the invention, the pharmaceutical compositions comprising the agents, such as one or more PANDA inhibitors and/or chemotherapeutic agents, is a sustained-release formulation, or a formulation that is administered using a sustained-release device. Such devices are well known in the art, and include, for example, transdermal patches, and miniature implantable pumps that can provide for drug delivery over time in a continuous, steady-state fashion at a variety of doses to achieve a sustained-release effect with a non-sustained-release pharmaceutical composition.

The pharmaceutical compositions comprising one or more PANDA inhibitors or chemotherapeutic agents may be administered using the same or different routes of administration in accordance with any medically acceptable method known in the art. Suitable routes of administration include parenteral administration, such as subcutaneous (SC), intraperitoneal (IP), intramuscular (IM), intravenous (IV), or infusion, oral and pulmonary, nasal, topical, transdermal, and suppositories. Where the composition is administered via pulmonary delivery, the therapeutically effective dose is adjusted such that the soluble level of the agent, such as the PANDA inhibitor in the bloodstream, is equivalent to that obtained with a therapeutically effective dose that is administered parenterally, for example SC, IP, 1M, or 1V. In some embodiments of the invention, the pharmaceutical composition comprising the PANDA inhibitor is administered by IM or SC injection, particularly by IM or SC injection locally to the region where the therapeutic agent or agents used in the cancer therapy protocol are administered.

Factors influencing the respective amount of the various compositions to be administered include, but are not limited to, the mode of administration, the frequency of administration (i.e., daily, or intermittent administration, such as twice- or thrice-weekly), the particular disease undergoing therapy, the severity of the disease, the history of the disease, whether the individual is undergoing concurrent therapy with another therapeutic agent, and the age, height, weight, health, and physical condition of the individual undergoing therapy. Generally, a higher dosage of this agent is preferred with increasing weight of the subject undergoing therapy.

Where a subject undergoing therapy in accordance with the previously mentioned dosing regimens exhibits a partial response, or a relapse following a prolonged period of remission, subsequent courses of concurrent therapy may be needed to achieve complete remission of the disease. Thus, subsequent to a period of time off from a first treatment period, a subject may receive one or more additional treatment periods comprising chemotherapy in combination with a PANDA inhibitor. Such a period of time off between treatment periods is referred to herein as a time period of discontinuance. It is recognized that the length of the time period of discontinuance is dependent upon the degree of tumor response (i.e., complete versus partial) achieved with any prior treatment periods of concurrent therapy with these therapeutic agents.

E. Kits

Any of the compositions described herein may be included in a kit. For example, PANDA, and/or at least one PANDA inhibitor, and/or at least one chemotherapeutic agent, or any combination thereof, may be included in a kit. The kit may also include one or more transfection reagents to facilitate delivery of oligonucleotides or polynucleotides to cells.

The components of the kit may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

Such kits may also include components that preserve or maintain the PANDA inhibitors or lncRNAs or that protect against their degradation. Such components may be RNAse-free or protect against RNAses. Such kits generally will comprise, in suitable means, distinct containers for each individual reagent or solution.

A kit will also include instructions for employing the kit components as well the use of any other reagent not included in the kit. Instructions may include variations that can be implemented. A kit may also include utensils or devices for administering a PANDA inhibitor by various administration routes, such as parenteral or catheter administration or coated stent.

EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Extensive and Coordinated Transcription of Noncoding RNAs within Cell-Cycle Promoters Introduction In this study, we create an ultrahigh-resolution tiling microarray to interrogate the transcriptional and chromatin landscape around the TSSs of 56 cell-cycle genes, including genes encoding all cyclins, cyclin-dependent kinases (CDKs) and cyclin-dependent kinase inhibitors (CDKIs). We analyze a diverse collection of cells and tissue samples that interrogate distinct perturbations in cell-growth control. Our results reveal a map of extensive and choreographed noncoding transcription and identify a specific set of lncRNAs that function in the DNA damage response.

Methods

Tiling Array Design and RNA Hybridization

A custom tiling array (Roche NimbleGen) was designed at 5 bp resolution across 25 kb of the 9p21 region (which encompasses CDKN2A, P14ARF and CDKN2B), as well as from 10 kb upstream to 2 kb downstream of each TSS from 53 other cell-cycle genes, including those encoding cyclins, CDKs and CDKIs (Table 1). In addition, the HOXA and HOXD loci were placed on the array as a control. Briefly, RNA was amplified (MessageAmp Kit, Ambion), reverse transcribed (RETROscript Kit, Ambion), labeled and hybridized according to the standard NimbleGen protocol.

TABLE 1

Tiling Array design

| Name | Chromosome | Feature Coordinates (Human March 2 006 NCBI Build 36.1 hg18) |
|---|---|---|
| 9p21 locus | 9 | 21900000-22150000 |
| CCNA1 | 13 | 35894632-35906659 |
| CCNA2 | 4 | 122962330-122974342 |
| CCNB1 | 5 | 68488668-68500750 |
| CCNB2 | 15 | 57174611-57186627 |
| CCNB3 | X | 50034275-50046275 |
| CCNC | 6 | 100121225-100133411 |
| CCND1 | 11 | 69155053-69167126 |
| CCND2 | 12 | 4243198-4255223 |
| CCND3 | 6 | 42015122-42027530 |
| CCNE1 | 19 | 34984740-34997400 |
| CCNE2 | 8 | 95974605-95986660 |
| CCNF | 16 | 2409440-2421471 |
| CCNG1 | 5 | 162787154-162799204 |
| CCNG2 | 4 | 78287401-78299550 |
| CCNH | 5 | 86742441-86754592 |
| CCNI | 4 | 78214148-78226149 |
| CCNJ | 10 | 97783140-97795329 |
| CCNJL | 5 | 159697177-159709177 |
| CCNK | 14 | 99007491-99019512 |

TABLE 1-continued

Tiling Array design

| Name | Chromosome | Feature Coordinates (Human March 2 006 NCBI Build 36.1 hg18) |
|---|---|---|
| CCNL1 | 3 | 158358577-158371176 |
| CCNL2 | 1 | 1322552-1334571 |
| CCNO | 5 | 54563265-54575265 |
| CCNT1 | 12 | 47395048-47407048 |
| CCNT2 | 2 | 135382862-135394875 |
| CCNY | 10 | 35565959-35577959 |
| CCNYL1 | 2 | 208274509-208286509 |
| CCNYL2 | 10 | 42268168-42280168 |
| CCNYL3 | 16 | 34105360-34117360 |
| CDK2 | 12 | 54636825-54648899 |
| CDK3 | 17 | 71499013-71511013 |
| CDK4 | 12 | 56430344-56442431 |
| CDK5 | 7 | 150383893-150395929 |
| CDK5R1 | 17 | 27828217-27840681 |
| CDK5R2 | 2 | 219522620-219534641 |
| CDK6 | 7 | 92299148-92311148 |
| CDK8 | 13 | 25716755-25728778 |
| CDK9 | 9 | 129578151-129590188 |
| CDK10 | 16 | 88270578-88282613 |
| CDKL1 | 14 | 49930367-49942367 |
| CDKL2 | 4 | 76772269-76784595 |
| CDKL3 | 5 | 133728113-133740664 |
| CDKL4 | 2 | 39308177-39320177 |
| CDKL5 | X | 18343677-18355677 |
| CDKN1A | 6 | 36744464-36756493 |
| CDKN1B | 12 | 12751575-12763663 |
| CDKN1C | 11 | 2861551-2873577 |
| CDKN2C | 1 | 51196148-51210203 |
| CDKN2D | 19 | 10538631-10550655 |
| CDKN3 | 14 | 53923462-53935475 |
| CNNM1 | 10 | 101070022-101082022 |
| CNNM2 | 10 | 104658064-104670853 |
| CNNM3 | 2 | 96835714-96848658 |
| CNNM4 | 2 | 96780365-96792606 |

Peak Calling

Robust multichip average normalized single channel data from each array were subjected to peak calling using the NimbleScan program (Roche NimbleGen) with a window size of 50. Peaks with a peak score greater than ten were considered significant transcriptional units. Peak calls from all 55 array samples were clustered using Galaxy (Carninci et al. (2005) Science 309:1559-1563, Taylor et al. (2007) Curr. Protoc. Bioinformatics Chapter 10, Unit 10.5; herein incorporated by reference), and only transcripts present in a minimum of 10% of the samples were considered for further analysis. Transcripts were annotated as follows: 'genomic location (upstream of TSS of cell-cycle protein-coding gene, upst; exon of cell-cycle protein-coding gene, exon; intron of cell-cycle protein-coding gene, int; downstream of cell-cycle protein coding gene, dst)'; 'gene symbol of nearest mRNA'; 'distance from TSS'.

Measuring Protein Coding Potential

To assess the coding potential of the new transcribed regions, we evaluated the evolutionary signatures in their alignments with orthologous regions in 20 other sequenced placental mammalian genomes using the codon substitution frequencies (CSF) method (Lin et al. Nature Precedings published online, doi:10.1038/npre.2010.4784.1 (18 Aug. 2010); Lin et al. (2007) Genome Res. 17:1823-1836; Lin et al. (2008) PLOS Comput. Biol. 4, e1000067, herein incorporated by reference in their entireties), which has also been applied to assess new transcribed regions in mouse 14. CSF produces a score for any region in the genome considering all codon substitutions observed within its alignment, based on the relative frequency of similar substitutions in known coding and noncoding regions. Briefly, CSF performs a statistical comparison between two empirical codon models (Kosiol et al. (2007) Mol. Biol. Evol. 24, 1464-1479), one estimated from alignments of known coding regions and the other based on noncoding regions, and reports a likelihood ratio that quantifies whether the protein-coding model is a better explanation while controlling for the overall level of sequence conservation (Lin et al. Nature Precedings published online, doi:10.1038/npre.2010.4784.1).

Module Map analysis

Figure 12:
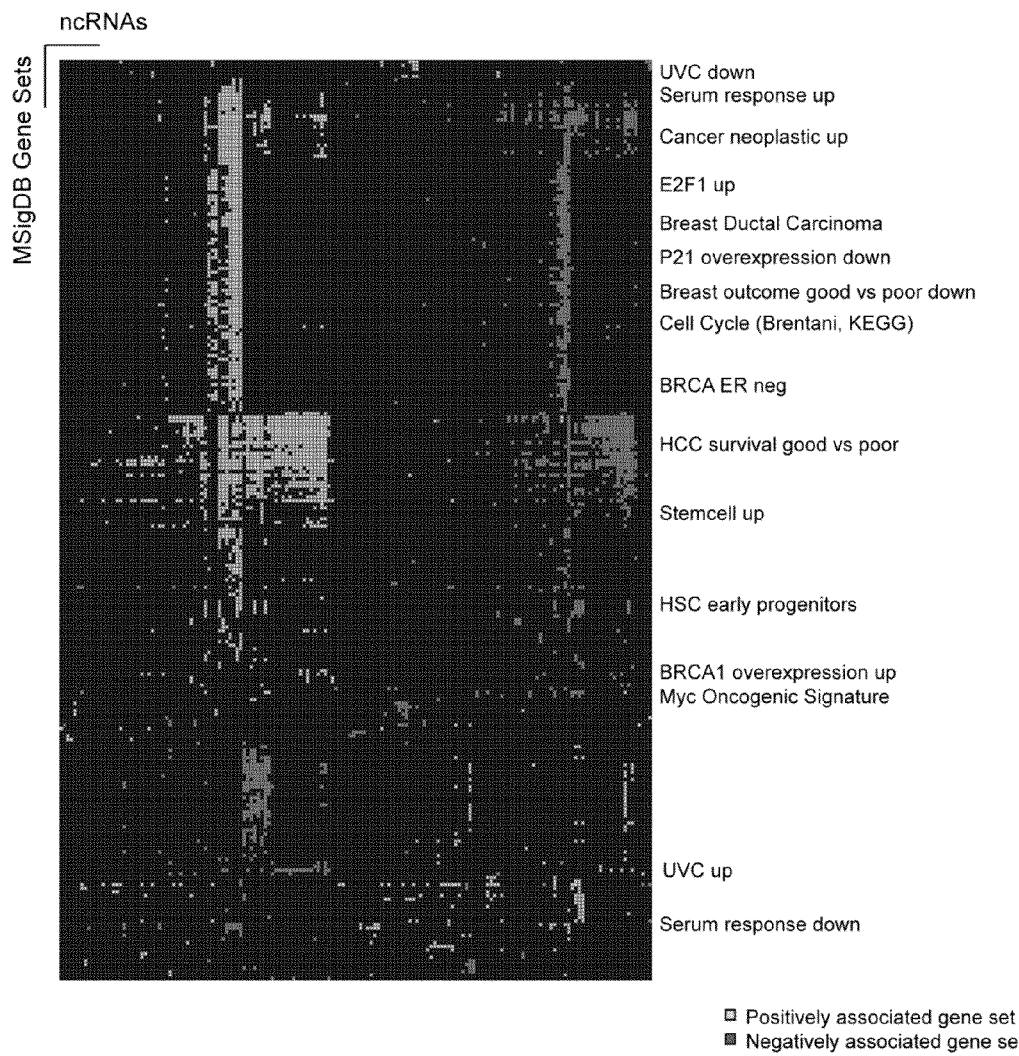
FIG. 12 shows a molecular Signature Data Base module map of gene sets associated with lncRNAs.

We generated a module map of the ncRNAs versus the protein-coding genes by computing the Pearson correlations for all pairwise combinations based on expression across 17 different samples. This map was clustered and visualized using the program Genomica (see URLs). For each ncRNA, we then defined gene sets of the protein-coding genes that had a Pearson correlation that was greater than or less than 0.5 with that ncRNA. To determine functional associations, we then generated a module map of these ncRNA gene sets with Gene Ontology Biological Processes gene sets (FIG. 3C) and with curated gene sets of metabolic and signaling pathways and biological and clinical states from the Molecular Signatures Database (MSigDB c2 collection) (FIG. 12) (Subramanian et al. (2005) Proc. Natl. Acad. Sci. USA 102:15545-15550). The P value of enrichment was determined by the hypergeometric distribution, and a false discovery rate (FDR) calculation was used to account for multiple hypothesis testing (P<0.05, FDR<0.05).

Tissue Samples and Cells

Informed consent was obtained for tissue donation, and we obtained approval from institutional review boards of Stanford University, Johns Hopkins University and Netherlands Cancer Institute. Human primary breast tumors from The Netherlands Cancer Institute (van de Vijver et al. (2002) N. Engl. J. Med. 347:1999-2009) and normal breast tissues and metastatic breast tumors from the Johns Hopkins University Rapid Autopsy Program are as described (Gupta et al. (2010) Nature 464:1071-1076). Human fetal pancreata were obtained from the Birth Defects Research Laboratory, University of Washington. Staged fetal pancreata were processed within 24 hours of receipt, minced, washed and processed for RNA isolation using standard methods. Human fetal lung fibroblasts FL3 (Coriell AG04393) or foreskin fibroblasts (ATCC CRL2091) were cultured in 10% FBS (Hyclone) and 1% penicillin-streptomycin (Gibco) at 37° C. in 5% $CO_2$.

PANDA Cloning and Sequence Analysis

3' and 5' RACE was performed using the FirstChoice RLM-RACE Kit (Ambion). RNA was extracted from 200 ng/ml doxorubicin (Sigma)-treated human fetal lung fibroblasts, polyA was selected using the Poly(A)Purist MAG kit (Ambion) and RLM-RACE was performed according to the standard manufacturer's protocol.

RT-PCR

Total RNA was extracted from cells using the TRIzol reagent (Invitrogen) and the RNeasy Mini Kit (Qiagen), and genomic DNA was eliminated using TURBO DNA-free (Ambion). RT-PCR using 50-250 ng of total RNA was performed using the One-Step RT-PCR Master Mix (Applied Biosystems) using TaqMan Gene Expression Assays and normalized to GAPDH. Strand-specific RT-PCR for PANDA was performed using the One-Step RT-PCR Master Mix SYBR Green (Stratagene)).

TaqMan® custom ncRNA Assays

A panel of TaqMan custom ncRNA assays was developed targeting 60 of the 219 new transcribed regions using the 'single-exon' design mode. The transcript specificity and genome specificity of all TaqMan assays were verified using a position-specific alignment matrix to predict potential cross reactivity between designed assays and genome-wide nontarget transcripts or genomic sequences. For gene expression profiling of these ncRNAs across different conditions, complementary DNAs (cDNA) were generated from 50 ng of total RNA using the High Capacity cDNA Reverse Transcription Kit (Life Technologies). The resulting cDNA was subjected to a 14-cycle PCR amplification followed by real-time PCR reaction using the manufacturer's TaqMan PreAmp Master Mix Kit Protocol (Life Technologies). Two replicates were run for each gene for each sample in a 384-well format plate on the 7900HT Fast Real-Time PCR System (Life Technologies). PPIA was used as an endogenous control for normalization across different samples.

RNA Blot

We obtained 5 µg of polyA RNA using an RNeasy Kit (QIAGEN) and PolyA Purist Mag (Ambion). RNA blots were performed using a NorthernMax Kit (Ambion) following the standard manufacturer's protocol. Probes were generated with full length PANDA using the Prime-It RmT Random Primer Labeling Kit (Agilent).

Antibodies

The following antibodies were used for chromatin immunoprecipitation assays: anti-H3K4me3 (Abcam ab8580), anti-H3K35me3 (Abcam ab9050) and anti-p53 (Abcam ab28). Protein blots were performed using anti-PARP (Cell Signal 9542), anti-B-tubulin (Abcam ab6046), anti LSD1 (ab17721), anti EZH2 (Cell Signal AC22), anti p21 (Santa Cruz Biotech) and anti NF-YA (Santa Cruz Biotech H-209).

RNA Interference

Human fetal lung fibroblasts were transfected with 50 nM of ON-TARGETPlus siRNAs (Dharmacon) targeting PANDA (Table 2). Validated siRNAs for mRNAs were obtained from Ambion (Table 2).

TUNEL

TUNEL assays were performed using the in situ Cell Death Detection Kit, TMR Red (Roche). Human fetal lung fibroblasts were cultured on chamber slides (Lab-Tek), treated with 200 ng/ml doxorubicin (Sigma) for 24 hours, fixed with methanol at −20° C. for 10 minutes and incubated with the TUNEL labeling mixture for 1 hour at 37° C. Slides were then washed with PBS and mounted in Prolong Gold antifade reagent with DAPI (Invitrogen) and imaged at 20× magnification.

RNA Immunoprecipitation

Ten million cells were treated with 200 ng/ml doxorubicin for 16 hours, trypsinized and crosslinked with 1% formaldehyde for 10 minutes, followed by the addition of 0.125 M glycine for 5 minutes. After two PBS washes, cells were lysed with 2× volume of Buffer A (10 mM HEPES pH 7.5, 1.5 mM $MgCl_2$, 10 mM KCl, 0.5 mM DTT, 1 mM PMSF) for 15 minutes on ice at 150 r.p.m. NP-40 was added to a final concentration of 0.25% for 5 minutes on ice. Lysates were centrifuged for 3 minutes at 2,000 r.p.m., and the supernatant (cytosol) was collected. Next, an equal volume of Buffer C as that used of Buffer A was added to the pellet for 20 minutes with frequent vortex (20 mM HEPES pH 7.5, 10% glycerol, 0.42 M KCl, 4 mM $MgCl_2$, 0.5 mM DTT, and 1 mM PMSF). Nuclear lysates were dounced for 5 seconds using a motorized pestle and sonicated for 7 minutes using a Diagenode Sonicator (30 seconds on, 30 seconds off, power setting H). Nuclear and cytoplasmic lysates were combined and centrifuged for 15 minutes at 13,000 r.p.m. Supernatants were transferred into micro spin columns (Pierce 89879), and 2 µg of antibody was added and incubated overnight. We washed 10 µl of Protein A/G UltraLink Resin (Pierce 53132) three times with RIP wash buffer (50 mM TrisHcl pH 7.9, 10% glycerol, 100 mM KCl, 5 mM $MgCl_2$, 10 mM B-me and 0.1%

NP-40) and added it to the immunoprecipitation reaction for 1 hour at 4° C. Samples were washed four times with RIP wash buffer and two times with 1 M RIPA (50 mM Tris pH 7.4, 1 M NaCl, 1 mM EDTA, 0.1% SDS, 1% NP-40, 0.5% sodium deoxycholate, 0.5 mM DTT and 1 mM PMSF). Beads were resuspended in 200 µl 150 mM RIPA (50 mM Tris pH 7.4, 150 mM NaCl, 1 mM EDTA, 0.1% SDS, 1% NP-40, 0.5% sodium deoxycholate, 0.5 mM DTT and 1 mM PMSF) plus 5 µl Proteinase K (Ambion) and incubated for 1 hour at 45° C. We added 1 ml of TRIzol to the sample, and RNA was extracted using the RNEasy Mini Kit (QIAGEN) with the on column DNAse digest (QIAGEN).

RNAse Mediated RNA Chromatography

RNAse mediated RNA chromatography (Michlewski et al. (2010) RNA 16:1673-1678, herein incorporated by reference in its entirety) was performed as previously described with the following modifications: 6 pmols of RNA (PANDA or a 1.2-kb fragment of LacZ) were used per reaction. RNA was folded (90° C. for 2 minutes, ice for 2 minutes), supplied with RNA structure buffer (Ambion) and shifted to room temperature (22-25° C.) for 20 minutes before conjugation to beads. RNAse digestion was performed with 5 µl of RNase A/T1 cocktail (Ambion) and 2 µl of RNase V1 (Ambion). Cellular lysates were prepared as follows: 10 million doxorubicin treated cells (16 hours) were incubated in 200 µl PBS, 600 µl $H_2O$ and 200 µl nuclear lysis buffer (1.28 M sucrose; 40 mM Tris-HCl pH 7.5; 20 mM $MgCl_2$; 4% Triton X-100) on ice for 20 minutes. Nuclei were pelleted by centrifugation at 2,500 g for 15 minutes. The nuclear pellet was resuspended in 1 ml RIP buffer (150 mM KCl, 25 mM Tris pH 7.4, 0.5 mM DTT, 0.5% NP40, 1 mM PMSF and protease inhibitor (Roche Complete Protease Inhibitor Cocktail Tablets)). Resuspended nuclei were sheared using a motorized douncer for 5 seconds. Nuclear membrane and debris were pelleted by centrifugation at 18,000 g for 10 minutes.

Chromatin Immunoprecipitation (ChIP)

ChIP was performed as previously described (Rinn et al. (2006) PLoS Genet. 2, e119). qPCR primers for FAS and CCNB1 and FAS-control NF-YA binding sites were obtained from Morachis et al. (Genes Dev. (2010) 24, 135-147). Primers for PUMA and BAX were designed to surround the NF-YA consensus motif CCAAT (Table 2).

TABLE 2

Primers and Oligos

RACE primers for PANDA

| | |
|---|---|
| Fwd | 5'-CAGAACTTGGCATGATGGAG-3' (SEQ ID NO: 4) |
| Rev | 5'-TGATATGAAACTCGGTTTACTACTAGC-3' (SEQ ID NO: 5) |
| Fwd2 | 5'-TGCACACATTTAACCCGAAG-3' (SEQ ID NO: 6) |
| Rev2 | 5'-CCCCAAAGCTACATCTATGACA-3' (SEQ ID NO: 7) |
| Rev3 | 5'-CGTCTCCATCAT GCCAAGTT-3' (SEQ ID NO: 8) |
| Rev4 | 5'-CATAGAGCTTCACCGACATAGC-3' (SEQ ID NO: 9) |

RT-PCR primers for PANDA

| | |
|---|---|
| Fwd | 5'-TGCACACATTTAACCCGAAG-3' (SEQ ID NO: 10) |
| Rev | 5'-CCCCAAAGCTACATCTATGACA-3' (SEQ ID NO: 11) | siRNAs for PANDA

| | |
|---|---|
| siRNA pool A | 5'-AAUGUGUGCACGUAACAGAUU-3' (SEQ ID NO: 12) |
| | 5'-GAGAUUUGCAGCAGACACAUU-3' (SEQ ID NO: 13) |
| siRNA pool B | 5'-GGGCAUGUUUUCACAGAGGUU-3' (SEQ ID NO: 14) |
| | 5'-GAGAUUUGCAGCAGACACAUU-3' (SEQ ID NO: 13) |
| siRNA pool C | 5'-AAUGUGUGCACGUAACAGAUU-3' (SEQ ID NO: 12) |
| | 5'-GGGCAUGUUUUCACAGAGGUU-3' (SEQ ID NO: 14) |
| siCTRL | Dharmacon D-001810-10 | siRNAs for mRNAs

| | |
|---|---|
| siNFYA pool | si9530 Ambion |
| | si9529 Ambion |
| | si9528 Ambion |
| siTP53 | S5606 Ambion |
| siCDKN1A | S417 Ambion |

Chip primers

| | |
|---|---|
| PUMA fwd | 5'-CGT GGA TTC CTG TCT CCT CT-3' (SEQ ID NO: 15) |
| PUMA rev | 5'-GTC ACT CTG GTG AGG CGA TT-3' (SEQ ID NO: 16) |
| NOXA fwd | 5'-TTT CCC TTC CCT GTT ACT GC-3' (SEQ ID NO: 17) |
| NOXA rev | 5'-CTT GGG TAA ACA AGC CCA GA-3' (SEQ ID NO: 18) |

Taqman assays

| | |
|---|---|
| PANDA | custom Taqman |
| TP53 | Hs99999147_m1 |
| LAP3 | Rh02870758_m1 |
| APAF1 | Hs00559441_m1 |
| LRDD | Hs00388035_m1 |
| FAS | Hs00163653_m1 |
| BIK | Hs00154189_m1 |
| CDKN1A | Hs01121168_m1 |
| GAPDH | Hs99999905_m1 |

Results
Extensive Noncoding Transcription Near Cell-Cycle Genes

To systematically discover functional ncRNAs in the regulatory region of human cell-cycle genes, we created a tiling array that interrogates at 5-nucleotide resolution across 25 kb of the 9p21 locus (which encompasses CDKN2A (p16), p14ARF and CDKN2B (p15)), as well as from 10 kb upstream to 2 kb downstream of each TSS from 53 cell-cycle genes to include those that encode all known cyclins, CDKs and CDKIs (FIG. 1A and Table 1). These genes are also critical for fundamental biological processes such as senescence, self-renewal, DNA damage response and tumor formation (Sherr et al. (1999) Genes Dev. 13:1501-1512; Hall et al. (1996) Adv. Cancer Res. 68:67-108; Johnson et al. (1999) Annu Rev. Pharmacol. Toxicol. 39, 295-312). Thus, we hybridized 54 pairs of polyadenylated RNAs from various human cells that were altered or perturbed through cell-cycle synchronization, DNA damage, differentiation stimuli, oncogenic stimuli or carcinogenesis (Table 3).

Figure 1B:
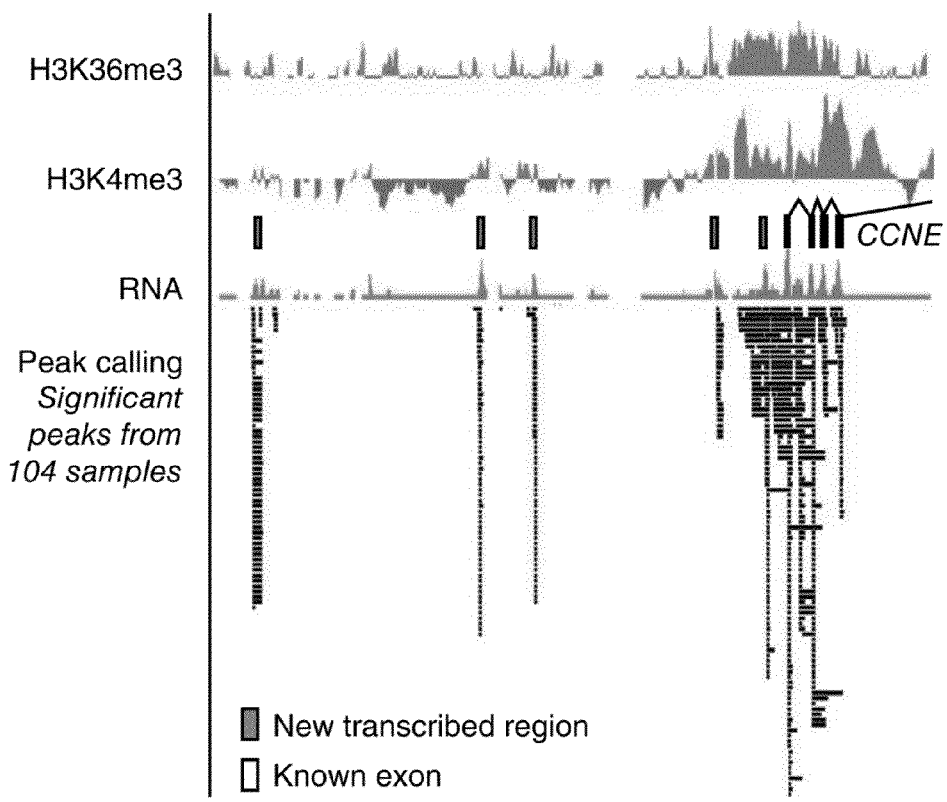
Figure 9:
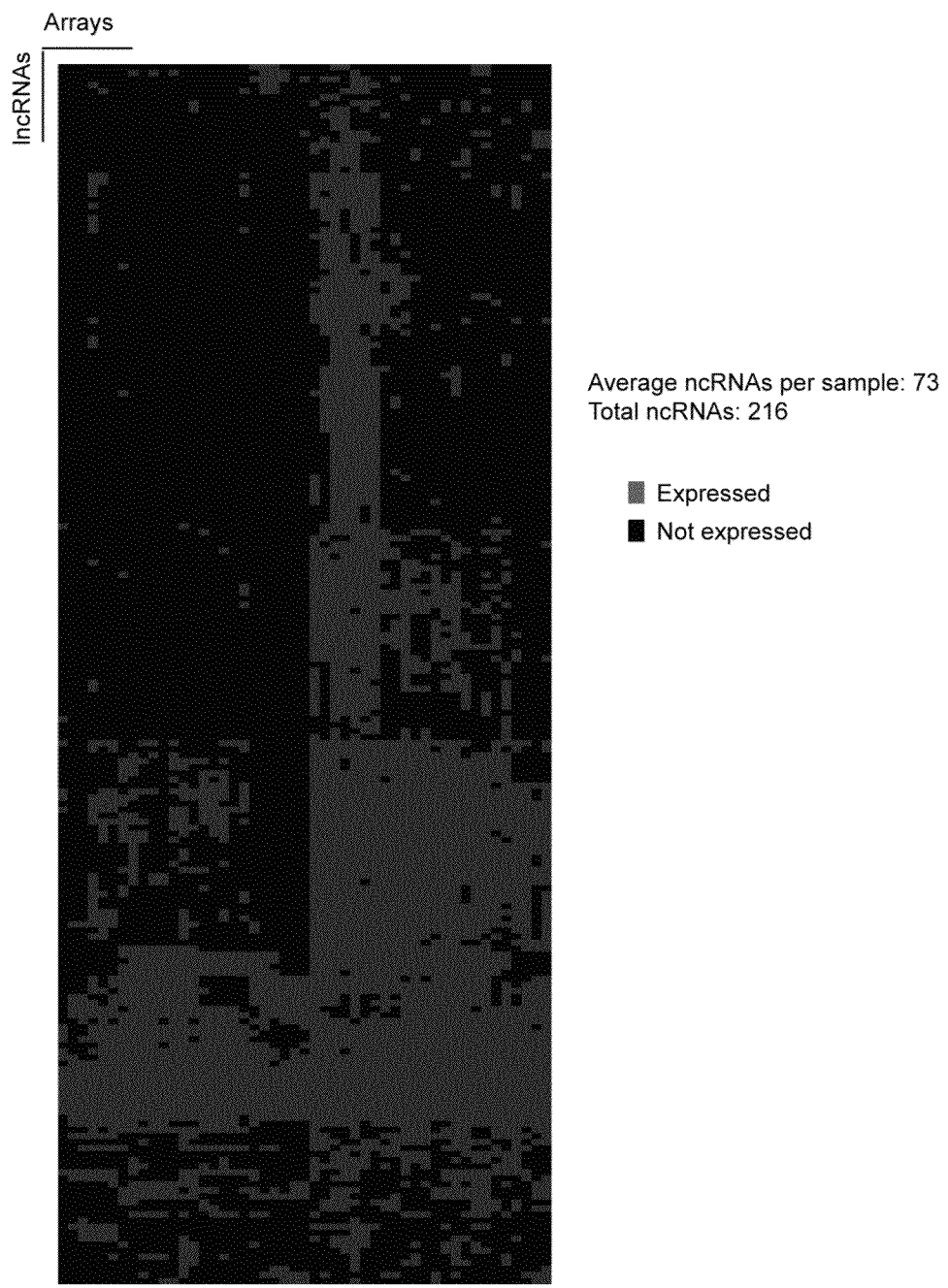
FIG. 9 shows a heatmap of lncRNAs expressed in each of the 104 different RNA tiling arrays as determined by peak calling analysis.

A peak calling algorithm searched for statistically significant signals above background and detected contiguous regions (peaks) of at least 50 bp. We then compiled statistically significant transcripts from all 108 channels of the 54 arrays, clustered all transcripts that overlapped by a minimum of 50 bases and identified clusters that were present in at least 10% of the samples. Averaging the signal intensity across all probes in a peak produced a quantitative estimate of transcript abundance. Despite possible 3' bias caused by polyadenylated RNA selection, our procedure detected exon 1 transcription from the majority of cell-cycle coding genes (41 of the 56), showing that this custom tiling array can detect previously reported transcribed regions. In each individual sample, we detected an average of 73 of the 216 transcribed regions (with a range of 14-189 transcribed regions) that did not overlap with known exons of the 56 cell-cycle genes (FIG. 9; an example of the CCNE1 locus in human fetal lung fibroblasts is shown in FIG. 1B). Across all 108 samples, we identified a total of 216 discrete transcribed regions (Table 4). The average transcript length was 234 nucleotides (with a range of 50-1,494 nucleotides). One hundred seventy one of the 216 (79%) previously unidentified transcribed regions were located 5' of the TSS of the cell-cycle genes ('upstream'), 40 of the 216 (19%) were located within introns (intronic), and 5 of the 216 (2%) were located downstream of the 3' end of CDKN2A.

Figure 1C:
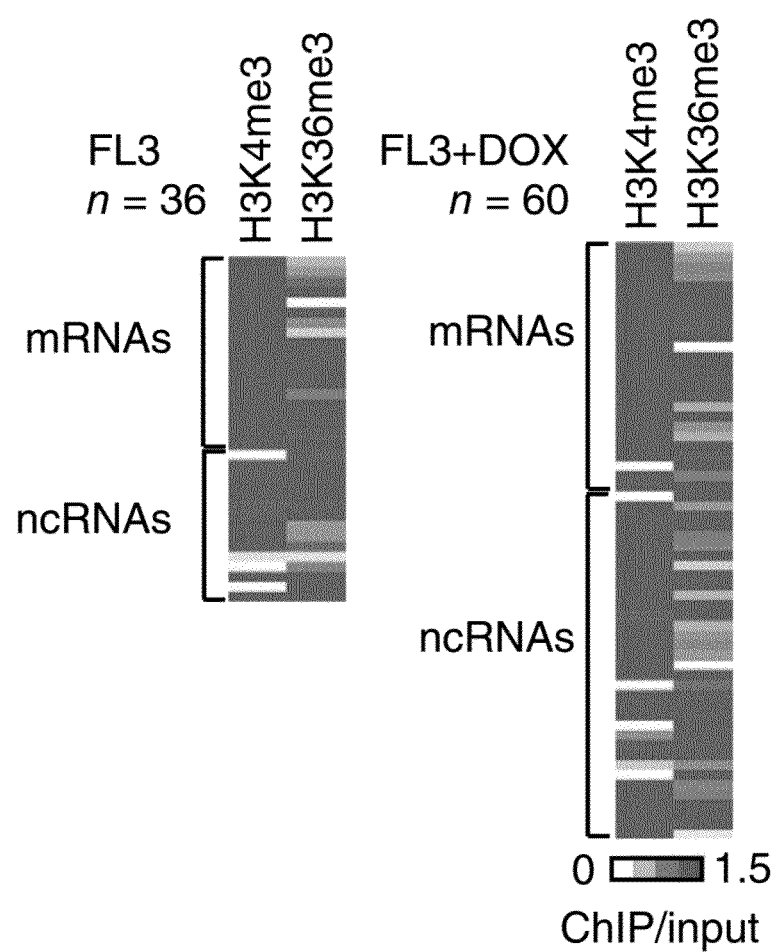

Genes actively transcribed by RNA polymerase II are marked by trimethylation of histone H3 on lysine 4 (H3K4me3) and lysine 36 of histone H3 (H3K36me3), which reflect gene starts and bodies, respectively (Rando et al. (2009) Annu Rev. Biochem. 78:245-271). These chromatin marks can be used to identify non-coding transcription (Guttman et al. (2009) Nature 458, 223-227, herein incorporated by reference). In a subset of our samples, we determined whether the 216 transcribed regions were similarly marked for active transcription by performing chromatin immunoprecipitation followed by hybridization to our custom tiling array (ChIP-chip). This analysis confirmed that the chromatin state at a majority of the newly defined transcripts was enriched in both H3K4me3 and H3K36me3 (FIGS. 1B and 1C). Using EpiGRAPH analysis to query our transcripts against approximately 900 published genomic attributes (Bock et al. (2009) Genome Biol. 10:R14), the 216 putative transcribed regions were enriched for H3K4me3 ($P<10^{-9}$) and RNA polymerase II binding ($P<10^{-7}$), providing further evidence that these genomic regions are actively transcribed.

Figure 1D:
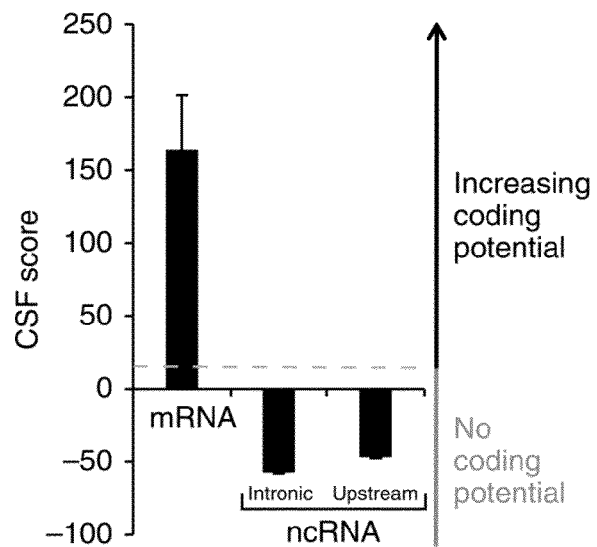
Figure 1E:
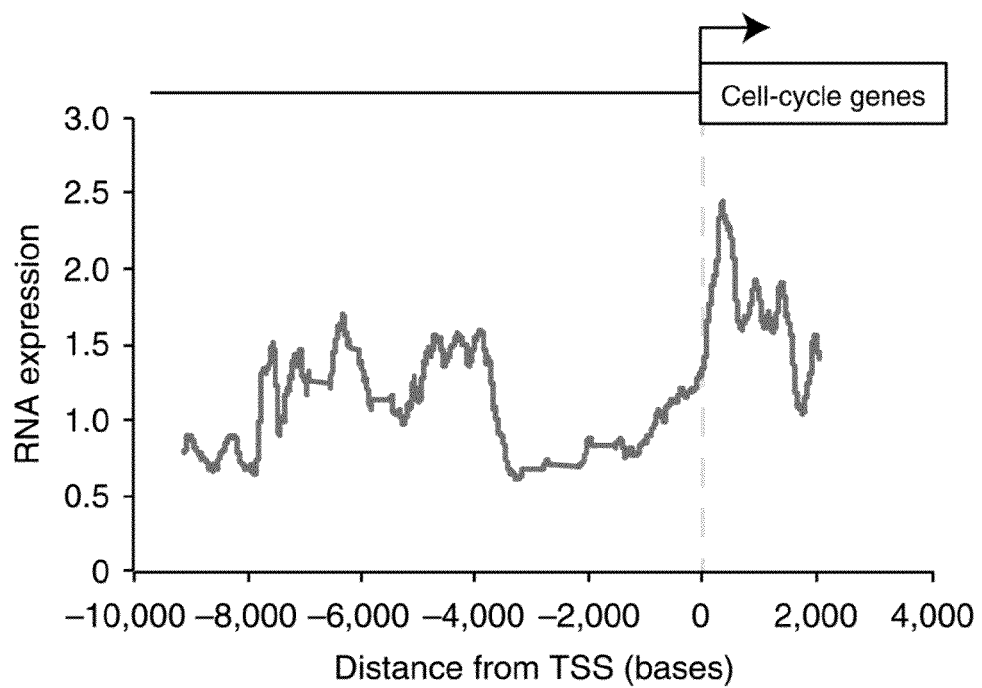

To determine whether the 216 transcripts may encode previously unknown protein-coding exons or noncoding RNAs, we used a codon substitution frequency (CSF) analysis to assess for characteristic evolutionary signatures of protein-coding sequences across 21 sequenced mammalian genomes (Lin et al. Nature Precedings published online, doi:10.1038/npre.2010.4784.1 (18 Aug. 2010), herein incorporated by reference in its entirety). As expected, the transcribed regions that coincided with annotated exons had high CSF scores. However, over 86% of the new transcribed regions had CSF scores well below the threshold of known protein-coding genes and resembled known ncRNAs (FIG. 1D and Table 5), suggesting that most of the new regions do not have protein-coding potential. BLAST analysis confirmed that the majority of the transcripts are not known protein-coding genes (Table 5). Furthermore, none of the transcripts intersect known pre-miRNAs, C/D box small nucleolar RNAs, H/ACA box small nucleolar RNAs or small Cajal-body specific RNAs as annotated in the UCSC genome browser. Thereafter, we referred to these transcribed regions as long noncoding RNAs (lncRNAs). We aligned the RNA hybridization signals at all 56 protein-coding loci of all 108 samples relative to their TSS (FIG. 1E). As expected, we found a peak immediately downstream of the TSS corresponding to exon 1 of the protein-coding gene. In addition, we found enrichment of non-coding transcription in the region 4-8 kb upstream of the TSS. Thus, unlike the previously described PASRs, tiny RNAs and TSSaRNAs, which are primarily located within 100 bp of the TSS, the majority of these ncRNAs are longer and are not clustered immediately around the TSS.

Expression Patterns of ncRNAs Suggest Specific Biological Functions

Figure 2A:
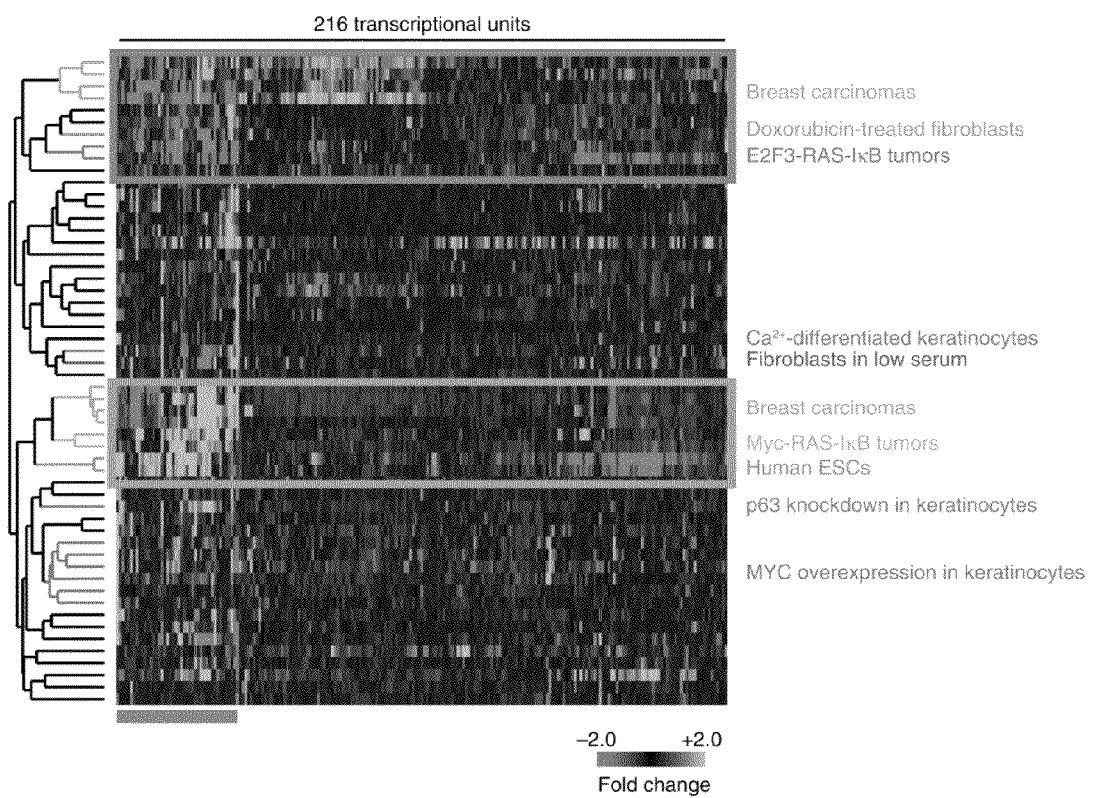
FIGS. 2A and 2B show an analysis of ncRNA expression across diverse cell cycle perturbations.

Next, we examined the biological conditions that regulate expression of these ncRNAs in order to infer possible biological functions. We assembled a matrix of the expression changes of the 216 new transcribed regions across all 54 perturbations and hierarchically clustered the genes and samples (FIG. 2A). Of the 216 new transcribed regions, 92 (43%) had at least a two-fold change in expression detected on the tiling array in at least one of the perturbations, suggesting that a large subset of the transcribed regions may have functional roles. The samples that had the most transcripts with at least twofold expression change were the embryonic stem cells (ESC) relative to day 152 fetal pancreas (40 of 216) and invasive ductal breast carcinomas relative to normal (as many as 35 of 216), suggesting that a subset of these lncRNAs may play a role in self-renewal and carcinogenesis (FIG. 2A). Notably, lncRNA expression profiles of keratinocytes with knockdown of P63, which inhibits keratinocyte differentiation, clustered with that of ESC, suggesting that these ncRNAs may have a role in the undifferentiated state. Expression patterns from five keratinocyte samples that were transduced with the oncogene MYC alone or in combination with other oncogenes relative to controls clustered together, showing that MYC has a dominant effect on ncRNA expression. MYC-RAS-IκBα transduced human keratinocytes activate an ESC-like mRNA gene expression program and acquire properties of cancer stem cells (Wong et al. (2008) Cell Stem Cell 2:333-344). Notably, the lncRNA expression profile of MYC-RAS-IκBα cells clustered with that of ESCs (FIG. 2), suggesting a shared lncRNA signature for embryonic and cancer stem cells. In contrast, the E2F3-RAS-IκBα transduced keratinocytes, which do not express the ESC-like mRNA gene expression program, had an inverse pattern of expression for the majority of lncRNAs. In addition, eight primary human invasive ductal breast carcinomas split into two different groups based on their lncRNA profiles: four of the cancers clustered with the ESCs and MYC-RAS-IκBα tumors, and the other four clustered with the E2F3-RAS- IκBα tumors, suggesting that these tumor models mimic the expression pattern of not only mRNAs but also these lncRNAs in bona fide human cancers.

Figure 2B:
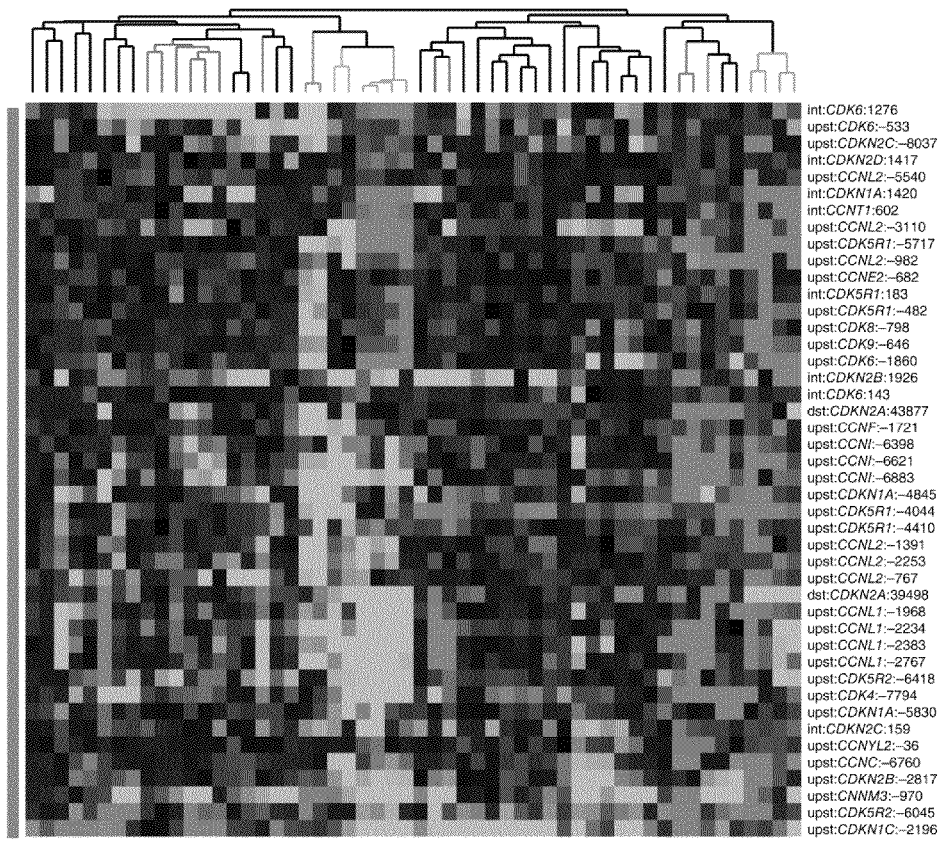

The 216 lncRNAs are divided into three main clusters based on their expression pattern across all samples (FIG. 2). Notably, cluster 1 is composed of lncRNAs that are strongly induced in ESCs, keratinocytes with P63-knockdown and MYC-RAS-IκB tumors relative to differentiated cells and GFP-RAS-IκB tumors, which we interpret to be a 'sternness cluster' (FIG. 2B). Notably, each cluster is composed of many of the ncRNAs from the same genomic locus, suggesting that multiple adjacent ncRNAs are either coordinately regulated in a shared response or are spliced together as exons of one transcript. High correlation of the dynamic expression patterns of these ncRNAs and different biological and cellular conditions suggest that these ncRNAs may be functional in the cell cycle, in self-renewal and in cancer.

TABLE 3

Experimental Samples And Conditions

| Sample pair # | Experimental sample |
|---|---|
| 1 | Human fetal lung fibroblasts treated with doxorubicin (200 ng/μl) for 24 hours |
| 2 | Human fetal lung fibroblasts in low serum (0.01%) |
| 3 | Human fetal lung fibroblasts transduced with HPV-E7 |
| 4 | Human fetal lung fibroblasts transduced with HPV-E6 |
| 5 | Human fetal lung fibroblasts transduced with HRAS |
| 6 | HeLa synchronized by double thymidine block: 0 hr |
| 7 | HeLa synchronized by double thymidine block: 2 hr |
| 8 | HeLa synchronized by double thymidine block: 4 hr |
| 9 | HeLa synchronized by double thymidine block: 6 hr |
| 10 | HeLa synchronized by double thymidine block: 8 hr |
| 11 | HeLa synchronized by double thymidine block: 10 hr |
| 12 | HeLa synchronized by double thymidine block: 12 hr |
| 13 | Primary human keratinocytes transduced with p63 shRNA |
| 14 | Primary human keratinocytes treated with $Ca^{2+}$ for 48 hours |
| 15 | U2OS synchronized by double thymidine block: 0 hr |
| 16 | U2OS synchronized by double thymidine block: 2 hr |
| 17 | U2OS synchronized by double thymidine block: 4 hr (A) |
| 18 | U2OS synchronized by double thymidine block: 4 hr (B) |
| 19 | U2OS synchronized by double thymidine block: 6 hr |
| 20 | U2OS synchronized by double thymidine block: 8 hr |
| 21 | U2OS synchronized by double thymidine block: 14 hr |
| 22 | U2OS synchronized by double thymidine block: 16 hr |
| 23 | Human ES (H9) |
| 24 | Human ES (H9) |
| 25 | Human ES (H9) |
| 26 | MCF7 cell line |
| 27 | Primary human keratinocytes transduced with MYC |
| 28 | Primary human keratinocytes transduced with MYC |
| 29 | Primary human keratinocytes transduced with HRAS |
| 30 | Primary human keratinocytes transduced with HRAS |
| 31 | Primary human keratinocytes transduced with E2F3 |
| 32 | Primary human keratinocytes transduced with E2F3 |
| 33 | Primary human keratinocytes transduced with IkB |
| 34 | Primary human keratinocytes transduced with IkB |
| 35 | Primary human keratinocytes transduced with MYC, RAS, and IkB |
| 36 | Primary human keratinocytes transduced with MYC, RAS, and IkB |
| 37 | Primary human keratinocytes transduced with E2F3, RAS, and IkB |
| 38 | Primary human keratinocytes transduced with E2F3, RAS, and IkB |
| 39 | Primary human keratinocytes transduced with SOX2, RAS, and IkB |
| 40 | Primary human keratinocytes transduced with SOX2, RAS, and IkB |
| 41 | MYC-RAS-IkB tumor 1 |
| 42 | MYC-RAS-IkB tumor 2 |
| 43 | E2F3-RAS-IkB tumor 1 |
| 44 | E2F3-RAS-IkB tumor 2 |
| 45 | Invasive ductal breast carcinoma P2 |
| 46 | Invasive ductal breast carcinoma P3 |
| 47 | Invasive ductal breast carcinoma P4 |
| 48 | Invasive ductal breast carcinoma P5 |
| 49 | Invasive ductal breast carcinoma P6 |
| 50 | Invasive ductal breast carcinoma P7 |
| 51 | Invasive ductal breast carcinoma P9 |
| 52 | Invasive ductal breast carcinoma P10 |

| Control samples |
|---|
| Human fetal lung fibroblasts untreated |
| Human fetal lung fibroblasts in normal serum |
| Human fetal lung fibroblasts transduced with vector control |
| Human fetal lung fibroblasts transduced with vector control |
| Human fetal lung fibroblasts transduced with vector control |
| HeLa asynchronous |
| HeLa asynchronous |
| HeLa asynchronous |
| HeLa asynchronous |
| HeLa asynchronous |
| HeLa asynchronous |
| HeLa asynchronous |
| Primary human keratinocytes transduced with control shRNA |
| Primary human keratinocytes without Ca2+ treatment |
| U2OS asynchronous |
| U2OS asynchronous |
| U2OS asynchronous |
| U2OS asynchronous |
| U2OS asynchronous |
| U2OS asynchronous |
| U2OS asynchronous |
| U2OS asynchronous |
| Human SOX17+ definitive endoderm |
| Human fetal pancreas day 76 |
| Human fetal pancreas day 152 |
| Human mammary epithelial cells |
| Primary human keratinocytes transduced with GFP |
| Primary human keratinocytes transduced with LacZ |
| Primary human keratinocytes transduced with GFP |
| Primary human keratinocytes transduced with LacZ |
| Primary human keratinocytes transduced with GFP |
| Primary human keratinocytes transduced with LacZ |
| Primary human keratinocytes transduced with GFP |
| Primary human keratinocytes transduced with LacZ |
| Primary human keratinocytes transduced with LacZ, RAS, and IkB |
| Primary human keratinocytes transduced with GFP, RAS, and IkB |
| Primary human keratinocytes transduced with LacZ, RAS, and IkB |
| Primary human keratinocytes transduced with GFP, RAS, and IkB |
| Primary human keratinocytes transduced with LacZ, RAS, and IkB |
| Primary human keratinocytes transduced with GFP, RAS, and IkB |
| GFP-RAS-IkB tumor pool |
| GFP-RAS-IkB tumor pool |
| GFP-RAS-IkB tumor pool |
| GFP-RAS-IkB tumor pool |
| Normal breast tissue |
| Normal breast tissue |
| Normal breast tissue |
| Normal breast tissue |
| Normal breast tissue |
| Normal breast tissue |
| Normal breast tissue |
| Normal breast tissue |

TABLE 4

216 Identified Transcribed Regions

| Gene ID | Unique ID | Name |
|---|---|---|
| GENE32X | chr7: 92301005-92301062 | int: CDK6: 143 (SEQ ID NO: 30) |
| GENE1X | chr9: 21921199-21921259 | dst: CDKN2A: 43877 (SEQ ID NO: 31) |
| GENE82X | chr16: 2417723-2417784 | upst: CCNF: −1721 (SEQ ID NO: 32) |

TABLE 4-continued

216 Identified Transcribed Regions

| Gene ID | Unique ID | Name |
| --- | --- | --- |
| GENE89X | chr4: 78222564-78222616 | upst: CCNI: −6398 (SEQ ID NO: 33) |
| GENE90X | chr4: 78222796-78222879 | upst: CCNI: −6621 (SEQ ID NO: 34) |
| GENE91X | chr4: 78223171-78223226 | upst: CCNI: −6883 (SEQ ID NO: 35) |
| GENE169X | chr6: 36750039-36750091 | upst: CDKN1A: −4845 (SEQ ID NO: 21) |
| GENE139X | chr17: 27834215-27834286 | upst: CDK5R1: −4044 (SEQ ID NO: 36) |
| GENE140X | chr17: 27833951-27834012 | upst: CDK5R1: −4410 (SEQ ID NO: 37) |
| GENE105X | chr1: 1325966-1326134 | upst: CCNL2: −1391 (SEQ ID NO: 38) |
| GENE106X | chr1: 1326824-1326881 | upst: CCNL2: −2253 (SEQ ID NO: 39) |
| GENE111X | chr1: 1325338-1325394 | upst: CCNL2: −767 (SEQ ID NO: 40) |
| GENE48X | chr19: 10539307-10539365 | int: CDKN2D: 1417 (SEQ ID NO: 41) |
| GENE109X | chr1: 1330111-1330167 | upst: CCNL2: −5540 (SEQ ID NO: 42) |
| GENE40X | chr6: 36756294-36756350 | int: CDKN1A: 1420 (SEQ ID NO: 43) |
| GENE23X | chr12: 47396450-47396506 | int: CCNT1: 602 (SEQ ID NO: 44) |
| GENE107X | chr1: 1327702-1327759 | upst: CCNL2: −3110 (SEQ ID NO: 45) |
| GENE142X | chr17: 27832743-27832798 | upst: CDK5R1: −5717 (SEQ ID NO:46) |
| GENE112X | chr1: 1325562-1325622 | upst: CCNL2: −982 (SEQ ID NO: 47) |
| GENE80X | chr8: 95977656-95977717 | upst: CCNE2: −682 (SEQ ID NO: 48) |
| GENE29X | chr17: 27838400-27838457 | int: CDK5R1: 183 (SEQ ID NO: 49) |
| GENE141X | chr17: 27837748-27837804 | upst: CDK5R1: −482 (SEQ ID NO: 50) |
| GENE154X | chr13: 25725961-25726018 | upst: CDK8: −798 (SEQ ID NO: 51) |
| GENE159X | chr9: 129587505-129587574 | upst: CDK9: −646 (SEQ ID NO: 52) |
| GENE151X | chr7: 92303843-92303900 | upst: CDK6: −1860 (SEQ ID NO: 53) |
| GENE30X | chr7: 92299944-92300005 | int: CDK6: 1276 (SEQ ID NO: 54) |
| GENE31X | chr7: 92302482-92302535 | upst: CDK6: −533 (SEQ ID NO: 55) |
| GENE202X | chr1: 51198111-51198165 | upst: CDKN2C: −8037 (SEQ ID NO: 56) |
| GENE99X | chr14: 99016592-99016918 | upst: CCNK: −899 (SEQ ID NO: 57) |
| GENE211X | chr2: 96845550-96845607 | upst: CNNM3: −248 (SEQ ID NO: 58) |
| GENE177X | chr11: 2868308-2868438 | upst: CDKN1C: −4619 (SEQ ID NO: 59) |
| GENE44X | chr9: 21958371-21958427 | int: CDKN2A: 6667 (SEQ ID NO: 60) |
| GENE5X | chr9: 21979973-21980169 | int: ARF: 4530 (SEQ ID NO: 25) |
| GENE188X | chr9: 22015449-22015506 | upst: CDKN2B: −15913 (SEQ ID NO: 61) |
| GENE33X | chr7: 92302831-92302887 | upst: CDK6: −1679 (SEQ ID NO: 62) |
| GENE166X | chr6: 36753254-36753315 | upst: CDKN1A: −1210 (SEQ ID NO: 63) |
| GENE45X | chr9: 21997580-21997644 | int: CDKN2B: 1926 (SEQ ID NO: 64) |
| GENE0X | chr9: 21925765-21925933 | dst: CDKN2A: 39498 (SEQ ID NO: 65) |
| GENE100X | chr3: 158363197-158363249 | upst: CCNL1: −1968 (SEQ ID NO: 66) |
| GENE101X | chr3: 158363410-158363460 | upst: CCNL1: −2234 (SEQ ID NO: 67) |
| GENE102X | chr3: 158363666-158363729 | upst: CCNL1: −2383 (SEQ ID NO: 68) |
| GENE103X | chr3: 158364054-158364109 | upst: CCNL1: −2767 (SEQ ID NO: 19) |
| GENE147X | chr2: 219526326-219526431 | upst: CDK5R2: −6418 (SEQ ID NO: 69) |
| GENE130X | chr12: 56440276-56440345 | upst: CDK4: −7794 (SEQ ID NO: 70) |
| GENE170X | chr6: 36748634-36748699 | upst: CDKN1A: −5830 (SEQ ID NO: 71) |
| GENE46X | chr1: 51206425-51206482 | int: CDKN2C: 159 (SEQ ID NO: 72) |
| GENE116X | chr10: 42270296-42270371 | upst: CCNYL2: −36 (SEQ ID NO: 73) |
| GENE121X | chr6: 100131015-100131072 | upst: CCNC: −6760 (SEQ ID NO: 74) |
| GENE191X | chr9: 22002466-22002532 | upst: CDKN2B: −2817 (SEQ ID NO: 22) |
| GENE212X | chr2: 96845025-96845087 | upst: CNNM3: −970 (SEQ ID NO: 75) |
| GENE146X | chr2: 219526647-219526700 | upst: CDK5R2: −6045 (SEQ ID NO: 76) |
| GENE175X | chr11: 2866110-2866163 | upst: CDKN1C: −2196 (SEQ ID NO: 77) |
| GENE8X | chr11: 69165927-69165983 | int: CCND1: 874 (SEQ ID NO: 78) |
| GENE9X | chr12: 4254403-4254460 | int: CCND2: 1205 (SEQ ID NO: 79) |
| GENE180X | chr11: 2864269-2864326 | upst: CDKN1C: −446 (SEQ ID NO: 80) |
| GENE17X | chr4: 78298022-78298078 | int: CCNG2: 390 (SEQ ID NO: 81) |
| GENE26X | chr17: 71505019-71505076 | upst: CDK3: −4148 (SEQ ID NO: 82) |
| GENE57X | chr4: 122964592-122964649 | upst: CCNA2: −250 (SEQ ID NO: 83) |
| GENE38X | chrX: 18353741-18353799 | int: CDKL5: 64 (SEQ ID NO: 84) |
| GENE67X | chr12: 4250076-4250132 | upst: CCND2: −3165 (SEQ ID NO: 85) |
| GENE20X | chr14: 99017701-99017769 | int: CCNK: 210 (SEQ ID NO: 86) |
| GENE39X | chr6: 36755581-36755639 | int: CDKN1A: 885 (SEQ ID NO: 20) |
| GENE150X | chr2: 219523426-219523488 | upst: CDK5R2: −9197 (SEQ ID NO: 87) |
| GENE49X | chr2: 96847177-96847234 | int: CNNM3: 1459 (SEQ ID NO: 88) |
| GENE58X | chr11: 69163558-69163614 | upst: CCND1: −1659 (SEQ ID NO: 89) |
| GENE108X | chr1: 1324135-1324191 | int: CCNL2: 463 (SEQ ID NO: 90) |
| GENE72X | chr19: 34993553-34993625 | upst: CCNE1: −1190 (SEQ ID NO: 91) |
| GENE149X | chr2: 219524610-219524666 | upst: CDK5R2: −8037 (SEQ ID NO: 92) |
| GENE164X | chr5: 133731711-133731768 | upst: CDKL3: −867 (SEQ ID NO: 93) |
| GENE16X | chr5: 162797800-162797857 | int: CCNG1: 381 (SEQ ID NO: 27) |
| GENE66X | chr12: 4250336-4250392 | upst: CCND2: −2874 (SEQ ID NO: 94) |
| GENE186X | chr9: 22130077-22130138 | upst: CDKN2B: −130736 (SEQ ID NO: 95) |
| GENE18X | chr4: 78215107-78215164 | int: CCNI: 1042 (SEQ ID NO: 96) |
| GENE68X | chr12: 4249397-4249454 | upst: CCND2: −4757 (SEQ ID NO: 97) |
| GENE36X | chr9: 129588503-129588560 | int: CDK9: 352 (SEQ ID NO: 98) |
| GENE10X | chr12: 4254887-4254947 | int: CCND2: 1689 (SEQ ID NO: 99) |
| GENE37X | chrX: 18355359-18355416 | int: CDKL5: 1682 (SEQ ID NO: 100) |
| GENE143X | chr2: 219528834-219528890 | upst: CDK5R2: −4541 (SEQ ID NO: 101) |
| GENE134X | chr7: 150394096-150394152 | upst: CDK5: −7855 (SEQ ID NO: 102) |

TABLE 4-continued

216 Identified Transcribed Regions

| Gene ID | Unique ID | Name |
|---|---|---|
| GENE157X | chr9: 129586747-129586804 | upst: CDK9: −1536 (SEQ ID NO: 103) |
| GENE65X | chr12: 4251907-4251963 | upst: CCND2: −1291 (SEQ ID NO: 104) |
| GENE62X | chr11: 69164970-69165027 | upst: CCND1: −377 (SEQ ID NO: 105) |
| GENE21X | chr3: 158360079-158360144 | int: CCNL1: 1097 (SEQ ID NO: 106) |
| GENE145X | chr2: 219532096-219532152 | upst: CDK5R2: −648 (SEQ ID NO: 107) |
| GENE110X | chr1: 1331923-1331980 | upst: CCNL2: −7336 (SEQ ID NO: 108) |
| GENE60X | chr11: 69162285-69162341 | upst: CCND1: −2768 (SEQ ID NO: 109) |
| GENE124X | chr12: 54645435-54645491 | upst: CDK2: −1390 (SEQ ID NO: 110) |
| GENE119X | chr16: 34107323-34107380 | upst: CCNYL3: −8181 (SEQ ID NO: 111) |
| GENE3X | chr9: 21956411-21956472 | dst: CDKN2A: 8650 (SEQ ID NO: 112) |
| GENE153X | chr13: 25726490-25726547 | upst: CDK8: −265 (SEQ ID NO: 113) |
| GENE129X | chr12: 56436900-56436957 | upst: CDK4: −4462 (SEQ ID NO: 114) |
| GENE182X | chr9: 21965167-21965225 | upst: CDKN2A: −44 (SEQ ID NO: 115) |
| GENE43X | chr9: 21959776-21959834 | int: CDKN2A: 5270 (SEQ ID NO: 116) |
| GENE93X | chr5: 159701961-159702018 | upst: CCNJL: −2749 (SEQ ID NO: 117) |
| GENE213X | chr2: 96788527-96788584 | upst: CNNM4: −1843 (SEQ ID NO: 118) |
| GENE148X | chr2: 219525252-219525310 | upst: CDK5R2: −7376 (SEQ ID NO: 119) |
| GENE22X | chr5: 54563848-54563906 | int: CCNO: 1417 (SEQ ID NO: 120) |
| GENE174X | chr11: 2863821-2863879 | upst: CDKN1C: −5 (SEQ ID NO: 121) |
| GENE179X | chr11: 2870355-2870412 | upst: CDKN1C: −6280 (SEQ ID NO: 122) |
| GENE55X | chr9: 21985446-21985507 | upst: ARF: −840 (SEQ ID NO: 123) |
| GENE64X | chr12: 4251368-4251433 | upst: CCND2: −1830 (SEQ ID NO: 124) |
| GENE137X | chr17: 27838057-27838134 | upst: CDK5R1: −206 (SEQ ID NO: 125) |
| GENE56X | chr13: 35903573-35903645 | upst: CCNA1: −1163 (SEQ ID NO: 126) |
| GENE15X | chr8: 95976064-95976125 | int: CCNE2: 647 (SEQ ID NO: 127) |
| GENE162X | chr9: 129587246-129587303 | upst: CDK9: −909 (SEQ ID NO: 128) |
| GENE118X | chr16: 34115099-34115155 | upst: CCNYL3: −293 (SEQ ID NO: 129) |
| GENE206X | chr14: 53933196-53933256 | upst: CDKN3: −271 (SEQ ID NO: 130) |
| GENE24X | chr2: 135393651-135393711 | int: CCNT2: 640 (SEQ ID NO: 131) |
| GENE59X | chr11: 69162503-69162560 | upst: CCND1: −2574 (SEQ ID NO: 132) |
| GENE113X | chr2: 135392543-135392600 | upst: CCNT2: −319 (SEQ ID NO: 133) |
| GENE138X | chr17: 27835198-27835254 | upst: CDK5R1: −3023 (SEQ ID NO: 134) |
| GENE158X | chr9: 129585474-129585543 | upst: CDK9: −3159 (SEQ ID NO: 135) |
| GENE161X | chr9: 129579484-129579540 | upst: CDK9: −8667 (SEQ ID NO: 136) |
| GENE77X | chr8: 95981621-95981682 | upst: CCNE2: −4956 (SEQ ID NO: 137) |
| GENE11X | chr6: 42015155-42015212 | int: CCND3: 2384 (SEQ ID NO: 138) |
| GENE172X | chr12: 12760224-12760281 | upst: CDKN1B: −1362 (SEQ ID NO: 139) |
| GENE92X | chr4: 78224048-78224105 | upst: CCNI: −7899 (SEQ ID NO: 140) |
| GENE114X | chr2: 135386111-135386168 | upst: CCNT2: −6751 (SEQ ID NO: 141) |
| GENE28X | chr7: 150383947-150384009 | int: CDK5: 1993 (SEQ ID NO: 142) |
| GENE160X | chr9: 129579642-129579699 | upst: CDK9: −8509 (SEQ ID NO: 143) |
| GENE61X | chr11: 69158023-69158080 | upst: CCND1: −7190 (SEQ ID NO: 144) |
| GENE181X | chr11: 2870788-2870849 | upst: CDKN1C: −7144 (SEQ ID NO: 145) |
| GENE207X | chr14: 53928983-53929043 | upst: CDKN3: −4479 (SEQ ID NO: 146) |
| GENE7X | chrX: 50041022-50041078 | upst: CCNB3: −3258 (SEQ ID NO: 147) |
| GENE14X | chr6: 42026838-42026902 | upst: CCND3: −9303 (SEQ ID NO: 148) |
| GENE155X | chr13: 25718422-25718479 | upst: CDK8: −8337 (SEQ ID NO: 149) |
| GENE47X | chr1: 51206791-51206847 | int: CDKN2C: 643 (SEQ ID NO: 150) |
| GENE117X | chr16: 34114348-34114405 | upst: CCNYL3: −1019 (SEQ ID NO: 151) |
| GENE132X | chr7: 150388302-150388358 | upst: CDK5: −2373 (SEQ ID NO: 152) |
| GENE50X | chr2: 96792179-96792239 | int: CNNM4: 1658 (SEQ ID NO: 153) |
| GENE79X | chr8: 95985217-95985273 | upst: CCNE2: −8552 (SEQ ID NO: 154) |
| GENE87X | chr5: 162788013-162788074 | upst: CCNG1: −9141 (SEQ ID NO: 155) |
| GENE69X | chr12: 4248317-4248374 | upst: CCND2: −4886 (SEQ ID NO: 156) |
| GENE98X | chr14: 99009355-99009417 | upst: CCNK: −8357 (SEQ ID NO: 157) |
| GENE135X | chr7: 150395034-150395090 | upst: CDK5: −9105 (SEQ ID NO: 158) |
| GENE183X | chr9: 22108313-22108371 | upst: CDKN2B: −108997 (SEQ ID NO: 159) |
| GENE6X | chr15: 57185158-57185215 | int: CCNB2: 547 (SEQ ID NO: 160) |
| GENE205X | chr14: 53931175-53931231 | upst: CDKN3: −2291 (SEQ ID NO: 161) |
| GENE52X | chr9: 21934843-21934899 | dst: CDKN2A: 30203 (SEQ ID NO: 162) |
| GENE125X | chr12: 54641615-54641672 | upst: CDK2: −5210 (SEQ ID NO: 163) |
| GENE104X | chr3: 158364606-158364664 | upst: CCNL1: −3430 (SEQ ID NO: 164) |
| GENE85X | chr16: 2415476-2415532 | upst: CCNF: −3964 (SEQ ID NO: 165) |
| GENE97X | chr14: 99013065-99013126 | upst: CCNK: −4426 (SEQ ID NO: 166) |
| GENE84X | chr16: 2415715-2415845 | upst: CCNF: −3743 (SEQ ID NO: 167) |
| GENE133X | chr7: 150389691-150389748 | upst: CDK5: −3754 (SEQ ID NO: 168) |
| GENE192X | chr9: 22034676-22034732 | upst: CDKN2B: −35359 (SEQ ID NO: 169) |
| GENE197X | chr9: 22086788-22086845 | upst: CDKN2B: −87467 (SEQ ID NO: 170) |
| GENE144X | chr2: 219527709-219527767 | upst: CDK5R2: −4915 (SEQ ID NO: 171) |
| GENE83X | chr16: 2417537-2417598 | upst: CCNF: −2075 (SEQ ID NO: 172) |
| GENE152X | chr7: 92309874-92309931 | upst: CDK6: −8726 (SEQ ID NO: 173) |
| GENE198X | chr9: 22089878-22089935 | upst: CDKN2B: −90566 (SEQ ID NO: 174) |
| GENE42X | chr9: 21960139-21960195 | int: CDKN2A: 4904 (SEQ ID NO: 175) |
| GENE41X | chr9: 21960611-21960667 | int: CDKN2A: 4432 (SEQ ID NO: 176) |
| GENE54X | chr9: 21986800-21986856 | upst: ARF: −2148 (SEQ ID NO: 177) |
| GENE185X | chr9: 22129741-22129797 | upst: CDKN2B: −130339 (SEQ ID NO: 178) |

TABLE 4-continued

216 Identified Transcribed Regions

| Gene ID | Unique ID | Name |
|---|---|---|
| GENE51X | chr2: 96836476-96836537 | upst: CNNM3: −9238 (SEQ ID NO: 179) |
| GENE86X | chr5: 162792622-162792678 | upst: CCNG1: −4532 (SEQ ID NO: 180) |
| GENE4X | chr9: 21968740-21968798 | int: ARF: 15754 (SEQ ID NO: 181) |
| GENE81X | chr16: 2418355-2418411 | upst: CCNF: −1085 (SEQ ID NO: 182) |
| GENE189X | chr9: 22023307-22023365 | upst: CDKN2B: −23831 (SEQ ID NO: 183) |
| GENE171X | chr6: 36745166-36745227 | upst: CDKN1A: −9569 (SEQ ID NO: 29) |
| GENE19X | chr4: 78214282-78214339 | int: CCNI: 1874 (SEQ ID NO: 184) |
| GENE2X | chr9: 21919179-21919235 | dst: CDKN2A: 45866 (SEQ ID NO: 185) |
| GENE25X | chr6: 100122671-100122732 | int: CCNC: 816 (SEQ ID NO: 186) |
| GENE120X | chr6: 100128825-100128888 | upst: CCNC: −5405 (SEQ ID NO: 187) |
| GENE127X | chr12: 56434070-56434128 | upst: CDK4: −1632 (SEQ ID NO: 188) |
| GENE96X | chr14: 99014441-99014506 | upst: CCNK: −3241 (SEQ ID NO: 189) |
| GENE122X | chr16: 88278773-88278830 | upst: CDK10: −1805 (SEQ ID NO: 190) |
| GENE95X | chr5: 159700005-159700083 | upst: CCNJL: −671 (SEQ ID NO: 191) |
| GENE209X | chr14: 53927762-53927822 | upst: CDKN3: −5723 (SEQ ID NO: 192) |
| GENE187X | chr9: 22014430-22014488 | upst: CDKN2B: −15114 (SEQ ID NO: 193) |
| GENE78X | chr8: 95982746-95982803 | upst: CCNE2: −5939 (SEQ ID NO: 194) |
| GENE94X | chr5: 159706600-159706661 | upst: CCNJL: −7299 (SEQ ID NO: 195) |
| GENE12X | chr6: 42021792-42021848 | upst: CCND3: −4248 (SEQ ID NO: 196) |
| GENE35X | chr9: 129589962-129590019 | int: CDK9: 1811 (SEQ ID NO: 197) |
| GENE203X | chr1: 51197610-51197664 | upst: CDKN2C: −8538 (SEQ ID NO: 198) |
| GENE53X | chr9: 21985885-21985942 | upst: ARF: −1395 (SEQ ID NO: 199) |
| GENE70X | chr12: 4246316-4246376 | upst: CCND2: −6904 (SEQ ID NO: 200) |
| GENE131X | chr12: 56433408-56433465 | upst: CDK4: −977 (SEQ ID NO: 201) |
| GENE74X | chr19: 34989349-34989406 | upst: CCNE1: −5422 (SEQ ID NO: 202) |
| GENE76X | chr8: 95979501-95979558 | upst: CCNE2: −2828 (SEQ ID NO: 203) |
| GENE128X | chr12: 56434864-56434921 | upst: CDK4: −2133 (SEQ ID NO: 204) |
| GENE156X | chr13: 25717125-25717182 | upst: CDK8: −9630 (SEQ ID NO: 205) |
| GENE27X | chr17: 71504535-71504596 | upst: CDK3: −4497 (SEQ ID NO: 206) |
| GENE13X | chr6: 42023953-42024020 | upst: CCND3: −6423 (SEQ ID NO: 207) |
| GENE63X | chr11: 69156135-69156265 | upst: CCND1: −8918 (SEQ ID NO: 208) |
| GENE184X | chr9: 22119409-22119474 | upst: CDKN2B: −119804 (SEQ ID NO: 209) |
| GENE208X | chr14: 53928196-53928270 | upst: CDKN3: −5438 (SEQ ID NO: 210) |
| GENE201X | chr1: 51198789-51198848 | upst: CDKN2C: −7397 (SEQ ID NO: 211) |
| GENE115X | chr2: 208280834-208280903 | upst: CCNYL1: −3709 (SEQ ID NO: 212) |
| GENE165X | chr2: 39316396-39316459 | upst: CDKL4: −6205 (SEQ ID NO: 213) |
| GENE168X | chr6: 36752378-36752435 | upst: CDKN1A: −2237 (SEQ ID NO: 214) |
| GENE176X | chr11: 2867781-2867838 | upst: CDKN1C: −4093 (SEQ ID NO: 215) |
| GENE71X | chr12: 4244159-4244216 | upst: CCND2: −9042 (SEQ ID NO: 216) |
| GENE34X | chr13: 25727477-25727542 | int: CDK8: 566 (SEQ ID NO: 217) |
| GENE196X | chr9: 22000124-22000184 | upst: CDKN2B: −804 (SEQ ID NO: 218) |
| GENE73X | chr19: 34990318-34990374 | upst: CCNE1: −4445 (SEQ ID NO: 219) |
| GENE194X | chr9: 22073848-22073931 | upst: CDKN2B: −74328 (SEQ ID NO: 220) |
| GENE193X | chr9: 22052663-22052719 | upst: CDKN2B: −53107 (SEQ ID NO: 221) |
| GENE75X | chr19: 34985345-34985401 | upst: CCNE1: −9426 (SEQ ID NO: 222) |
| GENE200X | chr1: 51202987-51203052 | upst: CDKN2C: −3161 (SEQ ID NO: 223) |
| GENE88X | chr4: 78294528-78294586 | upst: CCNG2: −2953 (SEQ ID NO: 28) |
| GENE210X | chr10: 101077377-101077444 | upst: CNNM1: −2645 (SEQ ID NO: 224) |
| GENE167X | chr6: 36752597-36752655 | upst: CDKN1A: −1902 (SEQ ID NO: 225) |
| GENE204X | chr14: 53931488-53931551 | upst: CDKN3: −1974 (SEQ ID NO: 226) |
| GENE123X | chr16: 88276535-88276599 | upst: CDK10: −4173 (SEQ ID NO: 227) |
| GENE163X | chr9: 129578646-129578704 | upst: CDK9: −9782 (SEQ ID NO: 23) |
| GENE178X | chr11: 2869277-2869335 | upst: CDKN1C: −5693 (SEQ ID NO: 228) |
| GENE136X | chr7: 150395804-150395862 | upst: CDK5: −9871 (SEQ ID NO: 229) |
| GENE215X | chr2: 96785614-96785671 | upst: CNNM4: −4755 (SEQ ID NO: 230) |
| GENE190X | chr9: 22030432-22030490 | upst: CDKN2B: −31120 (SEQ ID NO: 231) |
| GENE126X | chr12: 54638785-54638842 | upst: CDK2: −8040 (SEQ ID NO: 232) |
| GENE195X | chr9: 22074531-22074588 | upst: CDKN2B: −75214 (SEQ ID NO: 233) |
| GENE199X | chr1: 51206030-51206086 | upst: CDKN2C: −127 (SEQ ID NO: 234) |
| GENE173X | chr11: 2864676-2864748 | upst: CDKN1C: −1017 (SEQ ID NO: 26) |
| GENE214X | chr2: 96786532-96786600 | upst: CNNM4: −3840 (SEQ ID NO: 235) |

TABLE 5

Codon Substitution Frequency (CSF) Analysis

| NAME | Chromosome | Start coordinate | End coordinate | CSF Score | blast result ($E < 10^{-10}$) length |
|---|---|---|---|---|---|
| int: CDKL5: 64 | chrX | 18353741 | 18353799 | −114.14 | 58 |
| int: CDKL5: 1682 | chrX | 18355359 | 18355420 | −59.56 | 61 |
| upst: CCNB3: −3258 | chrX | 50041017 | 50041078 | −157.52 | 61 |
| dst: CDKN2A: 45866 | chr9 | 21919172 | 21919330 | 31.86 | 158 |

TABLE 5-continued

Codon Substitution Frequency (CSF) Analysis

| NAME | Chromosome | Start coordinate | End coordinate | CSF Score | blast result (E < 10$^{-10}$) | length |
|---|---|---|---|---|---|---|
| dst: CDKN2A: 43877 | chr9 | 21921161 | 21921271 | 14.97 | | 110 |
| dst: CDKN2A: 39498 | chr9 | 21925540 | 21925952 | 7.43 | | 412 |
| dst: CDKN2A: 30203 | chr9 | 21934835 | 21934908 | 0.00 | | 73 |
| dst: CDKN2A: 8650 | chr9 | 21956388 | 21956526 | 26.75 | | 138 |
| int: CDKN2A: 6667 | chr9 | 21958371 | 21958427 | −114.20 | | 56 |
| int: CDKN2A: 5270 | chr9 | 21959768 | 21959968 | −21.62 | | 200 |
| int: CDKN2A: 4904 | chr9 | 21960134 | 21960195 | −109.94 | | 61 |
| int: CDKN2A: 4432 | chr9 | 21960606 | 21960676 | −164.93 | | 70 |
| upst: CDKN2A: −44 | chr9 | 21965167 | 21965225 | −56.05 | | 58 |
| int: ARF: 15754 | chr9 | 21968736 | 21968809 | −196.59 | | 73 |
| int: ARF: 4530 | chr9 | 21979960 | 21980193 | −91.25 | | 233 |
| upst: ARF: −840 | chr9 | 21985330 | 21985704 | −14.20 | | 374 |
| upst: ARF: −1395 | chr9 | 21985885 | 21986116 | −109.72 | gi\|297684298\|ref\|XP_002819782.1\| | 231 |
| upst: ARF: −2148 | chr9 | 21986638 | 21986856 | −70.76 | | 218 |
| int: CDKN2B: 1926 | chr9 | 21997386 | 21997668 | −123.40 | | 282 |
| upst: CDKN2B: −804 | chr9 | 22000116 | 22000207 | −66.49 | | 91 |
| upst: CDKN2B: −2817 | chr9 | 22002129 | 22002592 | 63.29 | gi\|13569612\|gb\|AAK31162.1\| | 463 |
| upst: CDKN2B: −15114 | chr9 | 22014426 | 22014665 | 16.92 | | 239 |
| upst: CDKN2B: −15913 | chr9 | 22015225 | 22015826 | 21.20 | gi\|119593028\|gb\|EAW72622.1\| | 601 |
| upst: CDKN2B: −23831 | chr9 | 22023143 | 22023559 | 16.22 | | 416 |
| upst: CDKN2B: −31120 | chr9 | 22030432 | 22030493 | −79.49 | | 61 |
| upst: CDKN2B: −35359 | chr9 | 22034671 | 22034736 | −106.50 | | 65 |
| upst: CDKN2B: −53107 | chr9 | 22052419 | 22052723 | −37.43 | | 304 |
| upst: CDKN2B: −74328 | chr9 | 22073640 | 22073939 | −124.53 | | 299 |
| upst: CDKN2B: −75214 | chr9 | 22074526 | 22074600 | −87.12 | | 74 |
| upst: CDKN2B: −87467 | chr9 | 22086779 | 22086924 | −172.53 | | 145 |
| upst: CDKN2B: −90566 | chr9 | 22089878 | 22089940 | −104.21 | | 62 |
| upst: CDKN2B: −108997 | chr9 | 22108309 | 22108379 | −152.16 | | 70 |
| upst: CDKN2B: −119804 | chr9 | 22119116 | 22119482 | −38.44 | | 366 |
| upst: CDKN2B: −130339 | chr9 | 22129651 | 22129797 | −64.03 | | 146 |
| upst: CDKN2B: −130736 | chr9 | 22130048 | 22130158 | −27.37 | | 110 |
| upst: CDK9: −9782 | chr9 | 129578369 | 129578764 | −98.67 | | 395 |
| upst: CDK9: −8667 | chr9 | 129579484 | 129579540 | −69.73 | | 56 |
| upst: CDK9: −8509 | chr9 | 129579642 | 129579703 | −38.69 | | 61 |
| upst: CDK9: −3159 | chr9 | 129584992 | 129585555 | −115.94 | | 563 |
| upst: CDK9: −1536 | chr9 | 129586615 | 129586808 | −158.16 | | 193 |
| upst: CDK9: −909 | chr9 | 129587242 | 129587312 | 1.76 | | 70 |
| upst: CDK9: −646 | chr9 | 129587505 | 129587574 | 50.97 | | 69 |
| int: CDK9: 352 | chr9 | 129588503 | 129588560 | −74.33 | | 57 |
| int: CDK9: 1811 | chr9 | 129589962 | 129590019 | −135.53 | | 57 |
| int: CCNE2: 647 | chr8 | 95976013 | 95976740 | 47.62 | | 727 |
| upst: CCNE2: −682 | chr8 | 95977342 | 95978227 | −68.39 | | 885 |
| upst: CCNE2: −2828 | chr8 | 95979488 | 95979576 | −72.47 | | 88 |
| upst: CCNE2: −4956 | chr8 | 95981616 | 95981697 | −142.19 | | 81 |
| upst: CCNE2: −5939 | chr8 | 95982599 | 95982807 | −37.33 | | 208 |
| upst: CCNE2: −8552 | chr8 | 95985212 | 95985417 | −77.69 | | 205 |
| int: CDK6: 1276 | chr7 | 92299872 | 92300181 | −93.60 | | 309 |
| int: CDK6: 143 | chr7 | 92300772 | 92301101 | 64.35 | | 329 |
| upst: CDK6: −533 | chr7 | 92301681 | 92302693 | −50.77 | | 1012 |
| upst: CDK6: −1679 | chr7 | 92302827 | 92302910 | 24.85 | | 83 |
| upst: CDK6: −1860 | chr7 | 92303008 | 92304502 | −4.10 | gi\|169171680\|ref\|XP_001717196.1\| | 1494 |
| upst: CDK6: −8726 | chr7 | 92309874 | 92309931 | −145.14 | | 57 |
| int: CDK5: 1993 | chr7 | 150383936 | 150384009 | −120.12 | | 73 |
| upst: CDK5: −2373 | chr7 | 150388302 | 150388358 | −24.52 | | 56 |
| upst: CDK5: −3754 | chr7 | 150389683 | 150389748 | −134.91 | | 65 |
| upst: CDK5: −7855 | chr7 | 150393784 | 150394611 | 164.48 | gi\|297289681\|ref\|XP_001103478.2\| | 827 |
| upst: CDK5: −9105 | chr7 | 150395034 | 150395090 | −156.60 | | 56 |
| upst: CDK5: −9871 | chr7 | 150395800 | 150395870 | −70.35 | | 70 |
| upst: CDKN1A: −9569 | chr6 | 36744895 | 36745227 | −102.36 | | 332 |
| upst: CDKN1A: −5830 | chr6 | 36748634 | 36748699 | 9.40 | | 65 |
| upst: CDKN1A: −4845 | chr6 | 36749619 | 36750963 | 9.93 | gi\|1127256\|pdb\|1LCP\|A | 1344 |
| upst: CDKN1A: −2237 | chr6 | 36752227 | 36752462 | −114.64 | | 235 |
| upst: CDKN1A: −1902 | chr6 | 36752562 | 36752655 | −74.54 | | 93 |
| upst: CDKN1A: −1210 | chr6 | 36753254 | 36753322 | −170.24 | | 68 |
| int: CDKN1A: 885 | chr6 | 36755349 | 36755717 | 12.28 | | 368 |
| int: CDKN1A: 1420 | chr6 | 36755884 | 36756416 | 16.96 | | 532 |
| int: CCND3: 2384 | chr6 | 42015146 | 42015714 | 10.65 | | 568 |
| upst: CCND3: −4248 | chr6 | 42021778 | 42021857 | −70.48 | | 79 |
| upst: CCND3: −6423 | chr6 | 42023953 | 42024036 | −29.89 | | 83 |

TABLE 5-continued

Codon Substitution Frequency (CSF) Analysis

| NAME | Chromosome | Start coordinate | End coordinate | CSF Score | blast result (E < $10^{-10}$) | length |
|---|---|---|---|---|---|---|
| upst: CCND3: −9303 | chr6 | 42026833 | 42026919 | −46.71 | | 86 |
| int: CCNC: 816 | chr6 | 100122595 | 100122744 | −54.98 | | 149 |
| upst: CCNC: −5405 | chr6 | 100128816 | 100129047 | 7.35 | | 231 |
| upst: CCNC: −6760 | chr6 | 100130171 | 100131105 | 26.17 | gi\|38047525\| gb\|AAR09665.1\| | 934 |
| int: CCNO: 1417 | chr5 | 54563848 | 54563906 | −96.83 | | 58 |
| upst: CDKL3: −867 | chr5 | 133731531 | 133731787 | −45.41 | | 256 |
| upst: CCNJL: −671 | chr5 | 159699848 | 159700083 | −108.32 | | 235 |
| upst: CCNJL: −2749 | chr5 | 159701926 | 159702174 | −103.49 | | 248 |
| upst: CCNJL: −7299 | chr5 | 159706476 | 159706661 | −78.26 | | 185 |
| upst: CCNG1: −9141 | chr5 | 162788013 | 162788190 | −58.38 | | 177 |
| upst: CCNG1: −4532 | chr5 | 162792622 | 162792683 | −85.26 | | 61 |
| int: CCNG1: 381 | chr5 | 162797535 | 162798278 | −44.97 | | 743 |
| int: CCNI: 1874 | chr4 | 78214275 | 78214700 | −107.12 | | 425 |
| int: CCNI: 1042 | chr4 | 78215107 | 78215164 | −87.28 | | 57 |
| upst: CCNI: −6398 | chr4 | 78222547 | 78222634 | 23.04 | | 87 |
| upst: CCNI: −6621 | chr4 | 78222770 | 78222967 | 22.93 | gi\|109081011\| ref\|XP_001112542.1\| | 197 |
| upst: CCNI: −6883 | chr4 | 78223032 | 78223226 | 10.14 | gi\|297674039\| ref\|XP_002815047.1\| | 194 |
| upst: CCNI: −7899 | chr4 | 78224048 | 78224113 | 2.21 | | 65 |
| upst: CCNG2: −2953 | chr4 | 78294448 | 78294589 | −108.22 | | 141 |
| int: CCNG2: 390 | chr4 | 78297791 | 78298343 | −84.39 | | 552 |
| upst: CCNA2: −250 | chr4 | 122964592 | 122964728 | −42.04 | | 136 |
| int: CCNL1: 1097 | chr3 | 158360079 | 158360144 | −4.72 | | 65 |
| upst: CCNL1: −1968 | chr3 | 158363144 | 158363249 | 13.84 | | 105 |
| upst: CCNL1: −2234 | chr3 | 158363410 | 158363460 | 25.17 | | 50 |
| upst: CCNL1: −2383 | chr3 | 158363559 | 158363729 | 45.32 | gi\|34035\| emb\|CAA31369.1\| | 170 |
| upst: CCNL1: −2767 | chr3 | 158363943 | 158364477 | 63.96 | gi\|109076165\| ref\|XP_001084233.1\| | 534 |
| upst: CCNL1: −3430 | chr3 | 158364606 | 158364668 | −49.03 | | 62 |
| upst: CDKL4: −6205 | chr2 | 39316382 | 39316464 | −3.06 | | 82 |
| upst: CNNM4: −4755 | chr2 | 96785610 | 96785680 | −118.19 | | 70 |
| upst: CNNM4: −3840 | chr2 | 96786525 | 96786610 | −99.47 | | 85 |
| upst: CNNM4: −1843 | chr2 | 96788522 | 96788595 | −96.56 | | 73 |
| int: CNNM4: 1658 | chr2 | 96792023 | 96792456 | −142.58 | | 433 |
| upst: CNNM3: −9238 | chr2 | 96836476 | 96836537 | −28.88 | | 61 |
| upst: CNNM3: −970 | chr2 | 96844744 | 96845262 | −21.66 | gi\|297266562\| ref\|XP_001098957.2\| | 518 |
| upst: CNNM3: −248 | chr2 | 96845466 | 96846205 | 161.10 | gi\|40068047\| ref\|NP_951060.1\| | 739 |
| int: CNNM3: 1459 | chr2 | 96847173 | 96847265 | −94.67 | | 92 |
| upst: CCNT2: −6751 | chr2 | 135386111 | 135386176 | 3.59 | | 65 |
| upst: CCNT2: −319 | chr2 | 135392543 | 135392600 | −12.28 | | 57 |
| int: CCNT2: 640 | chr2 | 135393502 | 135393737 | −107.73 | | 235 |
| upst: CCNYL1: −3709 | chr2 | 208280800 | 208280910 | −111.99 | | 110 |
| upst: CDK5R2: −9197 | chr2 | 219523423 | 219523595 | −99.34 | | 172 |
| upst: CDK5R2: −8037 | chr2 | 219524583 | 219524900 | −187.33 | | 317 |
| upst: CDK5R2: −7376 | chr2 | 219525244 | 219525340 | −142.50 | | 96 |
| upst: CDK5R2: −6418 | chr2 | 219526202 | 219526431 | 40.49 | gi\|114688805\| ref\|XP_001152656.1\| | 229 |
| upst: CDK5R2: −6045 | chr2 | 219526575 | 219526998 | 88.39 | gi\|119591067\| gb\|EAW70661.1\| | 423 |
| upst: CDK5R2: −4915 | chr2 | 219527705 | 219527770 | −66.12 | | 65 |
| upst: CDK5R2: −4541 | chr2 | 219528079 | 219529078 | −19.83 | | 999 |
| upst: CDK5R2: −648 | chr2 | 219531972 | 219532912 | 160.37 | gi\|74005747\| ref\|XP_853120.1\| | 940 |
| int: CDKN2D: 1417 | chr19 | 10539238 | 10539446 | −94.96 | | 208 |
| upst: CCNE1: −9426 | chr19 | 34985314 | 34985518 | −27.88 | | 204 |
| upst: CCNE1: −5422 | chr19 | 34989318 | 34989418 | −142.01 | | 100 |
| upst: CCNE1: −4445 | chr19 | 34990295 | 34990379 | −42.05 | | 84 |
| upst: CCNE1: −1190 | chr19 | 34993550 | 34993681 | −33.48 | | 131 |
| upst: CDK5R1: −5717 | chr17 | 27832500 | 27833788 | −10.04 | | 1288 |
| upst: CDK5R1: −4410 | chr17 | 27833807 | 27834032 | −95.59 | | 225 |
| upst: CDK5R1: −4044 | chr17 | 27834173 | 27834421 | −40.59 | | 248 |
| upst: CDK5R1: −3023 | chr17 | 27835194 | 27835275 | −125.58 | | 81 |
| upst: CDK5R1: −482 | chr17 | 27837735 | 27837831 | 45.53 | | 96 |
| upst: CDK5R1: −206 | chr17 | 27838011 | 27838200 | 86.71 | | 189 |
| int: CDK5R1: 183 | chr17 | 27838400 | 27838457 | 40.97 | | 57 |
| upst: CDK3: −4497 | chr17 | 71504516 | 71504720 | −79.37 | | 204 |
| upst: CDK3: −4148 | chr17 | 71504865 | 71505136 | −87.60 | | 271 |
| upst: CCNF: −3964 | chr16 | 2415476 | 2415532 | −138.24 | | 56 |
| upst: CCNF: −3743 | chr16 | 2415697 | 2415850 | −103.12 | | 153 |
| upst: CCNF: −2075 | chr16 | 2417365 | 2417602 | −104.17 | | 237 |

TABLE 5-continued

Codon Substitution Frequency (CSF) Analysis

| NAME | Chromosome | Start coordinate | End coordinate | CSF Score | blast result (E < $10^{-10}$) | length |
|---|---|---|---|---|---|---|
| upst: CCNF: −1721 | chr16 | 2417719 | 2418099 | −66.81 | | 380 |
| upst: CCNF: −1085 | chr16 | 2418355 | 2418536 | −116.52 | | 181 |
| upst: CCNYL3: −8181 | chr16 | 34107179 | 34107406 | −27.05 | | 227 |
| upst: CCNYL3: −1019 | chr16 | 34114341 | 34114410 | 29.13 | | 69 |
| upst: CCNYL3: −293 | chr16 | 34115067 | 34115160 | 29.25 | | 93 |
| upst: CDK10: −4173 | chr16 | 88276405 | 88276870 | 26.25 | gi|119587116| gb|EAW66712.1| | 465 |
| upst: CDK10: −1805 | chr16 | 88278773 | 88278929 | 20.45 | | 156 |
| int: CCNB2: 547 | chr15 | 57185158 | 57185327 | −99.21 | | 169 |
| upst: CDKN3: −5723 | chr14 | 53927739 | 53927822 | −31.89 | | 83 |
| upst: CDKN3: −5438 | chr14 | 53928024 | 53928439 | −33.70 | | 415 |
| upst: CDKN3: −4479 | chr14 | 53928983 | 53929052 | 8.19 | | 69 |
| upst: CDKN3: −2291 | chr14 | 53931171 | 53931235 | 37.52 | | 64 |
| upst: CDKN3: −1974 | chr14 | 53931488 | 53931574 | −63.44 | | 86 |
| upst: CDKN3: −271 | chr14 | 53933191 | 53933452 | −53.81 | | 261 |
| upst: CCNK: −8357 | chr14 | 99009134 | 99009421 | −109.96 | | 287 |
| upst: CCNK: −4426 | chr14 | 99013065 | 99013134 | −138.67 | | 69 |
| upst: CCNK: −3241 | chr14 | 99014250 | 99014509 | −98.38 | | 259 |
| upst: CCNK: −899 | chr14 | 99016592 | 99016918 | 13.36 | | 326 |
| int: CCNK: 210 | chr14 | 99017701 | 99018238 | −0.57 | | 537 |
| upst: CDK8: −9630 | chr13 | 25717125 | 25717190 | 0.00 | | 65 |
| upst: CDK8: −8337 | chr13 | 25718418 | 25718483 | −122.01 | | 65 |
| upst: CDK8: −798 | chr13 | 25725957 | 25726089 | −2.39 | | 132 |
| upst: CDK8: −265 | chr13 | 25726490 | 25726547 | 29.46 | | 57 |
| int: CDK8: 566 | chr13 | 25727321 | 25727803 | −61.92 | | 482 |
| upst: CCNA1: −1163 | chr13 | 35903469 | 35904076 | 10.22 | | 607 |
| upst: CCND2: −9042 | chr12 | 4244156 | 4244216 | −60.32 | | 60 |
| upst: CCND2: −6904 | chr12 | 4246294 | 4246385 | −163.60 | | 91 |
| upst: CCND2: −4886 | chr12 | 4248312 | 4248374 | −81.37 | | 62 |
| upst: CCND2: −4757 | chr12 | 4248441 | 4249910 | 30.54 | | 1469 |
| upst: CCND2: −3165 | chr12 | 4250033 | 4250139 | −118.08 | | 106 |
| upst: CCND2: −2874 | chr12 | 4250324 | 4251151 | −5.17 | | 827 |
| upst: CCND2: −1830 | chr12 | 4251268 | 4251445 | 3.56 | | 177 |
| upst: CCND2: −1291 | chr12 | 4251907 | 4251963 | −73.06 | | 56 |
| int: CCND2: 1205 | chr12 | 4254403 | 4254460 | −16.55 | | 57 |
| int: CCND2: 1689 | chr12 | 4254887 | 4254947 | −12.75 | | 60 |
| upst: CDKN1B: −1362 | chr12 | 12760213 | 12760283 | −162.03 | | 70 |
| int: CCNT1: 602 | chr12 | 47396446 | 47396533 | −116.72 | | 87 |
| upst: CDK2: −8040 | chr12 | 54638785 | 54638842 | −98.60 | | 57 |
| upst: CDK2: −5210 | chr12 | 54641615 | 54641672 | −164.71 | | 57 |
| upst: CDK2: −1390 | chr12 | 54645435 | 54645491 | −65.27 | | 56 |
| upst: CDK4: −977 | chr12 | 56433408 | 56433465 | −45.37 | | 57 |
| upst: CDK4: −1632 | chr12 | 56434063 | 56434131 | −103.47 | | 68 |
| upst: CDK4: −2133 | chr12 | 56434564 | 56435185 | 127.35 | | 621 |
| upst: CDK4: −4462 | chr12 | 56436893 | 56436962 | −109.43 | | 69 |
| upst: CDK4: −7794 | chr12 | 56440225 | 56440345 | −116.15 | | 120 |
| upst: CDKN1C: −5 | chr11 | 2863582 | 2864004 | 88.97 | | 422 |
| upst: CDKN1C: −446 | chr11 | 2864023 | 2864511 | −41.83 | | 488 |
| upst: CDKN1C: −1017 | chr11 | 2864594 | 2864748 | −126.83 | | 154 |
| upst: CDKN1C: −2196 | chr11 | 2865773 | 2866560 | −62.22 | gi|119622932| gb|EAX02527.1| | 787 |
| upst: CDKN1C: −4093 | chr11 | 2867670 | 2867845 | −20.97 | | 175 |
| upst: CDKN1C: −4619 | chr11 | 2868196 | 2868608 | −34.51 | | 412 |
| upst: CDKN1C: −5693 | chr11 | 2869270 | 2869499 | −30.57 | | 229 |
| upst: CDKN1C: −6280 | chr11 | 2869857 | 2870421 | −8.76 | | 564 |
| upst: CDKN1C: −7144 | chr11 | 2870721 | 2870849 | −2.69 | | 128 |
| upst: CCND1: −8918 | chr11 | 69156135 | 69156265 | 6.45 | | 130 |
| upst: CCND1: −7190 | chr11 | 69157863 | 69158125 | −78.41 | | 262 |
| upst: CCND1: −2768 | chr11 | 69162285 | 69162341 | −11.64 | | 56 |
| upst: CCND1: −2574 | chr11 | 69162479 | 69162560 | −50.92 | | 81 |
| upst: CCND1: −1659 | chr11 | 69163394 | 69163640 | −18.16 | | 246 |
| upst: CCND1: −377 | chr11 | 69164676 | 69165039 | −21.36 | | 363 |
| int: CCND1: 874 | chr11 | 69165927 | 69165983 | −27.89 | | 56 |
| upst: CCNYL2: −36 | chr10 | 42270204 | 42270371 | −42.89 | | 167 |
| upst: CNNM1: −2645 | chr10 | 101077377 | 101077475 | −111.90 | | 98 |
| int: CCNL2: 463 | chr1 | 1324108 | 1324220 | −16.91 | | 112 |
| upst: CCNL2: −767 | chr1 | 1325338 | 1325394 | −48.64 | | 56 |
| upst: CCNL2: −982 | chr1 | 1325553 | 1325755 | −11.06 | | 202 |
| upst: CCNL2: −1391 | chr1 | 1325962 | 1326156 | −97.29 | | 194 |
| upst: CCNL2: −2253 | chr1 | 1326824 | 1326881 | 14.19 | | 57 |
| upst: CCNL2: −3110 | chr1 | 1327681 | 1327845 | −69.05 | | 164 |
| upst: CCNL2: −5540 | chr1 | 1330111 | 1330167 | −68.46 | | 56 |
| upst: CCNL2: −7336 | chr1 | 1331907 | 1332072 | 60.70 | gi|114575193| ref|XP_001156960.1| | 165 |
| upst: CDKN2C: −8538 | chr1 | 51197610 | 51197664 | −74.07 | | 54 |

TABLE 5-continued

Codon Substitution Frequency (CSF) Analysis

| NAME | Chromosome | Start coordinate | End coordinate | CSF Score | blast result (E < $10^{-10}$) | length |
|---|---|---|---|---|---|---|
| upst: CDKN2C: −8037 | chr1 | 51198111 | 51198165 | −16.04 | | 54 |
| upst: CDKN2C: −7397 | chr1 | 51198751 | 51199005 | −124.53 | | 254 |
| upst: CDKN2C: −3161 | chr1 | 51202987 | 51203052 | −34.49 | | 65 |
| upst: CDKN2C: −127 | chr1 | 51206021 | 51206095 | −156.53 | | 74 |
| int: CDKN2C: 159 | chr1 | 51206307 | 51206575 | −55.03 | gi\|239741164\|ref\|XP_002342150.1\| | 268 |
| int: CDKN2C: 643 | chr1 | 51206791 | 51206847 | −75.40 | | 56 |

Figure 3A:
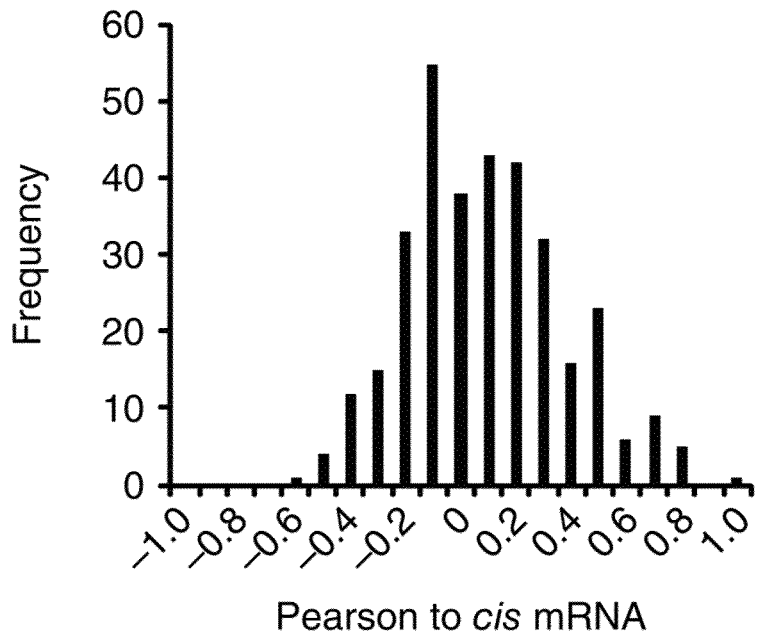
FIGS. 3A-3C show functional associations of the ncRNAs.
Figure 3B:
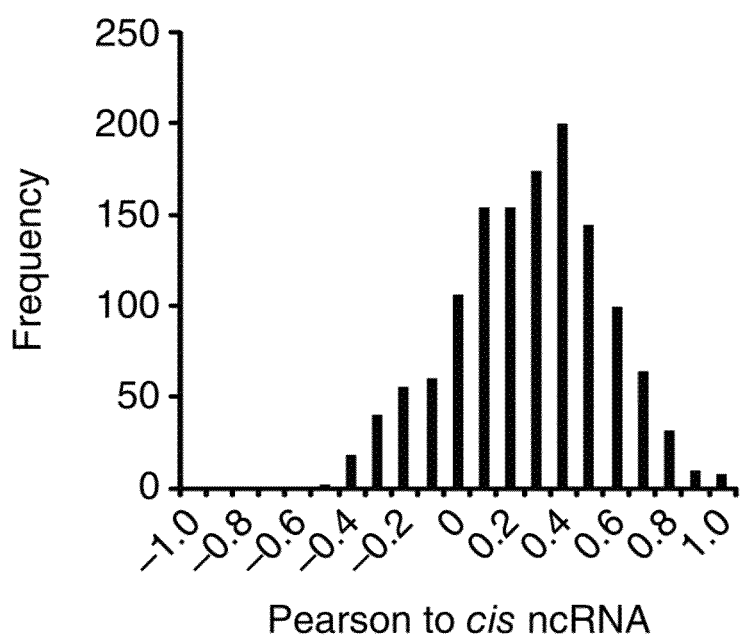
Figure 10:
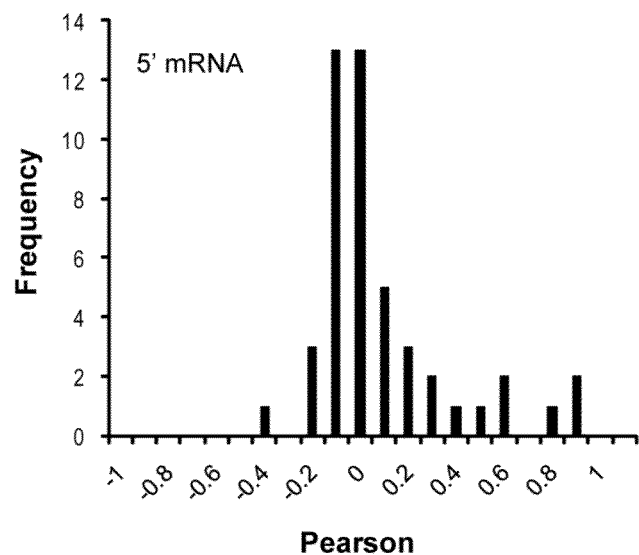
FIG. 10 shows that RT-PCR validated the expression correlation between 60 lncRNAs and their nearest 3' and 5' mRNAs across 34 RNA samples.
Figure 10:
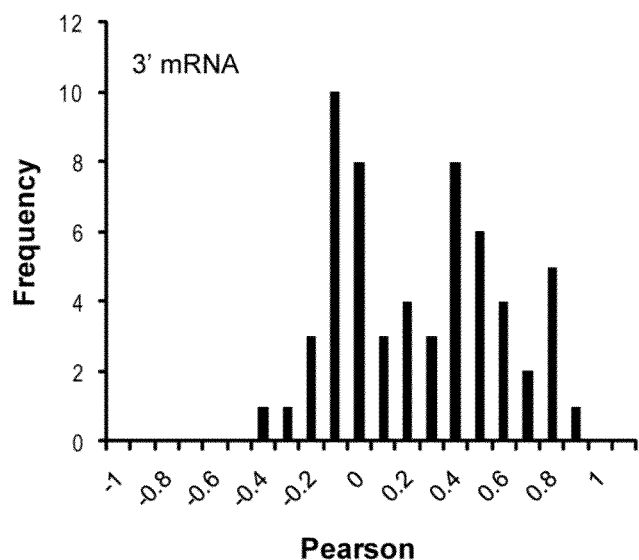

A Gene Co-Expression Map Infers Trans Regulatory Mechanisms and Biological Functions Multiple lncRNAs, including p15AS and the lncRNA upstream of CCND1, have been shown to regulate the transcription of the nearby coding gene. To determine whether gene-proximal lncRNAs are typically correlated with the expression of the nearest mRNA, we conducted whole-genome expression arrays on 17 samples that were also examined on our tiling array and calculated pairwise Pearson correlations between the expression patterns of each cell-cycle promoter lncRNA versus every mRNA genome wide. Notably, there was no significant correlation or anti-correlation between most of the 216 lncRNAs and the nearby protein-coding mRNA, suggesting that most of the lncRNAs may not function in cis to activate or repress nearby mRNA expression (FIG. 3A). Quantitative RT-PCR (qRT-PCR) analysis of lncRNAs and neighboring 5' and 3' mRNAs in 34 additional samples confirmed these findings (FIG. 10). In contrast, we found that the median correlation between two ncRNAs of the same locus was positive, supporting our hypothesis that neighboring ncRNAs may be coordinately regulated, positively regulate each other and/or are exons of the same transcript (FIG. 3B).

Figure 11:
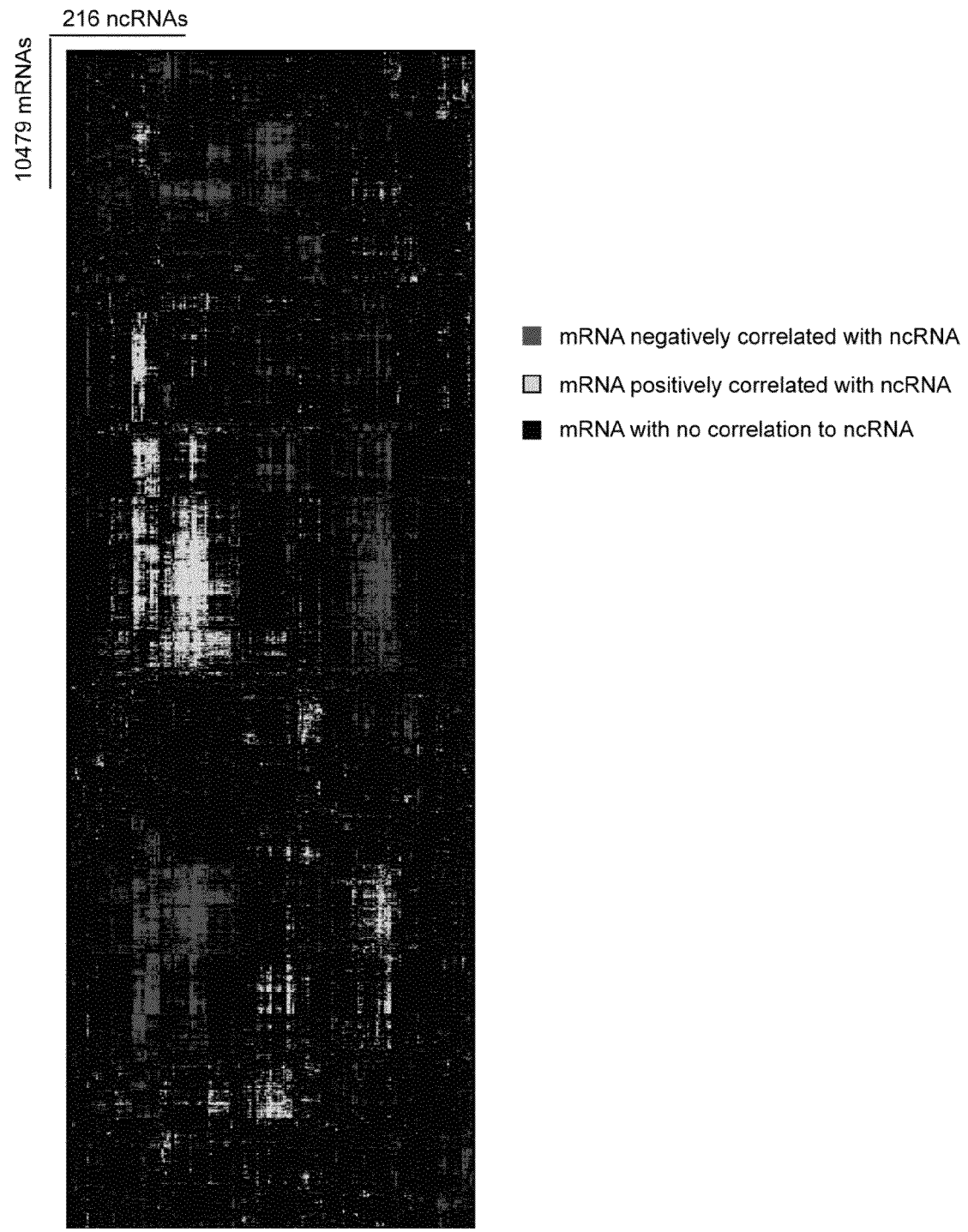
FIG. 11 shows gene sets of mRNAs positively or negatively correlated with each lncRNA as determined by pairwise Pearson correlation across 17 tiling and expression arrays.

Given that expression of the 216 ncRNAs does not generally correlate with the mRNA in cis, we further explored the genes and pathways that they may regulate using a guilt-by-association approach (Guttman et al. (2009) Nature 458:223-227, herein incorporated by reference). For each lncRNA, we defined a co-expression gene set as the group of mRNAs that are positively or negatively correlated with that lncRNA across the 17 samples (R>0.5 or R<0.5, respectively) (FIG. 11). We then constructed a gene module map of the association of each lncRNA co-expression gene set versus the Gene Ontology Biological Processes gene set and performed biclustering to identify lncRNAs that are associated with distinct Gene Ontology terms (FIG. 3C) (Segal et al. (2004) Nat. Genet. 36:1090-1098, herein incorporated by reference in its entirety). This analysis revealed multiple sets of lncRNAs that are associated with biological processes including cell cycle, DNA recombination, ribonucleoprotein complex biogenesis and assembly, RNA splicing, and response to DNA damage. Thus, despite having limited correlation in expression to their neighboring protein-coding gene, the expression patterns of these lncRNAs are still strongly related to the cell cycle. We constructed a similar module map with curated gene sets of metabolic and signaling pathways as well as biological and clinical states from the Molecular Signatures Database (MSigDB c2 collection) (Subramanian et al. (2005) Proc. Natl. Acad. Sci. USA 102, 15545-15550). This module map confirmed the enrichment for cell-cycle-related sets (for example, Cell Cycle Brentani or Cell Cycle KEGG). In addition, enriched modules included several poor prognosis breast cancer gene sets (BRCA estrogen receptor negative, BRCA prognosis negative and BRCA1 overexpressed up), DNA-damage-related gene sets (UVA/UVB), several oncogenic signatures.

Figure 4A:
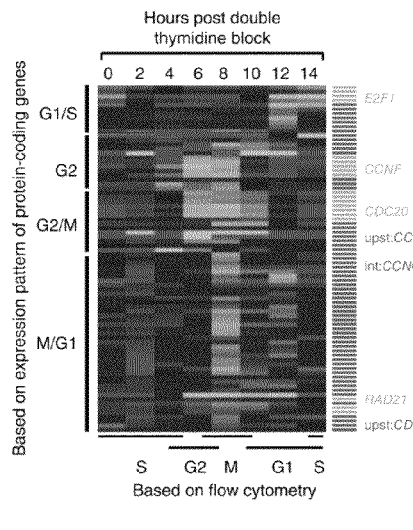
FIGS. 4A-4D show validated expression of ncRNAs in cell cycle progression, ESC differentiation and human cancers. We generated custom TaqMan probes and used them to interrogate independent biological samples for lncRNA expression.
Figure 4B:
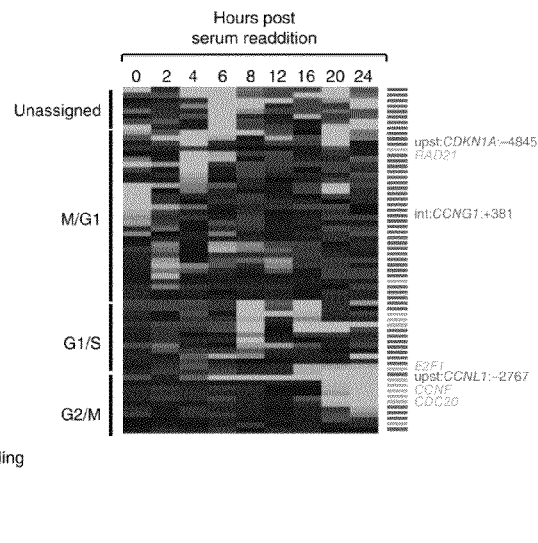
Figure 4C:
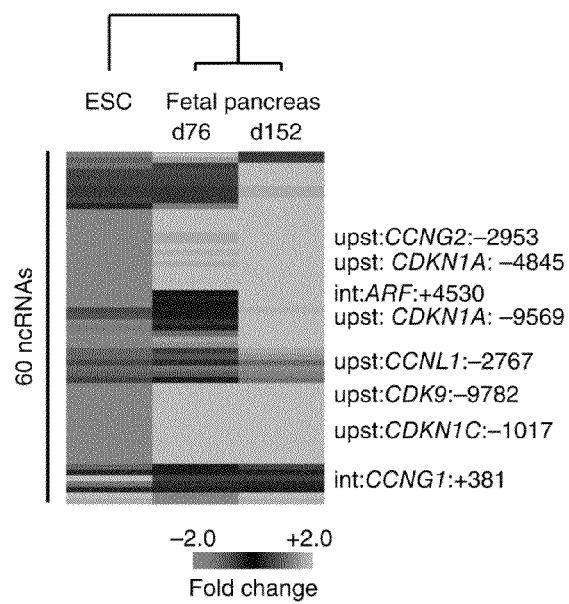
Figure 4D:
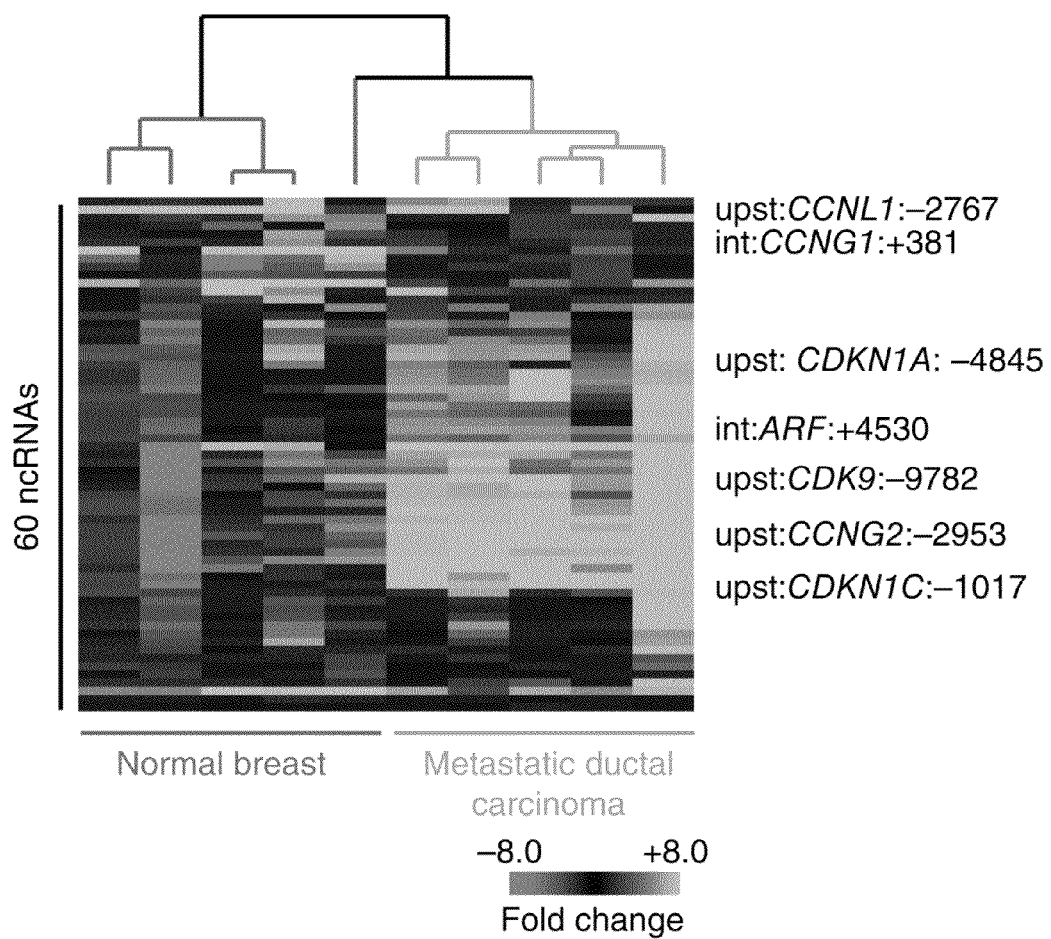

Validation of ncRNA Expression in Cell Cycle, ESC Differentiation, Cancer and DNA Damage Response To validate these inferred functional associations, we designed qRT-PCR assays for 60 of the 216 new transcribed regions (53 upstream and 7 intronic) to obtain a more quantitative measure of these lncRNAs across different conditions. Expression in HeLa cells synchronized in cell cycle progression by double thymidine block showed that most of the lncRNA have periodic expression peaking at different phases of the cell cycle (FIG. 4A) (Whitfield et al. (2002) Mol. Biol. Cell 13:1977-2000). Parallel analysis in primary human fibroblasts synchronized by serum stimulation confirmed the peak cell cycle phase of 74% of the lncRNAs with periodic expression pattern during the cell cycle (FIG. 4B). Next, comparison of human ESCs and fetal pancreas at days 76 and 152 showed that a majority of these lncRNAs are regulated during differentiation (FIG. 4C). In addition, unsupervised clustering of lncRNA expression patterns in five metastatic breast cancers and five normal mammary tissues readily distinguished the five metastatic breast cancers from the normal mammary tissues (FIG. 4D). Some of the lncRNAs, including upst:CCNL1:−2,767 and int:CDKN1A:+885 (Table 3), are repressed in the metastatic breast cancers relative to normal mammary tissues, whereas others, including upst:CDKN1A:−4,845, upst:CDKN2B:−2,817 and int:ARF:+4,517, are induced. Thus, the majority of these lncRNAs has periodic expression in the cell cycle and is differentially expressed in different states of cell differentiation and cancer progression.

Figure 3C:
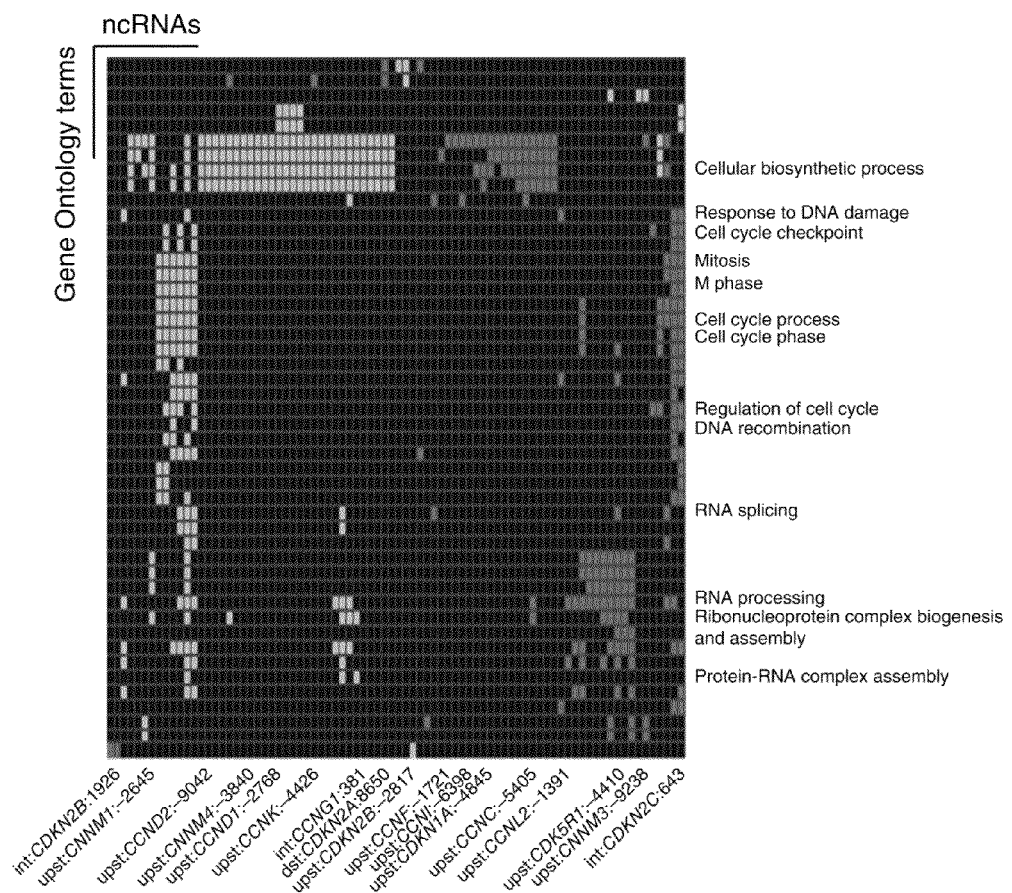
Figure 5A:
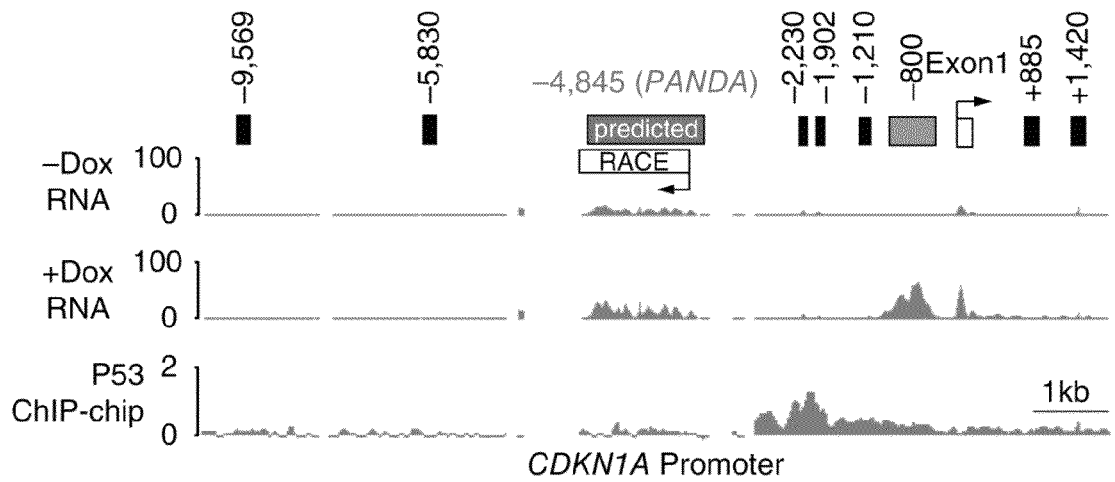
Figure 5B:
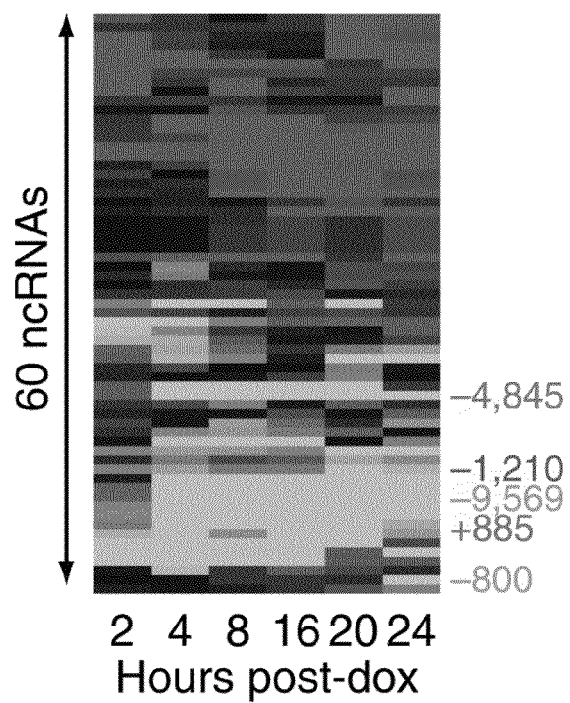

Our co-expression maps predicted associations of several lncRNAs with DNA damage response pathways (FIG. 3C and FIG. 11). In support of this finding, doxorubicin-treated human fetal lung fibroblasts showed at least two-fold change in 12 of the 216 ncRNAs on the tiling array and by qRT-PCR (FIG. 2). Notably, 2 of those 12 ncRNAs were located 5' of the TSS of the canonical p53 target gene CDKN1A (upst:CDKN1A:−1,210 and upst:CDKN1A:−4,845), and, similar to the CDKN1A mRNA, were induced by doxorubicin (FIG. 5A). In addition, a third lncRNA at the CDKN1A locus, upst:CDKN1A:−800, was also induced by doxorubicin but was not included in the 216 lncRNAs because it was only expressed in one of the 108 samples, the doxorubicin-treated fibroblasts. In order to confirm whether these lncRNAs may be responsive to DNA damage, we measured the expression changes of 60 lncRNAs predicted in the DNA damage pathway (as well as upst:CDKN1A:−800) by quantitative RT-PCR in human fetal lung fibroblasts treated with doxorubicin over a 24 hour time course. Most of the lncRNAs were either markedly induced or repressed by doxorubicin, and all five of the tested lncRNAs surrounding the CDKN1A TSS were induced, including the three that were previously detected on the tiling array (FIG. 5B). Notably, several lncRNAs upstream of CDKN1A are induced more rapidly and with substantially higher magnitude than CDKN1A upon DNA damage. Upst:CDKN1A:−4,845 is induced up to 40-fold upon DNA damage (FIG. 5C). These variations in expression patterns within the same locus suggest that the lncRNAs in the CDKN1A locus may play distinct roles in the DNA damage response from the CDKN1A protein, p21.

PANDA: a Long ncRNA Involved in the DNA-Damage Response

Figure 13:
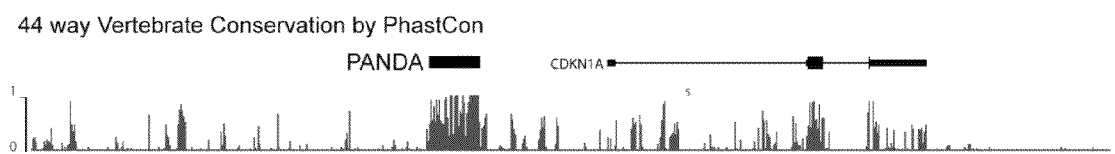
FIG. 13 shows that PANDA is evolutionarily conserved across vertebrates as determined by 44 way Vertebrate Conservation PhastCon score.
Figure 14A:
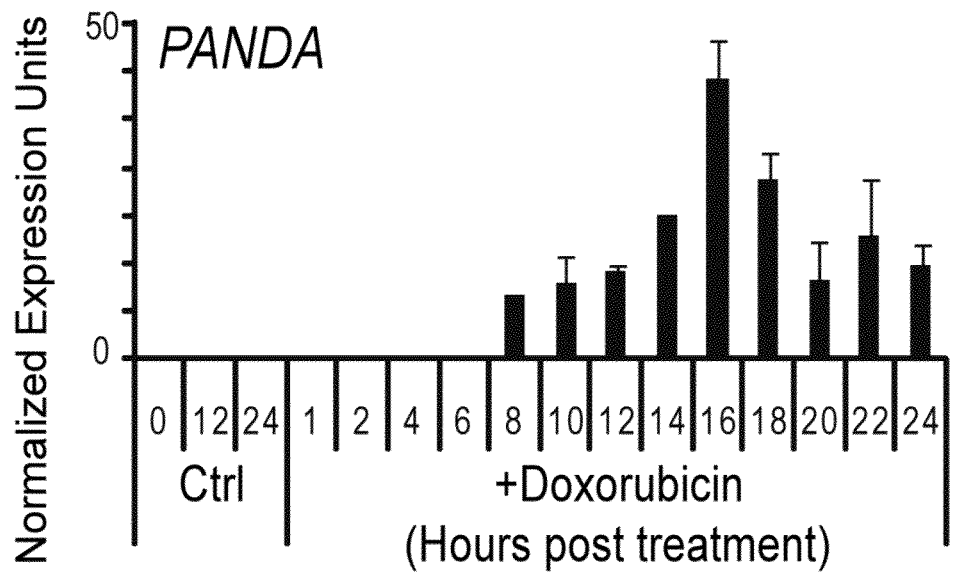
FIGS. 14A and 14B show 24 hour DNA damage time courses of PANDA (FIG. 14A) and LAP3 (FIG. 14B) expression. Human fetal lung fibroblasts (FL3) cells were treated with doxorubicin and collected at the indicated time points for RT-PCR analysis.
Figure 14B:
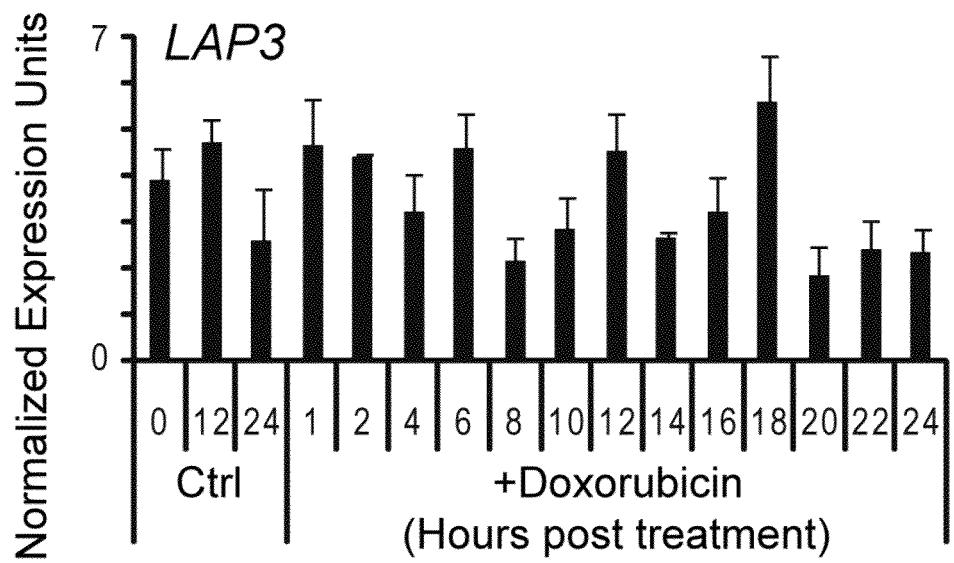

To investigate the functional relevance of these lncRNAs at the CDKN1A locus, we selected upst:CDKN1A:−4,845 (SEQ ID NO:1), hereafter termed PANDA (P21 associated ncRNA DNA damage activated), for further analysis. PANDA is located approximately 5 kb upstream of the CDKN1A TSS, coincides with a cluster of previously annotated expressed sequence tags and is evolutionarily conserved (FIG. 13). Although the PANDA locus intersects a computationally predicted pseudogene of LAP3, qRT-PCR showed that PANDA was specifically induced by DNA damage, whereas LAP3 expression did not significantly change, confirming that the change in expression detected by the tiling array was not caused by cross hybridization with LAP3 (FIG. 14). Furthermore, the CSF score of PANDA, 9.3, indicated very low protein-coding potential compared to LAP3 (with a CSF range of 117-1,343 for its 13 exons). Rapid amplification of the 5' and 3' complementary DNA ends (RACE, SEQ ID NO:2 and SEQ ID NO:3) and RNA blot analysis revealed a 1.5-kb transcript that is divergently transcribed from CDKN1A, antisense of the predicted LAP3 pseudogene (FIG. 5D). Thus, PANDA is a 5'-capped and polyadenylated non-spliced lncRNA that is transcribed antisense to CDKN1A.

Figure 15:
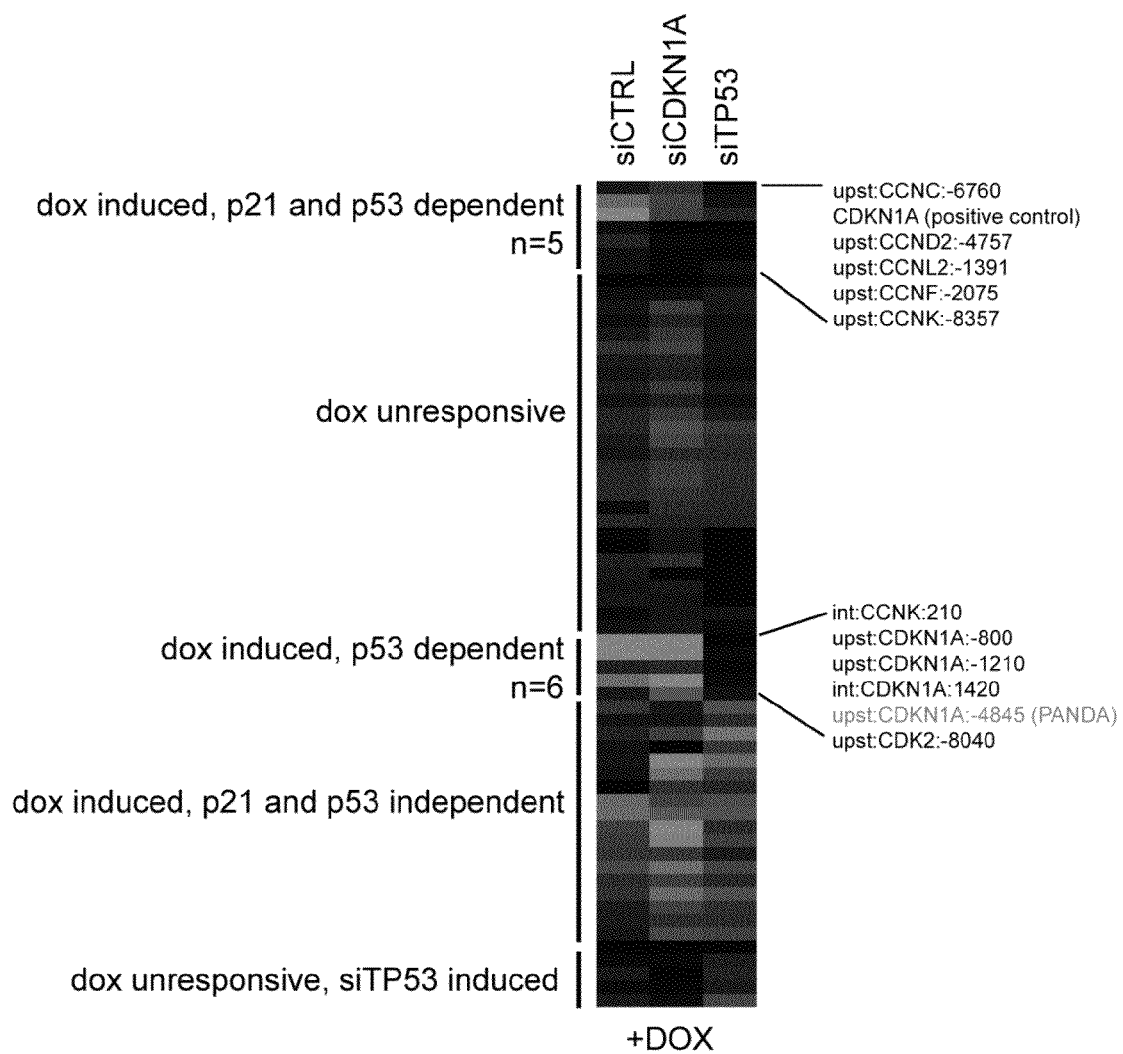
FIG. 15 shows p53-dependent DNA damage induction in a subset of lncRNAs. A heatmap is shown of lncRNA expression (as measured by RT-PCR) of human fetal lung fibroblasts (FL3) treated with doxorubicin in the presence of siCTRL, siCDKN1A, or siTP53. Light gray indicates induction relative to undamaged cells. Dark gray indicates repression.
Figure 16A:
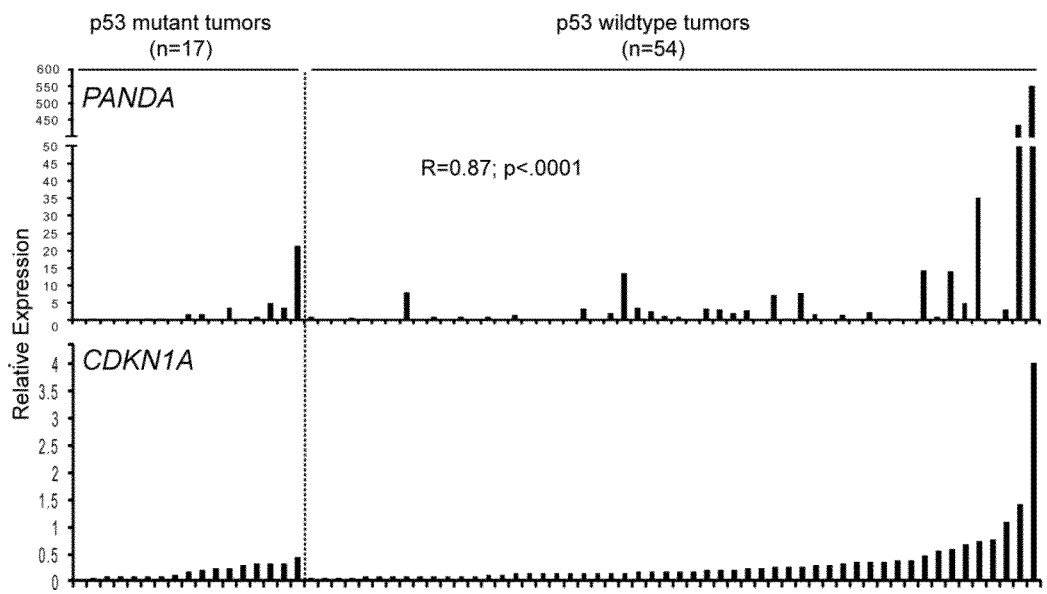
FIGS. 16A and 16B show PANDA expression levels in tumors.
Figure 16B:
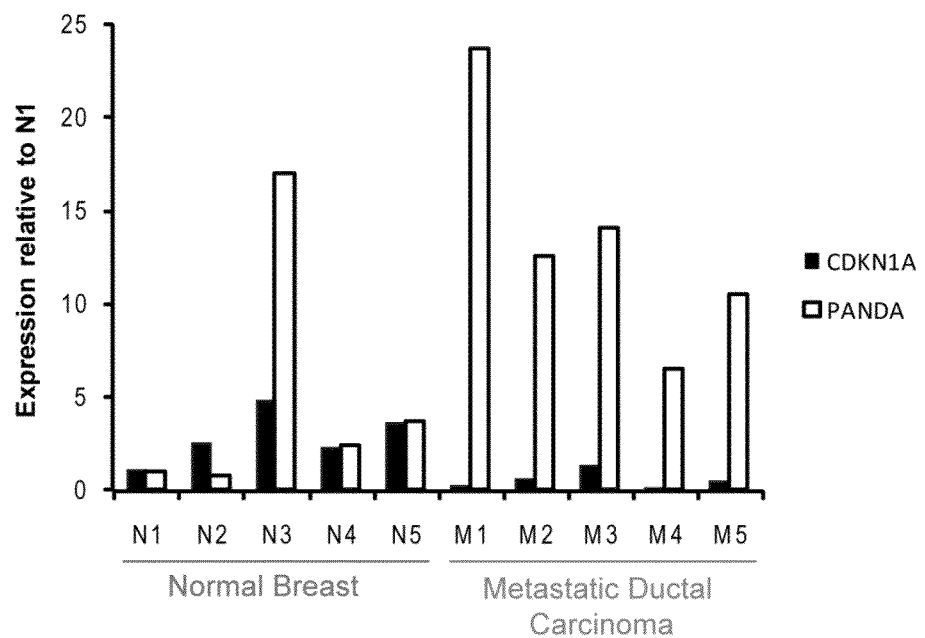

Because p53 is a positive regulator of CDKN1A during the DNA damage response, we asked whether p53 also regulates PANDA expression. ChIP-chip analysis confirmed the p53 binding site immediately upstream of the CDKN1A TSS (FIG. 5A) (Wei et al. (2006) Cell 124:207-219). PANDA and CDKN1A are diametrically situated 2.5 kb from this intervening p53 binding site, which supports the possibility of p53 co-regulation. Indeed, siRNA-mediated knockdown of p53 before DNA damage inhibited the induction of PANDA by 70% 24 hours after DNA damage (FIG. 5E and FIG. 15), which is similar to its effect on CDKN1A. In contrast, RNA interference of CDKN1A had no effect on PANDA expression, indicating that PANDA is not a linked transcript of CDKN1A nor is PANDA expression dependent on p21. PANDA level shows a trend of lower expression in human primary breast tumors harboring an inactivating mutation in TP53 as determined by exon 2-11 DNA sequencing (FIG. 16A) (Geisler et al. (2001) Cancer Res. 61, 2505-2512). Further, complementation of p53-null H1299 lung carcinoma cells by wild-type p53—but not the loss-of-function p53 (p.Val272Cys) mutant—restored DNA damage-inducible expression of PANDA (FIG. 5F). Notably, a gain-of-function p53 (p.Arg273His) mutant, observed in Li-Fraumeni syndrome (Olive et al. (2004) Cell 119, 847-860), abrogated the ability to induce CDKN1A but selectively preserved the ability to induce PANDA (FIG. 5F). We also observed selective induction of PANDA without concordant CDKN1A expression in metastatic ductal carcinomas but not in normal breast tissue (FIG. 16B).

Figure 6A:
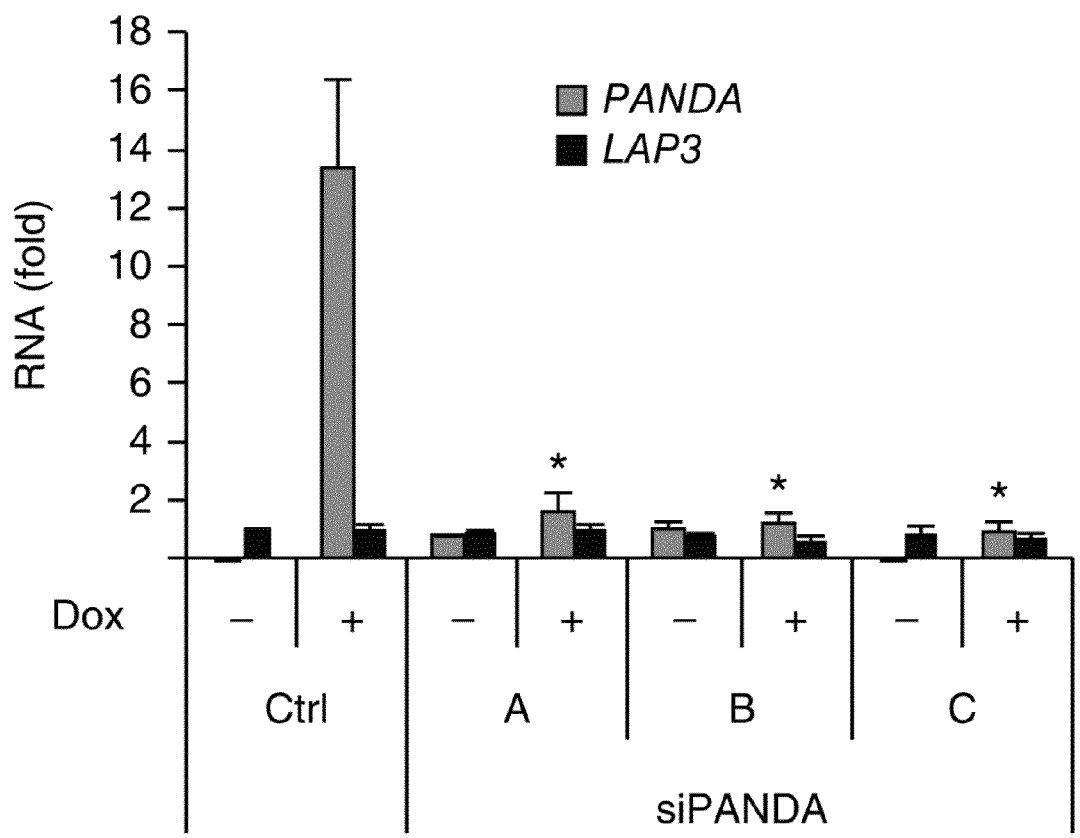
FIGS. 6A-6G show that the PANDA lncRNA regulates the apoptotic response to DNA damage.
Figure 6B:
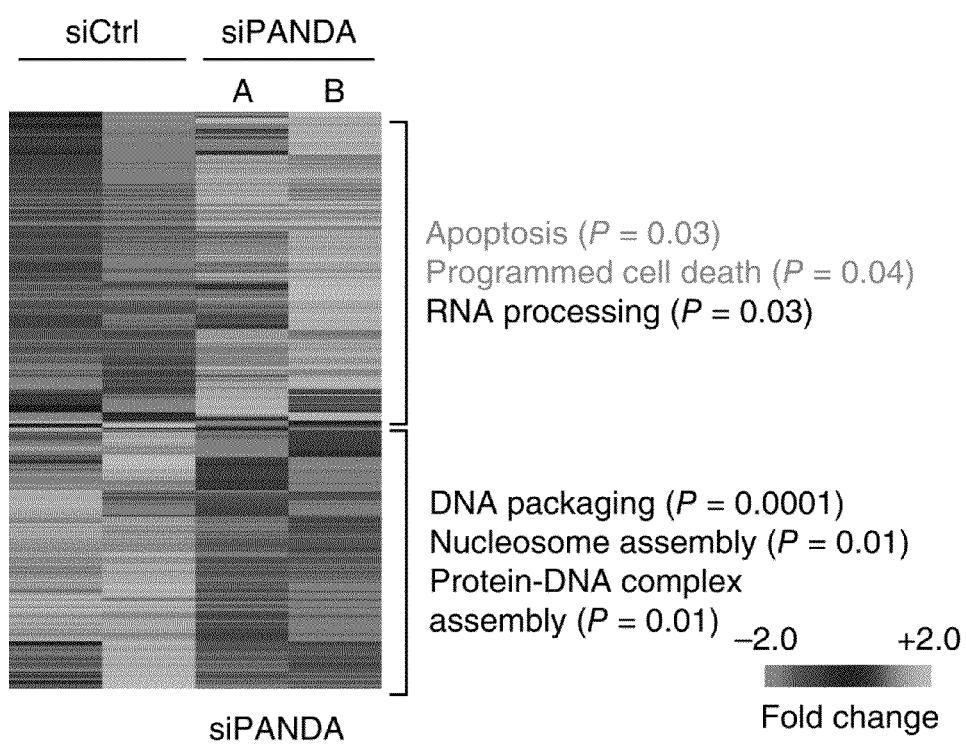
Figure 6C:
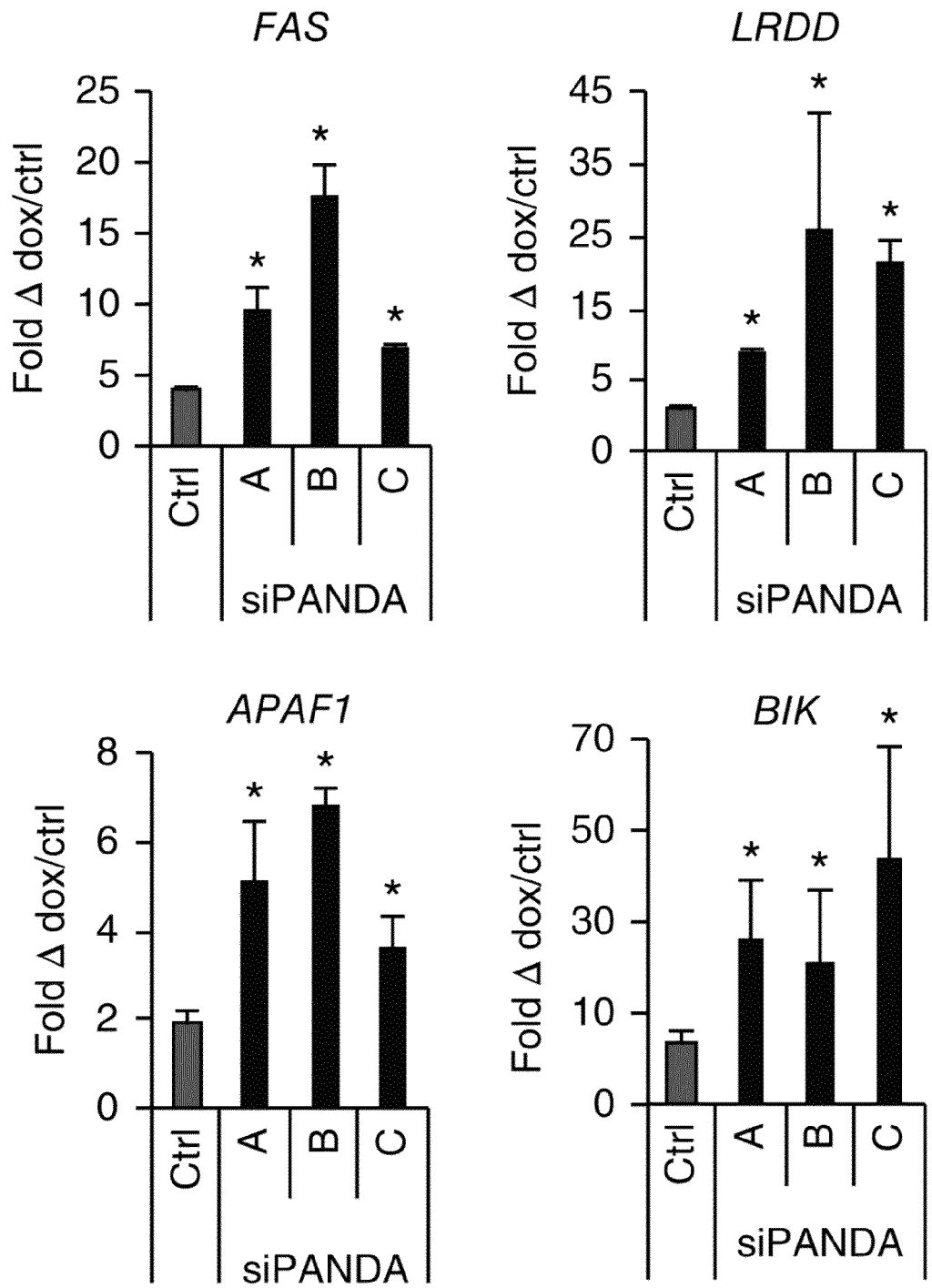
Figure 6D:
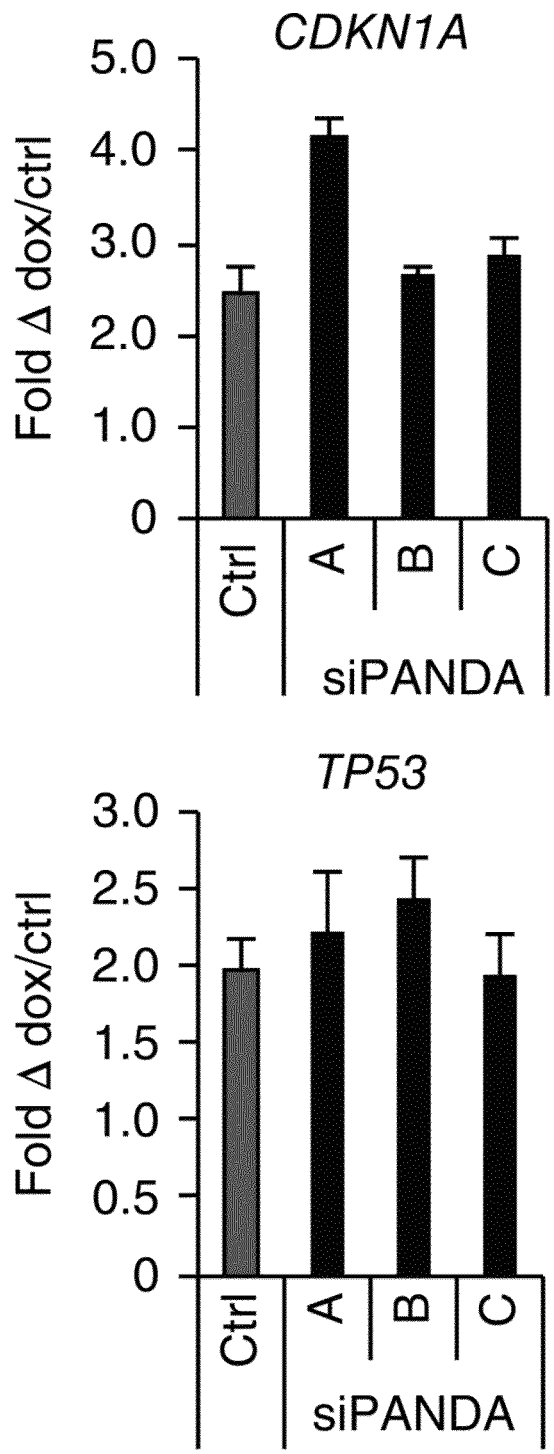

Next, we addressed whether PANDA affects the DNA damage response. We transduced human fetal fibroblasts (FL3) with custom siRNAs targeting PANDA and then applied doxorubicin for 24 hours following the knockdown (FIG. 6A). Global gene expression analysis showed that 224 genes were induced and 193 genes were repressed at least twofold by PANDA knockdown (FIG. 6B). Genes induced by PANDA knockdown were significantly enriched for those involved in apoptosis, such as the Gene Ontology terms 'cell death' (P<0.04) and 'apoptosis' (P<0.03) (FIG. 6B). qRT-PCR confirmed that PANDA depletion induced several genes encoding canonical activators of apoptosis, including APAF1, BIK, FAS and LRDD (FIG. 6C). On the other hand, expression of neither CDKN1A itself nor TP53 was affected by PANDA depletion (FIG. 6D), suggesting that PANDA is a P53 effector that acts independently of p21CDKN1A.

Figure 6E:
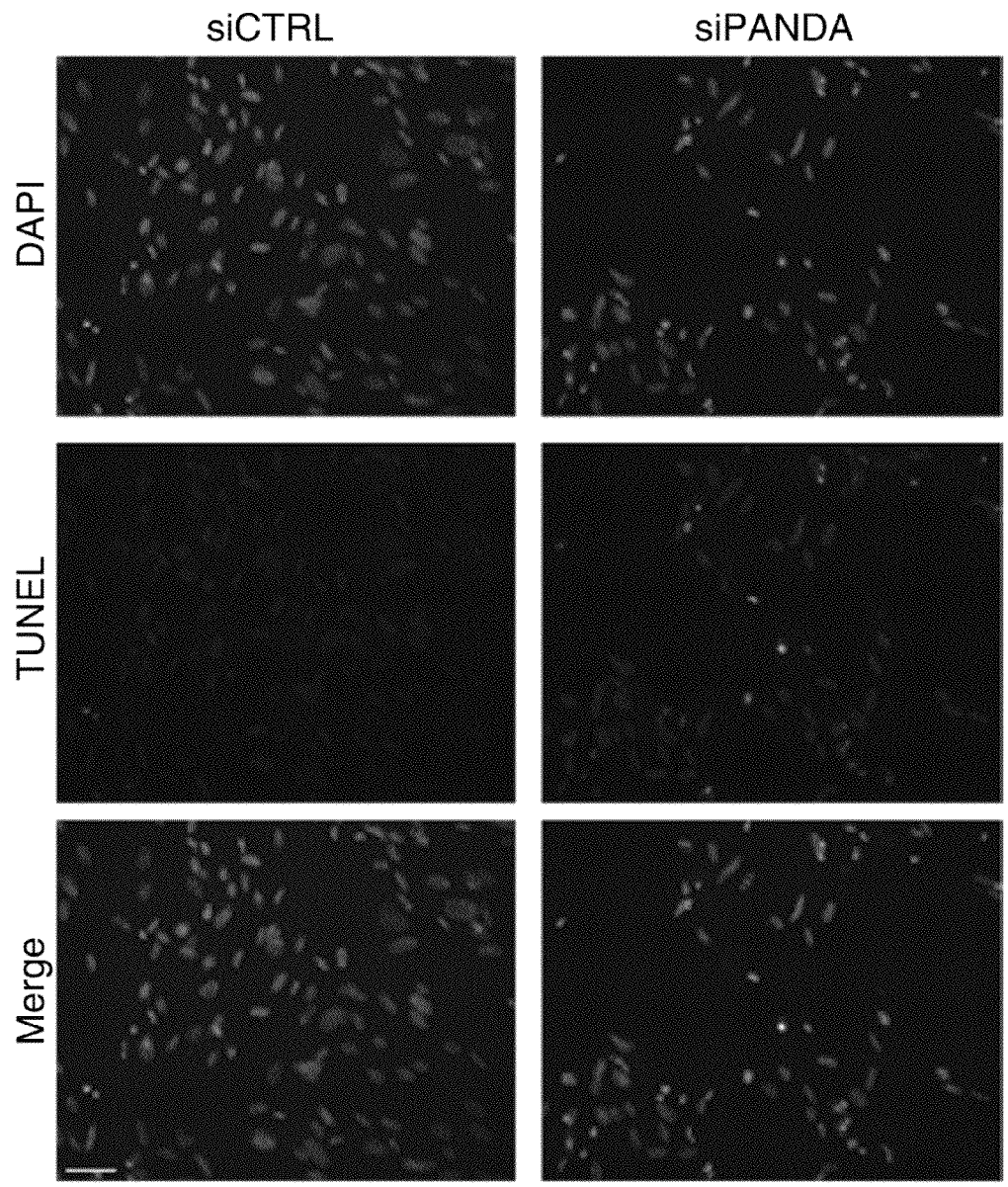
Figure 6F:
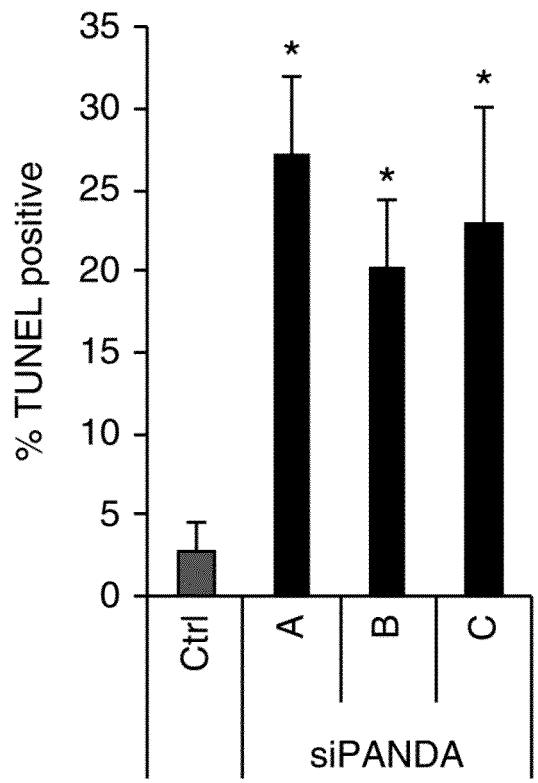
Figure 6G:
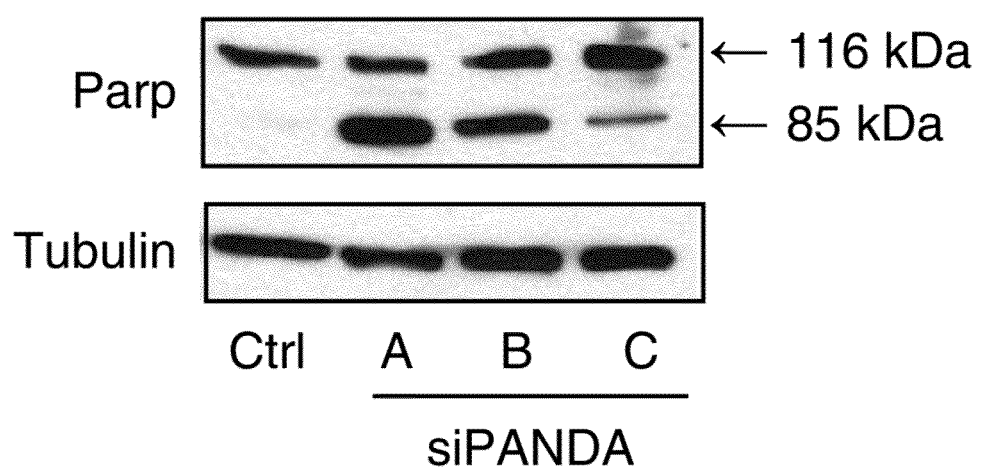
Figure 17:
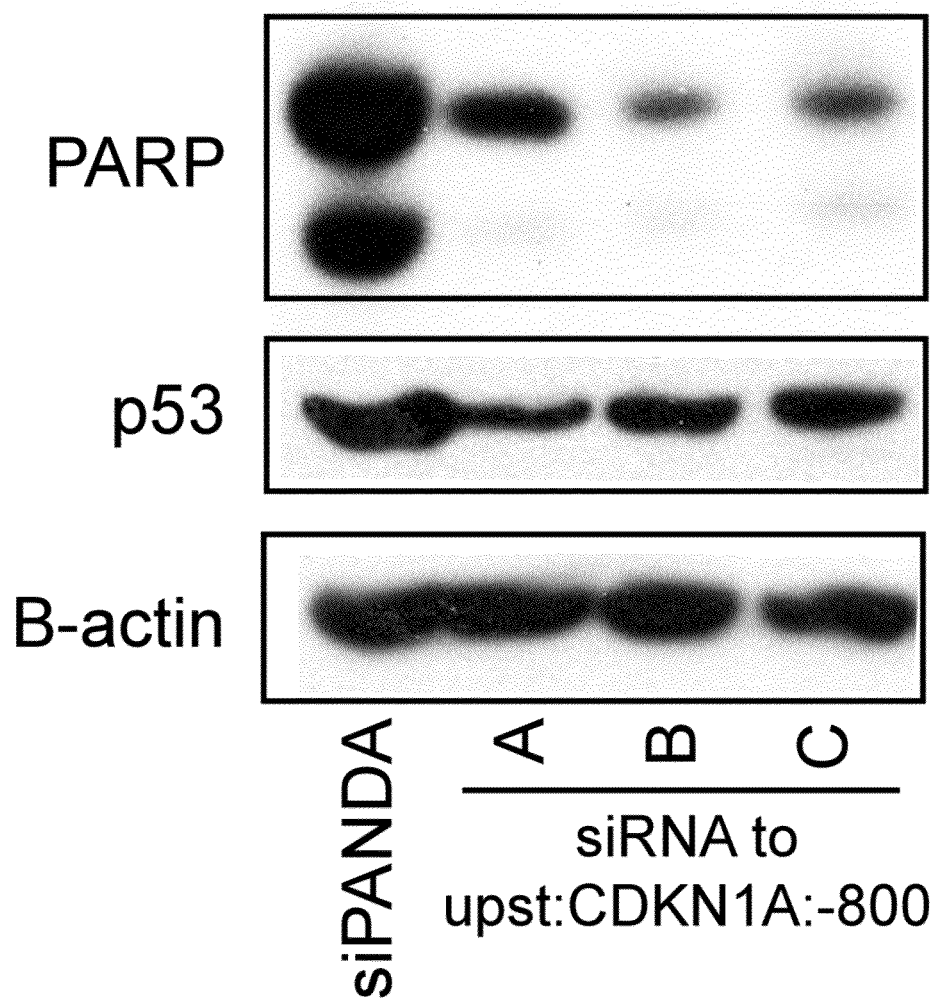
FIG. 17 shows that three independent siRNAs to upst:CDKN1A:−800 did not induce PARP cleavage in FL3 cells upon treatment with doxorubicin.
Figure 18:
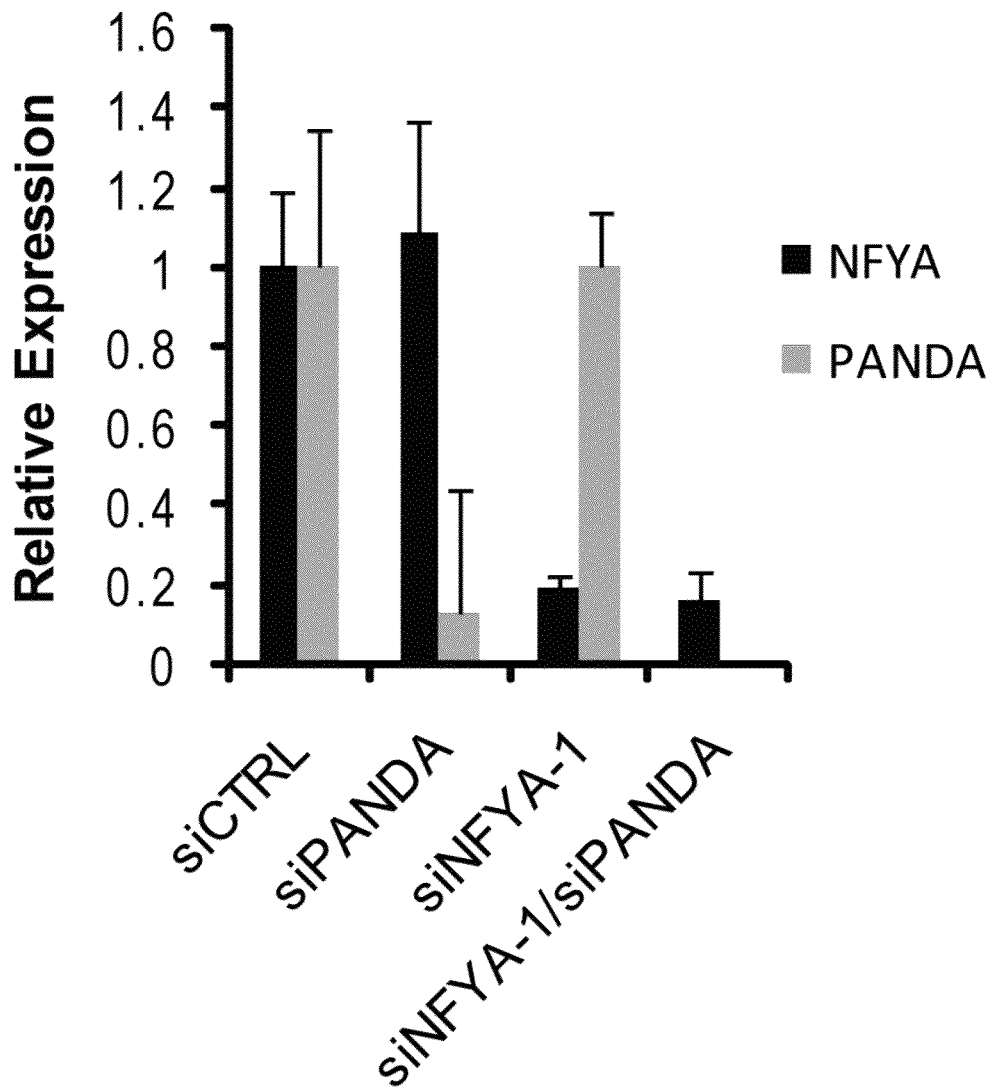
FIG. 18 shows the knockdown efficiency of NFYA and PANDA for FIGS. 7D and 7E.

DNA damage in human fibroblasts triggers p53-dependent G1 arrest but not apoptosis (Agarwal et al. (1995) Proc. Natl. Acad. Sci. USA 92:8493-8497; Di Leonardo et al. (1994) Genes Dev. 8, 2540-2551). Consistent with this finding, doxorubicin treatment in FL3 cells exposed to control siRNA had little to no apoptosis as measured by TUNEL. In contrast, PANDA knockdown resulted in fivefold to sevenfold increased TUNEL-positive cells (FIGS. 6E and 6F). Immunoblot analysis of PARP, a caspase substrate and marker of apoptosis, revealed PARP cleavage only in PANDA-depleted cells (FIG. 6G). In contrast, six additional siRNAs targeting other transcripts within the CDKN1A promoter had no effect on apoptosis (data not shown; FIG. 17). Thus, PANDA knockdown sensitized fibroblasts to DNA-damage-induced apoptosis. Altogether, these data suggest that in parallel with p53-mediated induction of CDKN1A for cell cycle arrest, p53-mediated induction of PANDA delimits apoptosis.

Figure 7A:
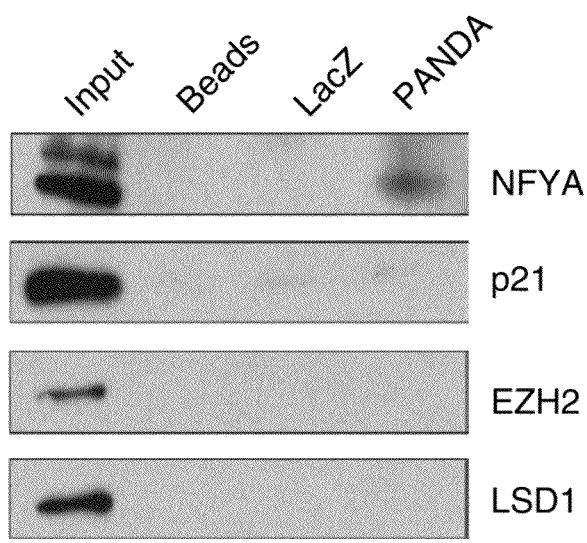
FIGS. 7A-7E show that PANDA regulates transcription factor NF-YA.
Figure 7B:
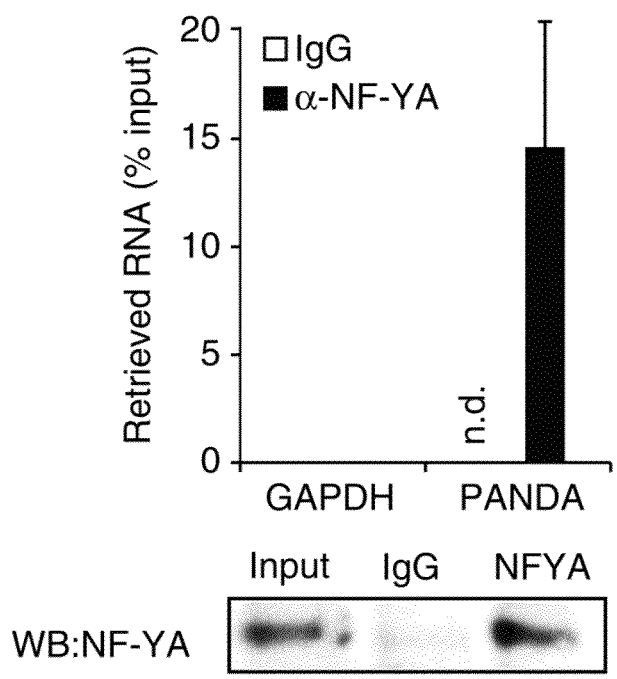
Figure 7C:
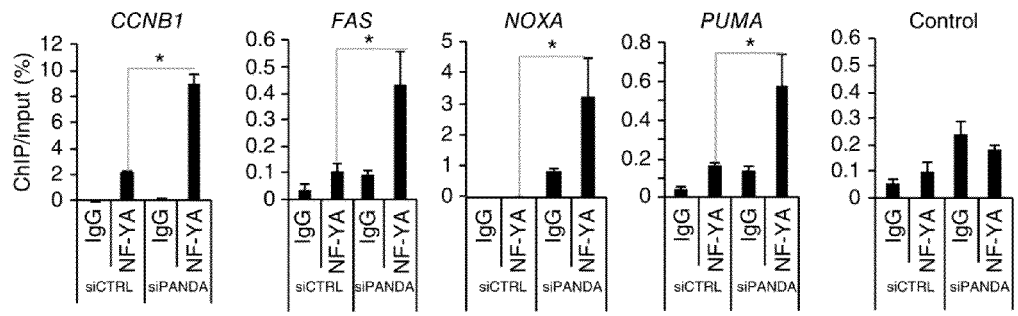
Figure 7D:
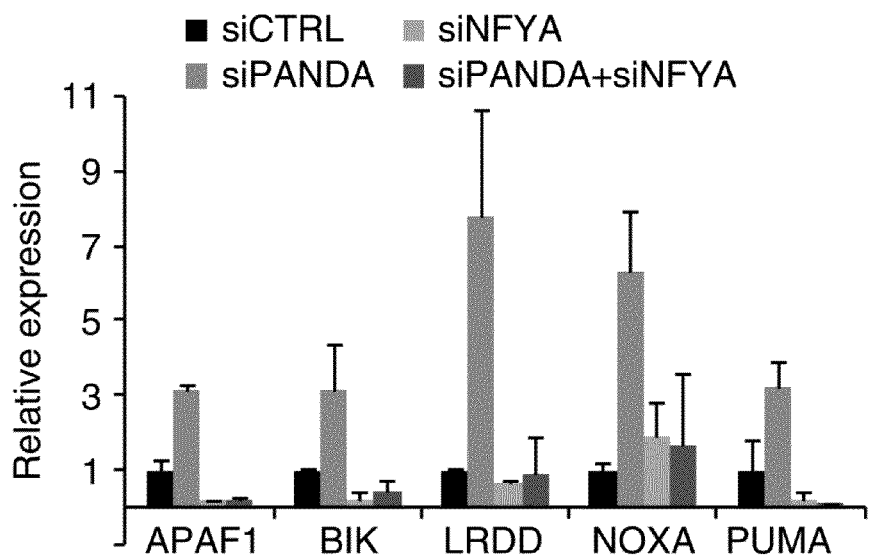
Figure 7E:
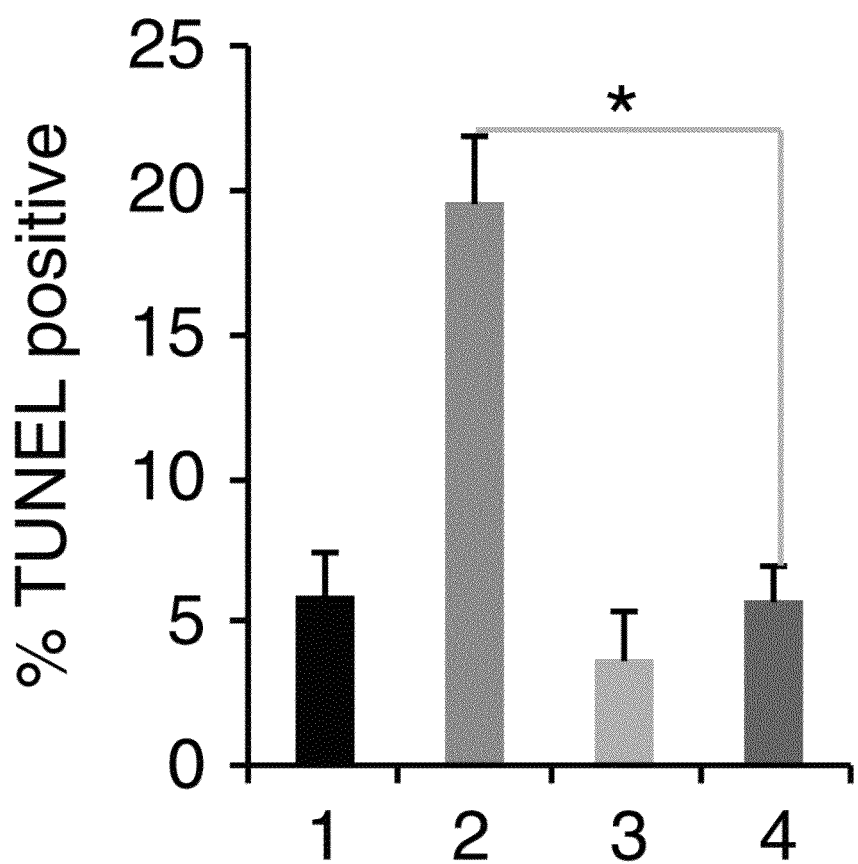
Figure 8:
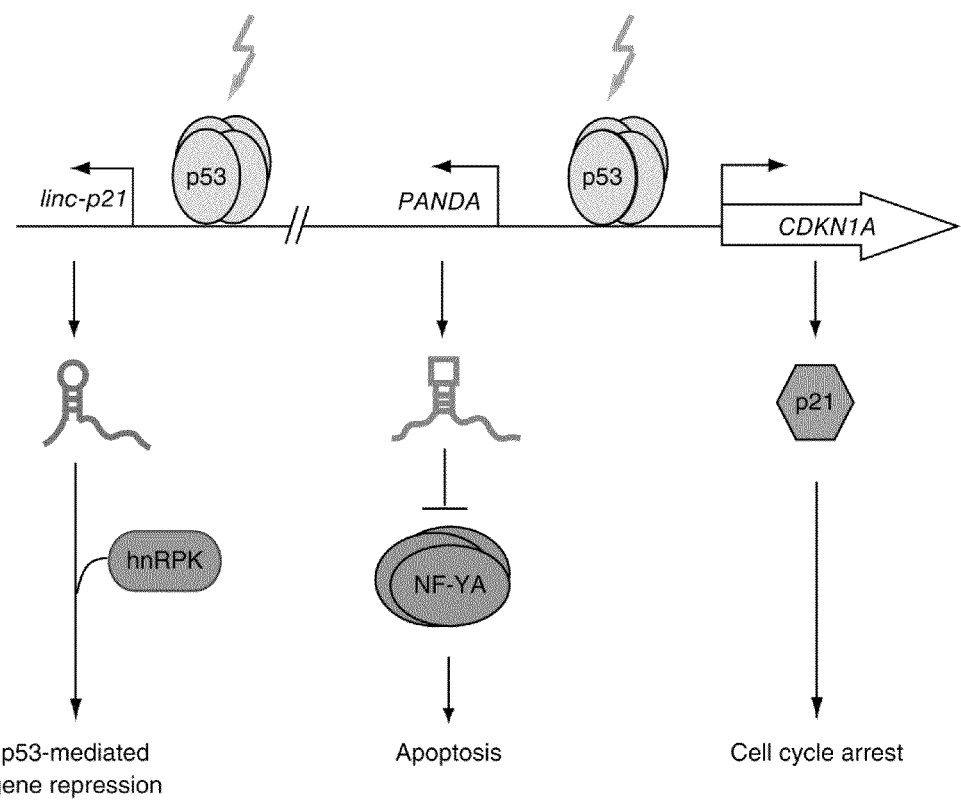
FIG. 8 shows a model of coding and noncoding transcripts at the CDKN1A locus coordinating the DNA damage response. After DNA damage, p53 binding at the CDKN1A locus coordinately activates transcription of CDKN1A as well as noncoding transcripts PANDA and linc-p21. CDKN1A mediates cell cycle arrest; PANDA blocks apoptosis through NF-YA; and linc-p21 mediates gene silencing through recruitment of hnRPK.

Core promoters of cell death genes downstream of p53 are distinguished from other p53 target genes by the binding site for the transcription factor NF-YA (Morachis et al. (2010) Genes Dev. 24:135-147), and we reasoned that PANDA may affect NF-YA function. RNA chromatography (Michlewski (2010) RNA 16:1673-1678, herein incorporated by reference) using purified, in vitro transcribed PANDA RNA, but not a 1.2-kb LacZ mRNA fragment, specifically retrieved NF-YA from cellular lysates of human fibroblasts induced by DNA damage (FIG. 7A). PANDA did not retrieve other chromatin modification complexes that can bind other lncRNAs, such as EZH2 or LSD1 (Khalil et al. (2009) Proc. Natl. Acad. Sci. USA 106:11667-11672; Tsai et al. (2010) Science 329: 689-693), or p21, illustrating the specificity of the interaction. Immunoprecipitation of NF-YA from doxorubicin-treated primary human lung fibroblasts specifically retrieved endogenous PANDA (FIG. 7B). NF-YA is a nuclear transcription factor that activates the p53-responsive promoter of FAS upon DNA damage (Morachis et al. (2010) Genes Dev. 24:135-147). Depletion of PANDA substantially increased NF-YA occupancy at target genes, including CCNB1, FAS, BBC3 (also known as PUMA) and PMAIP1 (also known as NOXA) (FIG. 7C). Moreover, concomitant knockdown of NF-YA and PANDA substantially attenuated induction of apoptotic genes and apoptosis as measured by TUNEL, indicating that NF-YA is required in part for cell death triggered by loss of PANDA (FIGS. 7D and E). Thus, PANDA binding to NF-YA may evict or prevent NF-YA binding to chromatin. These data suggest that DNA damage activates p53-mediated transcription at CDKN1A and PANDA that functions synergistically to mediate cell cycle arrest and survival. CDKN1A mRNA produces p21 to mediate arrest, whereas PANDA impedes NF-YA activation of apoptotic gene expression program (FIG. 8).

Discussion

Recent studies have revealed that a surprisingly large fraction of mammalian genomes is transcribed. In addition to small noncoding RNAs, long noncoding RNAs can be produced from gene promoters and enhancers, as well as stand-alone intergenic loci (Guttman et al. (2009) Nature 458:223-227; Katayama et al. (2005) Science 309:1564-1566; and De Santa et al. (2010) PLoS Biol. 8, e1000384). New approaches are needed that not only identify ncRNAs but also provide insight into their potential biological function.

Using an ultrahigh-resolution tiling array, we interrogated the transcriptional landscape at cell-cycle promoters in 108 samples that represent diverse perturbations. The ability to interrogate numerous and diverse biological samples in a rapid and economical fashion is advantageous for at least two reasons. First, many of the noncoding transcripts are induced only in highly specific conditions and may have been missed if only a few conditions were surveyed. Of the 216 new noncoding transcribed regions we identified, on average, only 73 of these are transcribed in any one biological sample. Second, comparison of lncRNA profiles amongst these diverse samples highlighted unexpected similarities in cell cycle promoter states among distinct perturbations. For instance, we identified a similarity of promoter states among ESCs, tumors induced by MYC and epithelial progenitors depleted of the differentiation regulator p63. Likewise, authentic human tumors can be classified based on the similarity of their promoter states to those of cells with defined oncogenic perturbation.

Noncoding transcription through regulatory elements may affect gene activity in a variety of ways. The act of transcription may open compacted chromatin over regulatory sequences or compete with transcription factor binding (so called transcriptional interference). In addition, the ncRNA product may modulate neighboring gene expression in cis (Lee (2009) Genes Dev. 23:1831-1842; Kanhere et al. (2010) Mol. Cell. 38:675-688), affect distantly located genes in trans (Rinn et al. (2007) Cell 129, 1311-1323) or even serve as a target for regulation by small regulatory RNAs (Han et al. (2007) Proc. Natl. Acad. Sci. USA 104, 12422-12427; Schwartz et al. (2008) Nat. Struct. Mol. Biol. 15, 842-848).

Because these different mechanisms predict distinct relationships between levels of ncRNAs and cognate mRNAs, we compared ncRNA and mRNA expression profiles across our samples. We found that most promoter ncRNAs are neither positively nor negatively correlated in expression with their neighboring mRNA but are rather correlated in expression with genes located elsewhere in the genome. The genes co-expressed (and presumably co-regulated) with promoter ncR-NAs function in specific biological pathways, including cell cycle, DNA damage response and stem cell differentiation, and have been associated with cancer prognosis. Quantitative RT-PCR analysis further validated that many of these ncR-NAs are differentially expressed in the cell cycle and in human cancers, and are regulated in response to DNA damage or ESC differentiation. These findings suggest that cell-cycle ncRNAs may participate in gene regulation in trans. In addition, noncoding transcription of cell-cycle promoters may be a form of regulatory anticipation or feedback to modulate the chromatin state of cell-cycle promoters.

Our results suggest that the human genome is organized into genomic units that code for multiple transcripts that function in the same biological pathways (FIG. 8). Forty nine of 56 cell-cycle protein-coding gene loci have at least one detected lncRNA and an average of four lncRNAs within 10 kb upstream and 2 kb downstream of the TSS. At the CDKN1A promoter, five lncRNAs, similar to the CDKN1A mRNA itself, are induced by DNA damage. One of these lncRNAs, which we named PANDA, is a non-spliced 1.5-kb ncRNA that is transcribed antisense to CDKN1A and is induced with faster kinetics than CDKN1A. Loss-of-function and complementation experiments show that PANDA induction during DNA damage is p53 dependent. In contrast, depletion of CDKN1A or depletion of PANDA had no effect on the other's response to DNA damage, indicating that their induction by p53 occurs in parallel. PANDA inhibits the expression of apoptotic genes by sequestering the transcription factor NF-YA from occupying target gene promoters. Whereas CDKN1A encodes a cell cycle inhibitor to mediate cell cycle arrest, PANDA promotes cell survival by impeding the apoptotic gene expression program. This linkage can be apparently exploited by tumors: the ability of the Li-Fraumeni gain-of-function p53 mutant R273H to selectively retain PANDA induction instead of CDKN1A in effect uncouples cell survival from cell cycle arrest, which was similarly observed in metastatic ductal carcinomas. Thus, lncRNAs like PANDA may provide new explanations for human cancer susceptibility.

Intriguingly, a recent study identified a distinct long intergenic noncoding RNA located 15 kb upstream of CDKN1A, named lincRNA-p21, that is induced by p53 and mediates p53-dependent gene repression (Huarte et al. (2010) Cell 142:409-419). Thus, the regulatory sequence upstream of CDKN1A drives the expression of multiple coding and noncoding transcripts that cooperate to regulate the DNA damage response (FIG. 8). These findings provide a vivid example that shows the blurring boundary between 'genes' and 'regulatory sequences' (Mattick (2003) Bioessays 25:930-939).

Our study provides an initial catalog of lncRNAs in cell-cycle promoters that may play diverse functions. At a minimum, promoter ncRNA expression provides a convenient means of tracking the chromatin state of promoters, which may be of use in cancer biology and regenerative medicine. Future studies are needed to pinpoint the functions of these and likely other ncRNAs emanating from regulatory sequences.

While the preferred embodiments of the invention have been illustrated and described, it will be appreciated that various changes can be made therein without departing from the spirit and scope of the invention.

What is claimed is:

1. An assay comprising:

a) measuring the amount of long non-coding RNA PANDA in a biological sample derived from a subject by performing polymerase chain reaction (PCR) using at least one set of oligonucleotide primers comprising a forward primer and a reverse primer capable of amplifying a long non-coding RNA PANDA polynucleotide sequence, wherein at least one set of primers is selected from the group consisting of:

i) a forward primer comprising the sequence of SEQ ID NO:4 and a reverse primer comprising the sequence of SEQ ID NO:5;

ii) a forward primer comprising the sequence of SEQ ID NO:6 and a reverse primer comprising the sequence of SEQ ID NO:7;

iii) a forward primer comprising the sequence of SEQ ID NO:8 and a reverse primer comprising the sequence of SEQ ID NO:9; and iv) a forward primer comprising the sequence of SEQ ID NO:10 and a reverse primer comprising the sequence of SEQ ID NO:11; and b) comparing the amount of the long non-coding RNA PANDA with a reference value, and if the amount of the long non-coding RNA PANDA is increased relative to the reference value, identifying the subject as having an increased probability of having metastatic ductal carcinoma.

2. A method of treating a subject suspected of having breast cancer, the method comprising:
  a) measuring the amount of the long non-coding RNA PANDA in a biological sample derived from the subject;
  b) analyzing the amount of the long non-coding RNA PANDA in conjunction with respective reference value ranges for the long non-coding RNA PANDA, wherein an increased amount of the long non-coding RNA PANDA in the biological sample compared to a control sample indicates that the subject has metastatic ductal carcinoma; and
  c) administering to the subject in need thereof a therapeutically effective amount of a chemotherapeutic agent in combination with a therapeutically effective amount of at least one small interfering RNA (siRNA) that inhibits the long non-coding RNA PANDA if the amount of the long non-coding RNA PANDA indicates that the subject has metastatic ductal carcinoma.

3. The method of claim 2, wherein at least one siRNA comprising a nucleotide sequence selected from the group consisting of SEQ ID NOS:12-14 is administered.

4. The method of claim 2, wherein measuring the amount of the long non-coding RNA PANDA in a biological sample comprises performing polymerase chain reaction (PCR) with at least one set of oligonucleotide primers comprising a forward primer and a reverse primer capable of amplifying a PANDA long non-coding RNA polynucleotide sequence, wherein at least one set of primers is selected from the group consisting of:
  a) a forward primer comprising the sequence of SEQ ID NO:4 and a reverse primer comprising the sequence of SEQ ID NO:5;
  b) a forward primer comprising the sequence of SEQ ID NO:6 and a reverse primer comprising the sequence of SEQ ID NO:7;
  c) a forward primer comprising the sequence of SEQ ID NO:8 and a reverse primer comprising the sequence of SEQ ID NO:9; and
  d) a forward primer comprising the sequence of SEQ ID NO:10 and a reverse primer comprising the sequence of SEQ ID NO:11.

5. A method of treating a subject suspected of having breast cancer, the method comprising:
  a) measuring the levels of the long RNA PANDA and one or more other biomarkers selected from the group consisting of a polynucleotide comprising an RNA equivalent of a nucleotide sequence selected from the group consisting of SEQ ID NOS:19-20 and 22-28, and a polynucleotide comprising an RNA equivalent of a nucleotide sequence that is complementary to a nucleotide sequence selected from the group consisting of SEQ ID NOS:19-20 and 22-28;
  b) analyzing the levels of the biomarkers in conjunction with respective reference value ranges for the long non-coding RNA PANDA and said one or more other biomarkers, wherein increased levels of the long non-coding RNA PANDA and decreased levels of one or more biomarkers selected from the group consisting of a polynucleotide comprising an RNA equivalent of a nucleotide sequence selected from the group consisting of SEQ ID NOS:19, 20, and 27, and a polynucleotide comprising an RNA equivalent of a nucleotide sequence that is complementary to a nucleotide sequence selected from the group consisting of SEQ ID NOS: SEQ ID NOS:19, 20, and 27 compared to a control sample indicate that the subject has metastatic ductal carcinoma, and wherein increased levels of the long non-coding RNA PANDA and increased levels of one or more biomarkers selected from the group consisting of a polynucleotide comprising an RNA equivalent of a nucleotide sequence selected from the group consisting of SEQ ID NOS:22-26 and 28, and a polynucleotide comprising an RNA equivalent of a nucleotide sequence that is complementary to a nucleotide sequence selected from the group consisting of SEQ ID NOS:22-26 and 28 compared to a control sample indicate that the subject has metastatic ductal carcinoma; and
  c) administering to the subject in need thereof a therapeutically effective amount of a chemotherapeutic agent in combination with a therapeutically effective amount of at least one small interfering RNA (siRNA) that inhibits the long non-coding RNA PANDA if the amounts of the long non-coding RNA PANDA and the one or more other biomarkers indicate that the subject has metastatic ductal carcinoma.

* * * * *

SEQUENCE LISTING

```
<160> NUMBER OF SEQ ID NOS: 235

<210> SEQ ID NO 1
<211> LENGTH: 1506
<212> TYPE: DNA
<213> ORGANISM: Homo sapiens
<300> PUBLICATION INFORMATION:
<308> DATABASE ACCESSION NUMBER: NCBI/JF803844
<309> DATABASE ENTRY DATE: 2011-07-21
<313> RELEVANT RESIDUES IN SEQ ID NO: (1)..(1501)
```

<400> SEQUENCE: 1

```
acgaattctt tcaggaatgc cgcagatgta catgctcccg cagatctata ttttccaatg      60
ttgttaacat cagccagctg gcaatctaca acctgtcttg tacaatgttt gaagagaggc     120
atcctccaga cacggtcccc tgtttcaatg ctggcctcga agagcttgtt ccagagccag     180
gatgaattgg taaagacccc agtggcacct gaccccaaag ctacatctat gacacctgtt     240
aaggtggtgg cattgaggat gaccttcggg ttaaatgtgt gcacgtaaca gagcgcatca     300
gccagtatga gcctcccctc agcatcagtg ttaccaacct ggatggtctt cctgttcctg     360
gctctaacaa catcccccag cttgttggcc ttgccgctgg gcatgttttc acagaggggc     420
cagacctata atattaatgg gcaaactgag atttgcagca gacacaatgg ctgagcatat     480
agttgtagct cctcccatgt cggccctcat gaggtccata tttgcagaag ccttgatgga     540
gataccacca ctgtcaaagg taattccttt cccaacaaac aaggggtggt ttgtctgcat     600
tggggctgcc tatgtagtga atttccaaga agactgaggg ctcgtcagat cctttggcca     660
cactgaggaa tgatcccatt gcctgttcct caatccaaga cctgggtctg atatgaaact     720
cggtttacta ctagcgcttt tgagattctt ctcaataatt tcggcaaatc tggttggcat     780
catctcgctg gctggcgtct ccatcatgcc aagttctgcc cagaagcaaa caggactcct     840
ttctgccagg cctcctgatc cccagttcca tagagcttca ccgacatagc catcttcttt     900
ttttgcttta ggtcatcgta ttcatagaga ccaagcaccg cgccctcctc agcagcctga     960
gcatctctac agggatccac ctccacggaa gagagctcca ggtcttgaat ctgcctgcat    1020
cctgctgcaa cagcagctct gatgttttct ttgccttcct gccagttttc ctgttcgtcg    1080
attctggctg cctttttgcc gaggccaact agcaccacgc tggggaagtc ctgatgcaga    1140
ccataaaagt ttcgagtctt gcctgccttc agaggtggtc cagatatgtt caaagtctct    1200
ctcagctttc cagctatcaa tttatcaaga ttctctcctg cacttgtgaa ctgtggcaca    1260
tcatcttctt tttctttgga atagattcct aaaacaaggc ccttcgtcat gtctgcagcg    1320
gagagacccc ggctcccgaa acatctcacg gccagacgtc agacgatgac tcgccccacc    1380
caatgtttgt attttagtag agagagggtt tctctatgtt ggtcaggctg gtctcaaacc    1440
tcgacctcag ttgatctgtc tgcctcggtc tcccaaagtg ctgagattac aggcgtgagc    1500
cactgc                                                              1506
```

<210> SEQ ID NO 2
<211> LENGTH: 229
<212> TYPE: DNA
<213> ORGANISM: Homo sapiens

<400> SEQUENCE: 2

```
tagatgtagc tttggggtca ggtgccactg gggtctttac caattcatcc tggctctgga      60
acaagctctt cgaggccagc attgaaacag gggaccgtgt ctggaggatg cctctcttca     120
aacattgtac aagacaggtt gtagattgcc agctggctga tattaacaac attggaaaat     180
atagatctgc gggagcatgt acatctgcgg cattcctgaa agaattcgt                 229
```

<210> SEQ ID NO 3
<211> LENGTH: 585
<212> TYPE: DNA
<213> ORGANISM: Homo sapiens

<400> SEQUENCE: 3

```
tcatagagac caagcaccgc gccctcctca gcagcctgag catctctaca gggatccacc      60
```

```
tccacggaag agagctccag gtcttgaatc tgcctgcatc ctgctgcaac agcagctctg    120
atgttttctt tgccttcctg ccagttttcc tgttcgtcga ttctggctgc cttttttgccg   180 aggccaacta gcaccacgct ggggaagtcc tgatgcagac cataaaaggt tcgagtcttg    240
cctgccttca gaggtggtcc agatatgttc aaagtctctc tcagctttcc agctatcaat    300
ttatcaagat tctctcctgc acttgtgaac tgtggcacat catcttcttt ttctttggaa    360
tagattccta aaacaaggcc cttcgtcatg tctgcagcgg agagacccccg gctcccgaaa   420 catctcacgg ccagacgtca gacgatgact cgccccaccc aatgtttgta ttttagtaga    480
gagagggttt ctctatgttg gtcaggctgg tctcaaacct cgacctcagt tgatctgtct    540
gcctcggtct cccaaagtgc tgagattaca ggcgtgagcc actgc                    585
```

```
<210> SEQ ID NO 4
<211> LENGTH: 20
<212> TYPE: DNA
<213> ORGANISM: Artificial
<220> FEATURE:
<223> OTHER INFORMATION: forward PANDA RACE primer 1

<400> SEQUENCE: 4
cagaacttgg catgatggag                                                20

<210> SEQ ID NO 5
<211> LENGTH: 27
<212> TYPE: DNA
<213> ORGANISM: Artificial
<220> FEATURE:
<223> OTHER INFORMATION: reverse PANDA RACE primer 1

<400> SEQUENCE: 5
tgatatgaaa ctcggtttac tactagc                                        27

<210> SEQ ID NO 6
<211> LENGTH: 20
<212> TYPE: DNA
<213> ORGANISM: Artificial
<220> FEATURE:
<223> OTHER INFORMATION: forward PANDA RACE primer 2

<400> SEQUENCE: 6
tgcacacatt taacccgaag                                                20

<210> SEQ ID NO 7
<211> LENGTH: 22
<212> TYPE: DNA
<213> ORGANISM: Artificial
<220> FEATURE:
<223> OTHER INFORMATION: reverse PANDA RACE primer 2

<400> SEQUENCE: 7
ccccaaagct acatctatga ca                                             22

<210> SEQ ID NO 8
<211> LENGTH: 20
<212> TYPE: DNA
<213> ORGANISM: Artificial
<220> FEATURE:
<223> OTHER INFORMATION: forward PANDA RACE primer 3

<400> SEQUENCE: 8
cgtctccatc atgccaagtt                                                20
```

```
<210> SEQ ID NO 9
<211> LENGTH: 22
<212> TYPE: DNA
<213> ORGANISM: Artificial
<220> FEATURE:
<223> OTHER INFORMATION: reverse PANDA RACE primer 3

<400> SEQUENCE: 9
catagagctt caccgacata gc                                          22

<210> SEQ ID NO 10
<211> LENGTH: 20
<212> TYPE: DNA
<213> ORGANISM: Artificial
<220> FEATURE:
<223> OTHER INFORMATION: forward PANDA RT-PCR primer

<400> SEQUENCE: 10
tgcacacatt taacccgaag                                             20

<210> SEQ ID NO 11
<211> LENGTH: 22
<212> TYPE: DNA
<213> ORGANISM: Artificial
<220> FEATURE:
<223> OTHER INFORMATION: reverse PANDA RT-PCR primer

<400> SEQUENCE: 11
ccccaaagct acatctatga ca                                          22

<210> SEQ ID NO 12
<211> LENGTH: 21
<212> TYPE: RNA
<213> ORGANISM: Artificial
<220> FEATURE:
<223> OTHER INFORMATION: siRNA for PANDA

<400> SEQUENCE: 12
aaugugugca cguaacagau u                                           21

<210> SEQ ID NO 13
<211> LENGTH: 21
<212> TYPE: RNA
<213> ORGANISM: Artificial
<220> FEATURE:
<223> OTHER INFORMATION: siRNA for PANDA

<400> SEQUENCE: 13
gagauuugca gcagacacau u                                           21

<210> SEQ ID NO 14
<211> LENGTH: 21
<212> TYPE: RNA
<213> ORGANISM: Artificial
<220> FEATURE:
<223> OTHER INFORMATION: siRNA for PANDA

<400> SEQUENCE: 14
gggcauguuu ucacagaggu u                                           21

<210> SEQ ID NO 15
<211> LENGTH: 20
<212> TYPE: DNA
<213> ORGANISM: Artificial
<220> FEATURE:
<223> OTHER INFORMATION: forward PUMA Chip primer
```

```
<400> SEQUENCE: 15
cgtggattcc tgtctcctct                                                    20

<210> SEQ ID NO 16
<211> LENGTH: 20
<212> TYPE: DNA
<213> ORGANISM: Artificial
<220> FEATURE:
<223> OTHER INFORMATION: reverse PUMA Chip primer

<400> SEQUENCE: 16
gtcactctgg tgaggcgatt                                                    20

<210> SEQ ID NO 17
<211> LENGTH: 20
<212> TYPE: DNA
<213> ORGANISM: Artificial
<220> FEATURE:
<223> OTHER INFORMATION: forward NOXA Chip primer

<400> SEQUENCE: 17
tttcccttcc ctgttactgc                                                    20

<210> SEQ ID NO 18
<211> LENGTH: 20
<212> TYPE: DNA
<213> ORGANISM: Artificial
<220> FEATURE:
<223> OTHER INFORMATION: reverse NOXA Chip primer

<400> SEQUENCE: 18
cttgggtaaa caagcccaga                                                    20

<210> SEQ ID NO 19
<211> LENGTH: 534
<212> TYPE: DNA
<213> ORGANISM: Homo sapiens

<400> SEQUENCE: 19
agcagcaaga tgggcattgt cagtctgcag aacgcattgt ccacaatatt tgtgaagatc        60
tgagccctca ggtcctcaat ggtcttgaaa taatggctcc agtctctgac ctggggtccc       120
tgcttctcca ggtgctcccg gattttgctc tctagcctcc ggttctcggt ctccaggctc       180
ctcactctgt ccaggtagga gaccaggtgg ttgtcaggtt ttgcatggtc tcctcggtct       240
ggatgcctcc cattcctgcc agaaccccgg ccatccccgc agtcaggccc ccggacctca       300
tgctgcccca gaagctggtg gagcgggaca tggagattcg gcagccagag ctcccggcgc       360
ctgcacagac gctggccatg ctgctcacca gccaggagtc gtagctgggt gcctggacag       420
agcccaggga ccggtagttg gtgtagaagg cggagtgagt ggtgaagctc atgctgtcca       480
gggaggaggg tgagaggaca gaactcaggc tttgccgacc aatttaactt attt            534

<210> SEQ ID NO 20
<211> LENGTH: 368
<212> TYPE: DNA
<213> ORGANISM: Homo sapiens

<400> SEQUENCE: 20
tcccaaggaa gccgggcact ggaggtccgg gacaccgcgt cgggtccccg ctccgcggcg        60
cgctgtaggg gtcggggagt cacggccctg ctctgggcgg gctctaacca gcctgtcagt      120
```

| | |
|---|---|
| cggggaaggg caagggtctc ctctacctct ttcccaccgc ggccgggaga atcgcggccc | 180 |
| agcctgtcct cgggtcgggg cgctggactc cggggcggga gcggagccca cgcctggatg | 240 |
| ggaggcgggg agggttcatg tctttgaggg gtggggggtc tgggggcac gacgctgctc | 300 |
| agggcctcta tcagctgcct cgggggctca gggcttcccg acctagccca gattccctct | 360 |
| ccgaaagc | 368 |

<210> SEQ ID NO 21
<211> LENGTH: 1344
<212> TYPE: DNA
<213> ORGANISM: Homo sapiens

<400> SEQUENCE: 21

| | |
|---|---|
| gatgtgccac agttcacaag tgcaggagag aatcttgata aattgatagc tggaaagctg | 60 |
| agagagactt tgaacatatc tggaccacct ctgaaggcag gcaagactcg aaacttttat | 120 |
| ggtctgcatc aggacttccc cagcgtggtg ctagttggcc tcggcaaaaa ggcagccaga | 180 |
| atcgacgaac aggaaaactg gcaggaaggc aaagaaaaca tcagagctgc tgttgcagca | 240 |
| ggatgcaggc agattcaaga cctggagctc tcttccgtgg aggtggatcc ctgtagagat | 300 |
| gctcaggctg ctgaggaggg cgcggtgctt ggtctctatg aatacgatga cctaaagcaa | 360 |
| aaaaagaaga tggctatgtc ggtgaagctc tatggaactg gggatcagga ggcctggcag | 420 |
| aaaggagtcc tgtttgcttc tgggcagaac ttggcatgat ggacgccac gccagcgaga | 480 |
| tgatgccaac cagatttgcc gaaattattg agaagaatct caaaagcgct agtagtaaac | 540 |
| cgagtttcat atcagaccca ggtcttggat tgaggaacag gcaatgggat cattcctcag | 600 |
| tgtggccaaa ggatctgacg agccctcagt cttcttggaa attcactaca taggcagccc | 660 |
| caatgcagac aaaccacccc ttgtttgttg ggaaaggaat tacctttgac agtggtggta | 720 |
| tctccatcaa ggcttctgca aatatggacc tcatgagggc cgacatggga ggagctacaa | 780 |
| ctatatgctc agccattgtg tctgctgcaa atctcagttt gcccattaat attataggtc | 840 |
| tggcccctct gtgaaaacat gcccagcggc aaggccaaca agctggggga tgttgttaga | 900 |
| gccaggaaca ggaagaccat ccaggttggt aacactgatg ctgaggggag gctcatactg | 960 |
| gctgatgcgc tctgttacgt gcacacattt aacccgaagg tcatcctcaa tgccaccacc | 1020 |
| ttaacaggtg tcatagatgt agcttttgggg tcaggtgcca ctgggtcttt taccaattca | 1080 |
| tcctggctct ggaacaagct cttcgaggcc agcattgaaa caggggaccg tgtctggagg | 1140 |
| atgcctctct tcaaacattg tacaagacag gttgtagatt gccagctggc tgatgttaac | 1200 |
| aacattggaa aatatagatc tgcgggagca tgtacatctg cggcattcct gaaagaattc | 1260 |
| gtgactcatc ctaagtgggc acatttagac atagcaggtg tgatgaccaa caaagatgag | 1320 |
| gttccctatc tatggaaagg catg | 1344 |

<210> SEQ ID NO 22
<211> LENGTH: 463
<212> TYPE: DNA
<213> ORGANISM: Homo sapiens

<400> SEQUENCE: 22

| | |
|---|---|
| ggcagccgag ctgcagacac agagatgcag atctttgtga agaccctcac gggcaagacc | 60 |
| atcacccttg aggtcgagcc cagtgacacc attgagaatg tcagtgcgaa aattcaagac | 120 |
| aaggagggta tcccccctga caagcagcgt ctgatatttg ccagcaaaca gctggaggat | 180 |
| ggccgcactc tctcagacta caacgtccag aaacagccca ccccgcacct ggtgctgcac | 240 |

```
ctgcgaggtg gcattattga gccttcactc ttccagctca cctagaaata cagctgaaac    300
aagatgatct gccataagcg ctatgctctc ctgcaccect atgctgtcaa ttgccgcaag    360
aagaagtgtg gccacaccaa caacctgcac cccaagaagg tcaaataagg ctcttccttc    420
ctcggagggc agcctcctgc ccaggcccca tggccctgga gcc                      463

<210> SEQ ID NO 23
<211> LENGTH: 394
<212> TYPE: DNA
<213> ORGANISM: Homo sapiens

<400> SEQUENCE: 23
accgagctca caccgctggt aggtggagca ggtgtgcgtg ttttgtgctc atgtaggggg     60
ttggggagtg ttccagccag cctctgtgca cctggggtgg gggtggaatg aggaggggt    120 tgttgtgagc ctgagggtcg cactgtctgt ggttctctcc ttcctgtcag ctgagcccag   180
ctccagactc aagaggaacg gctggggtga taccatctcc tggtttctgc ggggggtgtat  240 gtgagttccc tccccctgcc cccagctgtg ggactgtccc ttctcacagc caccaccaac   300
tgacttccca cagcctccag atgagcaaaa aggtaaaaact ccggcatttt ccacatcctc  360
agcatcctcc acctcctcag ctgttcgcac ccgt                                394

<210> SEQ ID NO 24
<211> LENGTH: 246
<212> TYPE: DNA
<213> ORGANISM: Homo sapiens

<400> SEQUENCE: 24
agcgtctcta ggaattgaga gagtggggaa gttaggatcc aggaggagga tggtgggggc    60
tgaggagtgg aggagcagcg tgcatctcat ctcttgtcgc cgggcgggcg ctctttcggg   120
tccagggccc ttgcaccccc agcgtggctc cggaggcggc gagacctgcc tgaaattgat   180 tggagggac tagagtgtgc ttgtggggtg gggtagtggg ggcggagaga agagatccca    240
agaagg                                                               246

<210> SEQ ID NO 25
<211> LENGTH: 233
<212> TYPE: DNA
<213> ORGANISM: Homo sapiens

<400> SEQUENCE: 25
attgagagag tggggaagtt aggatccagg aggaggatgg tgggggctga ggagtggagg     60
agcagcgtgc atctcatctc ttgtcgccgg gcggcgctc tttcgggtcc agggcccttg    120
cacccccagc gtggctccgg aggcggcgag acctgcctga aattgattgg aggggactag   180
agtgtgcttg tggggtgggg tagtgggggc ggagagaaga gatcccaaga agg           233

<210> SEQ ID NO 26
<211> LENGTH: 154
<212> TYPE: DNA
<213> ORGANISM: Homo sapiens

<400> SEQUENCE: 26
ggaccatgcc cctcccccgc ctgcagccct tcctggtaca gacctcggtc gtgcgcgcac     60
gcacacacac acacacacac acgcacgc acacacacgg tgcttcaccc cagccaggcc    120
agaccaaaag agaccattat ttcctgctgc ctcc                                154
```

<210> SEQ ID NO 27
<211> LENGTH: 743
<212> TYPE: DNA
<213> ORGANISM: Homo sapiens

<400> SEQUENCE: 27

| | | | | | |
|---|---|---|---|---|---|
| ggaggggcgg | agccggatcc | ggcctcctga | ggtgcctttc | gtgtctgccg | acccagtccc | 60 |
| agggactagc | ctggggagga | agaatggaac | ccctgcagtt | agaggttcct | cacatgacta | 120 |
| gctctgaaga | cctcctgcct | tcctgtctttt | agttggtgtg | ggagggacct | tccatgtatc | 180 |
| cagggcttag | cttgtgcccg | ggacatggtt | gtgttatgca | cacttaaatc | aatggaattc | 240 |
| ccaggttcat | ctttcagact | aggttagcaa | caacccaccg | cacccccccg | ccccaatacg | 300 |
| tgctcctaat | gtcacctttt | aagtttcctt | tcctaacaac | aataaaagtt | aagtaatatt | 360 |
| gagtattgtg | tgccaagcac | tgtgctatac | tctttaagtg | gtgaatcatc | ttgttcagtc | 420 |
| ttcacattca | gcgacagata | ttgttaccct | cattttataa | atctagaaag | aagctcaagc | 480 |
| tcattattat | tgttcagtgt | tttttaagcg | tctactgtat | gtgctaagct | ctttacgtga | 540 |
| tttcattttta | actcacaaat | ctgtgaggta | ggtcataaac | cttatcccta | ctttatcaat | 600 |
| gtggaactaa | gtacaattaa | gtaacttgaa | cagttcattt | tgttaatatg | tggcagaata | 660 |
| cttaactacc | atctgctttt | cactttcggt | atcctgtctt | acggtgttta | ttcgtggtta | 720 |
| tctattgaca | gtgaataact | tga | | | | 743 |

<210> SEQ ID NO 28
<211> LENGTH: 141
<212> TYPE: DNA
<213> ORGANISM: Homo sapiens

<400> SEQUENCE: 28

| | | | | | |
|---|---|---|---|---|---|
| tgagcacctt | ttagtttcag | tctcacatgt | cactgaggac | aatgggctgc | acatcaggct | 60 |
| ttcatggggt | tattggtgac | agtatcaccc | aaccccactg | caccctacc | acatgctgta | 120 |
| gaaaaccaag | tatcttaaat | t | | | | 141 |

<210> SEQ ID NO 29
<211> LENGTH: 332
<212> TYPE: DNA
<213> ORGANISM: Homo sapiens

<400> SEQUENCE: 29

| | | | | | |
|---|---|---|---|---|---|
| tgaacttggc | tctagtgtgg | ccactagcat | ttggggcttg | ggggttgcag | ctgtcgcatt | 60 |
| ccacagtggc | cccgatggca | ttacaattac | agatgacact | tagagccacc | ctagggaagc | 120 |
| aaaggcaagg | acaagcagct | gatgggaggg | ggagcagaag | ggctgcggcc | acagccagag | 180 |
| ccccggatct | gccctgaccc | tggtctgtgt | ccccttagcc | gaagccagca | cttcctaggg | 240 |
| tctccatttc | tctgtctgta | taagcgtcta | ataccctgc | cctggttggg | ggagggagga | 300 |
| gcatgtggat | ggtgaggagt | gagagaatgg | at | | | 332 |

<210> SEQ ID NO 30
<211> LENGTH: 329
<212> TYPE: DNA
<213> ORGANISM: Homo sapiens

<400> SEQUENCE: 30

| | | | | | |
|---|---|---|---|---|---|
| cgtaaccctg | gtgccgccgc | cgcgaaactc | cgcctgcaga | gtcgccgccg | ccgccgccgc | 60 |
| cggaggagcg | agccgatccc | tcctcttccc | tcctcgaagc | gaagtcctca | acacagacac | 120 |

```
gattacatag cctctgccca agcgcgtctc agtccagaat cattgcacct aaaggaggag    180
acgggaggat aagaagaaag tgcaatcaga cagcccagaa gccttcctcg ggttcctcc     240 agactcccct cctcctcctt tacgaagcct ccatcgctac cctccgcgcg ctcctgccct    300
ctcccaagcc gcttaatcct tcctggttc                                      329

<210> SEQ ID NO 31
<211> LENGTH: 110
<212> TYPE: DNA
<213> ORGANISM: Homo sapiens

<400> SEQUENCE: 31
ccaacaaccc atgcagccac cctgccctga cagctagcaa gaggccaaga cccacagaac    60
aatcaccatc acacctctgt cagcaggaag cagttacaga agactgacct               110

<210> SEQ ID NO 32
<211> LENGTH: 380
<212> TYPE: DNA
<213> ORGANISM: Homo sapiens

<400> SEQUENCE: 32
agccctggag gctcccactg ccagtgcagg gtgtggggcg agagcaggca tggctgcagt    60
caagacaact cctgctccct gaaaaagaaa tttgcctgtc catgttgaaa ggagagtgat    120
caggacacaa agcacaggat agagctaaac aacaacctag ggaccaagga tgctgttcta   180
gattctagag gcagctggtg tggctaatgt gctcatggct ggctctagtt gattaatccc    240
ttcaagatgc tatggaagct aaccctgaaa gtgcacctct gccctagggg gagacaggta   300
acagtgacaa gtaggaaac agtaacccag gaggacaaaa gtgagataag gggataataa    360 atctggggc tgagaacatg                                                 380

<210> SEQ ID NO 33
<211> LENGTH: 87
<212> TYPE: DNA
<213> ORGANISM: Homo sapiens

<400> SEQUENCE: 33
atttactgcc atttggcacc tgggtctggt tcagctggcg gatgagctga ttgatgcatt    60
caccctgata gccagctgtg cccatct                                        87

<210> SEQ ID NO 34
<211> LENGTH: 197
<212> TYPE: DNA
<213> ORGANISM: Homo sapiens

<400> SEQUENCE: 34
accaaacttc cccaggtgct cctcaatcac tgtgttttct gtcagagaga tggtcttatt    60
cttgaccttg gcttgtccac gtttcaaaat tcaaaattcc tggacagact tcagatttgg    120
aaatccctag gtcacataag gttccactat acgcagcatt tttaggttct tgggggtggc   180
ttttacaaag acaccat                                                   197

<210> SEQ ID NO 35
<211> LENGTH: 194
<212> TYPE: DNA
<213> ORGANISM: Homo sapiens

<400> SEQUENCE: 35
```

```
cttttgatgc acacaacaaa ggccaaggaa tgttcatctg gcaattccaa ggcatgaggt    60
ttcacttcta gttgtctgag aagcagcttg tcatgtttct gccaccagga atcatgttgg   120
aatgattcca gtcgcttaaa cctgagctct tttcctttgc tccttctttg ccaaaagtgc   180
ctgctttgcc tggg                                                     194
```

<210> SEQ ID NO 36
<211> LENGTH: 248
<212> TYPE: DNA
<213> ORGANISM: Homo sapiens

<400> SEQUENCE: 36

```
gtagcccttt tctcagttcc ctttgcgggt cttggtcaga tgatgccctc tagacccgtg    60
ctgtccaata tgtagccgct agccatgtgc agctgtcagg cccttgcaac gtggctggtt   120
cgagctgtga tacactgcaa gtgtaaacac aaaccagact tcgaaggctt agtatgataa   180
caaaagaaaa ggagtgtaaa atatgtcaat aactttttta tatatgtgtt gaaatatttt   240
gggtattg                                                            248
```

<210> SEQ ID NO 37
<211> LENGTH: 225
<212> TYPE: DNA
<213> ORGANISM: Homo sapiens

<400> SEQUENCE: 37

```
atgctgcttc cttggcaggt gattgtgatg tgaagcttag taagtcatag acgtgcaggt    60
gtctggagag tcctgacatg cagttgtggt ttcgtttcct tttggaatct tcaaaggcag   120 cgatttcat attgcctcac accctggcgg gggcgggggg ctctgggacc actggggac    180 ctgctaaatc ctcttcagtc tgagcagttc agccattgtc agttt                   225
```

<210> SEQ ID NO 38
<211> LENGTH: 194
<212> TYPE: DNA
<213> ORGANISM: Homo sapiens

<400> SEQUENCE: 38

```
ttgcccattc cctgagctgt gactgccaga ggagtgggag gttggtggtg cctccagccc    60
atcaggggca ggccctggga ccgcctggga acaggaggac tatggcacaa accgagtgag   120
tgatgggagc aacccgcagg gctctgccac atccctgtct tccttcactg acatgaaacg   180
cagaaaaggc agct                                                     194
```

<210> SEQ ID NO 39
<211> LENGTH: 57
<212> TYPE: DNA
<213> ORGANISM: Homo sapiens

<400> SEQUENCE: 39

```
agggaccagg ccaccaccca cctgatgtgg gagcatttcc cccaatccct gctgggc       57
```

<210> SEQ ID NO 40
<211> LENGTH: 56
<212> TYPE: DNA
<213> ORGANISM: Homo sapiens

<400> SEQUENCE: 40

```
cagggagacg gcgaggggt tcgtgcgttt gtaacgtctt gacatcgctg atcctc         56
```

```
<210> SEQ ID NO 41
<211> LENGTH: 208
<212> TYPE: DNA
<213> ORGANISM: Homo sapiens

<400> SEQUENCE: 41
tgcataagcc cccaggaaag ttcttctggg aatagggacc ccccccaaaa gctggtcact      60
cccttaagaa tgagaccccc caacccagag aacagccccc catggaaact ttcaaggaac     120
ctaagactct cccccaaggg accaaagacg cccccagata tgggcaatca ccaggaaaca     180
gaaaatcccc tccaggaaat gggccccc                                        208

<210> SEQ ID NO 42
<211> LENGTH: 56
<212> TYPE: DNA
<213> ORGANISM: Homo sapiens

<400> SEQUENCE: 42
gctcccagac ctgccagaac cccacaccaa gacagagtgc agctacggtg cagctg          56

<210> SEQ ID NO 43
<211> LENGTH: 532
<212> TYPE: DNA
<213> ORGANISM: Homo sapiens

<400> SEQUENCE: 43
tcccctctcc ttgcctccct ccacgtcgcg tttctgggag gacttgcgag cggttttgtt      60
ttcgttgctc ccgtctattt ttattttcca gggatctgac tcatcccgtg ctttgggcgt    120
ggagataagg tggaggggcc ggctcccggc gcgcgcgcgc gtgcgtgtct gcgcgggcgt    180
gtgtgtgtgt gtgtgtgtgt gtgtgtgtgt gtgtgtctgt gtcagagacg gcacaagagc    240
gcgcggtttc ccaacagcgg cgggagtttc ggaagcctgg ccggctcagc gtgacgtgtt    300
cgcggccccc cggtcccctc ccattctccc cctcccacc ccagggtgac gcgcagccgg     360
agtggaagca gttttggcgg gcgagcagcg ccttgcagga aactgactca tcactactcc    420
ctccagcggt ccgaggctct gcccacgcac ctcccactcc gcgcgtgatt tcctggaggc    480
cggcgccccc tccggccct ggcgggaata gcacacaggc tttcccgcgg ag              532

<210> SEQ ID NO 44
<211> LENGTH: 87
<212> TYPE: DNA
<213> ORGANISM: Homo sapiens

<400> SEQUENCE: 44
acatccagct tctgcccacc ttcttcccca ctttcgtccc cccacagag cctgagaccc       60 ggacgccaga gcatggcggg accaact                                         87

<210> SEQ ID NO 45
<211> LENGTH: 164
<212> TYPE: DNA
<213> ORGANISM: Homo sapiens

<400> SEQUENCE: 45
gtggacacgg gtgagggaag cacctgtgga atctgcaggg aggctggact ccagtcctga      60
tgtcggcccg gggaaccaaa caccttgttc agggtccttg gtcaccaccc tgactgagct    120
gactgctggc ctagggtaac cctttaagcc aacctggaag tgcc                      164

<210> SEQ ID NO 46
```

<211> LENGTH: 1288
<212> TYPE: DNA
<213> ORGANISM: Homo sapiens

<400> SEQUENCE: 46

```
cagcagcagc agcgcctgca tagctccact ctgacctgtg aaggaatggg gatgaggcca      60
ggagctagtg tctaccacgg ccacacaggg agcagtgtgg gcccttagcc cccaaggggc     120
ctgctatgca tgtggctttt tttttttttt taaacacagt aaactagatt agtcgtcagt     180
gttttaattg cccctcttct cctctcctgc attcctctcc tctcttcttt cctctctgtc     240
ccttctcttt cccctctcaa ccaggagacc atcatgtctc tctgccttcc tcctctcccc     300
tccaggggag tcaggctgtc tgtgaaagcc atgagcttct ctccctctcc cactcctcct     360
ctcctacttt cagatggatt tattcctttt ttaaacaatg aacatcggaa atgagactgt     420
ggggtgtggt ttctctctct cttttttttt taattttctt tgttgggttt ttgagcaacc     480
tcatgtcccc ttcccaggga gcttttaat ttacctctta gaactcaagt ggatgggaag      540
tagagcacta tgtgtcagta tgctttgttt tctgacacga ttacacagcg aggctttaat     600
gccatttggg taggtgagct ctgcacttc tgttgtgctg aactgtattt tcttctctca      660
tctcctcttt gtcttttct cttttcctct ccttcctgcc ttcttctgct ggcctccttt      720
tctctttctt taccttcctt ggattatcct tccaggtttt cataataaat ttatattttg     780
taaaaggatt ttgttgtacc aggttttgca tcctcactga atctgactgg cttttatttt     840
cctctccaaa atcaggtttt tgttctcaac atctttcccc atcatgtcta gtcactgttt     900
tggttttggc accatcagta tcaaatgtac aaacggttct tgctaaccaa caccaggtat     960
atctgatgtt cagatgagtt ccaataaaaa taatttttt ttttttcaaa aggtgtcttt     1020
ttcttgagtg ctggagggct tccaagcaag tccagacagc tctgtgtggc cccacactag     1080
tctagctctc atctggccaa agctgttatc tcatttgtgt aatgggagtc cttaaggtaa     1140
atttggggtc caaacttgga gggctttggg ggcaagaaag ttggtgtgtg agttctgagg     1200
ttggaaatga gttcaggtgt cttcttccag ggcagcatgg tccagtgagc acatgtaagt     1260
ttgggcagta gatcctctga gcctactt                                        1288
```

<210> SEQ ID NO 47
<211> LENGTH: 202
<212> TYPE: DNA
<213> ORGANISM: Homo sapiens

<400> SEQUENCE: 47

```
tggtggggaa gcctgcgtgg ggcagggaac ggtgaggcag gaagagggaa gggcagcaga      60
ggcctgagtg gttgcaggtt cacacactga gctgccagta actgcccagc tcagacgggc     120
tcaaattcag aagccaccat tgctcctcac ccccaccccc aggtcagctg tccactagct     180
ctgccatgac ttgatactgc ag                                              202
```

<210> SEQ ID NO 48
<211> LENGTH: 885
<212> TYPE: DNA
<213> ORGANISM: Homo sapiens

<400> SEQUENCE: 48

```
ccctgctttc cggctccctg ctcccctac cgggtttccc tcccatggg tcggtcgctc        60
ccccaacccg ccgctctgcc cctgcagtgg cctccagctg ccaccccgca gtccccgcgc     120
aggaaacgct cgcgccacgc cgcgccctcc ccttgcttcct ctcttctcca cctccaattc    180
```

```
cgggatccca gagggtaaaa cccctctccg gagcggggcc cgggaacggc attcctcctc    240
cccctgagcg cggtggtccc cggggacctg gccggtggg aagaaagatc gccaccacgt     300 gcaggcccg ggcccgcctg ccgcgccccg cccgccgcc gccgccagcg cgccctgcgg      360
agcccgcgcg agccggcagc gcgggagggc gccgttcgcg cccgagcgct gttgggagga    420 gggggcccg acgctcttcc tttatccttc cccgggtgtt taaacttagg ggtcccttcg     480
ctgcctctat gaatgccccc acaactggcg caccccaaaa ctgcacatcg tcaagtcaga    540
cttgcggcgg gtattccgca aacaggtttt gcggcgggag cagcgaggcg gggaacagct    600
ccgggaacaa agatccccg ggtggaggag cagtgcgaag gcgtctcgga acccgcggta     660
gctcgggcgg gccgcgtctg cccaggccct gagcgagccg gacggcgagc gggccgcgcc    720
gggagacgag agcctcgcgg gcgggagccc ttcccgagat gcaccgggag gcggcgcccg    780 gcgaccccg ctcccgcccg gccttttgtg ctgcgccgct cgagcgcgct tgaggcccgg     840
gaaatagccg ccgccggatg ggcgctttgg ggcgggcgaa gtcct                    885

<210> SEQ ID NO 49
<211> LENGTH: 57
<212> TYPE: DNA
<213> ORGANISM: Homo sapiens

<400> SEQUENCE: 49
ggcccctccc ggctgcgcct ggggaccgca gcggcggcgg cgggcggggg tgctgca       57

<210> SEQ ID NO 50
<211> LENGTH: 96
<212> TYPE: DNA
<213> ORGANISM: Homo sapiens

<400> SEQUENCE: 50
ctctccggcg gccgggctgc tgttgggcgg cggcgcggag cgggcggcga gctgtgcggg    60
aggggcggcc ccgaggggcg gggcgggccg acgccg                              96

<210> SEQ ID NO 51
<211> LENGTH: 132
<212> TYPE: DNA
<213> ORGANISM: Homo sapiens

<400> SEQUENCE: 51
cccatattcc caccgtgtgg ggcggagtcg tagaaggggc ggcagcggcg gcggcctgtg    60
cattctgggt attgtagtct ggggcccggc caccgctggg gctggttcca cgtggtgcat    120
ttggcggcag ct                                                        132

<210> SEQ ID NO 52
<211> LENGTH: 69
<212> TYPE: DNA
<213> ORGANISM: Homo sapiens

<400> SEQUENCE: 52
gcgccgaggg cggccggcgg acagcgagcg ggcgggcggt ggcggcggcg gcaggtgcgg    60
ccgcggagg                                                            69

<210> SEQ ID NO 53
<211> LENGTH: 1494
<212> TYPE: DNA
<213> ORGANISM: Homo sapiens
```

<400> SEQUENCE: 53

```
gcgcccatat gcacacggac gggcgcgctg cggggaccag ggctgctcac tgcggggcgt      60
gtgtttaact ccaatatttt aaattataaa agtaaacttg gaaactacag caaacgtgcg     120
tcttcgcggg gctccaagcc tgggcactgg ccggctgcgt gcacttttct gtgtataaca     180
cgcccgcagg aagcctgcgt taacatttat ctcgtggagg ggaaggtgga gcccacaccc     240
acacctcagc gagctggaga gggagttttc gaggggaaaa tgcaagcaca ttctccagca     300
tggagtccct agaggcagtg catttaaac cctaaatgtg aattattatg tgagtgtccg      360
agtagagttc cagttccgtt tggagaaact gtatgaggcg tgttccgtgt gggtgtgtgt     420
gcgtacggat acgtggaagc aggatctcgg tgtcgcgggt gtccctaggc tgggatctcc     480
ccctctcatc agataaggag aatcctctag ctccccaaaa ctggccccca taaccaatcc     540
cgtctcagtt cgtaaggggt taaccaaagc cgattccaag gaaacacagg tcccccccac     600
ccccgccac cctccactta ccccaccac agttctgcct cggaccccgg ccaatccccc       660
agatctcccc cgggacccc cacccgcag cccacccacc cgagcgcaca gctcctcacc       720
tgaggggccc agtcgcgtcg ggcctcccga ggggctgcg agtgtcagtc ggctctccgc      780
acgtgtccgc ggcctcgcgg agcaggtaat cagactctgg ggaaggagtt accagcactc     840
tctccggcga gggggtgggc acagcggcgg agggcggagg gacggcggag ggcgccgccc     900
gcgccgctcg ctggggcgg acgggggccg ctgggctccg gccggcgctg ggggcccag       960
ccggggaggc agctggggcg accgtgcggg gtggggcag ggacccgcga agccaactct      1020
gccggagacc cacccccgg cggggctggg ggctcgtggc gcagtggcaa gaaagtgtgc      1080
aaattaaagc cttccggaga gaaatgaggc ggccgagtcc cggcagtgct ccgagctccg     1140
ggctccctag ctcccttcta cgagtcgggg gctagaaggg cgcggtgggg gtgggggtgg     1200
gggggagagt taaatgaaaa tttccggctt tcgctgaaac tgtagtaggg ggatcctgcg     1260
actaaaataa gcggcattag tgggagagag tgggacgtgt cgtcgggagt cggcggagtt     1320
tccaaaccca gggtcgccca gagttggggt tttgacaggg tgaagcgggg ggcatcctca     1380
ctgtgtgacg tggacggatg ggaaaaacac aaaacaacca acaataatta tgagcggcca     1440
atgggggtgg taaataccaa tactttccaa gaaactgaaa aatcagacca aaaa           1494
```

<210> SEQ ID NO 54
<211> LENGTH: 309
<212> TYPE: DNA
<213> ORGANISM: Homo sapiens

<400> SEQUENCE: 54

```
ggctccaccc ataaagttcc cactgattat cacacggcat cctcattctc cagtctcacc      60
tactctgtct ttcaaaaatt ccccaacggc atggccacga aaaatatgcg ggggctagcg     120
gggcatgtct caggttggct tatcctgtcc ctaaaacgca cccacttccc ccagaccctc     180
cttcagggtg ggcagggaga aaacgcttct aagttgcaca gctgcaggga agcctgctca     240
ggtcatgttt ttttgacttg tctttcggct cgctgtctgg caaggtcacc ggctctggct     300
cgcggctct                                                            309
```

<210> SEQ ID NO 55
<211> LENGTH: 1012
<212> TYPE: DNA
<213> ORGANISM: Homo sapiens

<400> SEQUENCE: 55

```
tgggaagacc agccatctgg tcggggaggg ttgggggctta tcggggggtgg gcgagcgagc    60 ggtcctgggg gagggagac accgtccccc acgggatccc aagggtggga gaaaggggtg     120
ttcgccacaa tttcgcttgt cgtctcctta aagaataact tcaggaaggg gatagcataa     180
tcgcgcctcg tccttaagtt ttaaactgat ttcgacctga gcaaaactca acctcccttt     240
caaagggtgg ggggtggggg gttaaatcct gcgcctccag gggtgagaga gaaggtctct     300
gtcctcgggg cccggactcg cgaaccttt cccattccca ggacctcccc gctgtaggta     360
gcagaggtgg ctgccccatt cccctccgg ctaaaggccc ggtccagtct gcagccggac     420 gccccccggag ccctctgcac aacaaagcgc cagagtaggg taccctaact ttccctcccc     480
attcagcagc tatctgggac ctaggggggcc tccctcctcc agggccgccg cggcctcggc     540
aggactttca ccacgacggc cgcatgtccg gaattcccgg ggcacctcgg aattacctgc     600
ctcgcaaccg ctggcccgct cgccttttgc caggaattaa acaaacggcg cgaccccccac     660 gatgagcggt tggagcggac cgcggcgaga gcagagcttc tggcactcac tacattcaga     720
actttcctta aaagccgagg aaagagcccc cagggactgc ccgggggtct gagccaggtc     780
gagggccaca caggtagccg gggagccgcc gccggccgcc caacccgcct gtcctgcatc     840
cccccaaccc cctcccgctc gagtctagcc ccgggctccg cagcgaagga agcgtcgggg     900 acgtccacc cccgcaggga actgcgcctg ctgcccccgc cggggcccgc actgccctgg     960 ctctccccc actcgccccc cagacggtcg gcttcggcgg agagaaacgg ga            1012

<210> SEQ ID NO 56
<211> LENGTH: 54
<212> TYPE: DNA
<213> ORGANISM: Homo sapiens

<400> SEQUENCE: 56
acctgggagg cagacggcac ctcctgcgac cgtcgccgcc accgccgccg ccgc            54

<210> SEQ ID NO 57
<211> LENGTH: 326
<212> TYPE: DNA
<213> ORGANISM: Homo sapiens

<400> SEQUENCE: 57
cgccctccga ccccgccggg ccctcctcgc cctggccccc gagcgcacac ctgcccccttc     60 aagcccggg gccacagcgg ccggcgggga ccctggcggg ggcgcgggcc ggacttcggc     120 cgagggggcgc tggccaggggc gagggacggc ctcgcagagc tcggagacgc ggcgcgagtt     180 tccccccgcgg gccgcgcggg cgcagagacc gccgccagca ctcacctgcc cgcttcccct     240 agcgcagcg gaacgacgta ctccggcccg gaccccgccg tccgcctcaa ccaaccccca     300
ggcggtggcg gcggtggcgg cggcgg                                          326

<210> SEQ ID NO 58
<211> LENGTH: 739
<212> TYPE: DNA
<213> ORGANISM: Homo sapiens

<400> SEQUENCE: 58
tgggaggccc tgcccgccgc cccgcgtcct cccgccact gccaccccgc gcatccggag      60
ccgcagcaga ctcggcgggg cccggagccc cacgcccccg gccgcccct ggccgccact     120 tgtttactcc ccggcgcagc ctagtccgac cctgggggcc gccccgccc accgcctatt     180
```

```
ggccgaggag gcgcgaagag ccgtaacgat tggcccgggg aggcgcgggg cgagcggggt    240
aggctgcgcg agaggccgag aggggcagc aggcgatggc ggcggcggta gctgcggcgg     300
gtcggttagg ctggttgttc gccgcgctct gcctgggcaa cgccgcgggg gaggccgcgc    360
cgggcccgcg agtgctgggc ttctgcctgg aggaggatgg agcggcgggc gcgggttggg    420
tacgcggagg ggcggcgcgg gacacgccgg acgccacctt cctcctgcgc ctcttcggcc    480
cgggcttcgc caacagctct tggtcctggg tggccccgga gggggcgggc tgccgggagg    540
aggcggcctc ccccgcgggc gagtggcgcg cgctgctgcg cttgcgcctg cgggccgagg    600
ccgtgcgccc gcactcggcg ctgctggcgg tgcgcgtgga gccgggtggc ggggcggctg    660
aggaggcggc gccgccctgg gctctgggcc tgggggcggc cgggctgctg gcgctggcag    720
cgctggcgcg aggcctgca                                                 739

<210> SEQ ID NO 59
<211> LENGTH: 412
<212> TYPE: DNA
<213> ORGANISM: Homo sapiens

<400> SEQUENCE: 59
tctcccctga catctcccac cccaagccct agagccaggg ctgggcatct gtgcagggta     60
caaccctgcc cagggatgcc tgactctgga aaggccaccc ctttggcctc aaaccacatc    120
acccagcagc aggtcctcag accagccctg gacaggagct tgactggctg tgccccccaaa   180 ggccccagag ctccctgccc ccactgagcc tccaccttcc catccataag atggggtggg    240
gagtcatcca gcccagaggc cccaggggca tggggagtga cagattaacc caaggccccc    300
cctcccgcaa caggcggctc agcacacact tggcgggggg ccatgctggg ccaggagagc    360
tcccccgcac cagttccccg cgcgcaaggc tcgccccgcc ccccaggaca gg             412

<210> SEQ ID NO 60
<211> LENGTH: 56
<212> TYPE: DNA
<213> ORGANISM: Homo sapiens

<400> SEQUENCE: 60
cgtgcatgta cccgccgcca ccgctctccc acacctccct ggtccagcag ctagtc         56

<210> SEQ ID NO 61
<211> LENGTH: 601
<212> TYPE: DNA
<213> ORGANISM: Homo sapiens

<400> SEQUENCE: 61
ccaagccagg ggctctctgt ctggtgacga gcagctgggg ggtggggtgg gacctgtggg     60
agatggactg gcctcctctc cttgagtcaa ctgctgctta ttggaggtgt ggatgagaca    120
cttagggtct ttgctccttt attagtcaga gggtagcaag gacagttcca ttgcagaggt    180
agtggcagag aggctttcag ttgtccgtgg cggctctgtc cagggagttg ctgagttgct    240
attggcttga tatctctggt ggggtgtggc tagaggtcca ggcctggagg acctgctcgt    300
tgaagagatg tgggaatggg cacccacata acagtctgtt cacttttcca tagggctgct    360
gtagtatgct gggggccagc tccagtccct ggtcacttta gattttccag tacctggagg    420
tgtcaccagt gaaagctgcg aaacagcaaa gatggtggcc ttcctttctc tctgggagct    480
ccatccctgg gaaatacagg cctgttgctg gcccgaacac actggtagga catggctgaa    540
gacgctagtt gggagaccct cacccagccag gaggaatagg atcagggacc tgctttcaaa    600
``` a                                                               601

<210> SEQ ID NO 62
<211> LENGTH: 83
<212> TYPE: DNA
<213> ORGANISM: Homo sapiens

<400> SEQUENCE: 62
gcgactacaa aggctgcagc cgcctccttc tgctttctgt ctctgctctc tgtcttcaca    60
ctcaatgaaa tccttcatgc gcc                                           83

<210> SEQ ID NO 63
<211> LENGTH: 68
<212> TYPE: DNA
<213> ORGANISM: Homo sapiens

<400> SEQUENCE: 63
acagaaagga ggcaaaggtg aagtccaggg gaggtcaggg gtgtgaggta gatgggagcg    60
gatagaca                                                            68

<210> SEQ ID NO 64
<211> LENGTH: 282
<212> TYPE: DNA
<213> ORGANISM: Homo sapiens

<400> SEQUENCE: 64
tagagcttgg atgttagcag tcaatcagga tgatgcataa cttagaaaaa atgatgtttt    60
gcaggagtaa tcctgtagca gccatttgtg tacatgaaca ttatgaaaac atttgctgtc   120
atatttaaag tcaattataa gacaattttt ggtaactaaa tgtctaaaat cgagttattt   180
gttatgggtt tatgcacttt aaaatatacc atttaattga aaggcagtat acttctcatg   240
ttttgttggc ttgtttcatt aatattagaa atgttcattt ca                     282

<210> SEQ ID NO 65
<211> LENGTH: 412
<212> TYPE: DNA
<213> ORGANISM: Homo sapiens

<400> SEQUENCE: 65
tgggcatgga tttggggcag gatgtgacaa aaatctcata ctcatgtctc tctgggcctg    60
ataaattttg catactttat atagttcaga ctcttctgag ctacgtttct ttctcttcct   120
tttggttgag tttttttttc ttctgaaagt attgatgatc aacattttag atgtaagttt   180
gtcccatgtc actggaagac ttagttttag ttagtctcat cccacattgg aggaagagag   240
gagagataaa atggcttaag aatgcagtga agtctcaagg ccaagttgat tgcaacaca    300 aagggacagg gcaatggtat ttcaggtcat ctgcttacaa aggagctatg gcatgttgga   360
tcatttctaa gcatctagct atcattattt tagtgttttt gttgattttg ga          412

<210> SEQ ID NO 66
<211> LENGTH: 105
<212> TYPE: DNA
<213> ORGANISM: Homo sapiens

<400> SEQUENCE: 66
cttaatgtct cagaacttgg gtgtcgttgg tctcagatac cactttgcca tccactatcc    60
agcagatagt ggtcttttgg atggtttgca tggagttgct gctgt                  105

<210> SEQ ID NO 67
<211> LENGTH: 50
<212> TYPE: DNA
<213> ORGANISM: Homo sapiens

<400> SEQUENCE: 67
agcaggatcc cgttgagctg ctccatctgc agggcgtggc aggcctccac        50

<210> SEQ ID NO 68
<211> LENGTH: 170
<212> TYPE: DNA
<213> ORGANISM: Homo sapiens

<400> SEQUENCE: 68
agcagctcca acctcgacgg actgcgtggt gacccctgtg ttgctctcct caatctgtta        60
agaccagtac ttgtccagca cctattggtt cttcatgcca gctcatcata ttgggcccgg       120
atgtctgcca ttatcttggt gaggtcctga gatttgggga catctacctc                  170

<210> SEQ ID NO 69
<211> LENGTH: 229
<212> TYPE: DNA
<213> ORGANISM: Homo sapiens

<400> SEQUENCE: 69
aaaggaggtg tcccacgcag taaactcccc tgcaggtggg ctgagggcta gggctgagcc        60
tcaggtgggt ctcccattcc ctgtgctccc ctgcacagtg gcctcctcc cggactctgg        120 ggcagccaca aaggggcag gctgggaggg gctgccacag ctattcactt gggcaggacg        180
tcagaggact cggacaccag cttcccattt cccattgtgg gtctcgatc                   229

<210> SEQ ID NO 70
<211> LENGTH: 120
<212> TYPE: DNA
<213> ORGANISM: Homo sapiens

<400> SEQUENCE: 70
atcccggtgt gcccagccag tggtattaat ggatggcatt atgtttggag gcagcagcat        60
agaggactgt tgtttataga gaaaagattt gggaaggact gtttacaatg tgggtcagcc       120

<210> SEQ ID NO 71
<211> LENGTH: 65
<212> TYPE: DNA
<213> ORGANISM: Homo sapiens

<400> SEQUENCE: 71 gtattttag ttgtagattt ctttgctcct tctccactcc cactgcttca tttaactagc        60
cttaa                                                                    65

<210> SEQ ID NO 72
<211> LENGTH: 268
<212> TYPE: DNA
<213> ORGANISM: Homo sapiens

<400> SEQUENCE: 72
gagcactgtg cttagtggca gtccggattt ttccctccac ccccgcggcc accctgccc         60 accgcgccgt cgggcatgga tctggcaggt gcgaggccga ggcagggct cagcgaagga       120 cgccgagttt acagagcgcg cgcgcctaga ggaggcagca gcagccgcag cctgccgcc        180 cgaactttgc gagcctggcg ggggagcaca gaggcgggcc gacctgcccc gctagcgctg       240
aggaacgact ccctttatgc cagctcgc                                              268

<210> SEQ ID NO 73
<211> LENGTH: 167
<212> TYPE: DNA
<213> ORGANISM: Homo sapiens

<400> SEQUENCE: 73
gctcacaatg ccccgcccca cacttcacag tgccctcccc gacacctcac agtgccccac            60
cctggctgcc accctcccc cacagctcaa aatgtccctg cctgggctgc cccaccctgt           120
gacttatgct gctgctgctc tcctggcccc tcatgcagtg ccagtgg                        167

<210> SEQ ID NO 74
<211> LENGTH: 934
<212> TYPE: DNA
<213> ORGANISM: Homo sapiens

<400> SEQUENCE: 74
ggtcagaaag atcaaatttt ggcagggtgt ctgtgttcat ttcccattgt tgctataaca           60 aattaccta ttttacagtt ctggaggtca gaagtcctaa atgtcatcct ttcctttcac          120
tggtgtgcca cagcaagatg gtggtgcagt ttttcaagaa gaggaagttt gtcattgatg          180
gtatcttcaa agctgaactg aatgaagttc tcattcagga gctggctgaa gatagctact          240
ctggagttga ggtctgagtt acaccagcta ggacagaaat ctttacctta gccaccagaa          300
cacagaatgt tcttggtgag aagggctggc atatttggga attgactgct gtagttcaga          360
agaggtttgg cttttcagag ggtaaagtag agctttatgc tgaaaaggtg tctacaagag          420
atatgtgcca ttgtccaggc agagtctctg tgttacaaac ccctaggagg gcttgctgtg          480
cagaaggcct gctatggtgt gctgcggttc atcatggagt gtgggactaa aggcttcaag          540
gtcattgtgt ccaggaaact ctgaggacag agggctaaat ccatgaagtt tgtgaatggc          600
ctgatgatcc acagctggga ccctgttaat actatgttga caccgctgtg caccatgtgc          660
tgctccaaca ggctgtgctg ggcatcaagg tgaaggtcat gcttccctgg aaccagctg           720 gtaagattag ccctaggaag tccctgcccg accaggggca ggggacccat ctttgggttc          780
gtggaaccca aagatgagat actctccacc actcccatct cagaagagaa gggtaggaag          840
ccagagccac ctgccatgtc ccagccagtc cccacagcat aacagggtct acttagcagc          900
tgtgtctgga gtctggatgt tgttctgtaa agaa                                      934

<210> SEQ ID NO 75
<211> LENGTH: 518
<212> TYPE: DNA
<213> ORGANISM: Homo sapiens

<400> SEQUENCE: 75
atgggtaaag aatattccat actgtcaaca gaccacactg tcttctaaaa tcgcttcagc           60
agtgaggatc ctctggaata gatcttgtta atcctgagga attattctcc cagcggtgag          120
ctatgagaag tggaatcacc agatgtagta attcctgaca gaactgccgc ctgcttgtgt          180
ggctgagatg ctgacctagg tatcaggctg gtcgcgccgg aacccagcac ccacgctgag          240
tctttctgag ctccactctg ctcctgttag atattaacca cctgaggtag ctgtccagat          300
tcaaggcggt agtgattttg tgtgtctgtg tatttatcac ggggtccgcg gcgggaacgc          360
aggggctgtg tcccacgtcc ccaaacctct agtagggtac ggcgcgatga acatcttcca          420

```
taaaccttaa acctcccggc gctcagtcac tggttcttat ttcagccctc ttagccccgt      480
aggtcggcgc gctgaaaacc tttctggtac ctggggcc                             518
```

<210> SEQ ID NO 76
<211> LENGTH: 423
<212> TYPE: DNA
<213> ORGANISM: Homo sapiens

<400> SEQUENCE: 76

```
ggtggtcttc ttatggatac tcacgttctg catcccagac tccagacggc tctcctcgcc       60
ctccagcagc ttcctgtagg tggcgatctc gatgtccagg gccagcttct ggtactcacc      120
cagctgcgtg ccatgtcctg cttggcccgc tgcatggcgg cctccagctc agacagcttg      180
gtgttggcat ctttaatggc cagctccccc cactgctcgg catctgcgat ggcggcctcc      240
agggaagccc cctggccttt gaggccctca gtctcagcct ggagcctgct gatgttctgg      300
ttcatctcgg agatctgtct ttgcacaacg caggtcatcc ccatgcttcc cagccagcgt      360
ctgcagctcc tcatacttga tctggtacgt gctttcagcc tcagcccgac tgtggatggt      420
gat                                                                    423
```

<210> SEQ ID NO 77
<211> LENGTH: 787
<212> TYPE: DNA
<213> ORGANISM: Homo sapiens

<400> SEQUENCE: 77

```
gagcggggct gtgtcccccc agcccaagcc agggacacac ctggaggaag gcaccccagg       60 agctggggc tgggagttcc aggctctgag aggaggccca atgggcccag aagcaagcaa       120
acatctgtct aggtgcaaca atcaagctct attttgtaa ttaaaaatgt atccaaaggg       180 aaaaagaaa caaaaggaac aatatttgta ctctatgttg ctgcagagag cagaactgcg       240 gaggggtgc tagtcccaag gggtggactg tgctgtgcta gtgccctaaa tcctgcaagc       300
gcggggttgg ggggcgggg gagaccgctg tcggggtcg tgagttccgg gcccttgtgt        360
gcatgttcac gtcctgtcat tcttgccccc agctgagaga gcagtagagg aaaggcacta      420
catccaccag cctttgcatt ctcctcggag cacacagaaa gacattttcc agttatcttg      480
cacacaagtg ggcggcggga cccgttttgg ccgggaacgt tgtcaggaac gctgtacacc      540
acttccaggc ggtcacgtcc gagctgccca ggcagtcctt ctgcgccctc tgctggccag      600
atggaggctg cagaccctgc ggggccatca ggagagaacc accaagcacc ctctgcacac      660
cgcattgcct gtgttgggca caaagaataa acttttattg catcttaacc cactagaaat      720
gtaggcttgt ccatcacagt ggggcgttac ataccctaat acatagggaa ggcataggta      780
gatttca                                                                787
```

<210> SEQ ID NO 78
<211> LENGTH: 56
<212> TYPE: DNA
<213> ORGANISM: Homo sapiens

<400> SEQUENCE: 78

```
ttttattgca aagcaaaagt gtttattaat aattggggc agggtggggg cgggga            56
```

<210> SEQ ID NO 79
<211> LENGTH: 57
<212> TYPE: DNA
<213> ORGANISM: Homo sapiens

<400> SEQUENCE: 79

```
aatcgtgccc tctcccccac cccccacctc acgaagatta cttacagttt ggttttc      57
```

<210> SEQ ID NO 80
<211> LENGTH: 488
<212> TYPE: DNA
<213> ORGANISM: Homo sapiens

<400> SEQUENCE: 80

```
ccggctcctg gcgggtccgg tgtccggcca ggcccaactc gaccccggcc cggtccggac    60
cccggcgccc agctccgtcc cgcgctcgcc cgtgggcctc ctgcgccagc tgacgaggct   120
tggacccgcc gctgccagct cggccctggc ctgcgccgga tggggtcttc ggctgccccc   180
gcgcggcctg ctgctgctgg gctggtgtcc cttcgagggc tccgcgcgcc tggagccctc   240
acacacctgc tggccctaag gccctcgagt cgggaggggg acagggtc agctccactc     300
tttccccgag ggaccatgtg tgggacacct tgagagactc ccaccagccc cctggagctg   360
gagtctgaag ccgctatctg cggaggccca ccctgcccag tagatggaac aggggctgag   420
cccatcatgt cactgtcggg ggtcccagcc cttctcagcc ttgggccaga ccactccagc   480
cccgggat                                                             488
```

<210> SEQ ID NO 81
<211> LENGTH: 552
<212> TYPE: DNA
<213> ORGANISM: Homo sapiens

<400> SEQUENCE: 81

```
tccgctggag cgaccagggt gctgccctca gccccagccc cggggggagc tggcgcccgc    60
gatggacaga tagatgctcg tggggtggaa ggaggttgcg actaggttaa gggcagtctc   120
cgcctcggtg ccccccgccc ccgctcgtgt tgtcacgggg acttgctggc gtggtgcttc   180
tcgaattgac agccccgggg ctctgcagag ttgtggggcc ccggcatcag tgggtggacg   240
ggtgttgtcc ctacgggcgc ggggcgggcg ggctggactg gacttctctc cccggaccgt   300
agccgggtgt gccgcgccac cccagggctc ctggacgggg gtatccgcc tctcgggtaa    360
gtccggaatc ggcgctgcag cagcggacgg gaaaagctgg gggcgggact ctccgagagg   420
ggcttctgca gctgggcgcc ccgggcgggc ggggctcggg agtctcctcc ctccgcttct   480
ttgttcagtc gcgagactct ccctccccctc cccctattg tgcaacaccc catccccggg   540
acccgctgca gt                                                        552
```

<210> SEQ ID NO 82
<211> LENGTH: 271
<212> TYPE: DNA
<213> ORGANISM: Homo sapiens

<400> SEQUENCE: 82

```
gcttcactcc tgccccaaga ccccagcctc caccctcctg gttctgccaa ctgttgagtg    60
cagaaagatc acagaactcc aaggatttgg agctcaatga tttcaggggc tcactggcat   120
tccccctgctc tgcctagaaa tccttcctgt gtcctggcca cacccccctc ccggcgcca    180
ccacagctag tccagaaatt ccctgcctc acaagaaccc acttcctctc ctcccctgtc    240
cctcccggct tattgcttta tgagccagct a                                   271
```

<210> SEQ ID NO 83

```
<211> LENGTH: 136
<212> TYPE: DNA
<213> ORGANISM: Homo sapiens

<400> SEQUENCE: 83
gagtgaaggg taaaccaaag gaaactgagc aggggcgggg caggagggag aaacaaactg      60 gctgggcgg gagaaaacgc ctgcgcgggg cggggagagg taggatttag ggcccgacgc     120
ttccgattat tttaag                                                    136

<210> SEQ ID NO 84
<211> LENGTH: 58
<212> TYPE: DNA
<213> ORGANISM: Homo sapiens

<400> SEQUENCE: 84
tagtcgcgcc gccacccgcc cgccaagcct tcttacccctt acatcggccc cgcgtcca      58

<210> SEQ ID NO 85
<211> LENGTH: 106
<212> TYPE: DNA
<213> ORGANISM: Homo sapiens

<400> SEQUENCE: 85
ttccgtgaag ggtgaaaagg agataaggaa gaaccaacaa tctaccccct cccgccgccc      60 cccaccccg cgccacggtg atcagtttgg acttcaaagc cagagc                   106

<210> SEQ ID NO 86
<211> LENGTH: 537
<212> TYPE: DNA
<213> ORGANISM: Homo sapiens

<400> SEQUENCE: 86
ccggtacaca ttgaactttg cgggcgacgc ggggttgtgg ggcgggcgtg tagagagggt      60
ctgaggcgcc ggggcggggc agggaggccg gactcaccct agaactggta gcggccctcg     120
cactgggggg cagtcagagt tggggaactt tctaggggtt gggcaaaagg ggcagcggtg     180
ttaaccgcgc acagtctcac agccacagac ttctcatatc tccccgatta tttcgcggcg     240
tattagtccc aaccttggct aggcctgaaa cttttttggag gttgttccat gtctagggta    300
ctccgacttt ggagttttgg agagccacgt aacgagggtg cggctaagat gaggaaaagg     360
cacttccggg attagatttc gttcttgccc agacatcgtc tttacggacc cgctcctggt     420
ggttgatttg gtttgttatg agagaaattg ttctttagaa aattggagcg taagtctaga     480
ggttatgtga cagctcctaa acgattgtct gcccaagata ggctcggtaa tgctccc       537

<210> SEQ ID NO 87
<211> LENGTH: 172
<212> TYPE: DNA
<213> ORGANISM: Homo sapiens

<400> SEQUENCE: 87
tgcaactcaa attaccttaa gattagaaaa aaggtcaggg ggtgggggca gtgtggattt      60
atggcgtcat acaactgtat caggtttagc tggatctagg ggctaaaatt atgtcaggaa     120
tctgtccccc ccatctgttg actctgcttt cctgtgcatg acttcaggtg gc             172

<210> SEQ ID NO 88
<211> LENGTH: 92
<212> TYPE: DNA
<213> ORGANISM: Homo sapiens
```

```
<400> SEQUENCE: 88
tcctttagac agcgaacact ttaaccccg cgtcaggata gccccccccc cccatttgca       60
gggaggggta tgtccgcttg tcctctaatc cc                                   92

<210> SEQ ID NO 89
<211> LENGTH: 246
<212> TYPE: DNA
<213> ORGANISM: Homo sapiens

<400> SEQUENCE: 89
tggctatgcg ggggccaacg cgattgtggg tgctcgggga gtggggggg gcacgaccgt       60 aggtgctccc tgctggggca acccatcgct ccccatgcgg aatccggggg taattacccc      120
cccaggaccc ggaatattag taatcctaat tcccggcggg ggaggggcg cgggaggaat      180 tcaccctgaa aggtgggggt ggggggggtc gcatcttgct gtgagcaccc tggcgaaggg     240
gagagg                                                                246

<210> SEQ ID NO 90
<211> LENGTH: 112
<212> TYPE: DNA
<213> ORGANISM: Homo sapiens

<400> SEQUENCE: 90
tgggctggct agggaatggc gccgaggctg gggtcgggc aggggctggg gtcgggtct       60 aggcggggc ggtgcgggcc cgactcgccg ccaacaaagg cggctgccgc cc              112

<210> SEQ ID NO 91
<211> LENGTH: 131
<212> TYPE: DNA
<213> ORGANISM: Homo sapiens

<400> SEQUENCE: 91 caagaccta tccctacctg ccaccccca cccccgcca caataaaaaa tacaagtctt        60
gagggagaaa ggacagagga gctgtggaga ggaggcctga ggtctgaggg tggggatca     120 gggtcaggtc c                                                          131

<210> SEQ ID NO 92
<211> LENGTH: 317
<212> TYPE: DNA
<213> ORGANISM: Homo sapiens

<400> SEQUENCE: 92
gacagaggca agtgtaaatt aatgaacctg ctttgaagcc catccccac ccgcccccaa      60 ttctggacaa ataggaagtc aacaaaaggc ccctgtctaa gacgtcggag cagtaagcag    120
acctaccacg atcttcacac agaagttact cataacccct atcatgcaga gggggtagga    180 cccttttgtca ctgtgagcag ggggttgctg aggcctggtt ctaccttggg aacagtgctt    240
atcatcacag cctgggggttg gacaaggaag gccatgcact ggagcaaaca cagttccagg    300
tgcaggagcc agacccc                                                    317

<210> SEQ ID NO 93
<211> LENGTH: 256
<212> TYPE: DNA
<213> ORGANISM: Homo sapiens

<400> SEQUENCE: 93
```

```
aagtgcctag ggagtgcttt ctttattgaa tagggctttc tttgctttct tctataaaat    60
gagttaaatg taaaaaagcg aaatctcgct atgcttccgc taaataagag gaaaggcatt   120
atttaataaa tctagtctgg tgggtcccac ccagcatgca tatttaaatc acacctggag   180
agcttttaga aagcatccca accccccacct ccacacccct gccccaatgc cagagcacct   240
gatttaattg ggatag                                                    256

<210> SEQ ID NO 94
<211> LENGTH: 827
<212> TYPE: DNA
<213> ORGANISM: Homo sapiens

<400> SEQUENCE: 94
tagagacatt cctgccaacc tccgcaccct ctcacgcccc accccacgtg tgagagtctg    60
caaaaccacc ggggattgga ttcgatggcg agcttcacgc tcgggaacag tcagtaatcg   120 gaagggaag tggacagggg aacttcaaga ggcgagcctg ccacgcggga agcgcccgaa    180
cttgcgggtc tccatgaatg cagagggcgc cgggaagggg gggcatccgg ccgcgaccct   240
ctctgcccct cccattcgct gccccctcc ccgctggaat ttctctgtaa agcaagacgg    300
agtaggggga gggggagagg gaaggggcga gagggccctc ggctcactcc cgagacgtga   360
ggactcgcca cccaggcatt ctcctcgggg tgggctgggc cccgggacga ccacccgctt   420
cttcctcgcc cccgctgccc ccacttcggg agacccagag ctctgatgc ctttccccgg    480 agaaggggg gtgtgcggag tcgggtgga agagaccttg ctcgcagagc tatatcaagt    540
gatgtccaga ggctgggagc cccggcgcc tctgtcccctt gcctgtcggg ttagatttat    600
actttaaaaa tacctcccgc cctccctcct tctctcgcct ctccccgctg caactttctt   660
tgatccgctc aaaggtggct taggtgaaat tggagtaatt cccttatggg ggtcttaaaa   720
tgtaagtgaa tgtccttatc cggggtgact caaaagctta agtcgggaag cccaacgtga   780
ctaaaaccaa taggtgattg ttcggggccg actgtgtgcg ggtgtac                 827

<210> SEQ ID NO 95
<211> LENGTH: 110
<212> TYPE: DNA
<213> ORGANISM: Homo sapiens

<400> SEQUENCE: 95 gttttttaagc atagtacctg atagttttttt aatcttcacc cacacccacc ccttccccat   60 aactttttg attgattatg aaatatttca agcaaacaca gaaaataata                110

<210> SEQ ID NO 96
<211> LENGTH: 57
<212> TYPE: DNA
<213> ORGANISM: Homo sapiens

<400> SEQUENCE: 96
actcaaatct cacctcccc ggattccccc cacccacccg ccccaagccc tgggtaa        57

<210> SEQ ID NO 97
<211> LENGTH: 1469
<212> TYPE: DNA
<213> ORGANISM: Homo sapiens

<400> SEQUENCE: 97
cgactctcaa gtggagagag gatagaaagt caagtggcgg gggtcgcgac cagtgatcgg    60
gatttcagtc tgatctcagt acccagcgga acaggaccat aacctaaaga aatgagcttt   120
```

```
ttccggagca aagagcggcc ccgatttcaa agtagaaaaa ataaactgct tgggggtgga      180
agatggcgag gggcgggggg cggggaggga ggcgggtcgc ggcgctggct ccggggtccg      240
cggcacggcc tcctctgccg cgctgccagg gcccggacc ctgcccggcg ctgcgcccac       300
cgcgagggtg ccagacccgc cgcgccgccg ccgcgctctc ccagccgcgg ccccctcccc      360
cgccgcttcc tcttgctctc ccagccccctt ccccacgtg tggatgacgt caaaattccg      420
cgaaaaagcc gcgtggtggc tccccgagcg gaggcgcgat tccgccgccc agcggccccc      480
tcccgggggc gcctggaggg ggagaagggc ggaggcggcc ggttccttct cctcccggga      540
ggcaggaccc cccgacgccg accgccggac gccccccgcc ccaaagctta ttggaaaatt      600
cacttttgta aagcaaatgt atttccagag ctattttcgg ccgcgtgagg cgtgtcctaa      660
gctgaatcag acaggaagag ggggaagttc gggtctttta atttttttttt tttccgaagg    720 gaggggagtg agatgctagg tgggtgacag acggcaggcg ctcgccttct taactcacgc     780
ctgtcgcatc tgccgcctca gtaatccagc cccgtccaag ccgaaattcg ccgaagggag     840
tgcggatgca caggcctggc ggactctgcc ccctccaga acgcagcggc ccagcgcccc      900
ggcgggcgcg gctgcgacca gagggtcccg gaagcgagtg aacacctgca atcgcactgc    960
ccgtccccac ccaccctgct ccccgtgct ctccgcttcc cgacgttttc ctcttctcct     1020
tgtccgcatt tttctacttt gcctgcactc cctccttcct cttgatgtgc ctcctatgtg    1080
tcccctcgga tttatgtgtc ccctcgcatt ttgccagtcg ggttttcggt tttgattgac    1140
cgtccatccc tccacggaga aacacaaaca cagctccact cttggggga gccgagggga    1200 aggcagtggc tcccatttct gagcctgaac tcagtcacta cccgctcccc acctggccta    1260
ggcgcccctg cgcggagaag gcgggactcg aactcgcgct gctccgggc cttgagccga     1320 ccgcggaatc acctggctgg gaggcatcct ccaggtaagc ttgggagtat gtgtgcttag    1380
tgctgcaggc tcctgcagaa aagtgcctat aaacacccaa caccctgctg caccctccac   1440
ctccaggctt tgtacactttt ccaaccgaa                                      1469
```

<210> SEQ ID NO 98
<211> LENGTH: 57
<212> TYPE: DNA
<213> ORGANISM: Homo sapiens

<400> SEQUENCE: 98

```
ctggtgggga ggagcctgag gcccgtggtg ggggcgggga ggggctgcag agaggcg        57
```

<210> SEQ ID NO 99
<211> LENGTH: 60
<212> TYPE: DNA
<213> ORGANISM: Homo sapiens

<400> SEQUENCE: 99

```
cctccctccc cctctcttcc ccacctctcc tcacccgccc ccccaaaagc ggcccctggg     60
```

<210> SEQ ID NO 100
<211> LENGTH: 61
<212> TYPE: DNA
<213> ORGANISM: Homo sapiens

<400> SEQUENCE: 100

```
gcggggggttg gggggggaggt gagggtggtt gagggggggaa ggagccagaa gagagaagct  60
a                                                                     61
```

<210> SEQ ID NO 101
<211> LENGTH: 999
<212> TYPE: DNA
<213> ORGANISM: Homo sapiens

<400> SEQUENCE: 101

```
tatcccagaa aagcaacagc taccacccccc acccttcttg atctgctcct acatctgtag      60
tgctatgctg ggcgccagcg gggcctggga ggagaaggag tgggggacga aagggaggag     120
gcaaaaaggg ggcttggtgg aggcagaagg tgaaccaaga cttaaagctt ctggtgagtg     180
ctgggaggac tggacagaga gagctgttct caggggacag taaaggaggt gaaggcagga     240
gccagggagt tggagggaga tcaggacaga ggatgggaaa ggaagaaatg gccccccttc     300
catcaaggaa agcagcagag cttaaggcag ggaaaaggag tcaccagctc accectgtct     360
tctctgtccc cttcacectg ggccctccag catctcagca ttggtccctt ctctcccac      420
cccagagcat cacattcctc atctgtgctc ccagccctat tcactgttca aaagaaacta     480
tatttgggct ccttaattaa gtccttctag caaacagcct gcgaaatggg aagacatgag     540
aatttgggtc tccctcctga cagctagcag cacctcctct gtcaattcct ctcttctctc     600
tgcttacccc ctccccctc cactgttatc tgtagagggg ttctgctccc ctcctttgtt      660
ttagccaccc acttctcccc tggggtaagg tcctcaggag agggagagaa gtctgggctc     720
gtgcataccc accccctctg cacacctcag gagctgagac tgatgggcaa gggagttggg     780
ggtgccaggg tggggggggg ggcagcagga tccaggcact cagatgccca ggctgggtct     840
ccatcctggc tgttttaaga acctgtgtca tcattagcct ccttgtaggg gccectacag      900
ggaggtgcaa tgaccttggt ttctggggcc tttgatgttt actggggata tcctgggcct     960
cagccatctt gccctcctct tctttgcctt ctcacctttt                            999
```

<210> SEQ ID NO 102
<211> LENGTH: 827
<212> TYPE: DNA
<213> ORGANISM: Homo sapiens

<400> SEQUENCE: 102

```
ggcatcagga aagggtcggg tttgtgggcc agggcacgtg ggggctagga gagcctggtc      60
atgggagggg actctgatgt tgagtcagag cttggagctc tgggggctct tgatgttgag     120
agagaggggt aggaccacgt ggcagggccc tggccaccca gtgtggcaga gagaagggag     180
agagcagaag ctggcgtctg tgaagcctga ggcttacccc tcctcccagg gcaggaagct     240
gtctgccatc tccaaggccc ggtgccacgg actttattcc tcttgattaa acataggccc     300
ctgtgaacct ctgagtccca tgtctaggga tgtgccaggg ggtgaggggg caggggatg      360
aatgctgact gtcaggaagc agcgtcctga gctccttttc tgcaccagga cctgcactgg     420
gactttttcca aaatctcacc cctcatggca ccgccaaagg ctggtctcag ccctggctgc     480
tgaggagcag ttgacgttcg cagtggccgt tcagagggggc ctcgggtga ccgtttgggg      540
ctgcacagcc agaaaagggt ggagctgggg ttcggatgct ggcagtctgc atccagaatc     600
ctcccctcc ccgtgcccgc acctcccggg agtgggagct aggagggcct ggagtccgat      660
gtgggtcccc tccctggcta ccgcctgcgt gggtgctggg cgtggggag gaggccaggt      720
ttctcgggct cacggccatt ctgtctgcct agaacccagg tggaggaggc ggaggcggag     780
gcggtggcgg tggccagtgg cactgcaggg ggtgacgacg ggggtgc                    827
```

<210> SEQ ID NO 103
<211> LENGTH: 193
<212> TYPE: DNA
<213> ORGANISM: Homo sapiens

<400> SEQUENCE: 103

```
ccacccgcag agggctggag aggaggggc agattgaagc ggggcagagg aggcagaaaa      60
gacggctttg ctggaggctg tccttgggca gagctggagg gggaatctgg gggccgctgg     120
agccaggaag atgcgaggga agggatgggc gcgatggggg agggagatgg ggggggtgaa     180
cggtgagctc gcg                                                       193
```

<210> SEQ ID NO 104
<211> LENGTH: 56
<212> TYPE: DNA
<213> ORGANISM: Homo sapiens

<400> SEQUENCE: 104

```
cttcctcctg gagtgaaata caccaaaggg cgcggtgggg gtggggggtg acggga          56
```

<210> SEQ ID NO 105
<211> LENGTH: 363
<212> TYPE: DNA
<213> ORGANISM: Homo sapiens

<400> SEQUENCE: 105

```
cccagtcacc ccttctcgtg gtctccccag gctgcgtgtg gcctgccggc cttcctagtt      60
gtcccctact gcagagccac ctccacctca cccctaaat cccggggac ccactcgagg       120 cggacggggc cccctgcacc cctcttccct ggcggggaga aaggctgcag cggggcgatt     180
tgcatttcta tgaaaaccgg actacagggg caactccgcc gcaggcagg gcggcgcct      240 cagggatggc ttttgggctc tgcccctcgc tgctcccggc gtttggcgcc gcgccccct     300 ccccctgcgc ccgccccgc cccctcccg ctcccattct ctgccgggct ttgatctttg      360
ctt                                                                  363
```

<210> SEQ ID NO 106
<211> LENGTH: 65
<212> TYPE: DNA
<213> ORGANISM: Homo sapiens

<400> SEQUENCE: 106

```
aacagcccgc tgccaagtcc tccctccgcc tccgcagccc ccgccccgg cacgccccgg      60 ccgcg                                                                 65
```

<210> SEQ ID NO 107
<211> LENGTH: 940
<212> TYPE: DNA
<213> ORGANISM: Homo sapiens

<400> SEQUENCE: 107

```
tgagaccttg ctgctcccc tctcccctc aagctggaac ccccaagaag cgggttgtg       60 acctgcaaga aggctctgcc aggactccca acaggcagg gcagaaatgt gcctgctgca     120 gccccctag cgacctgggg ggtggggggc gaggtggggt cgcgaagagg aaacagacct     180
gacagtcaca ttggaggagc cagtgcaacg cgacccatct gggacctggg catccggtga    240
gggcactcac tgctcacact ggcccccac acaaattcaa aggcagaggg aaggagagct    300
gttcccatgg tttatctgct accgcgaccc agtgcatcag aacaagctgg tccaggccct   360
```

```
aggatccgga ggaggcagga gcagccacca ccccttctca actctgaccc tgaggaggcc    420
actcgaacga cgaccaccgc cttcccctte ctccgctcgg gggaagggaa aagactcagg    480
gcggagggtg gggattgggg cgggacttga aattgaagtg cgagagtcta ttggtcattg    540
gagctgccca tcaggagtgc aactcgggag cggattggcc gcgtgaggcg gggcacggcg    600
cgacgaaaaa aggggcccaa ggggtggggc tgacgctgca gctggcgcag ctcaggatta    660
gagcagcgga gccgcctagc agccaccttc ccccgccagt ccgcgcgccc gggccggggc    720 taggccccc accgccgggt ccccggggc tgcagtagca gcggcgccgc ccgcggctcc     780
cgctggggcc tgggcgccgg ccccgctctg caggatgggc acagtgctgt ctctttcgcc    840
tgcctcctcg gccaagggcc ggaggcccgg cgggctgccc gaggagaaga agaaggcgcc    900
gcccgcgggg gacgaggcgc tggggggcta cggggcgccg                          940

<210> SEQ ID NO 108
<211> LENGTH: 165
<212> TYPE: DNA
<213> ORGANISM: Homo sapiens

<400> SEQUENCE: 108
gcggctctgc agtggcccgg gcgaggggct ggagcagggg gtgacagtgg gggtggcggc    60
ggggcgggag aacggatgtc ccacagtttg cctgcggggc gacataattt gtcggagttt    120
cgaagcaagg tatgaaagga aggggctgag ggtggccggg cggct                    165

<210> SEQ ID NO 109
<211> LENGTH: 56
<212> TYPE: DNA
<213> ORGANISM: Homo sapiens

<400> SEQUENCE: 109
gactggtccc tgcaccaccc gccccaacc caagcccga gccccgcggc gcgcag           56

<210> SEQ ID NO 110
<211> LENGTH: 56
<212> TYPE: DNA
<213> ORGANISM: Homo sapiens

<400> SEQUENCE: 110
agaccctctc accaccccac ccccgcccct tgctcctgtc acgaggccca atcccc         56

<210> SEQ ID NO 111
<211> LENGTH: 227
<212> TYPE: DNA
<213> ORGANISM: Homo sapiens

<400> SEQUENCE: 111
gagcctcacc tctttcctga tccctcagcc acctgcagca aatgtctctc cagtaaagtg    60
ggggctccca gtgattttgg tggctttcac catgctgggg atagtttgac tgccatttca    120
atttctccta attcttttgg tggatggatg gatgatggag agggtagggg gtcggggtg     180 gggatgaagg aaaaaaaggc actagagctt tattaataag tggtaga                  227

<210> SEQ ID NO 112
<211> LENGTH: 138
<212> TYPE: DNA
<213> ORGANISM: Homo sapiens

<400> SEQUENCE: 112
cttccttcac gcccaaatgt tgcatatccc aagaccaccc tgtcccgcca cgcccccatc    60
```

```
ctttgcctat gaaaaccctg agaccctagc aggcagacac acaagcggct ctatgtccag    120
aggaactcat cggaggaa                                                  138
```

<210> SEQ ID NO 113
<211> LENGTH: 57
<212> TYPE: DNA
<213> ORGANISM: Homo sapiens

<400> SEQUENCE: 113

```
cagagacacc gctccccacc cccagccctc gtccctcggc tctccttcgc cggggga      57
```

<210> SEQ ID NO 114
<211> LENGTH: 69
<212> TYPE: DNA
<213> ORGANISM: Homo sapiens

<400> SEQUENCE: 114

```
agaggaggtt tccctgtcgg ggagcgcggc tgagtggggt cggggtggtg atggctgaca    60
gggcccctc                                                            69
```

<210> SEQ ID NO 115
<211> LENGTH: 58
<212> TYPE: DNA
<213> ORGANISM: Homo sapiens

<400> SEQUENCE: 115

```
tcctccccac ctgcccccca caccgccctc cggcctccct gctcccagcc gcgctccc     58
```

<210> SEQ ID NO 116
<211> LENGTH: 200
<212> TYPE: DNA
<213> ORGANISM: Homo sapiens

<400> SEQUENCE: 116

```
ccgggacctg gatgctagct gtaactggag ggaattggcg gggggagggg gaggaggggc    60
cgagtaaaga agaacttcgc gtctttaact tcgaaggtga ttttgcgttc tgtatttaca   120
gcatctccaa gcagagggct tagagctaac tcttcaccct gtcctcccca gctcccctat   180
ggcccaagga gcccaatgcc                                                200
```

<210> SEQ ID NO 117
<211> LENGTH: 248
<212> TYPE: DNA
<213> ORGANISM: Homo sapiens

<400> SEQUENCE: 117

```
gtctcatctg acctccacag gaactttgcc ttgggaggaa ccccgccccc caccccatac    60
cttccacagc tcctgacact ctcaaaggag tggatcagat cctggccaac agccagcagc   120
atccagtcct ggcagtgcca actgtgggtc agctgacttc atttcttctc ctctcactgg   180
tctgcaggct tggtctgcgt cagagggaag atggtgggca gggtgcggag atacagccct   240
gaagactc                                                             248
```

<210> SEQ ID NO 118
<211> LENGTH: 73
<212> TYPE: DNA
<213> ORGANISM: Homo sapiens

<400> SEQUENCE: 118

```
gataatagaa tgggaaagtt tctaagtatg ggaggtgggg gtaggggtgg agcagggcgc    60
tggtgttaca gct                                                      73

<210> SEQ ID NO 119
<211> LENGTH: 96
<212> TYPE: DNA
<213> ORGANISM: Homo sapiens

<400> SEQUENCE: 119
aatttaggac aagctggaga tggattagct gtgatggtgg aaggtggagg ggggcgggca    60
ggattagccg agtcatcaaa tcccattatc tgtaac                             96

<210> SEQ ID NO 120
<211> LENGTH: 58
<212> TYPE: DNA
<213> ORGANISM: Homo sapiens

<400> SEQUENCE: 120
gaatcgtgcg cgctggaaag acgggcggcc agggagtggc gggggagttt ggctgcgt     58

<210> SEQ ID NO 121
<211> LENGTH: 422
<212> TYPE: DNA
<213> ORGANISM: Homo sapiens

<400> SEQUENCE: 121
acgcccagcc cgcctgcgcc cccttatac gcgcgggccc caccccgtg cgcgcgggcc     60 cggccgcgat tagcataatg tagtattttc agtttcaaca acaccacggc gattggcggc   120
cgccccgctg ccccgccccg ccgcggcccg gccccgcgc accgcccatt ggccgcgcgc   180
acacccaccg ggggcgggc ggggcgcgcg gccggggcgc gcggctgatt ggcggccgcg   240
gggcgagcgc gctgtagcag gggaaggggg cggtgagcgg ggcgggggcg ggagttaaag   300
ggcgctgcgg gcggtaacgt gacaccgcga cgcccgcccc ctcgcccccat cccccctgca   360 acactccccc accccccgg ctcccgcccc ccgccggctc cttttgtctgc aggcggggc    420 ct                                                                  422

<210> SEQ ID NO 122
<211> LENGTH: 564
<212> TYPE: DNA
<213> ORGANISM: Homo sapiens

<400> SEQUENCE: 122
gccctggcgg cctcccaggt taacacactc ccaggtggct gcaccccaca ggcgagggct    60
gctcagagta gatgctcaac caagaggttg cccgtgcccc cttccccagc cgcaggggca   120
gccagaagcc aagcagcctc ccgcccactg gagcctggag cctgagggct gaagctgggc   180
gcctgctgcc ccctggcgtc ccgaaacggc acagccacca ggaccccccac ccacctcatt   240 catgcctcac acctgggggt gacttgggcc agggccttgc tctctggccc cgagtcccct   300
caagtgtaag atggggggctc tgcccagtgt ggctgtccgg gctgcagcgg gcaggagcgc   360 attttttcaca aaccccaaca cccctcggat ctggggtgg ggcggtgtca ctcgcacctc   420
agtgggaaac agcacgtggg cctcgcccgt ctccagggg tgggggaggg gagacaaaga    480
gcccgctctg cggagaggtg ggtacccgcc ctgccgcccc tccccattt cctctctgct    540 cccccctgccc ctcctcccct ccct                                         564
```

<210> SEQ ID NO 123
<211> LENGTH: 374
<212> TYPE: DNA
<213> ORGANISM: Homo sapiens

<400> SEQUENCE: 123

| | | | | | |
|---|---|---|---|---|---|
| tcttcctctt | tcctcttccc | ccgcgctccc | ctccctgct | ggccgctccc | ctcctgtcgc | 60 |
| cgcgtcctcg | cgtagaatgg | ttgtcttggc | gaccgttggc | cgctgccgcc | tccacgctct | 120 |
| gccccgcgcc | cagacacccc | gactccccctt | gatcccgccg | cctgactcct | cggcgtacgt | 180 |
| tctctctccg | gtctcccccct | ccatgtcccc | tcctcccctt | ttcttccaca | tcaccgatcc | 240 |
| tttctggact | ctctcccctc | ctcctttcca | gctgggagac | aggaaaagcg | gtcctgtttg | 300 |
| ggaacagtaa | aagcagggca | aggaaaggaa | ggagcggcag | aaaggagggg | tgagtcgagg | 360 |
| acacaggggc | agcc | | | | | 374 |

<210> SEQ ID NO 124
<211> LENGTH: 177
<212> TYPE: DNA
<213> ORGANISM: Homo sapiens

<400> SEQUENCE: 124

| | | | | | |
|---|---|---|---|---|---|
| gacattttcc | tcgcccgccc | cttccctccc | ctttctttac | atataggaga | tgggatactc | 60 |
| attcccgctg | ctattgataa | ggtcggaggc | ggccgggcct | ctccccagct | ttcgcccgcc | 120 |
| ccagcgcccg | ctctccctcc | gccctccctt | ggcttccttt | tgatgtagtg | gggaacg | 177 |

<210> SEQ ID NO 125
<211> LENGTH: 189
<212> TYPE: DNA
<213> ORGANISM: Homo sapiens

<400> SEQUENCE: 125

| | | | | | |
|---|---|---|---|---|---|
| ggcgctgagg | cgcgcgccgg | aagcgggagc | gggagcggga | gcgcggcggc | ggcggcgaag | 60 |
| gtgcgggcgg | ccgagcgggg | ggcggggctg | cggtgcctgc | agaaccttgg | acagaagctc | 120 |
| cctagctgcc | gccgccgccg | ccgccgccgt | cgccgccgcc | gagcgcgagc | ccagccgatc | 180 |
| cccgccgag | | | | | | 189 |

<210> SEQ ID NO 126
<211> LENGTH: 607
<212> TYPE: DNA
<213> ORGANISM: Homo sapiens

<400> SEQUENCE: 126

| | | | | | |
|---|---|---|---|---|---|
| tgtcagtcac | ctatgcaggc | gtctgagccc | ccgggttttcc | aggagccccc | cgtataagga | 60 |
| ccccagggac | tcctctcccc | acgcggccgg | gccgccgcc | cggcccccag | cccggagagc | 120 |
| tgccaccgac | cccctcaacg | tcccaagccc | cagctctgtc | gcccgcgttc | cttcctcttc | 180 |
| ctgggccaca | atcttggctt | tcccgggccg | gcttcacgca | gttgcgcagg | agcccgcggg | 240 |
| ggaagacctc | tcgtggggac | ctcgagcacg | acgtgcgacc | ctaaatcccc | acatctcctc | 300 |
| tgccgcctcg | caggccacat | gcaccggag | ccgggcgggg | caggcgcggc | ccgcaaggac | 360 |
| ccccgcgatg | gagacgcaac | actgccgcga | ctgcacttgg | ggcagcccg | ccgcgtccca | 420 |
| gccgcctccc | ggcaggaagc | gtaggtgtgt | gagccgaccc | ggagcgagcc | gcgccctcgg | 480 |
| gccagcgtgg | gcaggcgcc | gcagcctgcg | cagcccgag | gaccccgcgt | cgctctcccg | 540 |
| agccagggtt | ctcaggagcg | ggccgcgcag | gagacgttag | agggggttgt | tagcggctgt | 600 |

```
tgggaga                                                                      607

<210> SEQ ID NO 127
<211> LENGTH: 727
<212> TYPE: DNA
<213> ORGANISM: Homo sapiens

<400> SEQUENCE: 127
cctggaccag cggggagagg gggttgtgga ggcgaaatgc tgtggagaag ccggttccgc    60
gccaatttgg agagcggcgg tggcggggaa gcagggggcg gaggaaccaa gactggtgtc   120
acggcctcca gtctcctttc cctccttccc ggccctgccg cctaccgcc gctcggaggg    180 gcgccgggac cccaactcca gatgggaagc ggagggcgtg ggggagggca ggaaaaggag   240
ctaaagaaag gggagactgg gctggctggg aacttttctc cccatggagg ggacccggcc   300
tcccatcctc tctcccacgg gatagctccc caaatgaggg tgggatagag aagcccctag   360
aatgaggggc ggctctccat gcccagccgc ttcccggtcc cctgccaagg ttcctgacag   420
ggacggaacg cgggaaccca tgaccccag tcgtctagtt ctcagccctc ccgattttcc    480
tccctgaggc tcccgcctgt ggtaagtgat cggcccaact gggctttctt tcctcccaca   540 tccccctac gcgcagcaac tcctcaccgc cagaccagct accgctcggc tcagctggcg    600
ccggcgccaa cccaatatat aggccgggcc ggtcccgccc cgcacgcatg cgcctcagac   660
tgacacctcc ggacagcgcg ctcccctctc ccgcccgtcc gcccgcgtgc ccgcgcgccg   720
cgccctg                                                             727

<210> SEQ ID NO 128
<211> LENGTH: 70
<212> TYPE: DNA
<213> ORGANISM: Homo sapiens

<400> SEQUENCE: 128
ccgtcggttg ccatgtcaac ggagggtggc ggggaccggg ggaggcggag gcggggccg     60 ttctctcctc                                                           70

<210> SEQ ID NO 129
<211> LENGTH: 93
<212> TYPE: DNA
<213> ORGANISM: Homo sapiens

<400> SEQUENCE: 129
gccagcccgc ccgcccgtcc ctggccacga ggcgccccgg acctgaccac cgcccccgcc    60
acctccgccg gtgggcaagg agggtcccct ttc                                 93

<210> SEQ ID NO 130
<211> LENGTH: 261
<212> TYPE: DNA
<213> ORGANISM: Homo sapiens

<400> SEQUENCE: 130
gccgccttct gactcttccg ccccgcctcc gccccctgca ctctcccaac tggcgggagg    60
agggcgccct cccagccaat caacgtccca caggcccgc ctcccgcgcg tctttcaaag    120
gtcttctagg aaccagtcag cgattagagg ccgagtcttc ggccacccaa aggcggagta   180
agaaaccaga agcggatctg attggttgct ggaagacgcc gcgcccacct cacagaagga   240
cgaaccagtg agctaagctg c                                             261
```

```
<210> SEQ ID NO 131
<211> LENGTH: 235
<212> TYPE: DNA
<213> ORGANISM: Homo sapiens

<400> SEQUENCE: 131
cgtactggag ttctttatgt tcttggcgtg gttttgtatg ggtgtgtgcg cgcgcgtttc    60
aactgtttca ttttgagttt agttagtcgt agccattgat aaatagttcc agggccctca   120
gcgctgttag agtgaaaaga tcagcagttc ttattcccat ttatttggcg tcaagcctat   180
tctcttcctg ccgccccacc ccccgcgggc atttatttct ttatttccag tttgg        235

<210> SEQ ID NO 132
<211> LENGTH: 81
<212> TYPE: DNA
<213> ORGANISM: Homo sapiens

<400> SEQUENCE: 132
ccgaccatcc gcccaggccg cggtcaccgg ggcgggggcc aggggggcgag gaaagcgtga    60 aggtgatttc agttaatttt g                                              81

<210> SEQ ID NO 133
<211> LENGTH: 57
<212> TYPE: DNA
<213> ORGANISM: Homo sapiens

<400> SEQUENCE: 133
cccttccctc cccaccccctt cgccccgcca accctagacc cggcatgcgc tgcgccg      57

<210> SEQ ID NO 134
<211> LENGTH: 81
<212> TYPE: DNA
<213> ORGANISM: Homo sapiens

<400> SEQUENCE: 134
tgcttccagt tggagcagtg ataggaactg ggggtgggga ggtggtggtg ggttgaatga    60
aaagaggagc tctgtggtgt c                                              81

<210> SEQ ID NO 135
<211> LENGTH: 563
<212> TYPE: DNA
<213> ORGANISM: Homo sapiens

<400> SEQUENCE: 135
cagctgtcca gcgcctccct ttcctgtgct gccctcacct tctctgttaa atggcagcag    60
gaccagcggc tctcttgggg cagacatcta ccaaggactg gccacatgcc cagccttgcc   120
agcttagccg accctggga agcaggaaac gtttccagtc aatgagaaat cactcatttc    180
ttcttatttc tgcctgggtt ttgccagctt ggtgatctgg ggccccggac ctgggcagcc   240
tgggtagctt tctgacaggc ttccggcctt tcctgcctct cttgcctgcc tgcatcccac   300
agtggggact gaggccctga ggccccaagg ggaagtggcg ggcggatgct ggggttcaga   360
cgagggatgg cggggtgtag gtgacaactc caccggaact tctgctaggg cctttgccca   420
caggatgtga cttagggagg gctcatggga aacggcagge cctggcttga gatgtagtcg   480
gataatggag gccacacaag cccaccgcag atccccgccc accgcactac tgctcagacc   540
ccagcaatgc cgtggctcca ccc                                           563

<210> SEQ ID NO 136
```

```
<211> LENGTH: 56
<212> TYPE: DNA
<213> ORGANISM: Homo sapiens

<400> SEQUENCE: 136
gagacagcat cccatgacac ccccatcccc ctgccgcccc agtaactccc cacctg        56

<210> SEQ ID NO 137
<211> LENGTH: 81
<212> TYPE: DNA
<213> ORGANISM: Homo sapiens

<400> SEQUENCE: 137
tggaccgcaa ccctctttgt gggataaatg gaggggaggg ggcagaggtg tgctctcggt    60 gggggggccct tggaacctaa c                                             81

<210> SEQ ID NO 138
<211> LENGTH: 568
<212> TYPE: DNA
<213> ORGANISM: Homo sapiens

<400> SEQUENCE: 138
ataacctctt ccagatccag cagctccccc gcctcctccc caggctcctt ctgaggcggg    60
acagaaccgg tgactttcct gcccggcctg agcccagccc aagtttccag caagaggccc   120
agggagccac ttcccaaacc acaggagtga cagcagctcc ccacagggtt atgaaagacc   180
ttggtcagag agggcgggcc aggggagggg gcaccattat cacatcggaa gcagatgcag   240
ctcacctccc tgtctgtccc tcagcttggg ccttgggcta aggggggaag agggagctgt   300
ttccaccagg cccaaagcag ctgctccagt tcctcagaat gaggacgagg aaggattagg   360
aagaagctgt tcttccggg atataagagg aagcaaagaa ggtgggatga aatacatcag    420
cccttcctta aagcaatcag ggcctggctt taattggctc tgggaggctt ttctatcaca   480
aagtccacat gaggataaag actcaaccaa ggcaaaaccc cctcccccac atgaagcaca   540
ttccactccc ctactccagt gggggtgt                                      568

<210> SEQ ID NO 139
<211> LENGTH: 70
<212> TYPE: DNA
<213> ORGANISM: Homo sapiens

<400> SEQUENCE: 139
tgcattaact ttggctcaaa ccaagatgat gggtaccggg catggggtg gggaggcagt     60 tgaagatcca                                                           70

<210> SEQ ID NO 140
<211> LENGTH: 65
<212> TYPE: DNA
<213> ORGANISM: Homo sapiens

<400> SEQUENCE: 140
gtccagaaag gtgggataac tggaaacaag gagggtgggg ggtgagggga ttccaggtaa    60
taagt                                                                65

<210> SEQ ID NO 141
<211> LENGTH: 65
<212> TYPE: DNA
<213> ORGANISM: Homo sapiens

<400> SEQUENCE: 141
```

```
tcaaccatcc ccatatcccc acaagtccct ccgcccaccc ttctcagcct cgggtaacca    60
tcctt                                                                65

<210> SEQ ID NO 142
<211> LENGTH: 73
<212> TYPE: DNA
<213> ORGANISM: Homo sapiens

<400> SEQUENCE: 142
tcctctcctc accctgtgct tcgctccacc ccacccacct ttcagcacct ggttcagagt    60
gacaccattc att                                                       73

<210> SEQ ID NO 143
<211> LENGTH: 61
<212> TYPE: DNA
<213> ORGANISM: Homo sapiens

<400> SEQUENCE: 143
atcccatgac gcccccatcc ctctgctgcc ccagtaactc cccacctgag atcccatgtg    60
a                                                                    61

<210> SEQ ID NO 144
<211> LENGTH: 262
<212> TYPE: DNA
<213> ORGANISM: Homo sapiens

<400> SEQUENCE: 144
gaagatgcag ggcaggtgga gagcacagta agcgtctcgg ggggccacgc catcaccgcc    60
agcagggctc accagtatct ttgcccagag aatagccggg gtctagggag cagccagggt   120
ctagggagaa gggctgcttc cctgtggagg ctcctaactt tcccatctcc tccctgtttc   180 tccctgccc accccttact cctggaagtg tgactcgctg cctcctcccg tgactcccct    240
acattgcatc tccccagtta ct                                            262

<210> SEQ ID NO 145
<211> LENGTH: 128
<212> TYPE: DNA
<213> ORGANISM: Homo sapiens

<400> SEQUENCE: 145
tgggggccag caatcagggc agctggggaa gtggttaggg aggtggcggc acacaggccg    60
agctcagaga gtgagcagag aatgggccca ggggagggcg ctggagaggg ctgcagggct   120
tggggctg                                                            128

<210> SEQ ID NO 146
<211> LENGTH: 69
<212> TYPE: DNA
<213> ORGANISM: Homo sapiens

<400> SEQUENCE: 146
ttgaaagaac aaaccaccgg cagcccccct accacagaaa cagactccaa caagttacgt    60
gctagctcg                                                            69

<210> SEQ ID NO 147
<211> LENGTH: 61
<212> TYPE: DNA
<213> ORGANISM: Homo sapiens
```

```
<400> SEQUENCE: 147
ggctgtagtt ttcaaaatcc caactgggct ggtggagggt cgcaggtgtc aggttgagac      60
g                                                                      61

<210> SEQ ID NO 148
<211> LENGTH: 86
<212> TYPE: DNA
<213> ORGANISM: Homo sapiens

<400> SEQUENCE: 148
caacacccat cagaagtagg cagggtggtt tgtgtgacag gaagggtggg ctgtcctggg      60
actggtggag attggtggtt ctgatc                                           86

<210> SEQ ID NO 149
<211> LENGTH: 65
<212> TYPE: DNA
<213> ORGANISM: Homo sapiens

<400> SEQUENCE: 149
aggaaggatg atatctgatg gaacctgacc ttgggtggtg gaggcggggc agggaaaagg      60
ctact                                                                  65

<210> SEQ ID NO 150
<211> LENGTH: 56
<212> TYPE: DNA
<213> ORGANISM: Homo sapiens

<400> SEQUENCE: 150
agccggcgcg agagacttga cgggaggagg tggagagcgg gaggcgggaa tgaggg          56

<210> SEQ ID NO 151
<211> LENGTH: 69
<212> TYPE: DNA
<213> ORGANISM: Homo sapiens

<400> SEQUENCE: 151
ccggcgcggt tcctacaggg agcctggagg caggctgcgg ggtggctgtg ccgggagact      60
ggagcggct                                                              69

<210> SEQ ID NO 152
<211> LENGTH: 56
<212> TYPE: DNA
<213> ORGANISM: Homo sapiens

<400> SEQUENCE: 152
ctcccggggt cggtttgtcc aggcgggaag ttctgtgctg ggtgtgagag gcggca          56

<210> SEQ ID NO 153
<211> LENGTH: 433
<212> TYPE: DNA
<213> ORGANISM: Homo sapiens

<400> SEQUENCE: 153
agacccattc tcaagtgtct gccgtctgcc aggtagtgtg ctgtgtgctc ctgatgaatc      60
aaagctgaat aagacatact cgctcccttg gagggctgga gcaagacctc agggagctat     120
tgaagcaaga cagagtaaga cagatgcctg aaaagaggcc agggcgatgg agatttagag     180 tatgggtgg agtcaggaag gggctgggaa attggggaat ccacagggga aggagcattt      240
gaggagaatc ttaaaaggta gagaggcttg ctgcttgagg cagagggaac cccgcaagca     300
```

```
gagaaccgga gtggagaagc aaaagtgtgc ttgtggccca gcaggtggtc ctgtttggtg      360
ggtatagtgg ctctgatgct tagtggtcaa tggctggagt agtttggggc ccggtggtgg      420
acgctaagtt tgc                                                         433
```

<210> SEQ ID NO 154
<211> LENGTH: 205
<212> TYPE: DNA
<213> ORGANISM: Homo sapiens

<400> SEQUENCE: 154

```
actatttact cactcctccc caccctgtca acccctgctt ctgtaggtaa ttgatgctag       60
gctgaaccag gatgtgtggg gcaggcagca ctgtcctttc ccactcctgt gcctctctct      120
tcttagagac ccagggcaga gggatcctgt ggacaaagag cacctctgac ctgcccctgg      180
ctccctagtc ttgagataac ttcca                                            205
```

<210> SEQ ID NO 155
<211> LENGTH: 177
<212> TYPE: DNA
<213> ORGANISM: Homo sapiens

<400> SEQUENCE: 155

```
tagattccct gaacagtaga aaggtgattg ttagggctgg gagtggggga atggggaga        60 tattaaagca taaaaacttt cagtgataag atgaataatg caacattttt gtgggagaga     120
gatgaattag agggctgctt ctcatgaact gggggttggt ggagggcaga gaaactg         177
```

<210> SEQ ID NO 156
<211> LENGTH: 62
<212> TYPE: DNA
<213> ORGANISM: Homo sapiens

<400> SEQUENCE: 156

```
aaccaaccca gctgatactg agatggtgaa tggggcgggg gagcagggag gaatatgtcg       60
cg                                                                      62
```

<210> SEQ ID NO 157
<211> LENGTH: 287
<212> TYPE: DNA
<213> ORGANISM: Homo sapiens

<400> SEQUENCE: 157

```
aaacaccaca taccacttac aagtccacca acaacctccc catctaacag acaagacaca       60
ctttagaaga cagagaaatg aatgacaaac tcaattatta tttaaagtgc tgactaatat      120 acagggcat ctgtaatcaa ccaccacctc tgccaatcaa gcgattcttt tccatcgaat       180
ctgaatcgtg gaataaatgg gtcaggagaa acaagaaagc acatttagtg accttggcta      240
atgtgggcag tgggagcgga ggtgggtaa ggggtgctaa ataccta                     287
```

<210> SEQ ID NO 158
<211> LENGTH: 56
<212> TYPE: DNA
<213> ORGANISM: Homo sapiens

<400> SEQUENCE: 158

```
tcttccatca acttcccaca cgaccctgcc cctacctctc agaccagctg taatct           56
```

<210> SEQ ID NO 159

```
<211> LENGTH: 70
<212> TYPE: DNA
<213> ORGANISM: Homo sapiens

<400> SEQUENCE: 159
ttatggtatg ttccctgccc cacccactc cactccctct caacagggag aaagtacctg      60
aagaaaatca                                                            70

<210> SEQ ID NO 160
<211> LENGTH: 169
<212> TYPE: DNA
<213> ORGANISM: Homo sapiens

<400> SEQUENCE: 160
tacaactcct tgccaactaa gggacctgtg atggcggctg ggaggaggac tggaagggtt      60
ctgtaggcag taaagtgtac ggcgtgtttc atcaggcaac tgccaggctg ttttttcagat   120 tgttcacatt tcttttttgta tgagtttccc atttatttcg gcacgctaa                169

<210> SEQ ID NO 161
<211> LENGTH: 64
<212> TYPE: DNA
<213> ORGANISM: Homo sapiens

<400> SEQUENCE: 161
agcctcggtt cccgcccgcg cctccctctc tctccacact gccccgcaag cagagggagc      60
cagc                                                                  64

<210> SEQ ID NO 162
<211> LENGTH: 73
<212> TYPE: DNA
<213> ORGANISM: Homo sapiens

<400> SEQUENCE: 162
gagaatcccc ctggaccccc tggacacctg ccaccaccat gctcctagac tgaggcagag      60
agccaactag atg                                                        73

<210> SEQ ID NO 163
<211> LENGTH: 57
<212> TYPE: DNA
<213> ORGANISM: Homo sapiens

<400> SEQUENCE: 163
gcttttttcc tcatcccact cccaccatgc cctcccctgg aacttccaag ttcctac         57

<210> SEQ ID NO 164
<211> LENGTH: 62
<212> TYPE: DNA
<213> ORGANISM: Homo sapiens

<400> SEQUENCE: 164
aaggttcaca agcataggag ggagaagtct gggggatgag ggtgggagga aggtcccttt      60
ct                                                                    62

<210> SEQ ID NO 165
<211> LENGTH: 56
<212> TYPE: DNA
<213> ORGANISM: Homo sapiens

<400> SEQUENCE: 165
gaggccagcc cttcccaccc tctctcctcc cccgtgtgca tctgtgggac agcctg          56
```

<210> SEQ ID NO 166
<211> LENGTH: 69
<212> TYPE: DNA
<213> ORGANISM: Homo sapiens

<400> SEQUENCE: 166
aacatttctt cctgctctgt ccctctgccc tccctactt ccccatccca gtactgaggt    60
taggcttgc                                                          69

<210> SEQ ID NO 167
<211> LENGTH: 153
<212> TYPE: DNA
<213> ORGANISM: Homo sapiens

<400> SEQUENCE: 167
gagcaggtgg gctcctcatc gtgctcgctg cctccttccc tgcctccctc tcggctttcc    60
tctcagtctc cctccctgcc tccctctcag cttttctctc ggcctccctc cctgcctcct   120
ccctcagagc ctgtcctgct gtaataagga cag                               153

<210> SEQ ID NO 168
<211> LENGTH: 65
<212> TYPE: DNA
<213> ORGANISM: Homo sapiens

<400> SEQUENCE: 168
tgcggccttt cccacctcct ctctcctcct ccctctactc agcctctcgg ccctttttcgg    60 ccccc                                                                65

<210> SEQ ID NO 169
<211> LENGTH: 65
<212> TYPE: DNA
<213> ORGANISM: Homo sapiens

<400> SEQUENCE: 169
aatatgactt gcttctcctc cctccccctc cttcctgtgc ctgtatcccc atcattttt    60 tttct                                                              65

<210> SEQ ID NO 170
<211> LENGTH: 145
<212> TYPE: DNA
<213> ORGANISM: Homo sapiens

<400> SEQUENCE: 170
cctcagcctg ttttgttccc tctccctcc tccacctggc cttctccagc tcactcatca    60
atctattaga ctcaggcatc atctgcttgc cttcgtaacc ctccccaccc cgctcaccit   120 gctggattct gtgcctttgc ttgct                                        145

<210> SEQ ID NO 171
<211> LENGTH: 65
<212> TYPE: DNA
<213> ORGANISM: Homo sapiens

<400> SEQUENCE: 171
ggggttgctg ggggcagatg aaagaagagg gcctgggggc agagaggaga gggctgtgtt    60
ccact                                                                65

<210> SEQ ID NO 172

```
<211> LENGTH: 237
<212> TYPE: DNA
<213> ORGANISM: Homo sapiens

<400> SEQUENCE: 172
cccatggtcg ccaacccacc ctcctcagtc ctcgtttcag gtgactgctc cctgtgatga    60
aagccactcc ctgggctccc atatccagct ctcattcctc ccatgcccct ctctgcctcc   120
actgaaggcc catcttcttc tctgaatgtg ggatttctca ggctcccaag ctacttcact   180
ttcccttctc tcccctgccc ctcactaccc ataacgtttt caaccgacac ctcattc      237

<210> SEQ ID NO 173
<211> LENGTH: 57
<212> TYPE: DNA
<213> ORGANISM: Homo sapiens

<400> SEQUENCE: 173
gccagttgga ctccagtgag aaagtgggaa ggtgggggtg ggagggtcaa aggcaat       57

<210> SEQ ID NO 174
<211> LENGTH: 62
<212> TYPE: DNA
<213> ORGANISM: Homo sapiens

<400> SEQUENCE: 174
gaaacaaata cacccgtggg cttttagtgg ggggcattgg gtggctgagg gagaacagcg    60
gt                                                                   62

<210> SEQ ID NO 175
<211> LENGTH: 61
<212> TYPE: DNA
<213> ORGANISM: Homo sapiens

<400> SEQUENCE: 175
gctgtgggag tagggaactg gggccatgga atggggcgg agggaggatg ctttgagatc     60
a                                                                    61

<210> SEQ ID NO 176
<211> LENGTH: 70
<212> TYPE: DNA
<213> ORGANISM: Homo sapiens

<400> SEQUENCE: 176
ccgcagtcta ggccttgaac tagcagaggg taggtgtttg ggtggtggta tgctttggga    60
agtataatgt                                                           70

<210> SEQ ID NO 177
<211> LENGTH: 218
<212> TYPE: DNA
<213> ORGANISM: Homo sapiens

<400> SEQUENCE: 177
tctgcaccta tgccacgccc ccagcattcc cctcctacca ccaccttcag ccggcctccg    60
cctctgtagg ggggcattag gttttctgtc ccacagagga agggcgcttt agaaagggtt   120
agttcatcct ggaagaaaaa cgatgtcgga tgccagcata gtgtcattta aagatactgg   180
aggaatggag tgggagcggt gagggtttct tgggccta                           218

<210> SEQ ID NO 178
<211> LENGTH: 146
```

```
<212> TYPE: DNA
<213> ORGANISM: Homo sapiens

<400> SEQUENCE: 178
aagtgatata tctattatca aggaaatgct agggcatgat gcctgtcatc acaagctggg      60
agatggcatg gaacagattc ttccttaggg ccttccaaag gaaccaccac tgccacacct    120
tgacctcaga attttagcct ccagaa                                          146

<210> SEQ ID NO 179
<211> LENGTH: 61
<212> TYPE: DNA
<213> ORGANISM: Homo sapiens

<400> SEQUENCE: 179
tgactccata aaagcatttt cttttttggg tgttcggcgg gtggacagag tgtagtggta     60
c                                                                     61

<210> SEQ ID NO 180
<211> LENGTH: 61
<212> TYPE: DNA
<213> ORGANISM: Homo sapiens

<400> SEQUENCE: 180 tgttttcct ccacactcac ccaccaaccc ttggaatgcc aagggagggc tcctcactgc      60
c                                                                     61

<210> SEQ ID NO 181
<211> LENGTH: 73
<212> TYPE: DNA
<213> ORGANISM: Homo sapiens

<400> SEQUENCE: 181
ttcattcaac aagctcagaa actaagggca gacatggggt gggggcagag gggagtaggt     60
caaacatagt atc                                                        73

<210> SEQ ID NO 182
<211> LENGTH: 181
<212> TYPE: DNA
<213> ORGANISM: Homo sapiens

<400> SEQUENCE: 182
gaaggatgga agggtgcaga ctgagggaag cgtgagggag gggtgggcag ccttggccca     60
ggcccctgcc ttccccagga aaagccccct ctgtcctcca ccagacagtc aggaggctgc   120
gagtcttccc cttgacagcc tgtgccgtaa aagggtgcg gtgtggctga ctcctgaagg   180
a                                                                    181

<210> SEQ ID NO 183
<211> LENGTH: 416
<212> TYPE: DNA
<213> ORGANISM: Homo sapiens

<400> SEQUENCE: 183
aacagtttca acccagagca ccccccaccc acctgcagaa gaattgactt ttacgaaacc     60
agtccctggt gccaaaaagg ttggggacca ccgctgcact acactaccta aaagatttc   120 actttcacag tgttgcttgc ttctgtttta catgcacaag tagctaaagc tagccttctg   180
gtaaatggag gggcagagca gatggtgggg gaggagtaca tacggacgaa tttgaatcac   240
```

```
aatttcctca ctatatgcca gcaaaattta ataatagcac ctaaacatac acatgcatat      300
gtaaatgagt cacactataa aaacttttaa caagtactgg caagtcagat ggcagactta      360
ccctgaaacc tgccactcca ataaaaacct cataattaaa acaaggctg tctata           416
```

```
<210> SEQ ID NO 184
<211> LENGTH: 425
<212> TYPE: DNA
<213> ORGANISM: Homo sapiens

<400> SEQUENCE: 184
atgtattaca caatcaaaac aaaacacgga cacactcagc ttccaatctt gaccaacaca       60
catgctaagc tccattctaa cctactagga tgtcacatta ccacataaac tacctgtaac      120
tgcagatcat ttttactgaa cttccctaac acatgctgac tgtattagtc tgcccttcat      180
cggtatcaag aaatttctag tagaggggct cagaatctct cggagattct ctggtcccag      240
attagccaat ctcatctat tccgtccatt atttcttaat ctatttgtcc aatccttttct     300 atttcatctg ccacaaatga cctggaaaag ctagcagcag ataacactgc tatttcaaca     360
aactcatttt caggacagag accacacagc gtagaatcag acttaattct ggctactggg    420
tttta                                                                 425
```

```
<210> SEQ ID NO 185
<211> LENGTH: 158
<212> TYPE: DNA
<213> ORGANISM: Homo sapiens

<400> SEQUENCE: 185
ggaaaggcca tgcaacacca gagccagaac caacaccctc agctccagaa tacacttgtg      60
aggcactgga agacctgaaa ttcctctttt agtgaaaaca taagtaatgc cccctcaaca     120
tcctttcacc tcaaagtaag gtgatcctag tattagga                             158
```

```
<210> SEQ ID NO 186
<211> LENGTH: 149
<212> TYPE: DNA
<213> ORGANISM: Homo sapiens

<400> SEQUENCE: 186
agtaggcaga acaagccag actctctcct ctcctcataa tattaaatcc actcaagata      60
tacagtgaat gacaaaagac cacgacgccg atcacccgaa gaaaccccag gtaaaagcac    120
gccacaactg tcctgaacag gtagcctca                                       149
```

```
<210> SEQ ID NO 187
<211> LENGTH: 231
<212> TYPE: DNA
<213> ORGANISM: Homo sapiens

<400> SEQUENCE: 187
gatatcctca cagaaatact gtttttcgtg caaggttgct gtggtgtttg tgcaatgtta      60 tggttttttgc agcatctttt gtgatagttt ttgttaccag gcatttattt gtgagaaccc    120
ttccttcatg gccctttgag gctctatttt ttatttttgt tttttaacac aagtgactcc     180
attttgatct tgacaacttt cacataatga acagaaatgt attagctcat g              231
```

```
<210> SEQ ID NO 188
<211> LENGTH: 68
<212> TYPE: DNA
<213> ORGANISM: Homo sapiens
```

<400> SEQUENCE: 188
ttttcaaact cccttcccac accagcattc cccacttcag cctcaccttc cacataagac    60
cttcacag                                                              68

<210> SEQ ID NO 189
<211> LENGTH: 259
<212> TYPE: DNA
<213> ORGANISM: Homo sapiens

<400> SEQUENCE: 189
gcaaatatta taactggcca caagcaacat ccaaagtaac ataagaataa agataagttc    60
accgttctgt taaaaacatt taatgccata gcaataaatg actccgagtt ctctttgagg   120
gaacaaagtc accactccat tcccaggact tcggtccaag ggaaagaaac acacttgaaa   180
ctcttcctct ccaccctcaa cagaagcaca aggcacagca gccagggaac aggcaaacca   240
gtctctaaag ataaataac                                                 259

<210> SEQ ID NO 190
<211> LENGTH: 156
<212> TYPE: DNA
<213> ORGANISM: Homo sapiens

<400> SEQUENCE: 190
gctgatcaaa accaatctga atggagtcta ggtctggctg tgggctgttg ggaagaggcc    60
cccaaatctg gccatcaact ggccgcaaaa ctggccataa acaaaatctc tgctgcactg   120
tgacatgctc atgatggcca tgactcccac actgga                              156

<210> SEQ ID NO 191
<211> LENGTH: 235
<212> TYPE: DNA
<213> ORGANISM: Homo sapiens

<400> SEQUENCE: 191
aaaatgtaac aaagaagaca ggacctggct catgaggttg ctgtgaggat tcaatttgtt    60
aaagtgtggg gttgtctgta aagcatttcg gagtgtctgg accctagggc cgatgagggc   120
aagtgagaag ggctgcagcc tgagtgagga tgttccactt cctactcctg tgtgttgcta   180
agatctccac catcacctca ccgaacctga gcagaaaaag cccaggaaaa gcatc         235

<210> SEQ ID NO 192
<211> LENGTH: 83
<212> TYPE: DNA
<213> ORGANISM: Homo sapiens

<400> SEQUENCE: 192
acctgaggca gttaatgaca agaccaggaa gaagaagcac caccatcacc ccgcagacgc    60
tgcagtcagg gctggagttg aga                                            83

<210> SEQ ID NO 193
<211> LENGTH: 239
<212> TYPE: DNA
<213> ORGANISM: Homo sapiens

<400> SEQUENCE: 193
ggctcctgct atagactgtc tgtgcttttg cactggtgat ggtgttggtt tggtgagagg    60
cactgaccag tgcagatctg agtgcctcct tggtcacctg caagcaggag ggattgctca   120

```
gggtgtggga ggatcctctg ttctccatgc agcattacca caagagtgag gcactggcag    180
ctgcagggct tgctggctgt gtgctgctaa ggttctgtct gcaatggtgg ttgacagag    239
```

<210> SEQ ID NO 194
<211> LENGTH: 208
<212> TYPE: DNA
<213> ORGANISM: Homo sapiens

<400> SEQUENCE: 194

```
ttgtatggct ggaacgtagt gagcaaggga gtgatgggaa ggagatgcag tgagaatgtt    60
ttaaaagcat ccagctggct gctatgtgaa gcgtagactc cagcagggga aaagagtaga   120
agcagggaga ctggatagga gatgggtgca atgcaggaa ggggttagtt tgtgggagca    180
ggctgggtgg tggagattgg gagaagca                                      208
```

<210> SEQ ID NO 195
<211> LENGTH: 185
<212> TYPE: DNA
<213> ORGANISM: Homo sapiens

<400> SEQUENCE: 195

```
tgatcagcct gagacctcca gtggctcac caaggaggca gccatcctca gaagagtcag     60
gggataaaag gagtgctcat ctttgacatc actctctacc agagaccgc ctcaactgca    120 tcatctgctt ctgccccacc tgccacaaac ccaccatctg gagcaacgct agaccacatc   180
caagg                                                               185
```

<210> SEQ ID NO 196
<211> LENGTH: 79
<212> TYPE: DNA
<213> ORGANISM: Homo sapiens

<400> SEQUENCE: 196

```
accctccagg gcctggagcc acaccctct gccactccac tccctcactg tgtgaatttg     60
gctaagttaa accacctct                                                79
```

<210> SEQ ID NO 197
<211> LENGTH: 57
<212> TYPE: DNA
<213> ORGANISM: Homo sapiens

<400> SEQUENCE: 197

```
ggagcaggaa gaaagaagct ggttgtggga aagtgtgttg ggtgtggttt tcttgac       57
```

<210> SEQ ID NO 198
<211> LENGTH: 54
<212> TYPE: DNA
<213> ORGANISM: Homo sapiens

<400> SEQUENCE: 198

```
ataaatacac cacgcccata acaccacacg ctccacgctc acactccata catc           54
```

<210> SEQ ID NO 199
<211> LENGTH: 231
<212> TYPE: DNA
<213> ORGANISM: Homo sapiens

<400> SEQUENCE: 199

```
ctaaacctcg cgggctggac ccgcggcctg agtgggtggg tgtgtgccag aggattcggg    60
actaggccca gctccgggaa cctggaaatg tggcccgctt ctcagtggct tcctgttcat   120
```

```
gcgcttgggc ctagtggcct agttgaagaa gtggaaccac agcgtgagcc gacagggcct      180
tacagatcag acgtcaagcc ccccagacct tacaggggag gaaagtgagg c               231

<210> SEQ ID NO 200
<211> LENGTH: 91
<212> TYPE: DNA
<213> ORGANISM: Homo sapiens

<400> SEQUENCE: 200
caatttgatg acaatgttta aagaaataaa gtgaacatcc ccccacacac actcaccgaa      60
agaataagga agataatttt tattattatc a                                    91

<210> SEQ ID NO 201
<211> LENGTH: 57
<212> TYPE: DNA
<213> ORGANISM: Homo sapiens

<400> SEQUENCE: 201
agttaccacc acaccccctg caccctccag accaccacaa tgaatgaaaa tgacatg         57

<210> SEQ ID NO 202
<211> LENGTH: 100
<212> TYPE: DNA
<213> ORGANISM: Homo sapiens

<400> SEQUENCE: 202
ggtgctgaga gggtagcttc ctgctgcgta tctgcccagc caccccacc tccccaacct      60 catcacacac tcccactctt tcaagcatct tcaaattagt                           100

<210> SEQ ID NO 203
<211> LENGTH: 88
<212> TYPE: DNA
<213> ORGANISM: Homo sapiens

<400> SEQUENCE: 203
acttccatat actcactccc ctctcccacc caccacacat gcacagtttc ccctgttatt     60
gacatcttat agtatggcat atttatta                                         88

<210> SEQ ID NO 204
<211> LENGTH: 621
<212> TYPE: DNA
<213> ORGANISM: Homo sapiens

<400> SEQUENCE: 204
actcccatcc ctttagcacg cctacctccc ctgctccctc cctcacctcc ttcacacatt      60
acaatcacag gcttctgttt ctcagacaat ccgattccat tccttacaca cctctctttc     120
ccagtcccca tcgatcacac ttttcagccc tttgggtaaa gtgtatattg cttgagtccc     180
acccctgccc atgtacctcc ctcacacctc cgacacttgc acagtctttt ctttgcacat     240
tcccattttg cacaagcctc accctccctg gtacacctgc gtcatttaac cactcaccct     300
ccatgctcac ccgctcatcc cccactccca gacacacacc tagtcaactt gtgtgcacac     360
tccccttcct tggccactcc ccttcctcca ccctcctcgg gatcccacac ttgccccgc      420 ccctgggaca cctgctcgtg cggggcaggg cggggatgcg cagccgcggc cccttctcct     480 ctcccccctcc ccgccccgcc cctccctcca tccttcaccc gctccccggc gcccgccccg   540
cccgcccgcc actccggggg ggtctccgcc gccgccgccg ccggaaggag ccgccatttg     600
```

```
ccaccgccga gcgcacgggc c                                              621
```

```
<210> SEQ ID NO 205
<211> LENGTH: 65
<212> TYPE: DNA
<213> ORGANISM: Homo sapiens

<400> SEQUENCE: 205
atagaaacag agtagaatgg tggctgtcag gggttggtgg tgtgagggaa atggggagat    60
cttgg                                                               65
```

```
<210> SEQ ID NO 206
<211> LENGTH: 204
<212> TYPE: DNA
<213> ORGANISM: Homo sapiens

<400> SEQUENCE: 206
cagctctggg acttgcccaa acctttctcc ccaaaccaca cacccacaga gtctggagca    60
gggccggagt ttccccggct cctcgggtgt gtcagcatca cacatccctc cctgtctccc   120
tgctgccaac cagttccacc actgtgcacc tctgccccaa ttccacctcc cacgcctgct   180
gctgcacctt ggacttgttt tcct                                          204
```

```
<210> SEQ ID NO 207
<211> LENGTH: 83
<212> TYPE: DNA
<213> ORGANISM: Homo sapiens

<400> SEQUENCE: 207
tgcttgcata ttctgtttac agcttgtcta ctcccacacc acaccaccaa aacaggatgg    60
tatccagttc atagtagatg ttc                                           83
```

```
<210> SEQ ID NO 208
<211> LENGTH: 130
<212> TYPE: DNA
<213> ORGANISM: Homo sapiens

<400> SEQUENCE: 208
caaaatatca agtacttaag aagaaatcta ataaaagatg cacaacaccc aacacacaca    60
cacacactca cacacacaca cctgcaatta aattaaggac aatctaaata aacagaggtc   120
tatatcatgc                                                          130
```

```
<210> SEQ ID NO 209
<211> LENGTH: 366
<212> TYPE: DNA
<213> ORGANISM: Homo sapiens

<400> SEQUENCE: 209
tctagctcag aaaagcaaag atattctact ttcatatgta tgataattgg agctgagctg    60
actttaaaaa cagataattt ttcttttta tccctaataa ataatggtgc ttacagcaat   120
gagtgttgct ggtaacagat tccaccaatg ggtgtggtgt gaagtttagc atttgtggat   180
tttgcagctt ctgctattgt ctacagcatt tcctctcttg tctcggaggt tcatactttc   240
tcaggcaagg acactttaa ctccagataa atgtctgggt tttctcactc caaggataag   300 aaggtgggg tgatggagtg gtggtggtag ttgtggagtt gtcttcctgg cagggatttc   360
attgtg                                                             366
```

<210> SEQ ID NO 210
<211> LENGTH: 415
<212> TYPE: DNA
<213> ORGANISM: Homo sapiens

<400> SEQUENCE: 210

```
gttaaatgag cttattctac tgaatgtgaa gctgaatgtt agttgctttt gtggtctgct     60
atcattttca actttcctgg gccaggcccc cttttccaag ggtacaacct ggttcccatc    120
ttagaactca atttccattc aggggtactg tttttaagca tacttaaacg cacacctgag    180
tgtgcttcac catcccacac actccacagc ccacccactt tctggaacta ttcagccctc    240
agtagccttg tagcaaacca agaatggcaa atgtttccac cactcccttt cctccaata    300
caccagcccc accttaagga tcctcgcttt gaggggagga tcaaacataa ggaatgatag    360
cccgaaacac caacagccaa ccgtatttca gtgtttcacc cagagccagc ccggt         415
```

<210> SEQ ID NO 211
<211> LENGTH: 254
<212> TYPE: DNA
<213> ORGANISM: Homo sapiens

<400> SEQUENCE: 211

```
ccctagctga ggcggggacc agattgtgca cctcacgtgg ttagtcacac aaatacacac     60
caccctcaca aaccaactaa acacactgtt acaactcgtc taacaaacag catttcagaa    120
atatatgttt ttctctacaa tgtttcagca aaatacagct tcatatagtc tctcacgctc    180
aacctgtcaa aaccgaatcc acactgtcac acccagtccc aagctccctg acgtctgcat    240
cctcagactc cgta                                                      254
```

<210> SEQ ID NO 212
<211> LENGTH: 110
<212> TYPE: DNA
<213> ORGANISM: Homo sapiens

<400> SEQUENCE: 212

```
tattagaaca actagttatg atacctgaga tggaaccaat tagtcacaac acacacacaa     60
taaactgtat attcctgatc tcttgactgt cataaaattg ttcttgcatc                110
```

<210> SEQ ID NO 213
<211> LENGTH: 82
<212> TYPE: DNA
<213> ORGANISM: Homo sapiens

<400> SEQUENCE: 213

```
tgagaccttg tattgaaaca acaaccacaa caacaaccac aataacaaac accccacaat     60
tgctataata ttacctagaa tg                                              82
```

<210> SEQ ID NO 214
<211> LENGTH: 235
<212> TYPE: DNA
<213> ORGANISM: Homo sapiens

<400> SEQUENCE: 214

```
ctggcataga agaggctggt ggctattttg tccttgggct gcctgttttc aggtgaggaa     60
ggggatggta ggagacagga gacctctaaa gaccccaggt aaaccttagc ctgttactct    120
gaacagggta tgtgatctgc cagcagatcc ttgcgacagg gctgggatct gatgcatgtg    180
tgcttgtgtg agtgtgtgct gggagtcaga ttctgtgtgt gactttttaac agcct        235
```

<210> SEQ ID NO 215
<211> LENGTH: 175
<212> TYPE: DNA
<213> ORGANISM: Homo sapiens

<400> SEQUENCE: 215
agggctgggg attgcaggca cagggtcaag gtgggtagga ggtgagggct ggacaccatc     60
tgaatctgtg ctgttccagg gcccactaga gagtctccag gtacccggag cctgccctca    120
gcagtaccac cctcccacag caccccaggg accctgcaag aggtgtctgt gccct         175

<210> SEQ ID NO 216
<211> LENGTH: 60
<212> TYPE: DNA
<213> ORGANISM: Homo sapiens

<400> SEQUENCE: 216
accattttat atcggatttt tacatcctgg attttggtgg tggggtggga gtctttgaac     60

<210> SEQ ID NO 217
<211> LENGTH: 482
<212> TYPE: DNA
<213> ORGANISM: Homo sapiens

<400> SEQUENCE: 217
ctgtgatcct ttcccccacc agtttgtgat cgatttttta tcaaatttgt attttatttg     60
aggaaaggaa ggcagcgagt gaatgtggtt ctggagagag ttccccatag tgatcatctg    120
caacataaat gttgcaattg ctatttagat attattagct gtgaattttt acatagaaca    180
atggggtttt ggtgcagggt gggtggtggg gaagaaggca agtgacatag ggactatctc    240
gttcaggcgg tttcccccaa atttagcggc tggcagtgaa ctttaaataa tcccttttgct   300 ttaaatattc ttccctagta acaacttaat taaacctatg actggtaatg cttccaattt    360
agtttcttaa caggcaagtg aattgttcat ttttctctt tgtcagtaga tgaatgtctt     420
gtaatattga caaaagagaa ggcaattctt agttgggggg aaaatatatt ttattaactc    480
ca                                                                   482

<210> SEQ ID NO 218
<211> LENGTH: 91
<212> TYPE: DNA
<213> ORGANISM: Homo sapiens

<400> SEQUENCE: 218
aaaggaaatt tatgcagtaa taatgaaaca tcataagaga ggggtgtggt gctgggcttg     60
tcattaaaca ggctgaacct gtcattaaat t                                    91

<210> SEQ ID NO 219
<211> LENGTH: 84
<212> TYPE: DNA
<213> ORGANISM: Homo sapiens

<400> SEQUENCE: 219
ggccccacag caaggcctta gccagctcca ctgccagcca cagcccacac cttccctgat     60
caacctttgc tagcagcggg gctc                                            84

<210> SEQ ID NO 220
<211> LENGTH: 299
<212> TYPE: DNA
<213> ORGANISM: Homo sapiens

<400> SEQUENCE: 220
agctcgatca gcctatattt agatgtttgg ggtggagaat gagagaaaga aaagattttta    60 gggtggcatc caggtttctg aattttgtga ctcagtgaag ttttggagg gtaggtaaga     120 tgctgagttc agttttggat gtgttgagat ggactggtcc tgtggattta gttggatatt   180
agagtctaac gcttagaaca gaggtcaagg ctgtagattt agatatggag gacactggtg   240
tttgggtggt gatggcgcta tatattacat ggaattttca aaatactcaa aacttcagt    299

<210> SEQ ID NO 221
<211> LENGTH: 304
<212> TYPE: DNA
<213> ORGANISM: Homo sapiens

<400> SEQUENCE: 221
gtgttttatc tgaggaaaat ttaggttggt gttatgtttt gggctagctc tgctgaaaca    60
ttattctctt ttcttttaga gccagggctg tgggctgtgt cacttgtgac ttggcagccc   120
ttaatggggc tacatgagga agacatttcc ttacatgatt ccaagagtct ttctctgggg   180
ttctgaggta gtctctgtgt ttcttggaga tatcgttggc tctaaaattt cccctaagtg   240
aggtgatatt ctgtcatctc atgcatgggt tttggaggct gaggggtgtc tgggttggct   300
ccac                                                                304

<210> SEQ ID NO 222
<211> LENGTH: 204
<212> TYPE: DNA
<213> ORGANISM: Homo sapiens

<400> SEQUENCE: 222
tcagttgtcc ccaaacacag gaaattagct catcaatcac ccaccacccc accaaaaatt    60
aatcagggta aacttaagaa gggactcctt gtgggaacca aggaacagac cctgaaaata   120
tagaaaatat agctatcttc tccctaaagg ccaggcacac agaacccacc acggccctca   180
cgtcagcctc acattcatcc tctt                                          204

<210> SEQ ID NO 223
<211> LENGTH: 65
<212> TYPE: DNA
<213> ORGANISM: Homo sapiens

<400> SEQUENCE: 223
atcacagtca cttcacagaa ttgttgtaaa gattaatata tgcattggct gtgtgtggtg    60
gctca                                                               65

<210> SEQ ID NO 224
<211> LENGTH: 98
<212> TYPE: DNA
<213> ORGANISM: Homo sapiens

<400> SEQUENCE: 224
gttgactaca tacaatagga cggtaagaga atttgggggg tggtggtgat ggaattactt    60
tttattgtga tgtttacatg tatatgcatt tgtcaaca                           98

<210> SEQ ID NO 225
<211> LENGTH: 93
<212> TYPE: DNA
<213> ORGANISM: Homo sapiens

<400> SEQUENCE: 225
gtactagaca cttagtaggt acttaagaaa tattgaatgt cgtggtggtg gtgagctaga    60
agttataaaa aaaattcttt cccaaaaaca aca    93

<210> SEQ ID NO 226
<211> LENGTH: 86
<212> TYPE: DNA
<213> ORGANISM: Homo sapiens

<400> SEQUENCE: 226
aaatggaaac ctacatatca aaacaatagc tataaatacg tggtgggtgt ggtctgttcc    60
ttaaccctac taaggccttc atctga    86

<210> SEQ ID NO 227
<211> LENGTH: 465
<212> TYPE: DNA
<213> ORGANISM: Homo sapiens

<400> SEQUENCE: 227
gtagggaaac tgcaatagag aaagggttta attcacacag agacaagtga atgggagacc    60
agaatttgat gattactgaa atcagtctcc ccaagaattt ggggactagg gtgttccaaa   120
ggtagtttgg gggaaggggt ggggtagctt ggcagtgggt gcttgctgct gatgggttgt   180
gggggcgggg ggccatcgta gggtgtgaga caggatcctc ccgtgtgctg aaccgcttct   240
gggtggggct gcaggagtag ttggcaggtc caggtggagc catcatcagt cagtgggtcc   300
tgttggagcc gtaggtatca gacatgcaaa aaacccttgc gaggtactgc aaaaggccaa   360
tcttaggtta caatagcatt gttatctgca ggacctctgg aataatggct gataattgtt   420
tatgtctaca tcttagccaa attcaggctc ctctcctctc cctag    465

<210> SEQ ID NO 228
<211> LENGTH: 229
<212> TYPE: DNA
<213> ORGANISM: Homo sapiens

<400> SEQUENCE: 228
cctcaaagcc tctccaagcc actccctccc accctgcttt ccacacccaa gccacagcgt    60
tcagagaagc tcagggccta tttgaaatgc cagagagtgg ggatgcctcc agagaggtgg   120
catgagggcc cccagatgca ccccaccact ccctcctcca ctgcaggagg aggggcctgc   180
agttactgag gaagcctcac ccctactggg ccctcggggg tgaaggggc    229

<210> SEQ ID NO 229
<211> LENGTH: 70
<212> TYPE: DNA
<213> ORGANISM: Homo sapiens

<400> SEQUENCE: 229
acttggctcc ctctgacacc actcacctct gacacccacc ccagggctgc ctccggctct    60
gtaccctgaa    70

<210> SEQ ID NO 230
<211> LENGTH: 70
<212> TYPE: DNA
<213> ORGANISM: Homo sapiens

<400> SEQUENCE: 230
tcctggggta gccagtcttg gggacagagg acgggaggat ggtggcatga gagagggcag    60

```
gccgaaggac                                                            70

<210> SEQ ID NO 231
<211> LENGTH: 61
<212> TYPE: DNA
<213> ORGANISM: Homo sapiens

<400> SEQUENCE: 231
gatgttcaca aacaaccaga ctatagtgga gatgtgggtg gtgggttgag aaggagatca     60
t                                                                    61

<210> SEQ ID NO 232
<211> LENGTH: 57
<212> TYPE: DNA
<213> ORGANISM: Homo sapiens

<400> SEQUENCE: 232
ccatgatata accatttggg gtggtagttg ggggttgagg gtgtggaaac tacattt        57

<210> SEQ ID NO 233
<211> LENGTH: 74
<212> TYPE: DNA
<213> ORGANISM: Homo sapiens

<400> SEQUENCE: 233
gtaggctaca ttttttttac tctcagagaa aggggggtggg caggggtgtg atatgggttt    60
ttgtctctgg gagt                                                      74

<210> SEQ ID NO 234
<211> LENGTH: 74
<212> TYPE: DNA
<213> ORGANISM: Homo sapiens

<400> SEQUENCE: 234
gagagaccat tctagacacc ctccccaacc ccacatcccc aaaatccaag ccacttctaa     60
gtagtgagag aact                                                      74

<210> SEQ ID NO 235
<211> LENGTH: 85
<212> TYPE: DNA
<213> ORGANISM: Homo sapiens

<400> SEQUENCE: 235
agaatgtccc agagtcccag gtcacacagg caatcagcag ccaagccagc ccccagggtc     60
cttcaaagct gtgctctgaa cctcc                                          85
```